US 7,091,033 B2
Aug. 15, 2006

(12) United States Patent
Farr et al.

(10) Patent No.: US 7,091,033 B2
(45) Date of Patent: Aug. 15, 2006

(54) ARRAY OF TOXICOLOGICALLY RELEVANT CANINE GENES AND USES THEREOF

(75) Inventors: Spencer B. Farr, Santa Fe, NM (US); Gavin G. Pickett, Albuquerque, NM (US); Robin Eileen Neft, Albuquerque, NM (US); Robert Thomas Dunn, II, Rio Rancho, NM (US)

(73) Assignee: Phase-1 Molecular Toxicology, Inc., Santa Fe, NM (US)

( * ) Notice: Subject to any disclaimer, the term of this patent is extended or adjusted under 35 U.S.C. 154(b) by 0 days.

(21) Appl. No.: 09/911,904

(22) Filed: Jul. 23, 2001

(65) Prior Publication Data

US 2003/0096234 A1 May 22, 2003

Related U.S. Application Data

(60) Provisional application No. 60/220,057, filed on Jul. 21, 2000.

(51) Int. Cl.
*C07H 21/04* (2006.01)
*C12Q 1/68* (2006.01)

(52) U.S. Cl. ............ 435/287.2; 435/6; 435/174; 435/283.1; 435/2; 536/23.1; 536/24.3; 536/24.31

(58) Field of Classification Search .......... 435/6, 435/174, 283.1, 287.2; 536/23.1, 24.3, 24.31; 424/9.2
See application file for complete search history.

(56) References Cited

U.S. PATENT DOCUMENTS

| | | | |
|---|---|---|---|
| 5,143,854 A | 9/1992 | Pirrung et al. | |
| 5,252,743 A | 10/1993 | Barrett et al. | |
| 5,384,261 A | 1/1995 | Winkler et al. | |
| 5,412,087 A | 5/1995 | McGall et al. | |
| 5,424,186 A | 6/1995 | Fodor et al. | |
| 5,451,683 A | 9/1995 | Barrett et al. | |
| 5,474,796 A | * 12/1995 | Brennan ........... | 427/2.13 |
| 5,510,270 A | 4/1996 | Fodor et al. | |
| 5,545,531 A | 8/1996 | Rava et al. | |
| 5,585,232 A | 12/1996 | Farr | |
| 5,589,337 A | 12/1996 | Farr | |
| 5,599,695 A | 2/1997 | Pease et al. | |
| 5,624,711 A | 4/1997 | Sundberg et al. | |
| 5,631,734 A | 5/1997 | Stern et al. | |
| 5,654,401 A | 8/1997 | Clements et al. | |
| 5,677,195 A | 10/1997 | Winkler et al. | |
| 5,744,305 A | 4/1998 | Fodor et al. | |
| 5,811,231 A | 9/1998 | Farr et al. | |
| 6,114,114 A | 9/2000 | Seilhamer et al. | |
| 6,201,114 B1 | * 3/2001 | Aguirre et al. ........ | 536/23.5 |
| 6,228,589 B1 | 5/2001 | Brenner | |
| 6,251,632 B1 | * 6/2001 | Lillicrap et al. ........ | 435/69.1 |
| 6,465,178 B1 | * 10/2002 | Chappa et al. ........... | 435/6 |
| 2002/0187480 A1 | * 12/2002 | Brandon ............... | 435/6 |

FOREIGN PATENT DOCUMENTS

| | | |
|---|---|---|
| EP | 0 292 879 A2 | 11/1988 |
| WO | WO 92/10092 | 6/1992 |
| WO | WO 93/09668 | 5/1993 |
| WO | WO 97/10365 | 3/1997 |
| WO | WO 99/05320 | 2/1999 |
| WO | WO 00/12760 | 3/2000 |
| WO | WO 00/47761 A3 | 8/2000 |
| WO | WO 01/32928 A2 | 5/2001 |
| WO | WO 01/51667 A2 | 7/2001 |

OTHER PUBLICATIONS

Ding et al. "Unsupervised feature selection via two–way ordering in gene expression analysis." Bioinformatics. vol. 19, No. 10 pp. 1259–1266, 2003.*
Li et al. "Zipf's law in importance of genes for cancer classification using microarray data." J. Theor. Bil. vol. 219, pp. 539 551, 2002.*
Debouck et al. "DNA microarrays in drug discovery and development" Nature Genetics Supplement. vol. 21, pp. 48–50, Jan. 1999.*
Pirson et al. (Genbank Accession No. X95367, Oct. 1996).*
Yokota (Genbank Accession No. AB008451, Oct. 1997).*
Nakamura et al. (Genbank Accession No. AB012918, Oct. 1999).*
Van Leeuwen et al. (Genbank Accession No. L37107, Feb. 1997).*
Kobayashi et al. (Genbank Accession No. AB028042, Nov. 1999).*
Somberg et al. (Genbank Accession No. U28141, Jun. 1995).*
Kobayashi et al (Genbank Accession No. D84397, Jun. 1999).*
Manning et al. (Genbank Accession No. L31625, Apr. 1994).*
Puel et al. (Genbank Accession No. AF045016, Feb. 1998).*
Ortiz–Garcia et al. (Genbank Accession No. AF021873, Jul. 1999).*
BD Atlas Human cDNA expression array Gene list for cat #7740–1, 1999.*

(Continued)

*Primary Examiner*—Jeanine A. Goldberg
(74) *Attorney, Agent, or Firm*—Janeen Vilven; Peacock Myers, P.C.

(57) ABSTRACT

The invention provides for canine genes indicative of toxicological responses to agents such as drugs, pharmaceutical compounds, or chemicals. Methods of identifying and isolating toxicologically relevant canine gene are disclosed. In addition, an array comprising toxicologically relevant canine genes, methods of making a canine gene array, and methods of using a canine gene array in which toxicological responses can analyzed in a rapid and efficient manner are also provided. The methods disclosed herein are also useful for discovering and obtaining novel canine genes. Primers and sequences of novel canine genes are also disclosed.

5 Claims, 8 Drawing Sheets

(4 of 8 Drawing Sheet(s) Filed in Color)

OTHER PUBLICATIONS

Kraemer, et al., Regulation of Prostaglandin Endoperoxide H Synthase–2 Expression by 2,3,7,8–Tetrachlorodibenzo–p–dioxin, Archives of Biochemistry and Biophysics, 1996, 319–328, vol. 330, No. 2, Article No. 0259, Academic Press, Inc.

Bartosiewicz, et al., Development of a Toxicological Gene Array and Quantitative Assessment of This Technology, Archives of Biochemistry and Biophysics, 2000, 66–73, vol. 376, No. 1, Academic Press, Inc.

Schraml, et al., Tissue Microarrays for Gene Amplification Surveys in Many Different Tumor Types, Clinical Cancer Research: An Official Journal of the American Association for Cancer Research, 1999, 1966–1975, vol. 5, No. 8.

Farr, et al., Concise Review: Gene Expression Applied to Toxicology, Toxicological Sciences, 1999, 1–9, vol. 50, Society of Toxicology.

Marton, et al., Drug Target Validation and Identification of Secondary Drug Target Effects Using DNA Microarrays, Nature Medicine, 1998, 1293–1300, vol. 4, No. 11.

Schena, et al., Parallel Human Genome Analysis: Microarry–based Expression Monitoring of 1000 Genes, Proc. Natl. Acad. Sci. USA, 1996, 10614–10619, vol. 93.

Burczynski, et al., Toxicogenomics–Based Discrimination of Toxic Mechanism in HepG2 Human Hepatoma Cells, Toxicological Sciences, 2000, 399–415, vol. 58, Society of Toxicology.

U.S. Appl. No. 60/264,933, Farr et al., filed Jan. 29, 2000.
U.S. Appl. No. 60/220,057, Farr et al., filed Jul. 21, 2000.
U.S. Appl. No. 60/308,161, Farr et al., filed Jul. 26, 2000.
U.S. Appl. No. 60/254,232, Farr, filed Dec. 7, 2000.

Altshul, S. F. et al. (1997). "Gapped BLAST and PSI–BLAST: A New Generation of Protein Database Search Programs," *Nucleic Acids Res*. 25(17):3389–3402.

Amdur, M. O. et al., eds. (1991). *Casarett and Doull's Toxicology*, 4th edition, Pergamon Press, New York, p. 37. (Includes Table of Contents).

Bulera, S. J. (2001). "RNA, Expression in the Early Characterization of the Hepatotoxicants in Wistar Rats by High–Density DNA Microarrays," *Hepatology* 33(5):1239–1258.

Cortese, J. D. (2000). "The Array of Today," *The Scientist* 14(17):24–28.

Cortese, J. D.(2000),. "Array of Options," *The Scientist* 14(11):25–29.

Cunningham, M. J. (2000). "Gene Expression Microarray Data Analysis for Toxicology Profiling," *Ann. N.Y. Acad. Sci* 919:52–67.

Gennaro, A. R., ed. (1990). *Remington's Pharmaceutical Sciences*, 18th edition. Mack Publishing Co., Easton, Pennsylvania, pp. xv–xvi (Table of Contents Only).

Haab, B. B. et al. (2001). "Protein Microarrays for Highly Parallel Detection and Quantation of Specific Proteins and for Antibodies in Complex Solutions," *Genome Biol*. 2(2):Research 0004.1–0004.13.

Hayes, A. W., ed (2000). *Principles and Methods in Toxicology*, Corporate Product Integrity, The Gillette Co., Boston, Massachusetts, pp. v–vii (Table of Contents Only).

Heuvel, J. P. V., ed. (1997). *PCR Protocols in Molecular Toxicology*. (Table of Contents only).

Hough, C.D. et al. (2000). "Large–Scale Serial Analysis of Gene Expression Reveals Gnes Differentially Expressed in Ovarian Cancer," *Cancer Res*. 60(22):6281–6287.

http://cmgm.stanford.edu./pbrown.
http://www.comt.corning.com.

Johannes, G. et al. (1993). "Identification of Eukaryotic mRNAs that Are Translated at Reduced Cap Binding Complex elF4F Concentrations Using a cDNA Microarray," *Proc. Natl. Acad. Sci.* 96(23):13118–13123.

Kane, M. D. et al. (2000). "Assessment of the Sensitivity and Specificity of Oligonucleotide (50mer), Microarrays," *Nucleic Acids. Res.* 28(22):4552–4557.

Liang, P. and Pardee (1992). "Differential Display of Eurkaryotic Messenger RNA by Means of the Polymerase Chain Reaction," *Science* 257:967–971.

Liang, P. et al. (1993). "Distribution and Cloning of Eukaryiotic mRNAs by Means of Differential Display: Refinements and Optimization," *Nucleic Acids Res.* 21(14):3269–3275.

Lockhart, D.J. and Winzeler, E. A. (2000). "Genomics, Gene Expression and DNA Arrays," *Nature* 405(6788):827–836.

MacBeath, G. and Schreiber, S. L. (2000). "Printing Proteins as Microarrays for High–Throughput Function Determination," *Science* 289(5482):1760–1763.

Nadadur, S.S. et al.(2000). "A Pulmonary Rat Gene Array for Screening Altered Expression Profiles in Air Pollutant–Induced Lung Injury," *Inhalation Toxicology* 12:1239–1254.

Needleman, S. B. & Wunsh, C. D. (1970). "A General Method Applicable to the Search for Similarities in the Amino Acid Sequence of Two Proteins," *J. Mol. Biol.* 48:443–451.

Nuwaysir, E. F. et al. (1999). "Microarrays and Toxicology: The Advent of Toxicogenomics," *Molecular Carcinogenesis* 24:153–159.

Pearson, W. R. & Lipman, D. J. (1988). "Improved Tools for Biological Sequence Comparison," *Proc. Natal. Acad. Sci. USA*. 85:24444.

Sherlock, G. et al. (2001). "The Stanford Microarray Database," *Nucleic Acids Res.* 29(1)152–155.

Smith, T. F. and Waterman, M. S. (1981). "Comparison of Biosequences," *Adv. Appl. Math* 2:482–489.

Waring, J. F. et al.(1992). "Microarray Analysis of Hepatotoxins In Vitro Reveals a Correlation Between Gene Expression Profiles and Mechanisms of Toxicity," *Toxicol. Lett.* 120(1–3):359–368.

Welsh, J. et al. (1992). "Arbitrarily Primed PCR Fingerprinting of RNA," *Nucl. Acids Res.* 20(19):4965–4970.

Ausubel, F. M. et al. eds. (1987). *Current Protocols in Molecular Biology*. John Wiley & Wiley & Sons, Inc. pp. 1–9. (Table of Contents only).

Barnes, B. and Gordon, S. (1980). "Methods for Growth of Cultured Cells in Serum–Free Medium," *Anal. Biochem.* 102:255–270.

Coligan, J. E. et al, eds (1991). *Current Protocols in Immunology*, a Wiley & Sons, Inc. Publication. pp. 1–9. (Table of Contents only).

Diehn, M. et al. (1993). "Large–Scale Identification of Secreted and Membrane–Associated Gene Products Using DNA Microarrays," *Nat. Genet.* 25:58–62.

Feuerstein, G. Z., and Wang, X. (1997). "Use of Differential Display Reverse Transcription—Polymerase Chain Reaction for Discovery of Induced Adrenomedullin Gene Expression in Focal Stoke," *Can J. Physiol. Pharmacol.* 75:731–734.

Freshney, R. I. ed. (1987). *Animal Cell Culture, A Practical Approach*. IRL Press, Oxford Washington, DC, pp vii–xii. (Table of Contents only).

Gait, M. J. ed. (1990). *Oligonucleotide Synthesis*. IRL Press, Oxford Washington DC, pp vii–xiii. (Table of Contents only).

Ham, R. G. and Wallace, W. L. (1979). "Media and Growth Requirements" In *Methods in Enymology* vol. LVIII, Academic Press, Inc., pp. 44–93.

Harlow, E. and Lane, D. (1988). *Antibodies: A Laboratory Manual*, Harlow, E. and Lane, D. eds., Cold Spring Harbor Laboratory, pp. iii–ix. (Table of Contents only).

Hayes, A. W. ed. (2000). *Principals and Method in Toxicology*, Taylor & Frances, pp v–vii. (Table of Contents).

Hayward, R. E. et al. (1993). "Shotgun DNA Microarrays and Stage–Specific Gene Expression in *Plasmodium falciparum* Malaria," *Mol. Microbiol.* 35(1):6–14.

Heuvel, John P. Vanden, ed. (1997). *PCR Protocols in Molecular Toxicology*, National Library of Medicine.

Hough, C. D. et al. (2000). "Large–Scale Serial Analysis of Gene Expression Reveals Genes Differentially Expressed in Ovarian Canccer," *Cancer Res.* 60:6281–6287.

Johannes, G. et al. (1999). "Identification of Eukaryotic mRNAs that Are Translated at Reduced Cap Binding Complex ElF4F Concentrations Using a cDNA Microarray," *Proc. Nat. Acad. Sci. USA* 96(23):13118–13123.

Klein, P. E. et al. (2000). "A High–Throughput AFLP–based Method for Constructing Integrated Genetic and Physical Maps: Progress Toward a Sorghum Genome Map," *Genome Res.* 10:789–807.

Liang, P. and Pardee, A. B. (1992). "Differential Display of Eurkaryotic Messenger RNA by Means of the Olymerase Chain Reaction", *Science* 257:967–971.

Liang, P. et al. (1993). "Distribution and Cloning of Eukaryotic mRNAs by Means of Differential Display: Refinements and Optimization," *Nucl. Acids. Res.* 21(14):3269–3275.

Masseyeff, R. H. et al. eds. (1993). *Methods of Immunological Analysis*. Weinheim: VCH Verlags gesellschaft mbH, vol. 1–3. (Table of Contents only).

Miller, J. M. & Carlos, M. P. eds. (1987). *Gene Transfer Vectors for Mammalian Cells*. Current Communications in Molecular Biology, Cold Spring Harbor Laboratory, pp. vii–ix. (Table of Contents only).

Mullis, K. B. et al eds. (1994). *PCR: The Polymerase Chain Reaction*, Birkhäuser Boston, pp xv–xvii. (Table of Contents only).

Nadeau, J. H. (1992). "Multilocus Markers for Mouse Genome Analysis: PCR Amplification Based on Single Primers of Arbitrary Nucleotide Sequence," *Genome* 3:55–64.

Sambrook, J. et al (1989). *Molecular Cloning: A Laboratory Manual*, Cold Spring Harbor Laboratory Press, pp xi–xxxviii. (Table of Contents only).

Scherf, U. et al. (2000). "A Gene Expression Database for the Molecular Pharmacology of Cancer," *Nat. Genet.* 24:236–44.

Stahr, H. M. (1991). *Analytical Methods in Toxicology*. Wiley–Interscience Publication, John Wiley & Sons, Inc. pp. ix–xiii. (Table of Contents Only).

Wang, X. and Feuerstein, G. Z. (1997). "The Use of mRNA Differential Display for Discovery of Novel Therapeutic Targets in Cardiovascular Disease," *Cardiovasc. Res.* 35(3):414–421.

Weir, D. M. & Blackwell, C. C.eds. *Handbook of Experimental Immunology in Four Volumes*, vol. 1–4. Blackwell Scientific Publication, fourth edition. (Table of Contents only).

Welsh, J. et al. (1990). "Fingerprinting Genomes Using PCR with Arbitrary Primers," *Nucl. Acids Res.* 18(24):7213–7218.

Welsh, J. et al. (1992). "Arbitrarily Primed PCR Fingerprinting of RNA," *Nucl. Acid Res.* 20:4965–4970.

Wild, D. ed., (1994). *The Immunoassay Handbook*, Stockton Press NY, pp i–xix. (Table of Contents only).

Williams, J. G. K. et al. (1990). "DNA Polymorphisms Amplified by Arbitrary Primers Are Useful as Genetic Markers," *Nucl. Acids. Res.* 18(22):6531–6535.

Wilson, M. et al. (1999). "Exploring Drug–Induced Alterations in Gene Expression in *Mycobacterium Tuberculosis* by Microarry Hybridization," *Proc. Nat. Acad. Sci.* 96(22):12833–12838.

Woodward, S. R. et al (1992). "Random Sequence Olignucleotide Primers Detect polymorphic DNA products which Segregate in Inbred Strains of Mice," *Genome* 3:73–78.

Ye, S. Q. et al. (2000). "MiniSage: Gene Expression Profiling Using Serial Analysis of Gene Expression from 1 μg Total RNA," *Anal. Biochem.* 287(1):144–152.

* cited by examiner

Figure 2

| Gene | 0.1 µM | 1 µM | 10 µM |
|---|---|---|---|
| Alkaline phosphatase | 1.28 | 1.11 | 1.21 |
| BR-cadherin | 1.21 | -1.2 | 1.19 |
| BRCA1 | | 1.02 | 1.1 |
| Beta-glucuronidase | -1.03 | 1.05 | -1.09 |
| CD40 ligand | 1.27 | -1.05 | 1.3 |
| Catalase | -1.02 | 1.23 | -1.1 |
| Caveolin-2 | -1.02 | -1.13 | -1.02 |
| Cubilin | 1.1 | 1.06 | 1.08 |
| Cytochrome P450 2B | 1.07 | -1.68 | 1.11 |
| Cytochrome P450 2C21 | -1.37 | -1.01 | -1.44 |
| Cytochrome P450 2C41 | 1.28 | 1.08 | 1.18 |
| Cytochrome P450 2D | 1.02 | -1.75 | 1.12 |
| Cytochrome P450 3A | 1.29 | 1.04 | 1.17 |
| Decorin | 1.03 | -1.63 | 1.1 |
| Ear-3 (verbA related) OR Apolipoprotein A1 regulatory protein (ARP-1) | 1 | 1.06 | -1.1 |
| FGFR2 | -1.2 | -1.02 | -1.17 |
| GRP94 | -1.4 | -1.1 | -1.28 |
| Gadd45 | -1.21 | -1.15 | -1.26 |
| Glucose transporter | 1.06 | 1.29 | 1.06 |
| Glucose-6-phosphate | 1.14 | -1.51 | 1.23 |
| Glucose-regulated protein 94 | -1.32 | -1.04 | -1.27 |
| Glutathione S-transferase alpha subunit | -1.03 | 1.16 | 1 |
| IL-10 | 1.11 | -1.27 | 1.04 |
| IL-8 | -3.15 | -4.65 | -5.36 |
| Keratinocyte growth factor | 1.1 | -1.56 | 1.2 |
| Mek5 | 1.21 | 1.03 | 1.17 |
| Metallothionein 1 | -1.05 | 1.35 | 1.72 |
| Multidrug resistant protein-1 | -1.12 | -1.03 | -1.25 |
| N-cadherin | 1.08 | -1.06 | -1.03 |
| Paraoxonase1 (PON2) | -1.08 | 1.21 | -1.04 |
| Phenol sulfotransferase | -1.03 | 1.07 | -1.07 |
| Proliferating cell nuclear antigen gene | 1.07 | 1.01 | -1.02 |
| Prostaglandin D synthase | 1.06 | -1.36 | -1.05 |
| Rab2 | -1.14 | 1.12 | -1.14 |
| Rab5 | -1.02 | 1.24 | 1.02 |
| Rab7 | -1.1 | -1 | -1.13 |
| SHB (Src homology 2 protein) | -1.02 | -1.02 | -1.13 |
| Superoxide dismutase Mn | -1.05 | -1.02 | -1.16 |
| Tissue inhibitor of metalloproteinases-1 | -1.01 | -1.18 | -1.16 |
| Tumor necrosis factor-alpha | 1.2 | -1.02 | 1.02 |
| UV Excision repair protein RAD23 (XP-C) | -1.23 | 1.55 | 1.16 |
| Ubiquitin | -1.12 | 1.04 | -1.19 |
| Vascular cell adhesion molecule 1 (VCAM-1) | 1.23 | -1.18 | 1.33 |
| ZAP38/annexin IV | -1.08 | 1.15 | -1.12 |
| c-erb B-2 | 1.41 | 1.58 | 1.02 |
| p38 MAPK | 1.04 | 1 | 1.05 |
| p53 | 1.09 | 1.35 | 1.02 |

Dose Response Curve of Interleukin-8 (IL-8) Over Three Doses

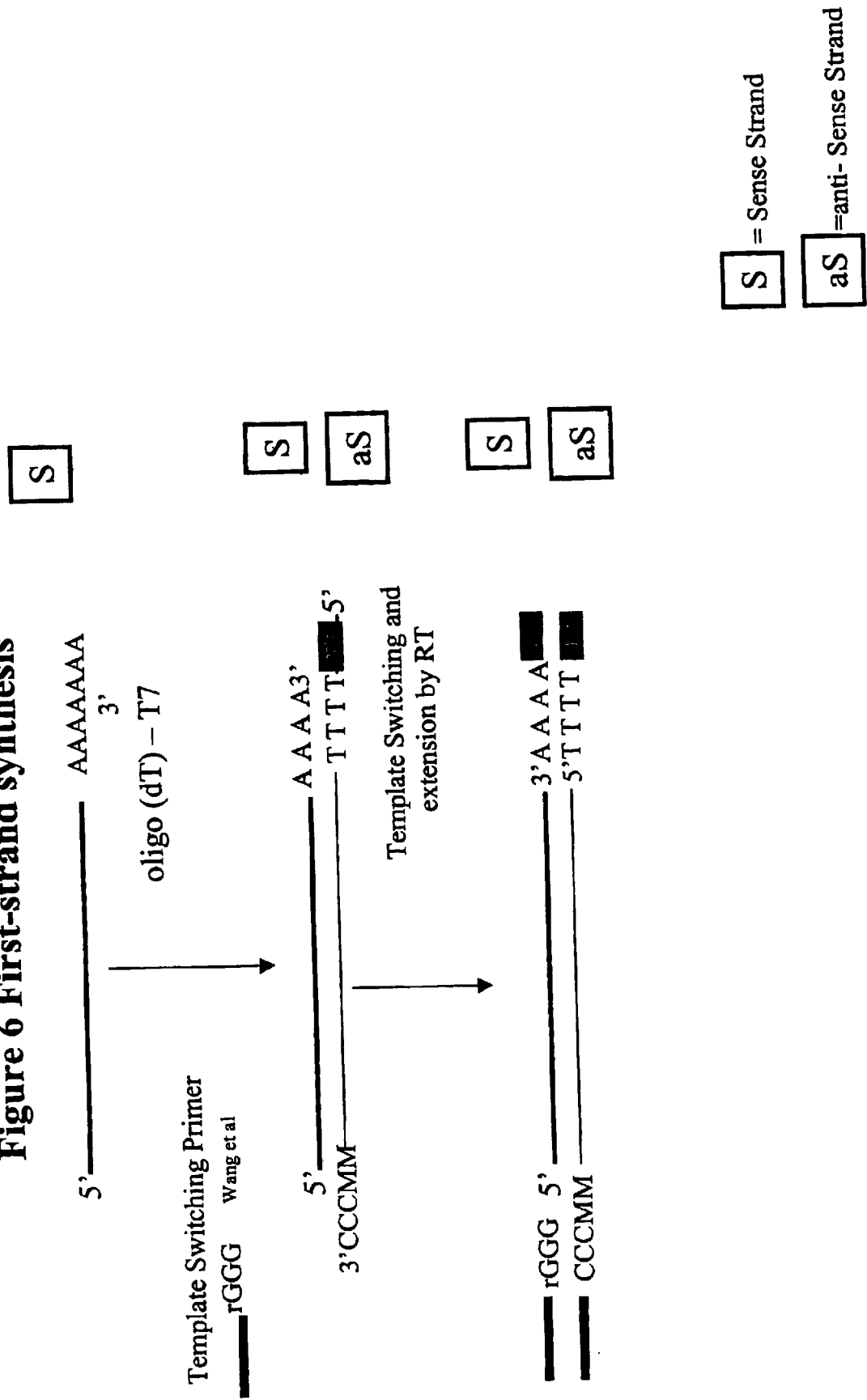

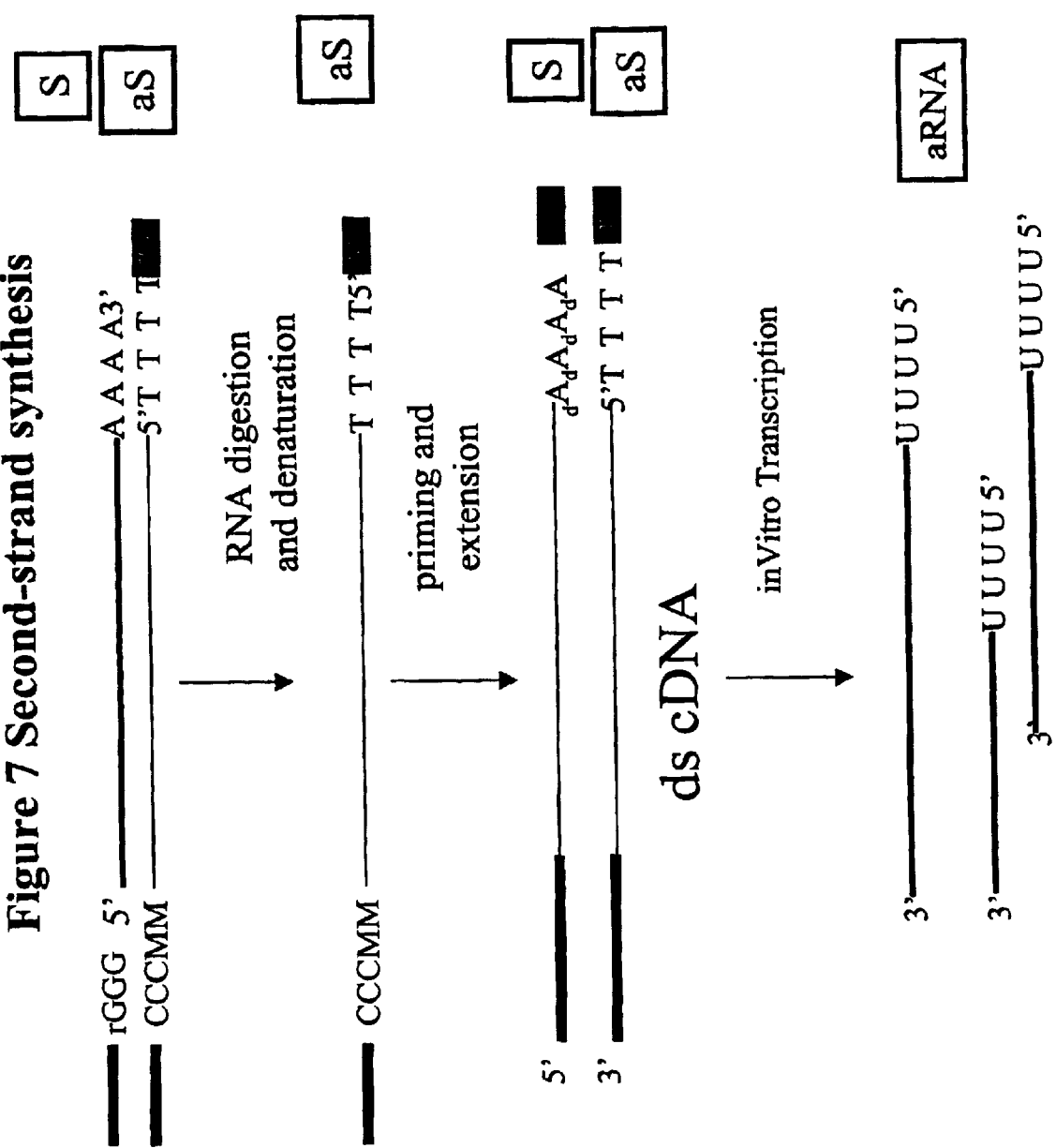

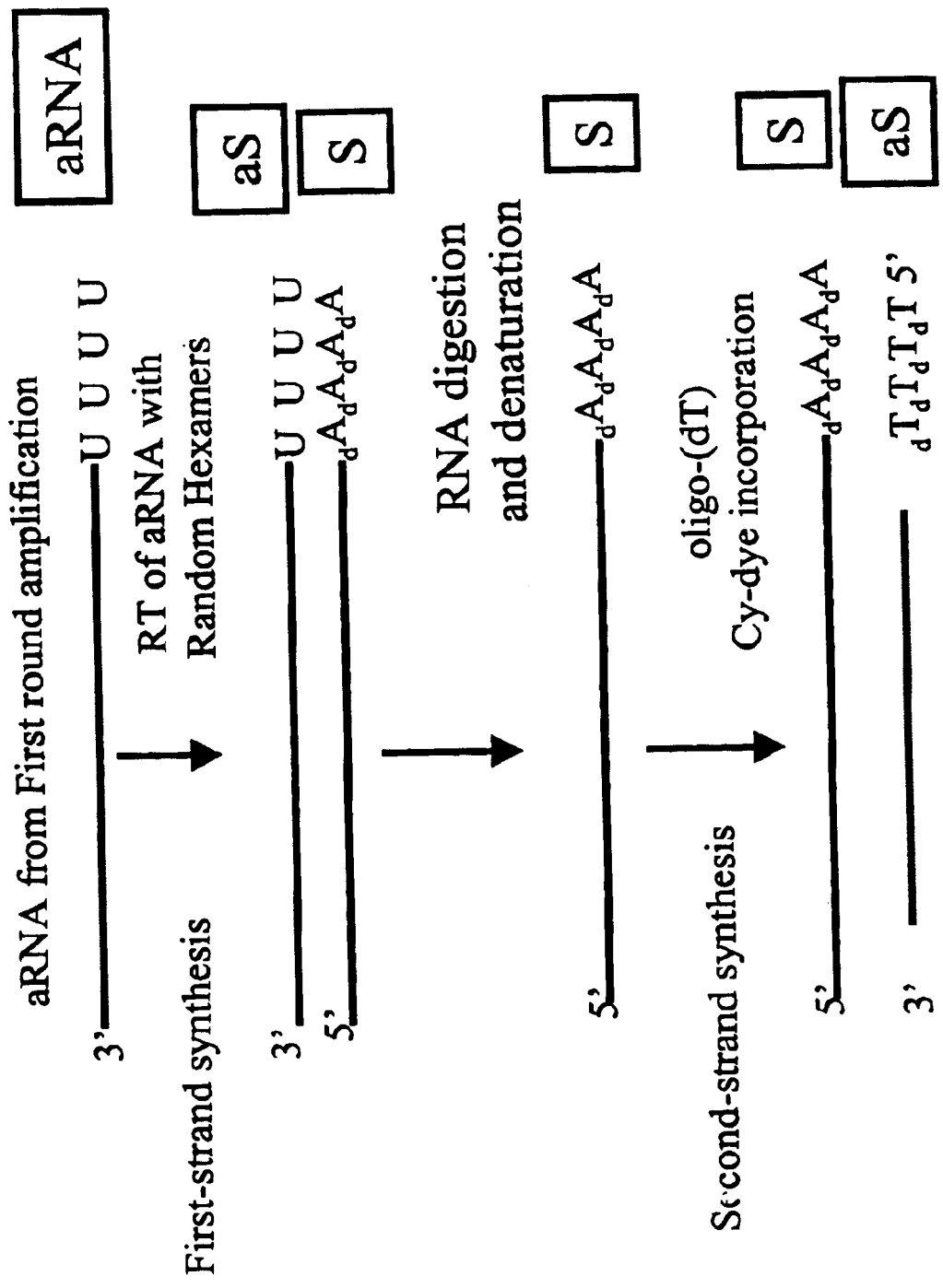

ARRAY OF TOXICOLOGICALLY RELEVANT CANINE GENES AND USES THEREOF

CROSS-REFERENCE TO RELATED APPLICATIONS

This application claims priority to U.S. provisional application Ser. No. 60/220,057, filed Jul. 21, 2000 which is incorporated by reference in its entirety.

TECHNICAL FIELD

This invention is in the field of toxicology. More specifically, the invention provides for methods for identifying canine genes which are toxic response genes, the genes themselves, and methods of using these genes. Also provided herein are primer sequences and sequence of canine genes which are useful for making and using arrays to determining toxicological responses to various agents and also useful for identifying novel canine gene sequences and novel canine genes.

BACKGROUND OF THE INVENTION

Individuals exhibit a high degree of variability in response to agents such as drugs, pharmaceutical compounds, and chemicals. The development of a drug or pharmaceutical compounds can take many years and cost millions of dollars. In addition, some companies use animals (e.g., mice, rabbits, dogs, cats, pigs, etc.) to test the efficacy and toxicity of drugs and/or pharmaceutical compounds to obtain data for Phase I trials. Many drugs that are being developed do not proceed beyond a Phase I trial for many different reasons. One plausible reason is a lack of data in an accepted animal model for the disease or symptoms which the drug is targeted to treat. Animals used in various disease models include, but are not limited to dogs, pigs, rabbits, cats, chimpanzees, and other primates. In addition, animals are used to test toxicity levels and toxicological responses to drugs and pharmaceutical compounds under development.

In animals, toxicity of a drug can be determined by observing several in vivo parameters, including but not limited to drug levels in blood, tissues, urine, and other biological fluids; enzymatic levels in tissues and organs; protein or sugar levels in blood and other biological fluids; elevation or depression in number, size, morphology, and/or function of cells (e.g., white blood cells, lymphocytes, red blood cells, etc.), tissues, or organs (e.g., liver, heart, kidney, etc.). Other physical and physiological parameters which may be useful include but are not limited to survival rate of animals, appearance (e.g., hair loss, brightness of eyes, etc.), and behavior (e.g., eating habits, sleeping habits, etc.).

With the advent of molecular and recombinant technology, genetic and molecular analysis provides another method by which toxicity may be measured. Differential gene expression technology involves detecting the change in gene expression of cells exposed to various stimuli. The stimulus can be in the form of growth factors, receptor-ligand binding, transcription factors, or exogenous factors such as drugs, chemicals, or pharmaceutical compounds. Differential gene expression can be observed by using techniques involving gel electrophoresis and polynucleotide microarrays.

A polynucleotide microarray may include genes for which full-length cDNAs have been accurately sequenced and genes which may be defined by high-throughput, single-pass sequencing of random cDNA clones to generate expressed sequence tags (ESTs). Bioinformatic algorithms such as Unigene group cDNA clones with common 3' ends into clusters which tentatively define distinct human genes. An ideal cDNA microarray might therefore contain one representative from each Unigene cluster. In practice, given the current complement of about 45,925 Unigene clusters, most microarrays contain at most one-third of the total Unigene set.

Researchers focused on detecting changes in expression of individual mRNAs can use different methods to detect changes in gene expression, for example, microarray, gel electrophoresis, etc. Other methods have focused on using the polymerase chain reaction (PCR) and/or reverse transcriptase polymerase chain reaction (RT-PCR) to define tags and to attempt to detect differentially expressed genes. Many groups have used PCR methods to establish databases of mRNA sequence tags which could conceivably be used to compare gene expression among different tissues (See, for example, Williams, J. G. K., *Nucl. Acids Res.* 18:6531, 1990; Welsh, J., et al. *Nucl. Acids Res.*, 18:7213, 1990; Woodward, S. R., Mamm. *Genome*, 3:73, 1992; and Nadeau, J. H., Mamm. *Genome* 3:55, 1992). This method has also been adapted to compare mRNA populations in a process called mRNA differential display. In this method, the results of PCR synthesis are subjected to gel electrophoresis, and the bands produced by two or more mRNA populations are compared. Bands present on an autoradiograph of one gel from one mRNA population, and not present on another, correspond to the presence of a particular mRNA in one population and not in the other, and thus indicate a gene that is likely to be differentially expressed. Messenger RNA derived from two different types of cells can be compared by using arbitrary oligonucleotide sequences of ten nucleotides (random 10-mers) as a 5' primer and a set of 12 oligonucleotides complimentary to the poly A tail as a 3' "anchor primer". These primers are then used to amplify partial sequences of mRNAs with the addition of radioactive deoxyribonucleotides. These amplified sequences are then resolved on a sequencing gel such that each sequencing gel has a sequence of 50–100 mRNAs. The sequencing gels are then compared to each other to determine which amplified segments are expressed differentially (See, for example, Liang, P. et al. Science 257:967, 1992; See also Welsh, J. et al., Nucl. Acid Res. 20:4965, 1992; Liang, P., et al., Nucl. Acids Res., 3269 1993; and U.S. Pat. Nos. 6,114,114 and 6,228,589).

The process of isolating mRNA from cells or tissues exposed to a stimulus (e.g., drugs or chemicals) and analyzing the expression with gel electrophoresis can be laborious and tedious. To that end, microarray technology provides a faster and more efficient method of detecting differential gene expression. Differential gene expression analysis by microarrays involves nucleotides immobilized on a substrate whereby nucleotides from cells which have been exposed to a stimulus can be contacted with the immobilized nucleotides to generate a hybridization pattern. This microarray technology has been used for detecting secretion and membrane-associated gene products, collecting pharmacological information about cancer, stage specific gene expression in Plasmodium falciparum malaria, translation products in eukaryotes, and a number of other scientific inquiries. See, for example, Diehn M, et al. Nat Genet. 25(1):58–62 (1993); Scherf, U., et al. Nat Genet. 24(3):236–44 (1993); Hayward R. E., et al. Mol Microbiol 35(1):6–14 (1993); Johannes G., et al. Proc Natl Acad Sci U S A 96(23):13118–23 (1993). Microarray technology has also been used in exploring drug-induced alterations in gene expression in Mycobacterium tuberculosis. See, for example, Wilson M., et al. Proc Natl Acad Sci. 96(22) :12833–8 (1999). The use of microarray technology with animal genes, e.g., canine genes, during drug development to detect drug-induced alternation in vertebrates, such as dogs, would provide a method that is fast, efficient, cost-effective and could spare many animals from being the subjects of laboratory tests.

The discovery and/or characterization of a set of toxicologically relevant genes would be useful in simplifying the development, screening, and testing of new drugs. While some genes are known to be differentially displayed in response to one agent, a more useful tool for assessing toxicity is a panel of genes which are identified as toxicologically relevant genes. The invention provided herein fulfills these needs and provides disclosure to novel canine genes as well.

The disclosure of all patents and publications cited herein are hereby incorporated by reference in their entirety.

SUMMARY OF THE INVENTION

Disclosed herein are methods of identifying and isolating canine genes which are toxicologically relevant and methods of using these toxicologically relevant canine genes to determine toxic responses to an agent. Further, arrays containing the canine genes, methods of making these arrays, and methods of using these arrays are provided. Also disclosed herein are primer sequences useful for obtaining canine genes, which in turn have a variety of uses, and gene sequences for novel canine genes discovered using these methods.

In one aspect, a method of identifying a toxicologically relevant canine gene is disclosed whereby the gene expression profile of untreated canine cells is obtained as well as a gene expression profile of canine cells treated with an agent. The gene expression profile of untreated canine cell is compared with the gene expression profile of the treated canine cells to obtain a gene expression profile indicative of a toxicological response. In some aspects, canine cells can be any type of cells including but not limited to biological samples from liver, lung, heart, kidney, spleen, testes, thymus, brain, or cells lines obtained from commercial sources (e.g., ATCC). The agent can be any type of synthetic or non-synthetic compound including but not limited to agents listed in Table 10.

In another aspect, a method of isolating canine genes indicative of a toxicological response to an agent is provided wherein sequences of mammalian, non-canine genes associated with toxicological responses are provided, primers homologous to said genes associated with toxicological responses are provided; and the primers are used to amplify canine genes from canine cDNA library.

In yet another aspect, a method for determining a toxicological response to an agent is provided wherein cells are exposed to an agent and a first gene expression profile is obtained and then compared to a gene expression profile of toxicologically relevant canine genes to determine if the first gene expression profile is indicative of a toxicological response. In one aspect, the gene expression profiles of one or more toxicologically relevant canine gene(s) are stored in a database. In another aspect, a database containing multiple gene expression profiles of toxicologically relevant canine genes is used.

In yet another aspect, a method for determining a toxicological response to an agent in an organ is provided wherein cells are exposed to an agent and a gene expression profile is obtained and then compared to a gene expression profile of toxicologically relevant canine genes to determine if the first gene expression profile is indicative of a toxicological response in an organ.

In another aspect, a method for screening an agent (e.g., drug, medicament, or pharmaceutical composition) for potential toxicological responses is provided wherein cells are exposed to an agent; and a gene expression profile is obtained and then compared to a gene expression profile of toxicologically relevant canine genes to determine if the first gene expression profile is indicative of a toxicological response in genes associated with toxicological responses. In one aspect, a database containing at least one gene expression profile of toxicologically relevant canine genes is used for comparison.

In one aspect, the invention relates to methods of identifying canine genes and gene sequences which are indicative of a toxicological response. These genes and their gene expression profiles are stored in a database. The database is useful for toxicological studies and analysis, particular when applied to the screening, development, and testing of potential new drugs. A panel of genes indicative of toxicity can vary between organs different in time of exposure to one or more agents resulting effects of agent(s) and, different compounds. In one aspect, the canine genes and gene sequences identified to be indicative of toxicological response (i.e., toxicologically relevant) are novel.

In another aspect, a method for generating a canine array comprising at least ten canine genes which are indicative of a toxicological response is provided. Genes indicative of toxicological response are immobilized to a substrate.

In another aspect, an array is provided comprising at least ten canine toxicological response genes or a portion thereof immobilized on a substrate. The canine genes are assembled in an array such that at least 2 genes, more preferably at least 5 genes, more preferably at least 10 genes, more preferably at least 20 genes, more preferably at least 30 genes, even more preferably at least 40 genes, more preferably at least 50 genes, more preferably at least 100 genes, more preferably at least 250 genes, more preferably at least 400 genes, more preferably at least 500 genes, more preferably at least 600 genes, more preferably at least 750 genes, more preferably at least 850 genes, and more preferably at least 1000 genes are assembled on such array. In one aspect, the toxicologically relevant genes are attached to the array substrate by covalent linkage. In another aspect, the genes or portions thereof are capable of hybridization to expressed nucleic acids derived from a cell and are capable of indicating a toxicological response of the cell to said agent.

In yet another aspect, a method for obtaining a gene expression profile is provided whereby a population of cells is exposed to an agent, cDNA from the population of cells is obtained, labeled, and contacted with the array comprising toxicologically relevant genes.

In still another aspect of the invention, primer sequences that are used for identifying canine genes are disclosed. These primer sequences can be used for probes, for PCR-related amplification, included on an array chip for identifying nucleotide sequences related to toxicological responses, or for identifying novel canine genes. Sequences of such primers and methods of using thereof are disclosed herein.

In yet another aspect of the invention, novel canine genes or portions of novel canine genes are disclosed and uses thereof. The sequences of novel canine genes are disclosed in Table 8. In one aspect, an array comprising at least 2, 5, 10, 25, 50, or 56 novel canine toxicologically relevant genes from Table 8 is provided. In one aspect, an array comprising at least 2, 5, 10, 25, 50, 60, 75, 90, 100, or 116 novel canine toxicologically relevant genes from Table 9 is provided.

In yet another aspect, novel canine sequences are cloned and/or maintained in expression vectors. In one aspect, novel canine sequences which are cloned in expression vectors are expressed and/or maintained in suitable eukaryotic host cells.

BRIEF DESCRIPTION OF THE TABLES

Table 1 depicts the primers used to isolate toxicologically relevant canine genes from a canine cDNA library.

Table 2 depicts target sequences obtained by using primers listed in Table 1.

Table 3 depicts 50-mer sequences for toxicologically relevant canine genes.

Table 4 depicts the accession numbers which correspond with toxicologically relevant canine genes.

Table 5 depicts toxicologically relevant genes that were identified and isolated using differential display.

Table 6 depicts canine genes that are identified and isolated by using primers to known toxicologically relevant human genes.

Table 7 depicts canine genes which have been identified as toxicologically relevant by differential display.

Table 8 depicts canine genes which have not been disclosed in a public sequence database, printed publications, or scientific conferences.

Table 9 depicts canine genes which are associated with specific agents.

Table 10 provides a list of agents which are used or can be used to determine toxicologically relevant canine genes.

Table 11 depicts the fold induction for canine genes in a canine array.

BRIEF DESCRIPTION OF THE FIGURES

The file of this patent contains at least one drawing executed in color. Copies of this patent with color drawing(s) will be provided by the Patent and Trademark Office upon request and payment of necessary fee.

FIG. 2 a chart which shows the fold induction in an analysis of toxicological responses to cadmium chloride using canine arrays.

FIG. 6 is a diagram of first strand synthesis for the design of an antisense probe from amplified antisense RNA for hybridization to microarrays with sense targets.

FIG. 7 is a diagram of second strand synthesis for the design of an antisense probe from amplified antisense RNA for hybridization to microarrays with sense targets.

FIG. 8 is a diagram of antisense probe synthesis for the design of an antisense probe from amplified antisense RNA for hybridization to microarrays with sense targets.

DETAILED DESCRIPTION OF THE INVENTION

Figure 1:
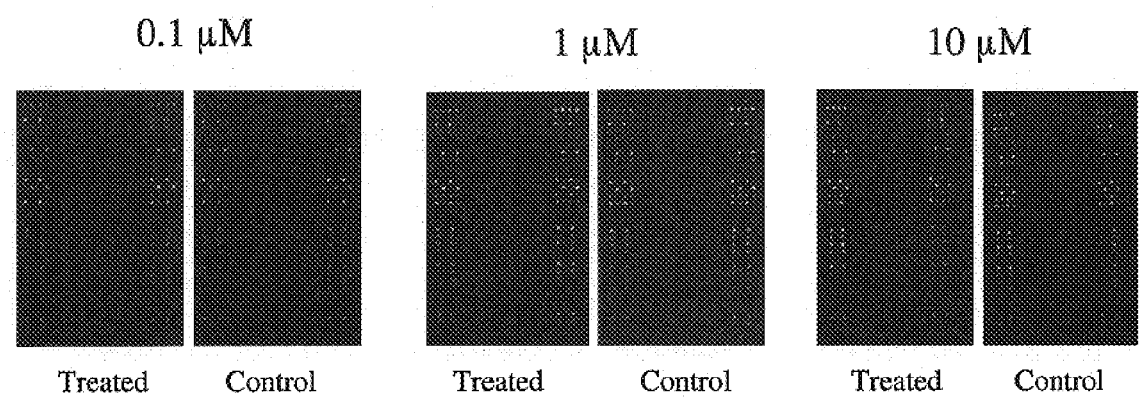
FIG. 1 is a scan of a microarray which shows toxicological responses to three doses of cadmium chloride using canine arrays.

The present invention discloses canine genes which are indicative of a toxicological response. Methods of identifying genes indicative of a toxicological response and isolating such genes are provided. Novel canine genes and methods of isolating the novel canine genes, including primers used, and methods of identifying them are also provided. Further, arrays which comprise canine genes for use in detecting gene expression indicative of toxicological response, the methods of making the array, and the canine genes which are included in the array are also provided.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, *Molecular Cloning: A Laboratory Manual*, second edition (Sambrook et al., 1989); *Oligonucleotide Synthesis* (M. J. Gait, ed., 1984); *Animal Cell Culture* (R. I. Freshney, ed., 1987); *Handbook of Experimental Immunology* (D. M. Weir & C. C. Blackwell, eds.); *Gene Transfer Vectors for Mammalian Cells* (J. M. Miller & M. P. Calos, eds., 1987); *Current Protocols in Molecular Biology* (F. M. Ausubel et al., eds., 1987); *PCR: The Polymerase Chain Reaction*, (Mullis et al., eds., 1994); *Current Protocols in Immunology* (J. E. Coligan et al., eds., 1991); *The Immunoassay Handbook* (David Wild, ed., Stockton Press NY, 1994); *Antibodies: A Laboratory Manual* (Harlow et al., eds., 1987); *Methods of Immunological Analysis* (R. Masseyeff, W. H. Albert, and N. A. Staines, eds., Weinheim: VCH Verlags gesellschaft mbH, 1993); *Principals and Methods in Toxicology* (A. Wallace Hayes, ed., 2000); *Analytical Methods in Toxicology* (H. M. Stahr, 1991); and *PCR Protocols in Molecular Toxicology* (John P. Vanden Heuvel, ed., 1997).

Definitions

"Toxicity", as used herein, refers to the exaggerated micro- or macroscopic responses of cells, tissues, organs or systems to low, average, or high doses of an agent. These responses may lead to observable symptoms such as dizziness or nausea and can also result in toxic outcomes. Toxicity often results in toxic side effects that are different, in either degree or kind, from the response of the majority of patients at the recommended dose. Toxicity may be characterized by, but is not limited to, the differential expression of genes when compared to the response of a similar individual who is not exposed to a given agent.

A "toxicological response", or "toxic response" used interchangeably herein, refers to a cellular, tissue, organ or system level response to exposure to an agent and includes, but is not limited to, the differential expression of genes and/or proteins encompassing both the up- and down-regulation of such genes; the up- or down-regulation of genes which encode proteins associated with the repair or regulation of cell damage; or the regulation of genes which respond to the presence of an agent.

The terms "toxicologically relevant gene", "toxicity gene", and "toxic response gene" are interchangeable as used herein. A toxic response gene can be defined as a gene whose message or protein level is altered by adverse stimuli (e.g, an agent). The specific set of genes that cells induce is dependent upon the type of damage or toxic threat caused by the agent and which organs are most threatened. In addition to the up-regulation of genes which respond to specific toxic threat, genes which encode functions not appropriate under conditions of toxic injury may be down regulated.

As used herein, "toxic outcome" refers to the cellular, molecular microscopic or macroscopic, molecular symptoms, physiological, morphological or pathological changes which are observed as a result of exposure to an agent.

As used herein, the term "agent" means a biological or chemical compound such as a simple or complex organic or inorganic molecule, a peptide, a protein, an oligonucleotide, an antibody, an antibody derivative, or antibody fragment. Various compounds can be synthesized, for example oligomers, such as oligopeptides and oligonucleotides, and synthetic organic compounds based on various core structures, and these are also included in the term "agent". In addition, various natural sources can provide compounds for screening, such as plant or animal extracts, and the like. Agents can be tested and/or used singly or in combination with one another. An "agent" to which an individual has a toxicological response can also be any substance to which an individual exhibits a toxicological response and includes, but is not limited to, drugs, pharmaceutical compounds, household chemicals, industrial chemicals, environmental chemicals, and other chemicals and compounds to which individuals may be exposed. Exposure to an agent can constitute physical contact as well as secondary contact, such as inhalation and environmental exposure.

As used herein, the term "gene" refers to polynucleotide sequences which encode protein products and encompass RNA, mRNA, cDNA, single stranded DNA, double stranded DNA and fragments thereof. Genes can include introns and exons. It is understood that the polynucleotide sequences of a gene can include complimentary sequences (e.g., cDNA).

The term "gene sequence(s)" refers to gene(s), full-length genes or any portion thereof.

The term "novel gene" refers to a gene and/or gene sequences that have not been disclosed in public sequence databases, in any printed publication, or a public forum (e.g., scientific conferences) as of June 2001.

"Differential expression" as used herein refers to the change in expression levels of genes, and/or proteins encoded by said genes, in cells, tissues, organs or systems upon exposure to an agent. As used herein, differential gene expression includes differential transcription and translation, as well as message stabilization. Differential gene expression encompasses both up- and down-regulation of gene expression.

"Gene expression indicative of toxicological response", as used herein, refers to the relative levels of expression of a gene, for example a toxic response gene. Profiles of gene expression profiles may be measured in a sample, such as samples comprising a variety of cell types and may, for example, comprise blood, urine, spinal fluid or serum.

The terms "polynucleotide" and "nucleic acid", used interchangeably herein, refer to a polymeric form of nucleotides of any length, either ribonucleotides or deoxyribonucleotides. These terms include a single-, double- or triple-stranded DNA, genomic DNA, cDNA, RNA, DNA-RNA hybrid, or a polymer comprising purine and pyrimidine bases, or other natural, chemically, biochemically modified, non-natural or derivatized nucleotide bases. It is understood that the double stranded polynucleotide sequences described herein also include the modifications described herein. The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidates and thus can be a oligodeoxynucleoside phosphoramidate (P-NH2) or a mixed phosphoramidate-phosphodiester oligomer. A phosphorothioate linkage can be used in place of a phosphodiester linkage. In addition, a double-stranded polynucleotide can be obtained from the single stranded polynucleotide product of chemical synthesis either by synthesizing the complementary strand and annealing the strands under appropriate conditions, or by synthesizing the complementary strand de novo using a DNA polymerase with an appropriate primer. The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers.

As used herein, "DNA" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides.

"Naturally occurring" refers to an endogenous chemical moiety, such as a carbohydrate, polynucleotide or polypeptide sequence, i.e., one found in nature. Processing of naturally occurring moieties can occur in one or more steps, and these terms encompass all stages of processing. Conversely, a "non-naturally occurring" moiety refers to all other moieties, e.g., ones which do not occur in nature, such as recombinant polynucleotide sequences and non-naturally occurring carbohydrates.

A polynucleotide is said to "encode" a polypeptide if, in its native state or when manipulated by methods well known to those skilled in the art, it can be transcribed and/or translated to produce the polypeptide or a fragment thereof. For purposes of this invention, and to avoid cumbersome referrals to complementary strands, the anti-sense (or complementary) strand of such a polynucleotide is also said to encode the sequence; that is, a polynucleotide sequence that "encodes" a polypeptide includes both the conventional coding strand and the complementary sequence (or strand).

"Hybridization" or "hybridize" refers to a reaction in which one or more polynucleotides react to form a complex that is stabilized via hydrogen bonding between the bases of the nucleotide residues. The hydrogen bonding is sequence-specific, and typically occurs by Watson-Crick base pairing. A hybridization reaction may constitute a step in a more extensive process, such as the initiation of a PCR, or the enzymatic cleavage of a polynucleotide by a ribozyme.

Hybridization reactions can be performed under conditions of different "stringency". Relevant conditions include temperature, ionic strength, time of incubation, the presence of additional solutes in the reaction mixture such as formamide, and the washing procedure. Higher stringency conditions are those conditions, such as higher temperature and lower sodium ion concentration, which require higher minimum complementarity between hybridizing elements for a stable hybridization complex to form. Conditions that increase the stringency of a hybridization reaction are widely known and published in the art: see, for example, "Molecular Cloning: A Laboratory Manual", Second Edition (Sambrook, Fritsch & Maniatis, 1989). When hybridization occurs in an antiparallel configuration between two single-stranded polynucleotides, those polynucleotides are described as "complementary". A double-stranded polynucleotide can be "complementary" to another polynucleotide, if hybridization can occur between one of the strands of the first polynucleotide and the second. Complementarity (the degree that one polynucleotide is complementary with another) is quantifiable in terms of the proportion of bases in opposing strands that are expected to form hydrogen bonding with each other, according to generally accepted base-pairing rules.

A "host cell" includes an individual cell or cell culture which can be or has been a recipient for vector(s) or for incorporation of polynucleotides and/or proteins. Host cells include progeny of a single host cell, and the progeny may not necessarily be completely identical (in morphology or in genomic of total DNA complement) to the original parent cell due to natural, accidental, or deliberate mutation. A host cell includes cells transfected in vivo with a polynucleotide (s) of this invention.

"Transformation" or "transfection" refers to the insertion of an exogenous polynucleotide into a host cell, irrespective of the method used for the insertion, for example, lipofection, transduction, infection or electroporation. The exogenous polynucleotide may be maintained as a non-integrated vector, for example, a plasmid, or alternatively, may be integrated into the host cell genome.

The terms "protein", "polypeptide", and "peptide" are used interchangeably herein to refer to polymers of amino acids of any length. The polymer may be linear or branched, it may comprise modified amino acids, and it may be interrupted by non-amino acids. It also may be modified naturally or by intervention; for example, disulfide bond formation, glycosylation, myristylation, acetylation, alkylation, phosphorylation or dephosphorylation. Also included within the definition are polypeptides containing one or more analogs of an amino acid (including, for example, unnatural amino acids) as well as other modifications known in the art.

As used herein, "array" and "microarray" are interchangeable and refer to an arrangement of a collection of nucleic acids (e.g., nucleotide sequences) in a centralized location. Arrays can be on a solid substrate, such as a glass slide, or on a semi-solid substrate, such as nitrocellulose membrane. The nucleotide sequences can be DNA, RNA, or any combination or permutations thereof. The nucleotide sequences can also be partial sequences from a gene, primers, whole gene sequences, non-coding sequences, coding sequences, published sequences, known sequences, or novel sequences.

An "individual" is a vertebrate, preferably a mammal, for example a dog. Mammals include, but are not limited to, humans, farm animals, sport animals, pets, primates, mice, and rats.

A "biological sample" encompasses a variety of sample types obtained from an individual. Biological samples or "samples" can be used in various manners (e.g., in the determination of toxicological response, analysis of one or more, toxicological responses, etc.). The definition encompasses blood and other liquid samples of biological origin, solid tissue samples such as a biopsy specimen, whole organs, tissue cultures or cells derived therefrom, and the progeny thereof. The definition also includes samples that have been manipulated in any way after their procurement, such as by treatment with agents, reagents, solubilization, or enrichment for certain components, such as proteins or polynucleotides. The term "biological sample" encompasses a clinical sample, and also includes cells in culture, cell supernatants, cell lysates, serum, plasma, biological fluid, and tissue samples.

METHODS OF THE INVENTION

Canine genes which are toxicologically relevant have been identified and disclosed herein. In some embodiments, canine genes which are disclosed are novel. Methods of identifying toxicologically relevant genes are described herein. In addition, methods of isolating and using toxicologically relevant genes are disclosed. In one embodiment, toxicologically relevant genes are used to make arrays. The arrays can be used for drug screening purposes to determine toxicological response.

Methods of identifying a set of toxicologically relevant genes

Identification of a set of toxicologically relevant genes can be achieved by several methods. One method which can be used is to clone genes previously described to be relevant in toxicology. Using published sequences, for example in literature or from GenBank, primers can be made and then used to PCR amplify from a relevant cDNA library to obtain the toxicologically relevant gene of interest which can then be cloned into a plasmid or an expression vector, depending on the use desired. The gene, i.e., nucleic acid, can be placed amongst other toxicologically relevant genes in an microarray for high-throughput testing, as disclosed infra. For example, using known toxicologically relevant canine sequences, primers can be designed and used in PCR reaction to amplify the canine gene from a cDNA library. The cDNA library can be made from different canine cells. In one embodiment, primary liver cells from a beagle are used as source for the cDNA library. The generation of a cDNA involves reverse transcribing isolated RNA and is well known in the art (see for example, Sambrook et al. supra). The canine gene fragments, amplified by PCR, are cloned into any standard plasmid expression vector which can be obtained from numerous commercial sources (e.g., Promega, InVitrogen, New England BioLabs, etc.) and sequenced. The resulting sequence information is then compared to the GenBank database to confirm that the cloned DNA is the specific canine gene for which the primers were designed. Upon positive confirmation of the sequence, the amplified gene is then added to the panel of genes to be included in the array. Methods of including toxicologically relevant genes in an array are disclosed below.

Alternatively, for replication to high copy numbers, a plasmid may be used to grow high copies of the toxicologically relevant gene of interest which can then be purified by any commercially available kit (e.g., from Qiagen or Promega). The purified toxicologically relevant gene may be used for "spotting" in a microarray or alternatively, the purified nucleic acid can then be inserted into an expression vector, transfected into mammalian cells, e.g., canine cells, and then the cells can be exposed to a compound and observed for toxicological responses. Toxicity may be ascertained by observing changes in cell morphology or re-arrangement of cytoskeleton, which can be determined by examination under a microscope, or alternatively, cell apoptosis or necrosis. In another alternative, "transcriptome profiling", described in greater detail below, may be used whereby nucleic acid can be isolated from both the exposed and unexposed cells and examined to determine which level of the compound causes the up-regulation or down-regulation of the toxicologically relevant gene of interest.

Another method which may be used to identify canine genes utilizes known sequences of toxicologically relevant non-canine (e.g., human) genes. These toxicologically relevant genes may be from a non-canine species including, but not limited to humans, primates, and other mammals. Primers to these toxicologically relevant non-canine genes are designed, synthesized, and are subsequently used in PCR reaction with canine cDNA libraries to amplify the homologous canine gene. The homologous canine gene may or may not be the exact sequence as the non-canine gene with which the primers were designed. It is understood that some changes in the nucleotide sequence can occur and the homologous canine gene can still be toxicologically relevant and/or retain the same function as the non-canine gene. The amplified canine genes can then be added to the panel of genes to be included in the array.

In yet another embodiment, target sequences for inclusion in a canine array are obtained by de novo synthesis of nucleotides and then immobilization on a substrate, e.g., a glass slide. The target sequences are from genes which can indicate one or more toxicological responses. Target sequences exemplifying this embodiment are shown in Table 3.

Another method which can be used to identify a set of toxicologically relevant genes is to analyze the gene expression profile from tissues in canine toxicity studies and select those genes with differential expression. Differential expression may be assessed by any number of methods. One method which may be used is by microarray analysis. Provided herein are methods of using microarray analysis to determine differential gene expression. Another method of determining differential gene expression is by reverse transcriptase-polymerase chain reaction (RT-PCR), e.g., Taqman® technology (Foster City, Calif.). Yet another method which could be used to detect differential gene expression is Invader® technology, commercially available from Third Wave (Madison, Wis.). Yet another method which may be used to determine differential expression is Northern blot analysis.

Other methods which may be used include open systems such as AFLP and SAGE (Klein, P. E., et al. *Genome Res.* 10(6):789–807 (2000); Wang, X. and Feuerstein, G. Z., *Cardiovasc Res.* 35(3):414–21 (1997)) Feuerstein, G. Z. and Wang X. *Can J. Physiol Pharmacol.* 75(6):731–4 (1997); Hough, C. D. et al., *Cancer Res.* 60(22):6281–7 (2000); Ye, S. Q., et al., *Anal Biochem.* 287(1):144–52 (2000)). An "open system" allows the entire transcriptome to be analyzed instead of a defined set of genes.

Alternatively, comparisons between gene expression profiles from control canine cells (or canine cell lines) and canine cells (or canine cell lines) treated with an agent can be used to select responsive genes. This is referred to herein as "transcriptome profiling". This method empirically determines which genes are toxicologically relevant by analyzing differential gene expression. In this embodiment, experimental canines are divided into two groups. One group is exposed to one agent (e.g., with a suitable vehicle) at different concentrations for different lengths of time. Another group of canines is exposed to vehicle only and serves as the control group. Canines are then sacrificed and organs such as liver, spleen, kidney, testes, heart, and thymus are harvested for cells to perform molecular analysis of gene expression. In addition, analysis of serum proteins in the circulating blood can provide another measure to compare with unexposed canines. Once the experimental group is exposed to at least one agent, then RNA of both groups is isolated and reverse transcribed in PCR reactions to generate cDNA which in turn is amplified to generate double stranded DNA. The PCR is performed in the presence of a radioactive or fluorescent DNA substrate that is incorporated into the double stranded DNA. On a polyacrylamide gel, the DNA derived from the treated cells is separated by length next to the DNA derived from untreated population. The intensity of the resulting band or bands is compared between the treated and untreated groups of cells. Bands that show different radioactive or fluorescent intensity are excised from the gel, amplified by PCR, cloned, and sequenced, as disclosed herein. The sequences are compared with known gene sequences in the public databases such as GenBank. In this manner, novel canine genes, in addition to known canine genes with varying degrees of similarity, which are toxicologically relevant are discovered and identified. The examples disclosed herein illustrates how this aspect of the invention may be practiced by the skilled artisan.

If a partial sequence of a novel canine gene is discovered, the technology, texts (see Sambrook et al. infra), and resources available to a skilled artisan would enable the skilled artisan to sequence the remainder of the gene and obtain a full-length gene without undue experimentation. One method of obtaining the remaining portion of a novel canine gene is to make primers corresponding to the part of the novel canine gene which are known combined with random primers and then use the primers in PCR reactions with a canine cDNA library. The PCR reaction are run on a standard agarose gel and amplified bands are identified, excised from the gel, and sequenced.

Other factors to consider in identifying toxicologically relevant genes include, but are not limited to, selection of one or more agent(s), the dosage amount to administer, routes of administration, time of exposure, and metabolism of the agent.

Selecton of agent(s)

The agent to be tested can selected on the basis of different criteria. One method of selecting which compound to test is damage observed in specific organs. For example, cisplatin, amphotericin B and gentamicin have been observed to cause kidney tubular epithelial cell damage. Another example, liver peroxisome proliferation has been observed to be affected by clofibrate, gemfibrozil, and WY 14643. Another basis for selection is function. For example, cisplatin causes apoptosis and reactive oxygen species, amphotericin B causes increased permeability of cell membranes to ions and renal vasoconstriction, and gentamicin causes phospholipid accumulation in lysosomes.

Other toxicants affect an organ in general, for example, some kidney toxicants include but are not limited to cisplatin, gentamicin, puromycin, and amphotericin B. Liver toxicant include but are not limited to chlorpromazine, clofibrate, diflunisal, tetracycline, erythromycin, and ethanol. Immunotoxicants include but are not limited to cyclosporin A, lipopolysaccharide (LPS), hydroxyurea, phenylhydrazine, dexamethasone, estradiol, and tamoxifen. Heart toxicant includes but is not limited to doxorubicin. Multiorgan toxicants include but are not limited to methotrexate and cadmium chloride.

Other criteria for selecting an agent to test is to select those agents to which an individual might be exposed to on a regular basis, either in the environment, by prescription or over-the-counter drug. Another criteria for selecting an agent is the need to obtain toxicity information for FDA-approval or alternatively for other toxicity requirements, for example in pre-clinical or clinical trials.

Determination of dosage

Dosages to use in canine experiments can be determined using several methods. One method is to use reported dosages as a starting point and dose incrementally above and below the reported dosage. Increments can be at least ±1%, 5%, 10%, 25%, 35%, 45%, 50%, 60%, 70%, 80%, 90%, or 95%. Upregulation or downregulation of markers in the blood including but not limited to serum chemistry values and hematology values can be used to determine if toxicity has been reached. Alternatively, examining the histopathology of organs, in particular, organs which are the specific targets of the compound of interest, may be used to determine if a pathological change has occurred in response to administration of the compound. Another method which may be used is to determine the molecular changes by analyzing the gene expression in response to administration of different doses of a compound by the methods disclosed infra.

Determination of the dosage experimentally using cell cultures is affected by many factors: the nature of the agent, its potency, mechanism of action, type of cell which is the target of the agent, and number of cells. To determine the dosage required experimentally, a low dosage level of the agent is added and then in a step-wise manner, the dosage is increased as well as length of time exposed to the agent. If the agent is lipophilic and easily crosses the lipid bilayer of cells, a lower initial concentration may be used and/or shorter length of time exposed to the agent. If the agent has the property of not being able cross the cell barrier easily (e.g., lipophobic) and would need to be actively or passively transported across cell membranes, then a slighter higher initial concentration may be used and/or longer length of time exposed to the agent. Increasing dosage step-wise while monitoring toxicological response and morphology of the cells, rate of death of the cells, and growth patterns allows the skilled artisan to determine the dosage at which a toxicological response occurs. However, it should be noted that toxicological responses may occur which are visible changes, including but not limited to, physical structure and integrity of the cells (i.e. morphology, growth pattern, etc.). Monitoring for cellular toxic responses as well as molecular toxic responses, e.g., differential gene expression increases the likelihood of finding preferable dosages. Combining visualization as well as monitoring for cellular changes and molecular changes (e.g., differential gene expression) increases the likelihood of finding preferable dosages.

Changes in gene expression may be toxicologically significant. The point at which toxicologically relevant gene expression becomes even more relevant is at that dosage at which removal or diminishment of the treatment no longer results in a return to normalcy, i.e., the state of a cell, organ, or system that existed prior to the treatment with the compound. Treatments beyond a certain dosages or time period may commit the cell to a toxicologically relevant fate. This toxic dosage will be reflected by an identifiable gene expression pattern, which will be distinct from the pattern observed below the toxic dosage.

Figure 3:
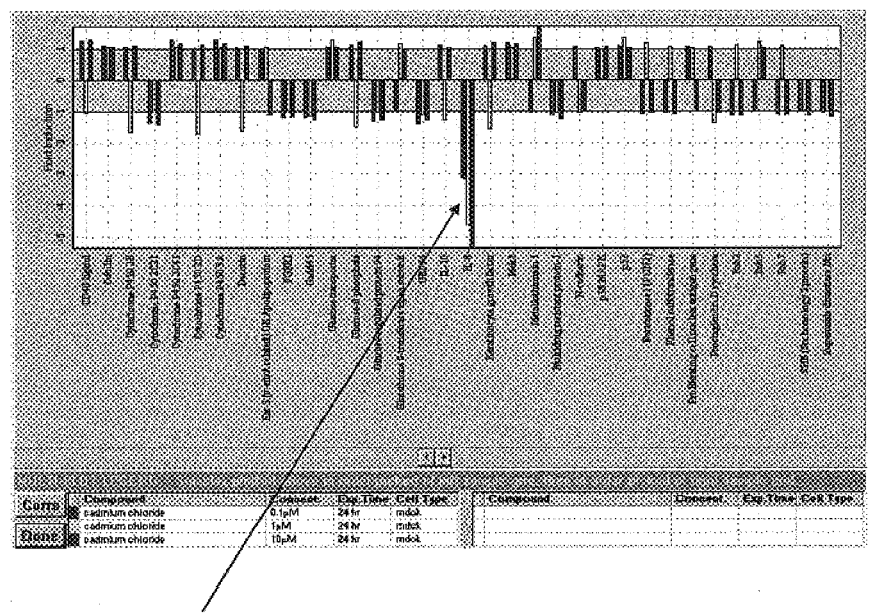
FIG. 3 is a graph which shows dose response of interleukin-8.

Dosage response is an important concept in toxicology. Depending on the dosage of a toxin or agent which may be toxic, the gene expression profile of a particular gene may vary. One way that this can be envisioned is by observing the changes in fold induction of a particular gene when analyzed using the arrays of this invention. The dosages determined in dose response curves may be useful in determining "threshold" levels of toxicity, for example for FDA approval. Example 15 and FIG. 3 illustrate this embodiment. Methods of analyzing gene expression and how to correlate gene expression data are provided herein.

Administration of an agent

Administration of one or more agents to dogs may be achieved by various routes. It will be readily appreciated by those skilled in the art that the route can vary, and can be intraperitoneal, intravenous, subcutaneous, topical, transcutaneously, intramuscular, enterally, transdermally, transmucously, sustained release polymer compositions (e.g., a lactide polymer or co-polymer microparticle or implant), perfusion, pulmonary (e.g., inhalation), nasal, oral, etc. Injectables can be prepared in conventional forms, either as liquid solutions or suspension, solid forms suitable for solution or suspension in liquid prior to injection, or as emulsions. If the agent to be test is a pharmaceutical composition or a drug, it may be administered with a suitable excipient (or vehicle). Suitable excipients include, for example, water, saline, aqueous dextrose, glycerol, ethanol or the like. Formulations for parenteral and non-parenteral drug delivery are known in the art and are set forth in Remington's Pharmaceutical Sciences, 18th Edition, Mack Publishing (1990). In testing for toxicity, the route of administration may be selected such that it is the same as the route of administration that will eventually be used in humans. For example, if administration of penicillin is generally by injection, it may be advantageous to administer penicillin to a dog via injection, obtain tissues samples (e.g., target tissue of the drug, if known), isolate cells and then obtain gene expression profiles. Once a series of gene expression profiles are compiled, cells may be used instead of whole animals and the gene expression profile of the cells, in response to an agent, may be compared to the compiled gene expression profiles of previous testing.

Methods of obtaining canine samples

Canine cells can be obtained from various sources. Different sources of cells can include, but are not limited to, biological samples such as tissue samples, blood, skin, biological fluids (e.g., semen), and cell lines. Immortalized cell lines can be obtained from commercial sources, e.g., Gibco BRL Life Sciences, or from non-commercial sources, e.g., American Type Culture Collection (ATCC). One example of a cell line which is used in this invention is MDCK (ATCC accession number CCL-34) which is a canine kidney cell line. Other methods of obtaining canine cells include isolating cells obtained from tissue biopsies, blood, skin, or biological fluids. As is well known to one of skill in the art, isolating cells from tissue samples can be achieved using any variety of techniques. One example is to digest a tissue sample in an enzymatic solution to break up connective tissue and then agitate cells in the digested tissue to separate the cells from the connective tissue. Examples of other enzymes that can be used to digest tissue include neutral proteases, serine proteases including, but not limited to, trypsin, chymotrypsin, elastase, collagenase, and thermolysin. Another method is to homogenize the tissue sample or apply mechanical stress forces to the tissue sample to separate the cells from the basement membranes and allow the cells to become separated from within the tissue. In the alternative, DNA or RNA can be directly isolated from tissue samples, as exemplified in Example 1. Isolating cells from blood can be achieved by layering blood over a gradient (e.g., Percoll™ or Ficoll™), spinning the blood-gradient layer in a centrifuge, and extracting the layer of cells from serum.

Sources from which cells are obtained can be any number of organs, including but not limited to liver, lung, heart, kidney, spleen, testes, thymus, and brain. In one embodiment, liver cells are used for toxicity studies where the agent to be administered is known or thought to induce liver malfunctions or liver toxicity. In other embodiments, when the target of the action delivered by the agent is known, the use of cells deriving from such target may yield more beneficial information regarding toxicological responses than if a tissue were selected at random. In another embodiment where the agent to be tested has unknown effects, a panel of cells isolated from different sources may be used. In the alternative, liver cells may be used in the absence of knowledge of the agent's target of action because the liver is known to process many toxins.

Canine cells obtained ex vivo or from a commercial or non-commercial source can cultured in media prior to being exposed to one or more agents. A wide variety of basal cell-sustaining media that can be used to keep the pH of the liquid in a range that promotes survival of canine cells. Non-limiting examples include F12/DMEM, Ham's F10 (Sigma), CMRL-1066, Minimal essential medium (MEM, Sigma), RPMI-1640 (Sigma), Dulbecco's Modified Eagle's Medium (DMEM, Sigma), and Iscove's Modified Eagle's Medium (IMEM). In addition, any of the basal nutrient media described in Ham and Wallace Meth. Enz., 58:44 (1979), Barnes and Sato Anal. Biochem., 102:255 (1980). In a preferred embodiment, Earle's Minimal Eagle's Medium (EMEM) supplemented with 10% fetal calf serum is used to culture canine cells. Cells can be grown in plates or in flasks. In a preferred embodiment, canine liver cells are grown in T-75 flasks contain Eagle's MEM supplemented with 10% fetal calf serum. Cells are grown and expanded to a level desired and needed for DNA or RNA isolation. Cells are removed from the plate or flask to isolate DNA or RNA. If the cells are adherent, trypsin or another equivalent may be used to release the cells from the plate or flask. Preferably at least about $1 \times 10^2$ cells, more preferably at least about $1 \times 10^3$ cells, more preferably at least about $1 \times 10^4$ cells, more preferably at least about $1 \times 10^5$ cells, more preferably at least about $1 \times 10^6$ cells, and even more preferably at least about $1 \times 10^7$ cells are used as sources for DNA and RNA.

Nucleotide sequences from tissue samples are isolated using any number of commercially available kits e.g., from Qiagen, GenHunter, Promega, etc. More detailed protocols on how to isolate DNA and/or RNA is disclosed in the Examples section. In general, a skilled artisan should take care to keep all reagents, tubes, and instruments sterile as to avoid contaminants which may affect how the results get interpreted. Once DNA or RNA has been isolated from cells which have been exposed to one or more agents, one or more toxicologically relevant genes are identified using the methods described above. The toxicologically relevant genes may be cloned into an expression vector, maintained in an expression vector or alternatively, the expression vector comprising the toxicologically relevant gene sequence may be transformed or transfected into a suitable host cell. Suitable host cells may be obtained from the ATCC or from commercial sources. Methods of isolating toxicologically relevant genes by cloning are further detailed in the Examples.

In some embodiments, the toxicologically relevant canine gene may be used to find a homologue in another animal, for example, in humans. The homologue may be then be used as a target for drug development or screening (e.g., antigen for antibody development or cellular regulation).

In other embodiments, canine genes identified to be toxicologically relevant may be used to generate an array of toxicologically relevant canine genes. In this case, the gene may be cloned to facilitate the process of generating an array.

Methods of making an array

The isolated DNA or RNA is amplified to generate a product which can be attached to a substrate. In a preferred embodiment, the substrate is a solid substrate (e.g., glass slide). The amplification process involves using primers which have a reactive group (e.g., amine group or derivative thereof on one end of the primer, which is incorporated into the amplification product. One example of reactive primers that can be used is Amine Primers from Synthegen (Houston, Tex.; catalog #5002). The gene fragments which are attached to the glass slide can vary in length. The more nucleotides of a gene that are in the array, the tighter the binding and the greater the specificity in binding can occur. However, it is important to consider that longer fragments are more difficult to amplify and may contain point mutations or other errors associated with amplification. Therefore, the desired length of a gene or a fragment thereof that is to be included in the array should take into consideration the balance between a high specificity of binding obtained with a long (e.g., >1 kb) gene sequence with the high mutational rate associated with a longer fragment. The gene fragments attached to the glass slide are at least about 50 base pairs (bp) in length, more preferably at least about 100 bp in length, more preferably at least about 200 bp, even more preferably at least about 300 bp, even more preferably at least about 400 bp, even more preferably at least about 500 bp in length. In a preferred embodiment, the gene fragments are about 500 bp in length. The region of a gene that is used to attach to a solid substrate to generate an array can be any portion of the gene, coding, non-coding, 5' end, 3' end, etc. In a preferred embodiment, about 500 base pairs of the 3' end of canine gene related to toxicological responses are selected to be included in an array.

In another embodiment, labeled antisense DNA probe may be made from amplified antisense RNA for hybridization to microarrays that contain sense targets. Exemplary protocols are disclosed in Examples 17 and 18. Methods of amplifying RNA are known in the art (see, for example Sambrook et al., infra) and methods of making microarrays with nucleic acids are disclosed herein.

Several techniques are well known to a skilled artisan for attaching a gene or a fragment thereof to a solid substrate such as a glass slide. One method is to attach an amine group, a derivative of an amine group, another group with a positive charge or another group which is reactive to one end of a primer that is used to amplify a gene or a gene fragment to be included in the array. Subsequent amplification of a PCR product will then incorporate this reactive group onto one end of the product. The amplified product is then contacted with a solid substrate, such as a glass slide, which is coated with an aldehyde or another reactive group which will form a covalent link with the reactive group that is on the amplified PCR product and become covalently attached to the glass slide. Other methods using amino propryl silicane surface chemistry are disclosed by Corning Company at their website found on the world wide web at cmt.corning.com; other methods for making microarrays which are readily accessible are found on the world wide web at cmgm.stanford.ecu/pbrownl.

In one embodiment of the invention, fluorescence-labeled single strand (or "first strand") cDNA probe is made from total or mRNA by first isolating RNA from control and treated cells, disclosed supra. This probe is hybridized to microarray slides spotted with DNA specific for toxicologically relevant genes. Methods for making the array and for labeling and making cDNA probes are disclosed in the Examples.

Method of using canine arrays to determine toxicological response

Once canine genes relevant to toxicological responses are identified, as disclosed supra, the genes or portions thereof are amplified and covalently attached to a substrate to produce an array as disclosed herein. In one embodiment, the substrate is a solid substrate including but not limited to glass slides, plastic slides, and metal chips. In a preferred embodiment, the solid substrate is a glass slide. Toxicological responses to agents are determined by isolating DNA or RNA from cells which have been exposed to one or more agents. The DNA or RNA is amplified and labeled (e.g., fluorescent) as cDNA probes. The labeled cDNA probes are then used to hybridize with the microarray containing a collection of genes or fragments thereof ("target sequences") that are toxicologically relevant. The differential expression of genes between exposed and unexposed provides information about a toxicological response.

By collecting many gene expression profiles from certain species, e.g., dogs, in response to one or more agents, a database can be built with collection of information about toxicological responses. With the database, it could be possible to predict toxicological response and/or stress response to specific agents or combinations thereof. The database can be stored on a computer and in a manner that allow for rapid searching when a comparison is desired. The database could store gene expression profiles for a particular toxin or alternatively, a group of toxins (e.g., kidney-specific toxins). The database could also store gene expression profiles for a group of genes known to be affected by a particular toxin. When a gene expression profile is obtained, it may be compared with the gene expression profiles stored in the database to determine what type of organ is likely to be affect, or alternatively, which genes could also be associated with the toxic response. One or more genes could be analyzed in this manner as well as one or more toxins. The database may be stored in a form that allows for rapid access and analysis with compatible software programs.

The instant invention of canine gene arrays provides an alternative to testing on live canine animals. The canine gene array can provide answers on how a canine species might respond to a particular agent by examining at the differential gene expression associated with that particular agent in the array or comparison with a database of information collected from testing with a canine array. Further, canine gene arrays can provide answers about toxicological responses faster and more efficiently than testing in vivo.

The information generated from using canine gene arrays can be used to predict cellular and pathological responses as well as histological changes induced by exposure to agents. This is accomplished by analyzing the differential gene expression observed when canine gene arrays are used. Potential drugs or pharmaceutical compounds can be tested and data gathered for FDA approval in an accelerated manner and can help pharmaceutical and biotechnology companies generate higher productivity with lower costs in research and development.

The canine gene array can also generate information that can be used to predict downstream effects, such as which pathways are affected by certain agents. This is accomplished by looking at the differential gene expression and analyzing which pathways contain the toxicological response genes and also which pathways the genes can affect. This information in turn can be used to predict tissue responses and ultimately whole organ responses. Examples of whole organ responses include but are not limited to organ functions, inflammatory responses, and autoimmune responses. Those of skill in the art can determine when the normal functions of an organ are compromised by exposure to one or more agents which are toxic. For example, a kidney's ability to filter toxins is compromised after an individual has been exposed to an agent. The ability to predict whole organ responses has great potential in the development of drugs, pharmaceutical compounds, and even in the use of chemicals.

The following Examples are provided to illustrate but not limit the present invention. It will be apparent to one of skill in the art that modifications can be made while keeping in the spirit and scope of the present invention.

EXAMPLES

Example 1

Isolation of Total RNA From Animal Tissues

To isolate high quality and high purity total RNA from tissue samples, the following materials are used: Qiagen RNeasy midi kits, 2-mercaptoethanol, liquid $N_2$, tissue homogenizer, dry ice.

It is important to take precautions to minimize the risk of RNA degradation by RNase. Samples should be kept on ice when specified, gloves are worn at all times and work areas and equipment are treated with an RNase inhibitor, e.g., RNase Zap (Ambion® Products, Austin, Tex.). In order to prevent RNA degradation, it is highly preferable that the work area and materials used for this procedure are clean and RNase-free. Autoclaving tips and microfuge tubes does not eliminate RNases. The following protocol is based on Qiagen® RNeasy® midi kit with modifications for optimal results. This total RNA isolation technique is used for RNA isolation from animal tissue and can be modified to accommodate smaller samples.

If tissue needs to be broken, it can be placed on a double layer of aluminum foil which is placed within a weigh boat containing a small amount of liquid nitrogen. The aluminum foil was placed around the tissue and then a blunt force was applied to the tissue with a small foil-wrapped hammer.

For liver or kidney, about 0.15–0.20 g of tissue was weighed and placed in a 15 ml conical tube. All tissue were kept on dry ice when other samples were being weighed.

About 3.8 ml of RLT buffer was added to the tube containing the sample. The RLT buffer® from Qiagen can be prepared beforehand by adding 10 μl betamercaptoethanol to each 1.0 ml of lysis buffer needed. The tissue was homogenized using the rotor-stator homogenizer for 45 seconds. A IKA Ultra Turrax T25 homogenizer set at speed 4 with the S25N-10G dispersing element can be used. Alternatively, a Virtishear Cyclone 750W rotor/stator homogenizer (Virtis item #278077) can be used with the 7 mm microfine sawtooth shaft and generator (195 mm long with a processing range of 0.25 ml to 20 ml, item #372718). After homogenization, samples were stored on ice until all samples were homogenized. To clean the homogenizing tip between samples, the tip was first run for a few seconds in 95% ethanol and then rinsed by squirting with fresh 95% ethanol. This process was repeated with nanopure water.

The tissue lysate was centrifuged at room temperature for 10 minutes at 3700–3800 rpm in a Beckman GS-6 (or equivalent) centrifuge to remove nuclei thus reducing DNA contamination.

The supernatant of the lysate was transferred to a clean 15 ml conical tubes containing an equal volume of 70% EtOH in DEPC treated $H_2O$, being careful not to include any of the pellet or fatty layer and mixed. About 3.8 ml of sample was added to the RNeasy spin column placed in a 15 ml centrifuge tube and centrifuged at 3000×g (3690–3710 rpm, Beckman GS-6) for 5 min. The flow-through was discarded. The remaining sample was added to the appropriate column and spun at 3000×g for 5 minutes and the flow-through was discarded.

About 4.0 ml of Buffer RW1 (Qiagen®) was added to the column and spun as before then about 2.5 ml of buffer RPE (Qiagen®) was added to column and spun at 3000×g (3690–3710 rpm, Beckman GS-6) for 2 minutes. In this example, RPE buffer was supplied as a concentrate so 4 volumes of 95% EtOH was added before use. For the midi kit, about 220 ml of 95% EtOH would be added to 55 ml of RPE. Another 2.5 ml of buffer RPE was added and spun for 5 minutes to also dry out column. The column, including the tip, should be dry for the next elution step.

For elution, the column that has the RNA bound to a clean 15 ml tube was transferred and 200 µl of RNase-free water was added to the column, allowed to sit for 1 minute, and spun for 3 minutes at 3000×g (3690–3710 rpm, Beckman GS6). This step was repeated into the same tube but with 200 µl RNase-free water.

To measure yield, the O.D. at 260 nm was taken and about 2.0 µl RNA was added to 98 µl H$_2$O. The following formula was used for calculations:

$$(\text{Absorbance}) \times (\text{dilution factor}) \times (40) / 1000 =$$
$$\text{amount of RNA in } \mu g/ml$$

For a sample calculation:

absorbance = 0.45 dilution factor = 50

$$\frac{(0.45) \times 50 \times 40}{1000} = RNA \text{ concentration in } \mu g/ml$$

This step is optional at this point in the procedure. It can be done after the LiCl precipitation step. The RNA solution was transferred to RNase-free 1.5 ml Eppendorf-type tubes and about ⅓ volume (~300 µl if RNA was eluted in a total volume of 1000 µl) of LiCl precipitation solution (Ambion Cat. #9480) was added. This mixture was placed at −20° C. for about 30 minutes and spun at 14,000 rpm for 10 minutes. The mixture was decanted of the supernatant and the pellet was washed with 1.0 ml 70% ethanol and spun at 14,000 rpm for 10 minutes. The supernatant was decanted again and the pellet was allowed to dry to a certain degree (not complete dryness). The pellet was resuspended in RNA storage buffer (10 mM sodium citrate, Ambion Cat #7000) starting with 300–400 µl and adding buffer as necessary until RNA is in solution. The RNA concentration was determined as disclosed using the RNA storage buffer as the blank. Samples were placed on ice until they were stored in the −80° C. freezer.

Example 2

LiCl Precipitation

Isolated RNA samples can be precipitated using the following lithium chloride (LiCl) process either before or after measuring absorbance reading for quantitation purposes. The volume of the sample was measured. To this, about ⅓ volume of LiCl PPT Solution from Ambion (Cat #9480) was added and mixed by inverting the tube. The LiCl should be in solution. If not, it may be necessary to adjust the pH to 8.0. The solution was placed at −20° C. for 30 minutes and centrifuged at 4° C. and 13,000 RPM for 10 minutes. If there is no visible pellet, it may help to return the sample to −20° C. overnight and then repeat the centrifugation. The supernatant was transferred to a separate tube and washed by adding 1 ml of ice cold 70% ethanol in DEPC treated water and gently inverted. Then the tube was centrifuged at 4° C. for 10 minutes and the supernatant was discarded and the pellet was air dried. The pellet was resuspended in RNA storage buffer (Ambion Cat #7000). To determine the amount of buffer necessary, it was estimated that ~50% of the RNA was lost during this process. The RNA amount was quantitated spectrophotometrically.

Example 3

Isolation of Total RNA From Adherent Cultured Cells

Total RNA of high quality and high purity was isolated from cultured cells by using Qiagen RNeasy midi kits and 2-mercaptoethanol. RNA degradation by RNases is not desirable when synthesizing fluorescent cDNA for hybridization with the canine array. Precautions were taken to minimize the risk of RNA degradation by RNases by wearing gloves, treating work areas and equipment with an RNase inhibitor, for example, RNase Zap (Ambion® Products, Austin, Tex.) and keeping samples on ice. This total RNA isolation technique was based on a Qiagen® RNeasy® midi kit and was used with some modification for HepG2 (human hepatocyte) cells in T-75 flasks and maxi kit RNA isolation for cells in T-175 flasks.

Cells were checked under the microscope to make sure that they were viable. Cells were dosed with an agent, which could be a drug, chemical, or pharmaceutical composition, when they reached 60–80% confluence. It is preferable to avoid isolating RNA from flasks that have reached 100% confluence.

For adherent cells, media was discarded and flasks were washed with 1x cold PBS twice (20 ml then 10 ml for T-75 flasks; 40 ml then 20 ml for T-175 flasks). After the second PBS wash, the remaining PBS was removed with a pipette. Freshly prepared RLT buffer (RLT buffer requires the addition of 10 µl beta mercaptoethanol for each 1.0 ml RLT) was added directly to the cell culture flask. T-75 flasks received 3 ml RLT buffer and T-1 75 flasks received 5.0 ml RLT buffer. It is preferable to lightly agitate the flasks at this point. Flasks were lightly agitated to distribute the RLT buffer and the cells became a gelatinous layer. The cells were allowed to sit for 4 minutes, then fluid was withdrawn and placed in RNase-free tubes. An equivalent volume of 70% ethanol was added to each tube and vortexed to distribute evenly. If a precipitate with a string-like appearance forms, it is acceptable to remove and discard this string-like precipitate. The fluid was applied to a spin column and spun for 5 min at 3650 rpm in the Beckman GS-6 (or a similar centrifuge). The flow-through was discarded. About 4 or 15 ml (T-75 or T-175, respectively) of RW1 buffer was applied and spun for 5 min at 3650 RPM. The flow through was discarded. About 2.5 ml RPE buffer (midi columns) or 10 ml RPE buffer (maxi columns) was applied and centrifuged for 3 minutes. The flow-through was discarded. Another 2.5 or 10 ml buffer RPE was applied and centrifuged for 5 minutes to dry out column before proceeding to the elution step. The column, including the tip, should be dry for the next step.

The column that has the RNA bound to it was transferred to a clean tube for elution. Then 150 µl of RNase-free water was added to midi columns and 500 µl of RNase-free water to columns, allowed to sit for 2–4 minutes and spun for 3 min at 3000×g (3690–3710 rpm, Beckman GS-6 or a similar centrifuge). The elution was repeated with another 150 µl or 500 µl of RNase-free water into the same tube. The elution was precipitated using the LiCl precipitation protocol, exemplified in Example 2, and resuspended in RNA storage buffer.

To measure yield, the O.D. reading was taken at 260 nm. About 2.0 µl RNA was added to 98 µl H2O and the O.D. reading was taken and calculated as follows:

$$(\text{Absorbance}) \times (\text{dilution factor}) \times (40) / 1000 =$$
$$\text{amount of } RNA \text{ in } \mu g/ml$$

Example: absorbance = 0.45 dilution factor = 50

$$\frac{(0.45) \times 50 \times 40}{1000} = RNA \text{ concentration in } \mu g/ml$$

The yield should be between 200–400 µg of total RNA from a T-75 flask with greater than 50% confluency. The sample was stored in −80° C. freezer.

Example 4

Identifying and Isolating Genes Involved in Toxicological Responses

CANINE KIDNEY CELLS MDCK (ATCC ACCESSION NUMBER CCL-34) WERE DIVIDED INTO TWO ALIQUOTS. ONE GROUP WAS TREATED WITH CADMIUM CHLORIDE (SIGMA C-2544) AT THREE DIFFERENT CONCENTRATIONS OF 0.1 µM, 1 µM, AND 10 µM FOR 24 HOURS AND THE OTHER GROUP OF CELLS REMAINED UNTREATED FOR CONTROL PURPOSES. RNA WAS ISOLATED FROM BOTH GROUPS OF CELLS USING MESSAGECLEAN® KIT FROM GENHUNTER®. THE PROTOCOLS FROM THE MESSAGECLEAN® KIT WERE MODIFIED TO GENERATE MORE OPTIMAL CONDITIONS FOR REMOVING DNA CONTAMINATION. THEN, THESE INGREDIENTS WERE ADDED: 50 ML TOTAL RNA, 5.7 ML 10X REACTION BUFFER, 1.0 ML DNASE I (10 UNITS/ML) FOR A TOTAL VOLUME OF 56.7 ML. THE INGREDIENTS WERE MIXED WELL AND INCUBATED FOR 30 MINUTES AT 370° CELSIUS. THEN 40 ML PHENOL/CHLOROFORM MIXTURE (1:1 VOLUME) WAS ADDED AND THE MIXTURE WAS VORTEXED FOR 30 SECONDS AND ALLOWED TO SIT ON ICE FOR 10 MINUTES. THEN THE TUBE CONTAINING THE MIXTURE WAS SPUN IN AN EPPENDORF CENTRIFUGE AT 4 DEGREES FOR 5 MINUTES AT MAXIMUM SPEED. THE UPPER PHASE WAS COLLECTED, TRANSFERRED TO A NEW TUBE AND 5 ML OF 3M NAOAC AND 200 ML 95% ETHANOL WAS ADDED TO THE UPPER PHASE. THE MIXTURE WAS ALLOWED TO SIT FOR AT LEAST ONE HOUR AT −80° C. AND THEN SPUN FOR ABOUT 10 MINUTES AT 4° C. THE SUPERNATANT WAS REMOVED AND THE RNA DRIED FOR A FEW MINUTES. SUBSEQUENTLY, THE RNA WAS SUSPENDED IN 11 ML DEPC $H_2O$. 1 ML WAS USED TO MEASURE $A_{260/280}$ IN 50 ML $H_2O$. THE RNA WAS STORED AS 1–2 MG ALIQUOTS AT −80° C. IMMEDIATELY PRIOR TO DIFFERENTIAL DISPLAY, THE APPROPRIATE AMOUNT OF RNA WAS DILUTED TO 0.1 MG/ML WITH DEPC $H_2O$. IT IS IMPORTANT TO AVOID USING THE DILUTED RNA AFTER FREEZE-THAW CYCLE.

RNAIMAGE® KITS WERE USED AND PROTOCOLS FROM THE RNAIMAGE® KITS WERE ALTERED TO OPTIMIZE MORE SUCCESSFUL MRNA DIFFERENTIAL DISPLAY. THE FOLLOWING SECTION DESCRIBES THE METHOD BY WHICH THIS WAS ACCOMPLISHED:

Reverse transcription

IN A TUBE, THE FOLLOWING INGREDIENTS WERE ADDED: 9.4 ML $DH_2O$, 4.0 ML 5X RT BUFFER, 1.6 ML DNTP (250 MM), 2.0 ML OF 0.1 MG/ML FRESHLY DILUTED TOTAL RNA THAT WAS DNASE-FREE, 2.0 ML H-$T_{11}$M (2 MM) FOR A TOTAL VOLUME OF 19 ML. THE INGREDIENTS WERE MIXED WELL AND INCUBATED AT 65° C. FOR 5 MINUTES, 37° C. FOR 60 MINUTES, 75° C. FOR 5 MINUTES, AND HELD AT 4° C. AFTER THE TUBES HAD BEEN AT 37° C. FOR 10 MINUTES, AND 1 ML OF SUPERSCRIPT II REVERSE TRANSCRIPTASE (LIFE TECHNOLOGIES INC.) WAS ADDED TO EACH REACTION, AND QUICKLY MIXED BY FINGER TAPPING THE TUBES BEFORE THE INCUBATION CONTINUED. AT THE END OF THE REVERSE TRANSCRIPTION, THE TUBES WERE SPUN BRIEFLY TO COLLECT CONDENSATION. THE TUBES WERE SET ON ICE FOR PCR OR STORED AT −20° C. FOR LATER USE.

PCR

THE FOLLOWING INGREDIENTS WERE USED FOR A PCR REACTION: 10 ML $DH_2O$, 2 ML 10X PCR BUFFER, 1.6 ML DNTP (25 MM), 2 ML OF 2 MM H-AP PRIMER, 2 ML OF 2 MM H-$T_{11}$M, 2 ML RT-MIX DESCRIBED ABOVE (MUST CONTAIN THE SAME H-$T_{11}$M USED FOR PCR), 0.2 ML $\alpha$-$^{33}$P DATP (2000 CI/MMOLE), 0.2 ML TAQ DNA POLYMERASE FROM PE BIOSYSTEMS FOR A TOTAL VOLUME OF 20 ML. THE TUBE CONTAINING ALL THESE INGREDIENTS WERE MIXED WELL BY PIPETING UP AND DOWN AND PLACED IN A THERMOCYCLER AT 95° C. FOR 5 MINUTES AND THEN AMPLIFIED FOR 40 CYCLES UNDER THE CONDITIONS OF 94° C. FOR 30 SECONDS, 40° C. FOR 2 MINUTES, 72° C. FOR 30 SECONDS AND FINALLY HELD AT 4° C. UNTIL THE SAMPLES ARE REMOVED FROM THE THERMOCYCLER.

Gel electrophoresis

A 6% DENATURING POLYACRYLAMIDE GEL IN TBE WAS PREPARED AND ALLOWED TO POLYMERIZE FOR AT LEAST 2 HOURS BEFORE USING. THEN THE GEL WAS RUN FOR ABOUT 30 MINUTES BEFORE ANY SAMPLES WERE LOADED. IT IS IMPORTANT FOR ALL THE SAMPLE WELLS IN THE GEL TO BE FLUSHED AND CLEARED OF ALL UREA PRIOR TO LOADING ANY SAMPLES IN THE WELLS. ABOUT 3.5 ML OF EACH SAMPLE WAS MIXED WITH 2 ML OF LOADING DYE AND INCUBATED AT 80° C. FOR 2 MINUTES IMMEDIATELY BEFORE LOADING ONTO THE 6% GEL. IN THIS EXAMPLE, THE LOADING DYE WAS XYLENE AND AFTER THE GEL WAS LOADED WITH THE SAMPLES OBTAINED FROM THE ROUNDS OF PCR, THE GEL WAS RUN AT 60 WATTS OF CONSTANT POWER UNTIL THE XYLENE DYE WAS ABOUT 6 INCHES FROM THE BOTTOM OF THE GEL. ONCE THE POWER WAS TURNED OFF, THE GEL WAS BLOTTED ONTO A LARGE SHEET OF EXPOSED AUTORADIOGRAPH FILM. THE GEL WAS COVERED WITH PLASTIC WRAP AND UNDER DARK CONDITIONS, THE GEL WAS PLACED IN A LARGE AUTORADIOGRAPH CASSETTE WITH A NEW SHEET OF UNEXPOSED FILM, MARKED FOR ORIENTATION, AND THE FILM WAS ALLOWED TO BE EXPOSED TO THE GEL AT −80° C. THE EXPOSURE PERIOD CAN BE ANYWHERE FROM OVERNIGHT TO 72 HOURS. ONCE THE FILM HAS BEEN DEVELOPED, BANDS OF INTEREST WERE IDENTIFIED BY ALIGNMENT WITH

THE DEVELOPED FILM AND SUBSEQUENTLY ISOLATED BY CUTTING THE BAND OF INTEREST OUT OF THE POLYACRYLAMIDE GEL WITH A CLEAN SCALPEL BLADE. THE ISOLATED BAND WAS PLACED IN 100 ML OF WATER AND BOILED AT 95% FOR 5 MINUTES.

PCR to amplify gel band

PCR WAS SET UP TO AMPLIFY THE GEL BAND. THE REAMPLIFICATION SHOULD BE DONE USING THE SAME PRIMER SET AND PCR CONDITIONS EXCEPT THE DNTP CONCENTRATIONS SHOULD BE AT 20 MM. THE FOLLOWING INGREDIENTS WERE COMBINED FOR THE PCR REACTION: 20.4 ML $H_2O$, 4 ML 10X PCR BUFFER, 3.2 ML OF 250 MM DNTPS, 4 ML OF 2 MM H-AP PRIMERS, 4 ML OF 2 MM $H-T_{11}M$, 4 ML TEMPLATE (OUT OF THE 100 ML CONTAINING GEL BAND), AND 0.5 ML TAQ POLYMERASE FOR A TOTAL VOLUME OF 40 ML. THESE INGREDIENTS WERE HEATED TO 95° C. FOR 5 MINUTES AND THEN CYCLED FOR 40 CYCLES UNDER THE CONDITIONS OF 94° C. FOR 30 SECONDS, 40° C. FOR 2 MINUTES, 72° C. FOR 30 SECONDS FOLLOWED BY A FINAL EXTENSION AT 72° C. FOR 5 MINUTES AND FINALLY HELD AT 4° C. UNTIL THE SAMPLES ARE REMOVED FROM THE THERMOCYCLER. ABOUT 4 ML OF THE PCR REACTION WAS REMOVED AND RUN ON A 1% AGAROSE GEL TO ASCERTAIN THE SUCCESS OF THE PCR REACTION.

Cloning amplified fragments

TO CLONE THE AMPLIFIED FRAGMENTS, PRODUCTS FROM DIFFERENT SOURCES (E.G., GENHUNTER OR INVITROGEN) MAY BE USED TO ACHIEVE THE DESIRED CLONED PRODUCT. IN THIS EXAMPLE, INVITROGEN'S TOPO TA CLONING KIT® WAS USED AND THE FOLLOWING MATERIAL WAS COMBINED IN A REACTION TUBE: 2 ML OF FRESHLY RUN PCR PRODUCT, 2 ML OF STERILE $H_2O$, 1 ML OF PCR-TOPO VECTOR FOR A FINAL VOLUME OF 5 ML. THE COMBINED INGREDIENTS WERE MIXED GENTLY AND INCUBATED FOR 5 MINUTES AT ROOM TEMPERATURE. THEN 1 ML OF 6X TOPO CLONING STOP SOLUTION WAS ADDED AND ALL COMBINED INGREDIENTS WERE MIXED FOR ABOUT 10 SECONDS AT ROOM TEMPERATURE AND THEN SET ON ICE. ONE SHOT™ CELLS WERE THAWED ON ICE. 2 ML OF THE TOPO CLONING REACTION WAS ADDED TO THE ONE SHOT™ CELLS, MIXED, AND INCUBATED ON ICE FOR 30 MINUTES. THE CELLS WERE HEAT SHOCKED AT 42° C. FOR 30 SECONDS WITHOUT SHAKING AND INCUBATED ON ICE FOR 2 MINUTES. THEN 250 ML OF ROOM TEMPERATURE SOC WAS ADDED TO THE HEAT SHOCKED CELLS AND MIXED. THE CELLS WERE THEN PLACED AT 37° C. FOR 30 MINUTES. ABOUT 50–100 ML OF THE CELLS WERE SPREAD ON 2 XYT PLATES CONTAINING 100 MG/ML AMPICILLIN AND X-GAL. THE PLATES WERE INCUBATED OVERNIGHT AT 37° C. AND THE NEXT MORNING, 3 WHITE COLONIES WERE SELECTED FOR ANALYSIS.

Screening colonies for correct recombinant plasmids

PCR WAS USED TO ASCERTAIN WHETHER THE WHITE COLONIES SELECTED CONTAINED THE CORRECT RECOMBINANT PLASMID. THE FOLLOWING INGREDIENTS WERE COMBINED FOR THE PCR REACTION: 21 ML $H_2O$, 2.5 ML 10X PCR BUFFER, 0.12 ML OF 10 MM DNTPS, 1 ML OF 25 NG/ML T7 PRIMER, 1 ML GENE SPECIFIC LEFT OR RIGHT PRIMER AT 25 NG/ML, TEMPLATE (A TOOTHPICK WAS USED TO TRANSFER COLONY FROM TRANSFORMATION PLATE TO TUBE BY SWISHING THE TOOTHPICK AROUND IN THE REACTION MIX), AND 0.5 ML TAQ POLYMERASE FOR A TOTAL VOLUME OF 25 ML. THE REACTION MIX WAS RUN AT 95° C. FOR 5 MINUTES AND THEN CYCLED 35 TIMES UNDER THE CONDITIONS OF 95° C. FOR 30 SECONDS, 45° C. FOR 30 SECONDS, 72° C. FOR 30 SECONDS, AND FOLLOWED BY 72° C. FOR 5 MINUTES AND FINALLY 4° C. UNTIL SAMPLES ARE REMOVED FROM THE THERMOCYCLER. ABOUT 4 ML OF THE PCR PRODUCT WAS REMOVED AND RUN ON A 1% AGAROSE GEL TO ASCERTAIN THE SUCCESS OF THE PCR REACTION. BACTERIAL COLONIES CORRESPONDING TO THE COLONIES WHICH YIELDED POSITIVE PCR RESULTS WERE GROWN OVERNIGHT IN LB MEDIA CONTAINING 100 MG/ML AMPICILLIN AT 370° C. WITH CONSTANT SHAKING. PLASMID DNA WERE ISOLATED FROM THE OVERNIGHT CULTURES AND SEQUENCED USING A T7 PRIMER. SEQUENCES WERE THEN COMPARED TO SEQUENCES IN THE GENBANK DATABASE TO CONFIRM THAT THE CORRECT GENE FRAGMENT WAS CLONED. GENE FRAGMENTS WERE THEN AMPLIFIED BY PCR FROM THE PLASMID DNA. THE UNINCORPORATED PRIMERS AND DNTPS WERE REMOVED AND THE RESULTING GENE FRAGMENTS WERE ARRAYED ON GLASS SLIDES FOR THE PURPOSES OF MEASURING DIFFERENTIAL GENE EXPRESSION USING THE PHASE-1 MOLECULAR TOXICOLOGY MICROARRAY PRODUCTS. TABLE 5 INDICATES TOXICOLOGICALLY RELEVANT GENES WHICH HAVE BEEN IDENTIFIED USING METHODS DISCLOSED IN THIS EXAMPLE.

Example 5

Identifying and Isolating Toxicologically Relevant Genes From Canine Databases

ONE METHOD THAT WAS USED TO IDENTIFY AND ISOLATE TOXICOLOGICALLY RELEVANT GENES FOR INCLUSION IN A CANINE ARRAY WAS TO SEARCH A PUBLIC DATABASE (E.G., GENBANK) FOR TOXICOLOGICALLY RELEVANT CANINE GENES. ONCE THESE GENES WERE IDENTIFIED, PRIMERS WERE OBTAINED AND USED IN AN AMPLIFICATION PROCESS WITH CDNA LIBRARY MADE FROM CANINE CELLS. AS DISCLOSED HEREIN, CDNA LIBRARY CAN BE MADE FROM A VARIETY OF SOURCES. IN THIS EXAMPLE, THE CDNA LIBRARY WAS MADE FROM BEAGLE LIVER CELLS. THE AMPLIFIED PRODUCT WAS CLONED INTO AN EXPRESSION VECTOR AND SEQUENCED TO CONFIRM THAT THE SEQUENCE MATCHED OR WAS SUBSTANTIALLY SIMILAR TO THE GENE SEQUENCE INFORMATION OBTAINED FROM GENBANK. CONFIRMED AMPLIFIED GENE PRODUCTS WERE THEN INCORPORATED INTO A CANINE ARRAY USING THE METHODS DISCLOSED HEREIN TO IMMOBILIZE THE GENE PRODUCT, OR TARGET SEQUENCE, TO A GLASS SLIDE. TOXICOLOGICALLY RELEVANT GENES WHICH HAVE BEEN IDENTIFIED AND ISOLATED IN THIS MANNER ARE LISTED IN TABLE 1.

Example 6

Identifying and Isolating Toxicologically Relevant Genes From Human Databases

ONE METHOD THAT WAS USED TO IDENTIFY AND ISOLATE TOXICOLOGICALLY RELEVANT GENES

FOR INCLUSION IN A CANINE ARRAY WAS TO SEARCH A PUBLIC DATABASE (E.G., GENBANK) FOR TOXICOLOGICALLY RELEVANT HUMAN GENES. ONCE THESE GENES WERE IDENTIFIED, PRIMERS WERE OBTAINED AND USED IN AN AMPLIFICATION PROCESS WITH CDNA LIBRARY MADE FROM CANINE CELLS. AS DISCLOSED HEREIN, CDNA LIBRARY CAN BE MADE FROM A VARIETY OF SOURCES. IN THIS EXAMPLE, THE CDNA LIBRARY WAS MADE FROM BEAGLE LIVER CELLS. THE AMPLIFIED PRODUCT WAS CLONED INTO AN EXPRESSION VECTOR AND SEQUENCED TO CONFIRM THAT THE SEQUENCE MATCHED OR WAS SUBSTANTIALLY SIMILAR TO THE GENE SEQUENCE INFORMATION OBTAINED FROM GENBANK. CONFIRMED AMPLIFIED GENE PRODUCTS WERE THEN INCORPORATED INTO A CANINE ARRAY USING THE METHODS DISCLOSED HEREIN TO IMMOBILIZE THE GENE PRODUCT, OR TARGET SEQUENCE, TO A GLASS SLIDE. TOXICOLOGICALLY RELEVANT GENES WHICH HAVE BEEN IDENTIFIED AND ISOLATED IN THIS MANNER ARE LISTED IN TABLE 6.

Example 7

Identifying and Isolating Toxicologically Relevant Genes Using de novo Primers

ANOTHER METHOD WAS USED TO IDENTIFY AND ISOLATE TOXICOLOGICALLY RELEVANT GENES. TOXICOLOGICALLY RELEVANT GENES WERE IDENTIFIED USING A PUBLIC DATABASE (E.G., GENBANK) AND SEQUENCES CORRESPONDING WITHIN THESE GENES WERE SYNTHESIZED DE NOVO AND USED IN AMPLIFICATION REACTIONS. THE AMPLIFIED PRODUCT WAS CLONED INTO AN EXPRESSION VECTOR AND SEQUENCED TO CONFIRM THAT THE SEQUENCE MATCHED OR WAS SUBSTANTIALLY SIMILAR TO THE GENE SEQUENCE INFORMATION OBTAINED FROM GENBANK. CONFIRMED AMPLIFIED GENE PRODUCTS WERE THEN INCORPORATED INTO A CANINE ARRAY USING THE METHODS DISCLOSED HEREIN TO IMMOBILIZE THE GENE PRODUCT, OR TARGET SEQUENCE, TO A GLASS SLIDE. TOXICOLOGICALLY RELEVANT GENES WHICH HAVE BEEN IDENTIFIED AND ISOLATED IN THIS MANNER ARE LISTED IN TABLE 3.

Example 8

Attaching Toxicologically Relevant Genes to Glass Slides

THE GENES TO BE ATTACHED TO THE GLASS SLIDES CAN BE AMPLIFIED AS PROVIDED HEREIN. AN IMPORTANT MODIFICATION TO THE AMPLIFICATION PROCESS WAS THE INCLUSION OF AMINE PRIMERS, WHICH CAN BE OBTAINED FROM ANY COMMERCIAL SOURCE, E.G., SYNTHEGEN, SUCH THAT A REACTIVE AMINE GROUP, A DERIVATIVE THEREOF, OR ANOTHER REACTIVE GROUP WAS INCLUDED IN THE AMPLIFIED PRODUCT. THE AMPLIFIED PRODUCT WAS PURIFIED BY ANY NUMBER OF METHODS DISCLOSED HEREIN AND IMMOBILIZED OR "SPOTTED" ONTO A SOLID SUBSTRATE, SUCH AS A GLASS SLIDE, WHICH CAN REACT WITH THE AMINE GROUP ON THE AMPLIFIED PRODUCT AND FORM A COVALENT LINKAGE.

MD Array Spotter Operation

The terminology and equipment used in this example comprised the following:

| | |
|---|---|
| Spotter: | MD Generation II Array Spotter main instrument |
| Spotting Chamber: | Area of spotter enclosed in glass which houses the pins, plates, trays and most spotter machinery. |
| Controller: | Dedicated Dell Computer and Monitor to right of Spotter Unit |
| Pins: | (6) fine tubes in the Spotter Unit which pick-up and spot the Target |
| Slides: | Std. size glass microscope slides with a special coating on one side |
| Plates: | Plastic 96 well plates which hold the Target solution to be spotted |
| Target: | A solution of PCR product which the spotter deposits on the slides. |
| N2 Tank: | 5 ft. high steel gas tank labeled "Nitrogen, Compressed" |
| N2: | The N2 gas from the N2 tank |
| Air Conditioner: | Kenmore air conditioner installed in window of spotting chamber |
| Humidifier 1: | Essick 2000 Evaporative Cooler against the window |
| Humidifier 2: | Bemis Airflow with white flexible duck into the Spotter Unit |
| Humidifier 3: | Bemis Airflow against the wall |
| Humidifier 4: | Kenmore QuietComfort 7 |
| Vacuum Pump: | Gast Laboratory Oilless Piston Vacuum Pump |
| Dampbox: | The plastic sealable container containing an NaCl/water slurry |

Materials used for reagent solutions were: Nanopure water, 0.2M KCl ($\frac{1}{10}$ dilution of Stock 2M KCL in water), and 95% EtOH Reagent. The temperature control was adjusted to 60°. The spotter chambers were adjusted to be greater than 39% relative humidity and less than 65° C. The spotting pins were pre-washed for 20 cycles.

Slide Preparation/Loading

When the pre-wash was completed, the slides were first each blown with N2 gas for about 2 seconds per side. The slides were inserted into the Spotter following Array Spotter Run Values. The slides were aligned using a clean narrow rod orienting it on the center right edge of the slide and gently pushed to the left until the slide was aligned vertically against the metal pins. After slides were loaded and straightened, a visual check was done to make sure no more debris had fallen. The humidity was confirmed to be greater than 39% relative humidity. The MD spotter recognizes 16 plates as a maximum for a run and will pause automatically after 8 plates. The MD spotter also advances sequentially to plates in an invariable order and is not programmable to accommodate unique plate sourcing scheme. Therefore, it was important to manually rotate (or shuffle) plates to accomplish the spotting for the canine arrays.

BLOCKING (SLIDE PREPARATION POST-SPOTTING)

THIS BLOCKING PROCEDURE IS IMPORTANT BECAUSE IT REDUCES THE NONSPECIFIC BACKGROUND SIGNALS. THE AMOUNTS PROVIDED IN THIS PROTOCOL ARE FOR 19 SLIDES, HOWEVER, A SKILLED ARTISAN MAY MAKE MODIFICATIONS ACCORDINGLY. MORE STAINING DISHES AND SLIDE RACKS WILL BE REQUIRED IF MORE THAN 19 SLIDES ARE TO BE BLOCKED. A CLEAN GLASS CONTAINER WAS OBTAINED AND FILLED WITH NANOPURE H2O. THE CONTAINER WAS PLACED ON A HOT PLATE AND HEATED TO A HIGH TEMPERATURE. A BLOCKING SOLUTION WAS MADE BY ADDING 2.5 ML OF 20% SDS TO 500 ML BLOCKING SOLUTION BOTTLE. THE BLOCKING SOLUTION WAS WARMED IN MICROWAVE FOR 2.5 MINUTES

AND CHECKED TO DETERMINE IF THE TEMPERATURE HAD REACHED 50° C. IF THE TEMPERATURE OF THE SOLUTION WAS NOT AT YET 50° C., THEN THE SOLUTION WAS WARMED IN THE MICROWAVE AT 10 SECOND INTERVALS UNTIL IT REACHED THE DESIRED TEMPERATURE. ONE STAINING DISH WAS PLACED ON AN ORBITAL SHAKER WITH 4X SSC SOLUTION AND TURNED TO AN AGITATION SPEED OF 75 RPM. SLIDES WERE PLACED IN METAL RACKS AND PLACED IN BOILING WATER FOR SEVERAL MINUTES (E.G., 2 MINUTES). THE SLIDES WERE TAKEN OUT OF BOILING WATER AND ALLOWED TO COOL BRIEFLY. THE SLIDES WERE THEN TRANSFERRED TO STAINING CONTAINER CONTAINING 4X SSC SOLUTION ON ORBITAL SHAKER FOR SEVERAL MINUTES (E.G., 2 MINUTES), RINSED WITH NANOPURE WATER IN A STAINING CONTAINER, AND THEN BRIEFLY PLACED IN BLOCKING SOLUTION FOR ABOUT 15 MINUTES. AFTER 15 MINUTES, THE SLIDES WERE TAKEN OUT OF THE BLOCKING SOLUTION AND RINSED THREE TIMES BY DIPPING INTO THREE SEPARATE CONTAINERS WITH NANOPURE WATER EACH TIME. THE TOPS OF THE SLIDES WERE DABBED LIGHTLY WITH A TISSUE AND THE SLIDES WERE PLACED IN A CENTRIFUGE FOR ABOUT 5 MINUTES AT A SPEED OF 1000 RPM.

Example 9

Microarray RT Reaction

Fluorescence-labeled first strand cDNA probe was made from total or mRNA by first isolating RNA from control and treated cells, disclosed supra. This probe is hybridized to microarray slides spotted with DNA specific for toxicologically relevant genes. The materials needed to practice this example are: total or messenger RNA, primer, Superscript II buffer, dithiothreitol (DTT), nucleotide mix, Cy3 or Cy5 dye, Superscript II (RT), ammonium acetate, 70% EtOH, PCR machine, and ice.

The volume of each sample that would contain 20 μg of total RNA (or 2 μg of mRNA) was calculated. The amount of DEPC water needed to bring the total volume of each RNA sample to 14 μl was also calculated. If RNA is too dilute, the samples are concentrated to a volume of less than 14 μl in a speedvac without heat. The speedvac must be capable of generating a vacuum of 0 Milli-Torr so that samples can freeze dry under these conditions. Sufficient volume of DEPC water was added to bring the total volume of each RNA sample to 14 μl. Each PCR tube was labeled with the name of the sample or control reaction. The appropriate volume of DEPC water and 8 μl of anchored oligo dT mix (stored at −20° C.) was added to each tube.

Then the appropriate volume of each RNA sample was added to the labeled PCR tube. The samples were mixed by pipeting. The tubes were kept on ice until all samples are ready for the next step. It is preferable for the tubes to kept on ice until the next step is ready to proceed. The samples were incubated in a PCR machine for 10 minutes at 70° C. followed by 4° C. incubation period until the sample tubes were ready to be retrieved. The sample tubes were left at 4° C. for at least 2 minutes.

The Cy dyes are light sensitive, so any solutions or samples containing Cy-dyes should be kept out of light as much as possible (e.g. cover with foil) after this point in the process. Sufficient amounts of Cy3 and Cy5 reverse transcription mix were prepared for one to two more reactions than would actually be run by scaling up the following recipes:

---

For labeling with Cy3

8 ul 5x First Strand Buffer for Superscript II
4 ul 0.1 M DTT
2 ul Nucleotide Mix
2 ul of 1:8 dilution of Cy3 (e.g.,, 0.125 mM Cy3dCTP).
2 ul Superscript II For labeling with Cy5

8 ul 5x First Strand Buffer for Superscript II
4 ul 0.1 M DTT
2 ul Nucleotide Mix
2 ul of 1:10 dilution of Cy5 (e.g.,, 0.1 mM Cy5dCTP).
2 ul Superscript II

---

About 18 μl of the pink Cy3 mix was added to each treated sanple and 18 μl of the blue Cy5 mix was added to each control sample. Each sample was mixed by pipeting. The samples were placed in a PCR machine for 2 hours at 45° C. followed by 4° C. until the sample tubes were ready to be retrieved. The samples were transferred to Eppendorf tubes containing 600 μl of ethanol precipitation mixture. Some of the EtOH precipitation mixture was used to rinse the PCR tubes. The tubes were inverted to mix. Samples were placed in −80° C. freezer for at least 20–30 minutes. If desired, samples may be left at −20° C. overnight or over the weekend.

The samples were centrifuged for 15 minutes at 20800×g (14000 rpm in Eppendorf model 5417C) and carefully the supernatant was decanted. A visible pellet was seen (pink/red for Cy3, blue for Cy5). It is a preferable to centrifuge the tubes at a fixed position so the pellet will be at a known area in the tube. In some rare instances, the probe is seen spread on one side of the tube instead of a tight pellet. If the pellet is white or nonexistent, the reaction has not occurred to maximal efficiency.

Ice cold 70% EtOH (about 1 ml per tube) was used to wash the tubes and the tubes were subsequently inverted to clean tube and pellet. The tubes were centrifuged for 10 minutes at 20800×g (14000 rpm in Eppendorf model 5417C), then the supernatant was carefully decanted. The tubes were flash spun and any remaining EtOH was removed with a pipet. The tubes were air dried for about 5 to 10 minutes. protected from light. The length of drying time will depend on the natural humidity of the environment. For example, an environment in Santa Fe would require about 2 to 5 minutes of drying time. It is preferable that the pellet are not overdried.

When the pellets were dried, they are resuspended in 80 ul nanopure water. The cDNA/mRNA hybrid was denatured by heating for 5 minutes at 95° C. in a heat block and flash spun.

Example 10

Purification of Cy-Dye Labeled cDNA

To purify fluorescence-labeled first strand cDNA probes, the following materials were used: Millipore MAHV N45 96 well plate, v-bottom 96 well plate (Costar), Wizard DNA binding Resin, wide orifice pipette tips for 200 to 300 μl volumes, isopropanol, nanopure water. It is highly preferable to keep the plates aligned at all times during centrifugation. Misaligned plates can lead to sample cross contamination and/or sample loss. It is also important that plate carriers are seated properly in the centrifuge rotor.

The lid of a "Millipore MAHV N45" 96 well plate was labeled with the appropriate sample numbers. A blue gasket and waste plate (v-bottom 96 well) was attached. Wizard DNA Binding Resin (Promega catalog #A151) was shaken immediately prior to use for thorough resuspension. About 160 µl of Wizard DNA Binding Resin was added to each well of the filter plate that was used. If this was done with a multi-channel pipette, wide orifice pipette tips would have been used to prevent clogging. It is highly preferable not to touch or puncture the membrane of the filter plate with a pipette tip. Probes were added to the appropriate wells (80 µl cDNA samples) containing the Binding Resin. The reaction is mixed by pipeting up and down ~10 times. It is preferable to use regular, unfiltered pipette tips for this step. The plates were centrifuged at 2500 rpm for 5 minutes (Beckman GS-6 or equivalent) and then the filtrate was decanted. About 200 µl of 80% isopropanol was added, the plates were spun for 5 minutes at 2500 rpm, and the filtrate was discarded. Then the 80% isopropanol wash and spin step was repeated. The filter plate was placed on a clean collection plate (v-bottom 96 well) and 80 µl of Nanopure water, pH 8.0–8.5 was added. The pH was adjusted with NaOH. The filter plate was secured to the collection plate with tape to ensure that the plate did not slide during the final spin. The plate sat for 5 minutes and was centrifuged for 7 minutes at 2500 rpm. If there are replicates of samples they should be pooled.

Example 11

Fluorescence Readings of cDNA Probe

To semi-quantitatively assess the incorporation of fluorescence into cDNA probes and to concentrate probes prior to hybridization, the following material was used: 384 well, 100 µl assay plate (Falcon Microtest catalog #35-3980) and Wallac Victor 1420 Multilabel counter (or equivalent).

It is preferable that a consistent amount of cDNA is pipeted into the 384-well plate wells because readings will vary with volume. Controls or identical samples should be pooled at this step, if required. The probes were transferred from the Millipore 96 well plate to every other well of a 384 well assay plate (Falcon Microtest). This was done using a multi-channel pipette. For replicate samples that have been pooled, 60 µl aliquots were transferred into wells of the assay plate.

The Cy-3 and Cy-5 fluorescence was analyzed using the Wallac 1420 workstation programmed for reading Cy3-Cy-5 in the 384-well format and the data was saved to disk. The typical range for Cy-3 (20 µg) is 250–700,000 fluorescence units. The typical range for Cy-5 (20 µg) is 100–250,000 fluorescence units. Settings for the Wallac 1420 fluorescence analyzer were as follows:

Cy3

CW lamp energy = 30445
Lamp filter = P550 slot B3
Emission filter = D572 dysprosium slot A4
Emission aperture = normal
Count time = 0.1 s Cy5

CW lamp energy = 30445

-continued

Lamp filter = D642 samarium slot B7
Emission filter = D670 slot A8
Emission aperture = normal
Count time = 0.1 s Dry-down Process Concentration of the cDNA probes is highly preferable so that they can be resuspended in hybridization buffer at the appropriate volume. The volume of the control cDNA (Cy-5) was measured and divide by the number of samples to determine the appropriate amount to add to each test cDNA (Cy-3). Eppendorf tubes were labeled for each test sample and the appropriate amount of control cDNA was allocated into each tube. The test samples (Cy-3) were added to the appropriate tubes. These tubes were placed in a speed-vac to dry down, with foil covering any windows on the speed vac. At this point, heat (45° C.) may be used to expedite the drying process. Time will vary depending on the machinery. The drying process takes about one hour for 150 µl samples dried in the Savant. Samples may be saved in dried form at −20° C. for up to 14 days.

Example 12

Microarray Hybridization

To hybridize labeled cDNA probes to single stranded, covalently bound DNA target genes on glass slide microarrays, the following material were used: formamide, SSC, SDS, 2 µm syringe filter, salmon sperm DNA, hybridization chambers, incubator, coverslips, parafilm, heat blocks. It is preferable that the array is completely covered to ensure proper hybridization.

About 30 µl of hybridization buffer was prepared per sample. Slightly more than is what is needed should be made since about 100 µl can be lost during filtration.

| Hybridization Buffer: | for 100 µl: |
|---|---|
| 50% Formamide | 50 µl formamide |
| 5X SSC | 25 µl 20X SSC |
| 0.1% SDS | 25 µl 0.4% SDS |

The solution was filtered through 0.2 µm syringe filter, then the volume was measured. About 1 µl of salmon sperm DNA (10 mg/ml) was added per 100 µl of buffer. Materials used for hybridization were: 2 Eppendorf tube racks, hybridization chambers (2 arrays per chamber), slides, coverslips, and parafilm. About 30 µl of nanopure water was added to each hybridization chamber. Slides and coverslips were cleaned using $N_2$ stream. About 30 µl of hybridization buffer was added to dried probe and vortexed gently for 5 seconds. The probe remained in the dark for 10–15 minutes at room temperature and then was gently vortexed for several seconds and then was flash spun in the microfuge. The probes were boiled for 5 minutes and centrifuged for 3 min at 20800×g (14000 rpm, Eppendorf model 5417C). Probes were placed in 70° C. heat block. Each probe remained in this heat block until it was ready for hybridization.

Pipette 25 µl onto a coverslip. It is highly preferable to avoid the material at the bottom of the tube and to avoid generating air bubbles. This may mean leaving about 1 µl remaining in the pipette tip. The slide was gently lowered, face side down, onto the sample so that the coverslip covered that portion of the slide containing the array. Slides were placed in a hybridization chamber (2 per chamber). The lid of the chamber was wrapped with parafilm and the slides were placed in a 42° C. humidity chamber in a 42° C. incubator. It is preferable to not let probes or slides sit at room temperature for long periods. The slides were incubated for 18–24 hours.

Post-Hybridization Washing

To obtain single stranded cDNA probes on the array, all non-specifically bound cDNA probe should be removed from the array. Removal of all non-specifically bound cDNA probe was accomplished by washing the array and using the following materials: slide holder, glass washing dish, SSC, SDS, and nanopure water. It is highly preferable that great caution be used with the standard wash conditions as deviations can greatly affect data.

Six glass buffer chambers and glass slide holders were set up with 2X SSC buffer heated to 30–34° C. and used to fill up glass dish to ¾th of volume or enough to submerge the microarrays. It is important to exercise caution in heating of the 2X SSC buffer since a temperature of greater than 35° C. might strip off the probes. The slides were removed from chamber and placed in glass slide holders. It is preferable that the slides are not allowed dry out. The slides were placed in 2X SSC buffer but it is recommended that no more than 4 slides be placed per dish. Coverslips should fall off within 2 to 4 minutes. In the event that the coverslips do not fall off within 2 to 4 minutes, very gentle agitation may be administered. The stainless steel slide carriers were placed in the second dish and filled with 2X SSC, 0.1% SDS. Then the slides were removed from glass slide holders and placed in the stainless steel holders submerged in 2X SSC, 0.1% SDS and soaked for 5 minutes. The slides were transferred in the stainless steel slide carrier into the next glass dish containing 0.1X SSC and 0.1% SDS for 5 minutes. Then the slides are transferred in the stainless steel carrier to the next glass dish containing only 0.1X SSC for 5 minutes. The slides, still in the slide carrier, was transferred into nanopure water (18 megaohms) for 1 minute.

To dry the slides, the stainless steel slide carriers were placed on micro-carrier plates with a folded paper towel underneath. The top of the slides were gently dabbed with a tissue. Then the slides were spun in a centrifuge (Beckman GS-6 or equivalent) for 5 minutes at 1000 rpm. It is very important that the slides do not air dry, as this will lead to increased background.

When the examples are practiced by a skilled artisan as disclosed, an analysis of a toxicological response to an agent, for example, cadmium chloride, can be obtained as shown in FIGS. 1 and 2.

Example 13

Reverse Transcription of mRNA

This procedure was used prior to the step of acrylamide gel electrophoresis and after the step of RNA isolation. Reverse transcription of mRNA transforms mRNA to cDNA. The following were used in this procedure:

| | |
|---|---|
| H-T$_{11}$ Primer: | Arbitrary primers marked either G, A, or C. 2 µM concentration. |
| H-AP Primer: | Arbitrary primer, 2 µM concentration. Marked numerically. |

-continued

| | |
|---|---|
| RH-T11: | Arbitrary primer, marked either G, A, or C. 2 µL concentration. |
| Thermocycler: | MJ Research DNA Engine, PTC-200 Peltier Thermal Cycler. Programmed at 65° C. for 5 min→37° C. for 60 min→75° C. for 5 min→4° C. for the RT reaction. Another program is needed at 94° C. for 30 sec→40° C. for 2 min→72° C. for 60 sec→for 40 cycles followed by 72° C. for 5 min→4° C. |
| MMLV: | Reverse transcriptase enzyme, 100 units/µL. One unit is the amount of enzyme that incorporates 1 nmole of TTP (Thrombotic Thrombocytopenic purpura) into acid-insoluble form in 10 minutes at 37° C. using a Poly-A-oligo(dt)12-18 as a substrate. |
| Total RNA (DNA free): | Obtained from RNA isolation and purification. |
| DH$_2$0: | 18 Ω super filter in glass room. |
| DNTP mix: | Oligonucleotide mix, containing in 250 µM concentrations, A, T, G, and C. |
| 5X RT buffer: | 250 mM Tris-HCL (pH 8.3), 375 mM, 50 mM DTT, 15 mM MgCl$_2$. |
| 10X PCR Buffer: | 100 mM Tris-HCL (pH 8.8 at 25° C., 500 mM KCL, 0.8% Nonidet P40, 15 mM MgCl$_2$. |
| Taq DNA polymerase: | Enzyme used in PCR amplifications, 1000 units 5 U/µL. |
| RT Mix: | Obtained from the reverse transcription(RT) of mRNA. |
| Pipette: | VWRbrand ®; Pipette tips: ART ® 10 REACH ™, 20P, 100P, 200P, 1000E. |
| Set-up: | Countertops were wiped down with 70% ethanol prior to experiment. All tubes and pipettes were sterile before start. |
| General set-up: | The reagents were arranged in ice container and all tubes to be used in the experiment were labeled. |

| RT Reaction: (for 20 µl final volume) | µl |
|---|---|
| dH$_2$O | 9.4 |
| 5X RT buffer | 4.0 |
| dNTP Mix | 1.6 |
| Total RNA (DNA-free) | 2.0 (.1 µg/µl freshly diluted) |
| H-T$_{11}$M primer (clear tubes) | 2.0 |
| Total | 19.0 µL |

The following procedure was followed: Thaw components and set them on ice. Set up 3 RT reactions for each RNA sample in three PCR tubes. Each tube should contain each of the three different H-T$_{11}$ primers (G, A, or C). A master mix with out the RNA template is recommended to reduce pipeting errors. Duplicate reverse transcriptions for each RNA sample can also be done and run side-by-side on a 1.5% agarose gel. Program a thermocycler to: 65° C. for 5 min→37° C. for 60 min→75° C. for 5 min→4° C. After the tubes have been at 37° C. for 10 min, pause the thermocycler and add 1 µL of MMLV reverse transcriptase to each tube. Primers and samples are light sensitive and it is recommended that they be kept in the dark. Samples can be stored at −20° C. until ready to proceed with the PCR reaction.

PCR Reaction (From RNAspectra Red Kit™ from GenHunter)

| For a 20 μl final volume | μL |
|---|---|
| dH$_2$O | 10.2 |
| 10X PCR buffer | 2.0 |
| dNTP Mix | 1.6 |
| H-AP primer (2 μM) | 2.0 |
| RH-T$_{11}$ primer (pink tubes) | 2.0 |
| RT Mix | 2.0 |
| Taq DNA Polymerase | 0.2 |
| Total | 20.0 μL |

It is important that RT mix contains the same H-T$_{11}$M primer used for PCR. Master Mixes without the RT mix is recommended to avoid pipeting errors. Program a thermocycler for 94° C. for 30 sec→40° C. for 2 min→72° C. for 60 sec→for 40 cycles followed by 72° C. for 5 min→4° C. indefinitely. Examples of genes which were subjected to this protocol are shown in Tables 5 and 7.

Example 14

Reamplifying cDNA

This procedure was used prior to the cloning step and after acrylamide gel electrophoresis. The following were used in this procedure:

| | |
|---|---|
| DH$_2$0: | 18 Ω super filter in glass room. |
| 10X PCR buffer: | 100 mM Tris-HCL (pH 8.8 at 25° C., 500 mM KCL, 0.8% Nonidet P40, 15 mM MgCl$_2$. |
| DNTP mix: | Oligonucleotide mix, containing in 250 μM concentrations, A, T, G, and C. |
| H-AP Primer: | Arbitrary primer, 2 μM concentration. Marked numerically. |
| RH-T11: | Arbitrary primer, marked either G, A, or C. 2 μL concentration. |
| Thermocycler: | MJ Research DNA Engine, PTC-200 Peltier Thermal Cycler. Programmed at 94° C. for 30 sec→ 40° C. for 2 min→72° C. for 1 min→39 cycles→72° C. for 5 min→4° C. |
| cDNA template: | Obtained from the reverse transcription reaction. |
| Taq DNA polymerase: | Enzyme used in PCR amplifications, 1000 units 5 U/μL. |
| Centrifuge: | Eppendorf centrifuge 5417C. |
| Pipette: | VWbrand ®; Pipette tips: ART ® 10 REACH ™, 20P, 100P, 200P, 1000E |
| Glass plates: | Acrylamide long jumbo gel ™ system, Hitachi genetic systems. |
| Hot plate: | VWR scientific products, Dyla dual hot plate/stirrer. |
| Set-up: | Countertops were wiped down with 70% ethanol prior to experiment. All tubes and pipettes were sterile before start. |
| General set-up: | The reagents were arranged in ice container and all tubes to be used in the experiment were labeled. |

The following procedure was followed: Take off smaller glass plate, leaving the gel attached to the larger plate. Lay the glass plate with the gel attached to the paper printout of the gel. Align the printout of the gel with the glass plate, using the tape fragments. Cut out the bands of interest with a clean razor blade, or small bore needle. Transfer each gel slice to a 1.5 ml microcentrifuge tube filled with 100 μL of dH$_2$O. Soak the gel slice for 10 min at room temperature. Make sure the gel slice is completely covered by dH$_2$O. Boil the tube for 15 minutes to elute DNA from the gel slice. Spin the tube for 2 min (~14,000 rpm) to pellet the gel. Transfer the supernatant to a new 1.5 ml tube. Add 10 μl of 3M sodium acetate, 5 μL of glycogen (10 mg/ml), and 450 μL of 100% EtOH. Let sit for 30 min in a −80° C. freezer. Centrifuge at 14,000 rpm for 10 min at 4° C. to pellet the DNA. Remove the supernatant, then rinse the pellet with 200 μL of ice-cold 85% EtOH. Spin 1 min at 14,000 rpm and remove the residual EtOH. Dissolve the pellet in 10 μl of dH$_2$O. You can use 4 μL for reamplification. Save the rest in a −20° C. freezer.

| Reamplification PCR Reaction | μL |
|---|---|
| dH$_2$O | 23.4 |
| 10X PCR buffer | 4.0 |
| dNTP Mix | 0.2 |
| H-AP primer, 2 μM | 4.0 |
| H-T$_{11}$M (clear tubes) | 4.0 |
| cDNA Template | 4.0 |
| Taq DNA Polymerase | 0.4 |
| Total | 40.0 μL |

The reamplification was done using the same primer combinations as the PCR protocol of Example 13. 10 μL of sample was added to 3 μL of loading dye and run on a 1.5% agarose gel and then stained with ethidium bromide for confirmation. PCR product was then sequenced. The PCR product can also be used for cloning. A commercial source Sequetech (Mountain View, Calif.; 1-800-697-8685) was used for direct sequencing. If the samples are to be cloned, they can be stored at −80° C. for great periods of time, or used directly for ligations.

Examples of genes which were subjected to this protocol are shown in Tables 5 and 7.

Example 15

Measurement of IL-8 Dose Response

MDCK cells were dosed with cadmium chloride for 24 hrs at three different dosages (0.1 μM, 1 μM, and 10 μM) and then RNA was isolated from the cells according to protocol detailed in Example 1. cDNA probes were made according to the methods described herein and the Examples above and IL-8 gene expression was measured. FIG. 3 shows the result of the dosages and that the fold induction varies with the dosage.

Example 16

Erythromycin Estolate Dosing

Figure 4:
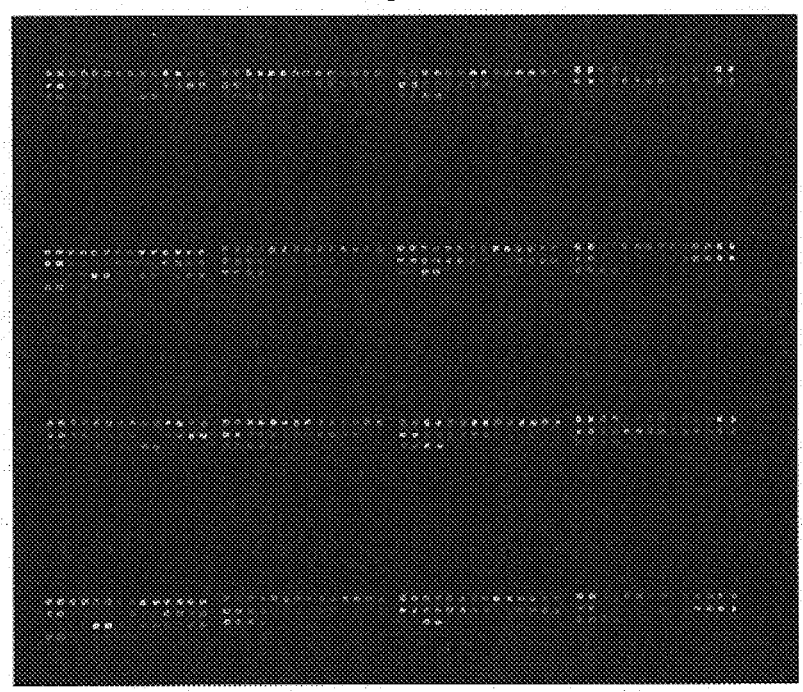
FIG. 4 is a scan of a microarray which shows the gene expression profile of a canine liver dosed with erythromycin estolate (100 mg/kg).
Figure 5:
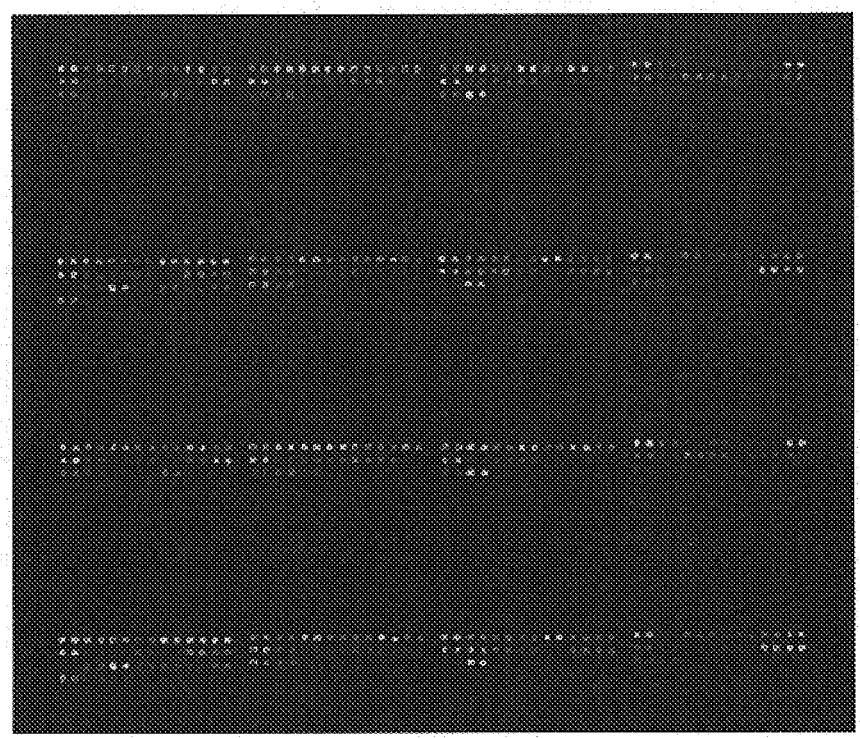
FIG. 5 is a scan of a microarray which shows the gene expression profile of a canine kidney dosed with erythromycin estolate (100 mg/kg).

Liver and kidney organs were isolated from a dog which was dosed with erythromycin esolate at 100 mg/kg/day for 2 or 10 days. The dog was euthanized 16 hours after the last dosage and the organs were harvested according to standard sterile procedure. RNA was isolated from the kidney and liver as detailed in Example 1. cDNA was made from the RNA and used as probes as detailed in the Examples above. Results are shown in FIGS. 4 and 5.

Example 17

Amplification of RNA

Amplification of RNA is accomplished by using the following protocol:

1. Combine in a microfuge tube:

1 ug total RNA/8 ul DEPC treated water (Ambion #9922)
2 ul (1 ug) Oligo d(T)$_{22}$-T7 (Operon, 5' TCT AGT CGA CGG CCA GTG AAT TGT AAT ACG ACT CAC TAT AGG GCG 3') (SEQ ID NO: 385)
Heat to 70° C. for 3 minutes.

2. While reaction is cooling to room temperature to synthesize first strand cDNA add the following:

4 ul First Strand Synthesis buffer (Gibco, supplied with SSII)
2 ul 0.1M DTT (Gibco, supplied with SSII)
2 ul 10 mM dNTP's
1 ul Anti-RNase (Ambion catalog #2690)
1 ul Template Switching Primer (1 ug/ul) (Operon, 5'-AAG CAG TGG TAT CAA CGC AGA GTA CGC GGG-3') (SEQ ID NO: 386)
2 ul Superscript II (Gibco catalog #18064-022)
cDNA synthesis is completed at 4° C. for 60 minutes.

3. Place reaction on ice and add the following:

106 ul dH$_2$O
15 ul Reaction 2 buffer (Gibco, supplied with Klenow)
3 ul 10 mM dNTP's
1 ul RNase H (Gibco catalog #18021-014)
1 ul T4 DNA Polymerase (Gibco catalog #18005-017)
2 ul Klenow (Gibco catalog #18012-021)
*2$^{ND}$ Strand Synthesis is completed by using the 2$^{ND}$ SS PCR program (see appendix).

4. End the above reaction with 7.5 ul of 1M NaOH/2 mM EDTA, heat to 65° C. for 10 minutes.
5. Add 15 ul 3M NaOAC and extract with 150 ul Phenol: chloroform: isoamyl alcohol 1:1 (see appendix).
6. Precipitate with 1 ul linear acrylamide (Ambion #9520 ) and 300 ul 100% EtOH (Aldrich #E7023), put in 95% EtOH/dry ice bath and place at −80° C. for 20 minutes or O/N.
7. Centrifuge at 14000 rpm for 10 minutes, decant supernatant.
8. Wash with 70% EtOH, centrifuge at 14000 rpm for 10 minutes and decant again.
9. Let pellet completely air dry and resuspend in 500 ul dH$_2$O.
10. Clean and remove unincorporated nucleotides using a Microcon 100 (Amicon #42412) concentrator.
11. Lyophilize sample to 16 ul using a Speedvac at 45° C.
12. To perform the amplification: 16 ul of ds-cDNA sample is combined with the following: 4 ul 10X Reaction buffer, 3 ul 100 mM dATP, 3 ul 100 mM dCTP, 3 ul 100 mM dGTP, 3 ul 100 mM dTTP, 4 ul. 1M DTT, 4 ul T7 enzyme mixture (Ampliscribe T7 Transcription kit, Epicentre Technologies #AS3107) for a total volume of 40 ul.
13. Incubate at 41° C. for 4–5 hours.
14. Place sample in a 1.5 ml centrifuge tube and bring volume up to 100 ul by adding 60 ul DEPC treated water.
15. Extract with 100 ul Phenol: chloroform: isoamyl alcohol 5:1.
16. Precipitate with 1 ul linear acrylamide (Ambion #9520) and 300 ul 100% EtOH (Aldrich #E7023), put in 95% EtOH/dry ice bath and place at −80° C. for 20 minutes or O/N.
17. Centrifuge at 14000 rpm for 10 minutes, decant supernatant.
18. Wash with 70% EtOH, centrifuge at 14000 rpm for 10 minutes and decant again.
19. Let pellet air dry and resuspend in 100 ul DEPC dH$_2$O. To verify products: OD sample and run on a formaldehyde gel.
20. Store samples at −80° C. About 300–400 ug aRNA can be expected from 1 ug total RNA

Example 18

Anti-Sense RNA Probes

1. Combine in a microfuge tube:

20 ug aRNA(1x)/8 ul DEPC water (Ambion #9922)
6 ul Random Hexamers (Gibco #48190-011)
Heat to 70° C for 10 minutes, put on ice for 2 minutes.

2. Keep reaction on ice while adding the following:

20 ul First Strand Buffer (Gibco, supplied with SSII)
10 ul 0.1M DTT (Gibco, Supplied with SSII)
10 ul 10 mM dNTP's
4 ul Superscript II (Gibco #18064-022)
2 ul Anti-Rnase (Ambion #2690)
Heat to 41° C. for 60 minutes 3. Add 8 ul Oligo d(T)$_{12}$ (1 ug/ul) to the reaction.
4. Heat to 70° C. for 10 minutes, put on ice for 2 minutes
5. Place reaction on ice and add the following:

38 ul DEPC water
30 ul 2$^{ND}$ Strand Synthesis buffer (Gibco, supplied with Klenow)
6 ul 10 mM dNTP's
2 ul Rnase H (Gibco #18021-014)
2 ul T4 DNA Polymerase (Gibco #18005-017)
4 ul Klenow (Gibco #18012-021)
2 ul 0.125 mM CyDye (Cy3 or Cy5, Pharmacia #27-2692-01) for a total volume of 150 ul.

6. Place in PCR machine and use program 2$^{ND}$SS (see Appendix).
7. Place reaction into a 1.5 ml centrifuge tube and add 600 ul of precipitation mix (see appendix). Place in −80° C. for 1 hour.
8. Centrifuge for 10 minutes at 14,000 rpm
9. Decant supernatant
10. Wash with 500 ul 70% EtOH. Centrifuge again.
11. Decant supernatant, and let samples air dry.
12. At this point you can resuspend samples in dH$_2$O to read fluorescence or go directly to hybridization.

APPENDIX

Phenol Chloroform Extraction is performed as follows:

1. Add 1 volume of Phenol: chloroform: isoamyl alcohol (use 5:1, Sigma #P-1944, if extracting RNA and 1:1, Sigma #P-2069, if extracting DNA).
2. Vortex to mix.
3. Centrifuge at 14000 rpm for 5 minutes.
4. Remove the upper, aqueous layer to a clean 1.5 ml centrifuge tube, be careful to avoid the denatured proteins which are found at the aqueous/phenol interface.

5. Centrifuge tube again and remove any more aqueous layer that may be present.
6. Follow with precipitation.

$2^{ND}$ SS PCR Program is as follows: 37° C. for 2 minutes→95° C. for 3 minutes→65° C. 3 minutes→75° C. 30 minutes.

Precipitation Mix is as follows: 68 ul water, 92 ul ammonium acetate (filtered), and 440 ul 95% EtOH.

To use the Microcon 100 concentrator, the following is done:
1. Prepare column with 500 ul dH20 centrifuge at 3000 K for 10 minutes
2. Add sample to column and centrifuge at 3000 K for 10 minutes
3. Invert column into 1.5 ml collection tube and centrifuge at 4500 K for 3 minutes.

TABLE 1

| ID# | Gene Name | Accession Number | Size of insert | Left PCR primer sequence | Right PCR primer sequence |
|---|---|---|---|---|---|
| C1 | c-myc | X95367 | 503 | caagaggacgaagaagaaattgatgtt | cgcttccgcaacaagtccttt |
| C2 | c-erb B-2 | AB008451 | 507 | gtgtttgatggtgacttgggaatg | gtactccgggttctctgctgtagg |
| C3 | Catalase | AB012918 | 506 | gacaaaatgcttcagggtcgtctt | ccatgctgcataaaggtgtgaatc |
| C4 | p53 | AF060514 | 506 | acttttcgacacagtgtggtggtg | cgagaggtagattgccccttcttt |
| C5 | Metallo thionein 2 | Ab028042 | 330 | gactccagccgccccttct | aggaatgtagtagcaaacgggtca |
| C6 | Interleukin-2 | U28141 | 490 | tcacagtaacctcaactcctgcca | gtcagtgttgagaagatgctttgaca |
| C7 | Metallo-thionein 1 | D84397 | 376 | gctctgactctcctgtggtctg | caaacgggaatgtagaaaacaagtca |
| C8 | Intercellular adhesion molecule-1 | L31625 | 507 | caagtcagagctggaatttcccat | tggaaagaactcccaactggacat |
| C9 | Multidrug resistant protein-1 | AF045016 | 510 | ggcaaagagataaagcacctgaatg | atagatgcctttctgagccagcag |
| C10 | Beta-actin | AF021873 | 509 | aagtattctgtgtggatcggaggc | caacttcaaggcaattaaccaccc |
| C11 | Tumor necrosis factor-alpha | S74068 | 510 | caaattgcctccaactaatcagcc | acagggcaatgatcccaaagtaga |
| C12 | Nitric oxide synthase-1, inducible | AF077821 | 510 | gtccttgcatcctcattggacct | gctgttttgctgcaccatcttttt |
| C13 | BRCA-1 | U50709 | 499 | tttctgggtattgcaggaggaaaa | agtctgcagcagttctgggaatct |
| C14 | Metallo-thionein-IV | AB028041 | 385 | ctgtgacagcattggagcttcttg | tttacatgagtgtcaccaccacca |
| C15 | Tumor necrosis factor receptor | AF013955 | 507 | ggctctgttgttggaaatataccc | cagttcacacaagagacgcattca |
| C16 | c-kit | AF099030 | 504 | gagacttggctgctagaaatatcctcc | aattgatccgcacggaatggt |
| C17 | CD40 ligand | AF086711 | 508 | ccaatttgaagcctttctcaagga | gagtaagccaaaagacgtgaagcc |
| C18 | Cubilin | AF137068 | 508 | tgaatgcacacatgacttcttgga | tgatggatacactgcatactctgcg |
| C19 | Alkaline phospha-tase | AF149417 | 499 | cagatgtggagtatgagatggacga | agaccaaagatagagttgccccg |

TABLE 1-continued

| ID# | Gene Name | Accession Number | Size of insert | Left PCR primer sequence | Right PCR primer sequence |
|---|---|---|---|---|---|
| C20 | Pancreatic lipase | M35302 | 490 | actcagagagcatcctcaaccctg | cagaagctgtgcactgttttctcct |
| C21 | Apolipoprotein CIII | M17178 | 236 | agccctggaggaagaggaccct | cagaggctggagttggtttggcc |
| C22 | Interleukin-4 | AF054833 | 301 | tcacctcccaactgattccaactctgg | gtcttgtttgccatgctgctgaggttc |
| C23 | Tissue inhibitor of metalloproteinases-1 | AF077817 | 492 | cttgtgcaactcccaaatcgtcatca | gtgcatatccctggctctcttggcag |
| C24 | Ubiquitin | AB032025 | 341 | gcagattttgtaaagaccctgacggg | acttcttcttgcggcagttgacagcac |
| C25 | Matrix metalloproteinase-2 | AF095638 | 260 | agcggtcagtgtgaaggaggtgg | tgtcccagggcacgatgaagtca |
| C26 | Interleukin-6 | U12234 | 493 | cctggtccagatgctaaagagcaaggt | acctggctccgaaacatcgaggatatt |
| C27 | Vascular cell adhesion molecule 1 (VCAM-1) | U32086 | 517 | tggaatttgaacccaaacaaaggca | cccgcatcctctaactggaccttgt |
| C28 | Phenol sulfotransferase | D29807 | 495 | gctccccagaccttgttggatc | gcatcaaagcgctcattctgggc |
| C29 | GRP94 | U01153 | 503 | aatcccagacatcccctgatcaaagac | cacttctttctgtgacccacaatccca |
| C30 | E-selectin | L23087 | 506 | ttacacggttgctgtcactggatgaaa | cacccaggtgccccactatcatgttt |
| C31 | gastric lipase | Y13899 | 501 | tgcactatcatcagagcatgcctccct | tccatcctaggaccccgagatcatgac |
| C32 | HSP27 | U19368 | 503 | ggacccttccgcgactggtacc | tgatttctgccgactgggtggct |
| C33 | IL-10 | U33843 | 472 | cgggtccctgctggaggactttaaga | ggtatgacggggttctccaagcagtt |
| C34 | caveolin-1 | U47060 | 470 | tccgaggggcacctctacaccgt | ttgccaacagcctcaaagaacgg |
| C35 | H-ras, p21 | U62092 | 193 | accatccagctcatccagaaccacttc | tggcaaatacacagagaaagccctccc |
| C36 | rab2 | M35521 | 514 | agacaagaggtttcagccagtgcatga | gtgtgtggcattagtagcagcgtgctg |
| C37 | rab5 | M35520 | 521 | aagcctagtgcttcgttttgtgaaggg | ttggctgcgtgggttcagtaaggtcta |
| C38 | rab7 | M35522 | 508 | ccccaacacattcaaaacccctcgata | tgtgtgtgtcagggtgaagtgtttgg |
| C39 | APO CII | M17177 | 256 | ctggttctgttgcttgtcctcctggggtcagtgaaaatccctgcta | gtaagtgc |
| C40 | endothelin-2 | X57038 | 330 | ctgtccgcctctgtccccctgtt | ggagtagggacaacacccagccg |
| C41 | FGFR2 | AF211257 | 498 | tgattgttcttctgccaccaaaatgcc | taaatacagaacgcacaacacggcgac |
| C42 | leptin | Ab020986 | 503 | gccttaccctcagggaccttgca | gcatgaacaaaacagcctccgcc |

TABLE 1-continued

| ID# | Gene Name | Accession Number | Size of insert | Left PCR primer sequence | Right PCR primer sequence |
|---|---|---|---|---|---|
| C43 | prostaglandin D synthase | AB026988 | 510 | aggtgtccctgcagcccaacttc | gggcggcggtcacctacttgttc |
| C44 | paraoxonase-2 (PON2) | L48515 | 472 | caggactccacagcttttcccagata | ggtgaaatattgatcccatttgctgca |
| C45 | beta-glucuronidase | AF019759 | 493 | cgccgtatgtggacgtcatctgtgt | agacagaggcttcagaggcgaacg |
| C46 | caveolin-2 | AF039223 | 359 | ctccaggtgggcttcgaggacgt | tggggtccaagtgctcagtcgtg |
| C47 | matrix metalloproteinase 14 | AF032025 | 350 | ttcttcaaaggagacaagcactgggtg | tagcctggctctaccttcagcttctgg |
| C48 | matrix metalloproteinase-9 | AB006421 | 471 | gattctccaagggcaagggacgc | tcacgtagcccacttcgtccacc |
| C49 | IL-8 | U10308 | 498 | gtggcccacattgtgaaaactcagaaa | gaccaaggcaaggttgaaaagggactc |
| C50 | keratinocyte growth factor | U80800 | 482 | caatgacatgactccagcaaatggc | ttgccataggaagaaagtgggctgttt |
| C51 | decorin | U83141 | 505 | gattgaaaatggagccttccagggaat | ataatttccaagctggatggcagagcg |
| C52 | glucose-6-phosphatase | U91844 | 508 | ctggggatctcagctgcaggattttct | atcctttcctctccttgccctctcctc |
| C53 | TGFB-1 | L34956 | 489 | gacccttcctgctcctcatggcc | cttaaatacagcccggcgcagcg |
| C54 | ZAP36/annexin IV | D38223 | 488 | gacacgtccttcatgttccagagggtg | ccagatgtgtcacccttgatgaaggag |
| C55 | N-ras | U62093 | 224 | gttggagcaggtggtgttgggaaaag | gcaaatacacagaggaagccttcgcc |
| C56 | K-ras | U62094 | 228 | gtagttggagctggtggcgtagcaa | ggcaaatacacaaagaaagccctccc |
| C57 | p38 MAPK | AF003597 | 506 | ctggtgacccatcttatgggagcagat | tttgcaaagttcatcttcggcatctgg |

TABLE 2

TARGET SEQUENCES FOR CANINE ARRAY

| ID# | Gene Name | Accession Number | Target Sequence | |
|---|---|---|---|---|
| C1 | c-myc | X95367 | caagaggacgaagaagaaattgatgttgtttctgtggaaaaaaggc aggcccctgccaaaaggtccgaatcggggtcccccctctgctggagg ccacagcaaacctcctcacagcccactggtccttaagagatgccat gtgtccaccatcagcacaactacgcggcacccccctccaccagga aggactatcccgccgccaagagggcgaggttggacagtggtagagt cctgaaacagatcagcaacaaccgcaaatgtgccagcccaggtct tcggacacggaggagaatgacaagaggcgaacacacaacgtcttgg agcgccagaggaggaacgagctgaaacggagcttctttgccctgcg tgatcagatcccggagttggaaaacaatgaaaaggccccccaaggta gtgatccttaaaaaagccaccgcgtacatcctgtccgtccaagccg aggagcaaaagctcctttccgaaaaggacttgttgcggaagcg | (SEQ ID NO: 115) |
| C2 | c-erb B-2 | AB008451 | gtgtttgatggtgacttgggaatgggggcagccaaggggctgcaga gccttcccctcacagacccagcccctctccagcggtacagtgagga | (SEQ ID NO: 116) |

TABLE 2-continued

TARGET SEQUENCES FOR CANINE ARRAY

| ID# | Gene Name | Accession Number | Target Sequence | |
|---|---|---|---|---|
| | | | ccctacggtaccccttgcccccctgagattgatggtaaggttgccccc<br>ctgacctgcagcccccagcctgaatatgtgaaccagccagaagttt<br>ggccgcagcccccccttgccctagaaggcccctttgcctccttcccg<br>accggctggtgccactctggaaaggcccaagactctgtcccccaag<br>actctctcccctggcaagaatgggggttgtcaaagacgttttttgcct<br>ttgggagtgctgtggagaatccggagtacctggcaccccggggcag<br>agctgcccctcagcccccaccctcctccagccttcagcccagccttt<br>gacaacctgtattactgggaccaggatccatcagagcggggctctc<br>cacccagcacctttgaagggacccctacagcagagaacccggagta<br>c | |
| C3 | Catalase | AB012918 | gacaaaatgcttcagggtcgtcttttttgcctatcctgacactcacc<br>gccaccgcctgggacccaactatcttcagatacctgtgaactgtcc<br>tttccgggctcgagtggccaactaccaacgggatggccccatgtgc<br>atgctcgacaatcagggtggtgctccaaattactaccccaatagct<br>ttagtgctcctgaacaacagcgttgtgtcctagagcatagcagcca<br>atgttcgccagatgtgcagcgcttcaacagtgccaatgaagataat<br>gtcactcaggtgcggaccttctatttgaaggtacttggtgaagagg<br>agaggaaacgcctgtgcgagaacattgctggccatctgaaggacgc<br>acaacttttcatccagaagaaagcggtcaagaacttcagtgatgtc<br>caccctgactacggggcccgcattcaggctcttttggacaaataca<br>atgctgagaaacctaagaacgcgattcacacctttatgcagcatgg | (SEQ ID NO: 117) |
| C4 | p53 | AF060514 | acttttcgacacagtgtggtggtgccttatgagccacccgaggttg<br>gctctgactataccaccatccactacaactacatgtgtaacagttc<br>ctgcatgggaggcatgaaccggcggcccatcctcactatcatcacc<br>ctggaagactccagtggaaacgtgctgggacgcaacagctttgagg<br>tacgcgtttgtgcctgtcccggagagaccgccggactgaggagga<br>gaatttccacaagaagggggagccttgtcctgagccaccccccggg<br>agtaccaagcgagcactgcctcccagcaccagctcctctcccccgc<br>aaaagaagaagccactagatggagaatatttcacccttcagatccg<br>tgggcgtgaacgctatgagatgttcaggaatctgaatgaagccttg<br>gagctgaaggatgcccagagtggaaaggagccaggggggaagcaggg<br>ctcactccagccacctgaaggcaaagaaggggcaatctacctctcg | (SEQ ID NO: 118) |
| C5 | Metallothionein 2 | AB028042 | gactccagccgccccttctcgccatggatcccaactgctcctgcgc<br>cgcgggggctcctgcacgtgcgccggctcctgcaaatgcaaagag<br>tgcagatgcacctcctgcaagaagagctgctgctcctgctgcccccg<br>tgggctgtgccaagtgtgcccagggctgcatctgcaagggcgcatc<br>ggacaagtgcagctgctgtgcctgatgtgggggagagcctattcct<br>gatgtaaatagagcgacgtgtacaaacctacagtttgtgggggggtt<br>ttttggtgcttttttgtttgggtccaactctgacccgtttgctact<br>acattcct | (SEQ ID NO: 119) |
| C6 | Interleukin-2 | U28141 | tcacagtaacctcaactcctgccacaatgtacaaaatgcaactctt<br>gtcttgcatcgcactgacgcttgtacttgtcgcaaacagtgcacct<br>attacttcaagctctacaaaggaaacagagcaacagatggagcaat<br>tactgctggatttacagttgctttttgaatggagttaataattatga<br>gaaccccccaactctccaggatgctcacattttaagtttttacacgccc<br>aagaaggccacagaatttacacaccttcaatgtctagcagaagaac<br>tcaaaaacctggaggaagtgctaggttttacctcaaagcaaaaacgt<br>tcacttgacagacaccaaggaattaatcagcaatatgaatgtaaca<br>cttctgaaactaaagggatctgaaacaagttacaactgtgaatatg<br>atgacgagacagcaaccattacagaatttctgaacaaatggattac<br>cttttgtcaaagcatcttctcaacactgac | (SEQ ID NO: 120) |
| C7 | Metallothionein 1 | D84397 | gctctgactctccctgtggtctgcctgggacctccgtcctcgcctc<br>gcctcgcctcgcctcgcctcgcctgggctcgagatgggccgact<br>gctcctgctccaccggtggctcctgcacgtgcgctggctcctgcaa<br>atgcaaggagtgcaaatgcacctcctgcaagaagagttgctgctcc<br>tgctgccccgtgggctgtgccaagtgtgcccagggctgcatctgca<br>agggtgcgtcggacaagtgcagctgctgtgcctgatgtgtgagaac<br>acctgttcctgatgtatatagagcaagcaacatgtacaaacctgca<br>gttttaaagcatttttttcatatcactctgacttgttttctacatt<br>cccgtttg | (SEQ ID NO: 121) |
| C8 | Intercellular adhesion molecule-1 | L31625 | caagtcagagctggaatttcccattccattggctaagctgctttcc<br>tccagaggaggactggcaatggtgatacagtttagttggcgacatg<br>cccagggacaacccactgagccccatactcctccccgtcactgaca<br>ctgacctctgttagccgtctctctcccatacgcatctctgctagt<br>gctcacgatgacatcgctgcatgcctgaacacgaatgaccactcac<br>tggcagctaaactgtggagtcccatgaaactgcccaacccctatgt<br>gtccctgcctggtcctgtttccatctcggtggcaccatacaaggac<br>acagcactctggcagcccaaattcctgcagagacgagggccctgca<br>ggcagttggcagaagaggccggcgaggattcctgtcccagctccgg<br>aagcttctcttgtagtaataaagcttgtctgtgggcgcttgtct<br>tgtgtgagtggaggggaggtgtcatgtccagttgggagttctttcc<br>a | (SEQ ID NO: 122) |
| C9 | Multidrug resistant protein-1 | AF045016 | ggcaaagagataaagcacctgaatgtccagtggctccgagcacacc<br>tgggcatcgtgtctcaggagcccatcctgtttgactgcagcattgc | (SEQ ID NO: 123) |

TABLE 2-continued

TARGET SEQUENCES FOR CANINE ARRAY

| ID# | Gene Name | Accession Number | Target Sequence | |
|---|---|---|---|---|
| C10 | Beta-actin | AF021873 | cgagaacattgcctatggagacaacagccgggtcgtatcacatgaa gagattatgcaggcagccaaggaggccaacatacaccacttcatcg agacactccctgagaaatacaacaccagagtaggagacaaaggaac ccagctctctggtggccagaaacagcgcattgccatagctcgcgct cttgttagacagaaaaggttgtccaagaagccctggacaaagccag agaaggccgcacctgcattgtgatcgcccaccgcttgtccaccatc cagaatgcagatttaatagtggtgtttcagaatggcaaagtcaagg agcatggcacacatcaacagctgctggctcagaaaggcatctat aagtattctgtgtggatcggaggctccatcctggcctcgctgtcca ccttccagcagatgtggatcagcaagcaggagtacgacgagtcggg ccctccatcgtccatcgcaaatgcttctagatcgactgcgagcag atgcgtagcatttgctgcatgagtgaattccgaagtataaattggc cctggcaaatggctagcctcatgaaactggaataagcgctttgaaa agaaatttgtccttgaagctngtatctgatatatcagcantggatt gtagaacttgttgctgatcttgacnttgtatccaagttaactgttc ccttggtatatgtttaataccgcctattccaggattctctagaggc tggcaagagtctgaaccagttgtcatttctgtcttgccggtctaac agggttgggaaggtccgagccttaggacccactttcctgtcttacc caatgttttcctgccagaacaccgtgggtggttaattgccttgaag ttg | (SEQ ID NO: 124) |
| C11 | Tumor necrosis factor-alpha | S74068 | caaattgcctccaactaatcagccctcttgcccagacagtcaaatc atcttctcgaacccccaagtgacaagccagtagctcatgttgtagca aaccccgaagctgaggggcagctccagtggctgagccgacgtgcca atgacctcctggccaatgacgtggagctgacagacaacaacagctgat agtgccgtcagatgggttgtacctcgatagctcccaggtcctcttc aagggccaagggtgcccttccacccatgtgctcctcacccacacca tcagccgcttcgccgtctcctaccagacaaaggtcaacctactctc tgccatcaagagcccttgccaaagggagaccccagaggggaccgag gccaagcccctggtacgagcccatctacctgggaggggtcttccaac tggagaagggtgatcgactcagcgctgagatcaatctgcctaacta tctggactttgccgagtctgggcaggtctactttgggatcattgcc ctgt | (SEQ ID NO: 125) |
| C12 | Nitric oxide synthase-1, inducible | AF077821 | gtccttgcatcctcattggacctggcacaggcatcgcccccttccg cagtttctggcagcagcggctccatgacatcaagcacaaagggctc cggggcagccgcatgaccctggtgtttgggtgccgccgcccagatg aggaccacctgtatcgggaggagatgttggagatggcccagatgg ggtgctgcatgaggtgcacacagcctattctcgcctgcctggccag cccaaggtctatgttcaagacatcctgcggcagcagctggccagcc aggtgctccgcatgctccatgaggagcagggccaccttttatgtctg tggggatgtgcgtatggcccgggatgtggcccataccctgaagcac ctggctgccaagctgagcctgagtgaagagcaagttgaggact atttttttccagcttaagagccagaagcgctatcatgaagatatctt tggtgctgtgtttccctatgaggtgaaaaaagatggtgcagcaaaa cagc | (SEQ ID NO: 126) |
| C13 | BRCA1 | U50709 | tttctgggtattgcaggaggaaaatgggtagttagctatttctggg taacccagtctattaaagaaagaaagatactagatgagcatgattt tgaagtcagaggagatgttgtgaatggaagaaatcaccagggtccg aagcgagcaagagaatcccaggacagagaatcccaagacagaaaga tcttcaggggcctagaaatctgttgctatgaccctttaccaacat gcccacagatcaattagagtggatggtgcacctctgtggggcttct gtggtgaaggagccttcgttattcaccctcagcaagggcactcatc cagtggtagtcgtgcagccggacgcctggacagaggacagtggctt ccatgcgattgggcagatgtgtgaggcacctgtggtgacccgagag tgggtactggacagtgtagccctctaccagtgccaggagctggaca cctacctgatcccgcagattcccagaactgctgcagact | (SEQ ID NO: 127) |
| C14 | Metallothionein-IV | AB028041 | ctgtgacagcattggagcttcttggacacctggacatggaccccgg ggaatgcacctgcatgtctggaggaatctgtatctgtggacaat tgcaaatgtacaacctgcaactgtaaaacatgtcgaaaaagctgct gtccttgctgccccccggctgtgccaagtgtgcccagggctgcat ctgcaaaggaggctcggacaagtgcagctgctgtgcctgaaccgca tccgtggtgctggggctggcgggggcgggggttgtggatgccacag ccccggaaatgtctgtacagtgcattagttgagaaactgaaattat tgtaccataggttatgcttttttatatatttgctcagaggtggtggt ggtgacactcatgtaaa | (SEQ ID NO: 128) |
| C15 | Tumor necrosis factor receptor | AF013955 | ggctctgttgttggaaatatacccccataagcgttactgcacttgtt cctcaccccccggaacagggtgaagagagctattctgtgctcccagg gaaaatatattcaccctgaagacgattccatttgctgtacgaagtg ccacaaagggacctacctgtacaatgactgtccaggcccagggctg gacacagactgcagggaatgtgaaaacggaacttttacagcttcag agaaccacctcagacaatgtcttagctgctgccaaatgccgaaaaga aatgaaccaggtggagatttctcccttgtactgtgtaccgggacacg gtgtgtggctgcaggaagaaccagtaccggttttattggagtgaaa cccttttccagtgcaataactgcagcctctgcctcaatggcacggt gcagatctcctgccaagagaagcagaacaccatatgcacctgccac | (SEQ ID NO: 129) |

TABLE 2-continued

TARGET SEQUENCES FOR CANINE ARRAY

| ID# | Gene Name | Accession Number | Target Sequence | |
|---|---|---|---|---|
| | | | gcggggttctttctaagagagcatgaatgcgtctcttgtgtgaact g | |
| C16 | c-kit | AF099030 | gagacttggctgctagaaatatcctccttactcatggtcgaatcac aaagatttgtgattttggtctagccagagacatcaagaatgattct aattatgtggtcaaaggaaacgctcggctacctgtgaagtggatgg cccctgagagcatttcaactgtgtgtacacatttgaaagtgatgt ctggtcctatgggatttttctgtgggagctcttctctttaggaagc agccctacctgggatgccagtcgattcaaagttctacaagatga tcaaggaaggcttccggatgctcagccctgagcatgcacctgctga aatgtatgacatcatgaagacgtgctgggatgctgatcccctgaaa aggccgacgtccaagcagatcgtgcagctaattgagaagcagattt cagatagcaccaatcatatttattccaacctcgcgaactgcagccc caacccagagcgccccgtggtggaccattccgtgcggatcaatt | (SEQ ID NO: 130) |
| C17 | CD40 ligand | AF086711 | ccaatttgaagcctttctcaaggagataatgctaaacaacgaaatg aagaaagaagaaaacattgcaatgcaaaaaggtgatcaggatcctc gaattgcagcccatgtcataagtgaggctagtagtaacccagcgtc cgttctgcggtgggcgccaaaagggtactacaccataagcagcaac ctggtgagcctcgagaatgggaaacagttggccgtgaaaagacaag gactctattacgtctatgcccaagtcaccttctgctccaatcgggc agcttcgagtcaagctccgttcgtcgccagcctatgcctccattcc ccgagtggaacggagagagtcttactccgcgccgcgagctcccgcg gctcgtccaaaccttgcggccaacagtccatccacttgggaggagt atttgaattgcatccaggtgcttcggtgttcgtcaacgtgactgat ccaagccaagtgagccacgggaccggcttcacgtcttttggcttac tc | (SEQ ID NO: 131) |
| C18 | Cubilin | AF137068 | tgaatgcacacatgacttcttggaggtaagaaatggaagtgatagc agttcaccattatttggcacatactgtggaactctgttgccagatc ctatcttctctcgaaacaacaaactataccatacgtgttaagaccga tagcgcaacttccaatcgtgggtatgaaattgtctggacctcatca ccctctggctgtggtggaacccttatggagacagtggttcdttca ccagcccggctatcccggcacttaccccaacaacactgactgtga atgggccatcatcgctcctgctggaagacctgtcaccgtcaccttt tactttatcagcatcgatgatcccggagactgtgtccagaactatc tcatactctacgatggaccggatgctaattctccatcctttggacc atactgtggggcagacaccaacatagctcccttttgtggcctcttca catccgtgtcttcataaaatttcacgcagagtatgcagtgtatccat ca | (SEQ ID NO: 132) |
| C19 | Alkaline phosphatase | AF149417 | cagatgtggagtatgagatggacgagaagtccaggggcacgaggct ggatggcctgaacctcatcgacatctggaagaacttcaaaccgaga cacaagcactctcactacgtctggaaccgcacggaactcctggccc tcgaccctacaccgtggactacctcttgggtctctttgagccggg ggacatgcagtacgagctgaacaggaacaacgtgactgacccgtca ctctccgagatggtggaaatagccatcaagattctgagcaagaacc ccagaggcttcttcttgctggtggaaggaggcaggattgaccacgg gcatcacgagggcaaggccaagcaggcgctgcacgaggcagtggag atggaccgggcaattgggaaggcaggcgtcatgacctccttggaag acacgctgaccgtcgtcactgcggaccactcccacgtcttcaccttt tggcgggtacaccccccggggcaactctatctttggtct | (SEQ ID NO: 133) |
| C20 | Pancreatic lipase | M35302 | actcagagagcatcctcaaccctgatggatttgcttcctaccctg tgcttcctacagggccttttgaatctaacaagtgcttcccctgccca gatcaagggtgcccacagatgggtcactatgctgataaatttgctg tcaagacaagtgatgagacacagaaatacttcctgaacaccggaga ttccagcaattttgctcgctggagatacggggttttctataacattg tctgggaaaagagccactggtcaggctaaagttgctttgtttggaa gtaagggaaatactcatcaattcaatatcttcaaggggattctcaa accaggctctactcattccaatgagtttgatgcaaagcttgatgtt ggaacaattgagaaagtcaagtttctttggaataacaacgtggtaa acccaaccttcccaaagtgggtgcagccaagatcaccgtgcaaaa gggagaggagaaaacagtgcacagcttctg | (SEQ ID NO: 134) |
| C21 | Apolipoprotein CIII | M17178 | agccctggaggaagaggaccccctcctcctgggccttatgcagggt tacatgcagcacgccaccaagacggcccaggacacgtcgaccagcg ttcaggagtccaggtggcgcagcgggccagggggctggatgaccga tagcttcagttccctgaaagactactgcagcacgtttaagggcaag ttcactgggttctgggattcagcctctgaggccaaaccaactccaa gcctctg | (SEQ ID NO: 135) |
| C22 | Interleukin-4 | AF054833 | tcacctcccaactgattccaactctggtctgcttactagcactcac cagcacctttgtccacggacataacttcaatattactattaaagag atcatcaaaatgttgaacatcctcacagcgagaaacgactcgtgca tggagctgactgtcaaggacgtcttcactgctccaaagaacacaag cgataaggaaatcttctgcagagctgctactgtactgcggcagatc tatacacacaactgctccaacagatatctcagaggactctacagga acctcagcagcatggcaaacaagac | (SEQ ID NO: 136) |
| C23 | Tissue inhibitor of metalloproteinases-1 | AF077817 | cttgtgcaactcccaaatcgtcatcagggccaagttcgtgggacc gcagaagtcaaccagaccgacttaaaccggcgttatgagatcaaga | (SEQ ID NO: 137) |

TABLE 2-continued

TARGET SEQUENCES FOR CANINE ARRAY

| ID# | Gene Name | Accession Number | Target Sequence | |
|---|---|---|---|---|
| C24 | Ubiquitin | AB032025 | tgaccaagatgttcaagggtttcagcgccttggggaatgcctcgga<br>catccgcttcgtcgacaccccgccctggaaagcgtctgcggatac<br>ttgcacaggtcccagaaccgcagcgaggagtttctggtcgccggaa<br>acctgcgggacggacacttgcagatcaacacctgcagtttcgtggc<br>cccgtggagcagcctgagtaccgctcagcgccggggcttcaccaag<br>acctatgctgctggctgtgaggggtgcacagtgtttacctgttcat<br>ccatcccctgcaaactgcagagtgacactcactgcttgtggacgga<br>ccacttcctcacaggctctgacaaggtgtttccagagccgccacctg<br>gcctgcctgccaagagagccagggatatgcac<br>gcagattttgtaaagaccctgacgggcaaaactatcaccttgag<br>gtcgagcccagtgacaccattgaaaatgtcaaagccaaaatccaag<br>acaaggagggcatcccgcctgaccagcagcgtctgattttttgcggg<br>caaacagctagaagatggccgaactctgtcagactacaatatccag<br>aaagagtccaccttgcacttggtgcttcgcctgcgaggtggcatca<br>ttgagccttcactccgccagctggcccagaaatacaactgcgacaa<br>gatgatctgccgcaagtgttatgctcgcctgcaccccgtgctgtc<br>aactgccgcaagaagagt | (SEQ ID NO: 138) |
| C25 | Matrix metalloproteinase-2 | AF095638 | agccggtcagtgtgaaggaggtggactctgggaatgacatctacggc<br>aaccccatcaagcggattcagtatgagatcaagcagataaagatgt<br>tcaaaggaccagacaaggacatagagtttatctacacggctccttc<br>ctccgccgtatgcgggtctccctggacatcggaggaaagaaggag<br>tatctcattgcgggaaaggccgaggggaacggcaagatgcacatca<br>cccttttgtgacttcatcgtgccctggggaca | (SEQ ID NO: 139) |
| C26 | Interleukin-6 | U12234 | cctggtccagatgctaaagagcaaggtaaagaatcaggatgaagtg<br>accactcctgacccaaccacagacgccagcctgcaggctatcttgc<br>agtcgcaggatgagtgcgtgaagcacacaacaattcacctcatcct<br>gcggagtctggaggatttcctgcagttcagtctgagggctgttcgg<br>ataatgtagcctgggcatctaagattgctgtagttcatgggcattc<br>ctttctccagtcagaaacctgtgcagtgggcacaaaaacttatgttg<br>ttctctgtgaggaactaaaagtatgagcgttaggacactattttaa<br>ttattttaattattgatatttaaatatgtgatatggagttaatt<br>tatataagtaatagatatttatattttttatgaagtgccacttgaa<br>atattttatgtattcattttgaaaaagttaacgtaaaatgctatgc<br>ggcttgaatatcctcgatgtttcggagccaggt | (SEQ ID NO: 140) |
| C27 | Vascular cell adhesion molecule 1 (VCAM-1) | U32086 | tggaatttgaacccaaacaaaggcagagtacacagacactttatgt<br>taatgttgcccccagggataacaacgtcgtggtcagcccctcctcc<br>atcgtggaggaaggtagtcctgtgaacatgacctgctctagcgatg<br>gccttccagctccgaacatcctgtggagcaggcggctaagtaatgg<br>gcgcctgcagtctctttctgaggatccaattctcaccttaacttct<br>gcaaaaatgaagattctggtatttatgtgtgtgaagggattaacc<br>aggctggaataagcagaaaagaagtagaattaattatccaagttgc<br>tccgaaaagacatacagcttatagcttttccttctgagagtgtcaag<br>gaaggagacactgtcattatctcctgtacatgtgaaatgttccaa<br>aaacttggataatcctgaagaaaaaagcagagacgggagacacagt<br>gctaaagtccagagatggtgcatataccatccacaaggtccagtta<br>gaggatgcggg | (SEQ ID NO: 141) |
| C28 | Phenol sulfotransferase | D29807 | gctccccagacccttgttggatcagaaggtcaaggtggtctacgtc<br>gcccgcaacgcaaaagatgtagctgtctcctattaccacttctacc<br>gcatggccaaggtgcaccctgaccctgacacctgggacagcttcct<br>ggagaagttcatggctggggaagtgtcctatgggtcctggtatcag<br>catgtgcaggaatggtgggagctgagtcacactcaccctgttctct<br>acctcttctatgaggacatgaaagagaaccccaaaagggagattca<br>gaagatcctgaagtttgtggggcgctccctgccagaggagactgtg<br>gatctcattgtccagcacacgtctttcaaggagatgaagaacaact<br>ccatggctaactacaccaccttatctcctgacatcatggaccacag<br>catttctgccttcatgaggaaaggcatctcgggggactggaagacc<br>accttcactgtggcccagaatgagcgctttgatgc | (SEQ ID NO: 142) |
| C29 | GRP94 | U01153 | aatcccagacatcccctgatcaaagacatgctgcgacgagttaagg<br>aagatgaagatgacaaaacggtatcggatcttgctgtggttttgtt<br>tgagacagcaacgctgagatcaggctatctgctaccagacactaaa<br>gcatatggagatcgaatagaaagaatgcttcgcctcagttttaaaca<br>ttgaccctgatgcaaaggtggaagaagaaccagaagaagaacccga<br>agagacaaccgaggacaccacagaagacacagagcaggacgatgaa<br>gaagaaatgggatgcaggaacagacgacgaagaacaagaaacagtaa<br>agaaatctacagctgaaaaagatgaattataaattatactctcacc<br>atttggaacctgtgtggagagggaatgtgaaatttaagtcatttct<br>ttcgagagactttgtttggatgctccccgcagccccttctccc<br>ctgcactgtaaaatgttgggattgtgggtcacagaaagaagtg | (SEQ ID NO: 143) |
| C30 | E-selectin | L23087 | ttacacggttgctgtcactgatgaaataattgccaaggagtttag<br>ggggaaacaacttggtcaaagtattctatcaccaacatgcaaaaaaa<br>tattttaaatgccacaggcgagtacatggggaaatcctgcttaat<br>actttgtgcaaggattgctaaacacagtcctaatcccttttaccc<br>tgtgggattcagtgcatttaaagtgttcttagagatttaaagtg | (SEQ ID NO: 144) |

TABLE 2-continued

TARGET SEQUENCES FOR CANINE ARRAY

| ID# | Gene Name | Accession Number | Target Sequence | |
|---|---|---|---|---|
| C31 | gastric lipase | Y13899 | ttcttttatttgcattggctaaagtacaattttccctaattcttaa<br>ttcagtgtaagtgtttagagactttaaaatatatgcatgttagagc<br>tatgatagggtaaaagttacttatcagggatctttgtttatgaagg<br>gactctaatgttatatctgtagtaaattcattttaaaaggggcaaa<br>tgctgtccccagtattacgtgaatcagtgtaaagttgtgaatgttt<br>ttactatagttgcttttaaaaacatgaatagtggggcacctgggtg<br>tgcactatcatcagagcatgcctccctactacaacctgacagacat<br>gcatgtgccaatcgcagtgtggaacggtggcaacgacttgctggcc<br>gaccctcacgatgttgacctttgctttccaagctccccaatctca<br>tttaccacaggaagattcctccttacaatcacttggactttatctg<br>ggccatggatgcccctcaagcggtttacaatgaaattgtttccatg<br>atgggaacagataataagtagttctagatttaaggaattattcttt<br>tattgttccaaaatacgttcttctctcacacgtggttttctatcat<br>gtttgagacacggtgattgttcccatggttttgatttcagaaatgt<br>gttagcatcaacaatcttccattggtaattttgaatttaaaatg<br>attttaaatttggggcatctgggtggctcagtcggctaagtcgtc<br>tgccttcggcttaagtcatgatctcggggtcctaggatgga | (SEQ ID NO: 145) |
| C32 | HSP27 | U19368 | ggacccttccgcgactggtacccggcccacagccgcctcttcgac<br>caggccttcgggctgccccggctgccggaggagtgggcgcagtggt<br>tcggccacagcggctggccgggctacgtgcgcccagtcccccccgc<br>ggtcgagggccccgccgcggccgccgcggccgccgcgcccgcctac<br>agccgcgcgctcagccggcagctcagcagcggcgtgtcggagatcc<br>ggcagacggccgaccgctggcgcgtgtccctggacgtcaaccactt<br>cgcccccgaggagctgacggtcaagacgaaggacggcgtggtggag<br>ataactggcaagcacgaagagaggcaggatgagcatggctacatct<br>cccgccgcctcactcccaaatacaccctgcccctggtgtggatcc<br>taccctggtctcctcctccctgtccctgagggcactctcacggtg<br>gaggctcccatgcccaagccagccacccagtcggcagaaatca | (SEQ ID NO: 146) |
| C33 | IL-10 | U33843 | cgggtccctgctggaggactttaagagttacctgggttgccaagcc<br>ctgtcggagatgatccagttttacttggaggaggtgatgccccggg<br>ctgagaaccacgacccagacatcaagaaccacgtgaactccctggg<br>agagaagctcaagacccctcaggctgagactgaggctgcgacgctgt<br>caccgatttcttccctgtgagaataagagcaaggcggtggagcagg<br>tgaagagcgcatttagtaagctccaggagaaaggtgtctacaaagc<br>catgagtgagtttgacatcttcatcaactacatagaaacctacatg<br>acaatgaggatgaaaatctgaaacgtgctggagaacaaaacaccca<br>ggatggcaactcttctcgactctaggacatgaattggagatctgca<br>aaataccatcccgagatgtaggagagccgaccaactgcttggagaa<br>ccccgtcatacc | (SEQ ID NO: 147) |
| C34 | caveolin-1 | U47060 | tccgaggggcacctctacaccgttcccatccgggagcagggcaaca<br>tctacaagcccaacaacaaggccatggcggaggagatgagcgagaa<br>gcaggtgtacgacgcgcacaccaaggaaatcgacctggtcaaccgc<br>gacccccaagcatctcaacgacgacgtggtcaagattgattttgaag<br>atgtgattgcagaaccagaaggaacacacagttttgatggcatctg<br>gaaggccagcttcaccacctcactgtgacaaaatactggtttttac<br>cgcttgctgtctgccctctttggcatcccaatggcactcatatggg<br>gcatttactttgccattctttcttcctgcacatctgggcagttgt<br>gccgtgcattaagagtttcctgattgagattcagtgcatcagccgt<br>gtctattccatctacgtccacaccttctgtgacccgttctttgagg<br>ctgttggcaa | (SEQ ID NO: 148) |
| C35 | H-ras, p21 | U62092 | accatccagctcatccagaaccacttcgtggatgagtacgaccca<br>ccatcgaggactcctatcggaagcaagtggtcattgacggggagac<br>gtgcctgctgggacatcctggacacagcgggccaggaggagtacagc<br>gccatgcgggaccagtacatgcgcacgggggagggctttctctgtg<br>tatttgcca | (SEQ ID NO: 149) |
| C36 | rab2 | M35521 | agacaagaggtttcagccagtgcatgacctgactatcggtgtagag<br>tttggtgctcgaatgataactattgatgggaaacagataaaacttc<br>agatatgggatacggcagggcaagagtcctttcgttccatcacaag<br>gtcatattacagaggtgcagcaggggctttactagtgtatgatatt<br>acaaggagagatacattcaaccacttgacaacctggttagaagatg<br>cccgccagcattccaattccaacatggtcattatgcttattggaaa<br>taaaagtgatttagaatcaagaagagaagtaaaaaaagaagaggt<br>gaagcttttgcacgagaacatggacttatcttcatggaaacttctg<br>ctaagactgcttccaatgtagaagaggcatttattaatacagcaaa<br>agaaatttatgagaaaatccaagaaggagtctttgacattaataat<br>gaggcaaacggcattaaaattggccctcagcacgctgctactaatg<br>ccacacac | (SEQ ID NO: 150) |
| C37 | rab5 | M35520 | aagcctagtgcttcgttttgtgaagggccaatttcatgaatttcaa<br>gagagtaccataggggctgcttttctaacccaaactgtgtgtcttg<br>atgatacaacagtaaagtttgaaatatgggatacagctggtcaaga<br>acgataccatagcttagcaccaatgtactacagaggagcacaagca<br>gccatagttgtatatgatatcacaaatgaggagtcctttgccagag<br>ccaaaaactgggttaaagaacttcagaggcaagccagtcctaacat<br>tgtaatagctttatcaggaaacaaggctgatcttgcaaataaaaga | (SEQ ID NO: 151) |

TABLE 2-continued

TARGET SEQUENCES FOR CANINE ARRAY

| ID# | Gene Name | Accession Number | Target Sequence | |
|---|---|---|---|---|
| | | | gctgtcgatttccaggaagcacagtcctatgcagatgacaacagtt tattattcatggagacatcagctaaaacatcgatgaacgtaaatga aatattcatggcaatagctaaaaagttgccaaagaacgaaccacag aatccaggagcaaattctgccagaggaagaggagtagaccttactg aacccacgcagccaa | |
| C38 | rab7 | M35522 | ccccaacacattcaaaaccctcgatagctggagagatgagtttctc atccaggccagtccccgggatcctgaaaacttcccttcgttgtgt tgggaaacaagattgacctcgaaaacagacaagtggccacaaagcg ggcacaggcctggtgctacagcaaaaacaacattccctacttcgag accagtgccaaggaggccatcaatgtggagcaggcgttccagacga ttgcaaggaatgcacttaaacaggaaacagaggtggagctgtacaa tgaattccctgaacccatcaaactggacaagaaccacgggccaag acctcagcggaaagctgcagttgctgaaggggcagtgagagcagag cacagagtccttcacaaacaaagaacacacttaggccttccaacac gagccccttcttctcttccaaacaaaacataaagtcatctctcga atccagctgccaaaagaccctaccaaacacttcaccctgacacaca ca | (SEQ ID NO: 152) |
| C39 | APO CII | M17177 | ctggttctgttgcttgtcctcctggtattgggatttgaggtccagg gggcccatgagtcccagcaagatgaaaccaccagctccgccctgct cacccagatgcaggaatcactctacagttactggggcacagccaga tcggctgccgaggacctgtacaagaaggcataccccaactaccatgg atgagaaaatcagggacatatacagcaaaagcacagcagctgtgag cacttacgcagggattttcactgacc | (SEQ ID NO: 153) |
| C40 | endothelin-2 | X57038 | ctgtccgcctctgtccccctgttgcgcacgcaggcaagggccaggt ggccgctgccccggagcatccagcaccctcagcccgggcccgaggc tcccacctgcggcctcggcgttgctcctgcagctcctggctcgaca aggagtgcgtctacttctgccacctggacatcatctgggtgaacac tcccggggtgagctcccgcggggacccaggcggggctgctagaggcg gggcaggggtggggaacctgtagctagcacagctctccctgggcc tccagacggatcgctgagctgacatgaagagcggctgggtgttgtc cctactcc | (SEQ ID NO: 154) |
| C41 | FGFR2 | AF211257 | tgattgttcttctgccaccaaaatgccagtagtaaacaaacccatc gataggaaagtattttgttttgctgtgcagctctgtcattgggccc atggagcgcggaactggacttccaagacaaatggtaccagcgttc tcttaaaaagatgccttaatccattcctcgagggtggaccttagtt gagatgatagcagactgtactccctcggcagctgccctttctgcc ctgagttgcacgttaatcagattagcctgtattctcttcagtggat tttgataatggcttccagattcattggcgttagggaagcctttag aatcttcacgtgtcatcgtcgaaattgaaacactgagttgttctgc tgatggttttggagatacttccatctttttaaggttgctctgt ctaattctggcaggacctcaccaaaagatcgggcctcgtaccaacg tcagacacgatgtcgccgtgttgtgcgttctgtattta | (SEQ ID NO: 155) |
| C42 | leptin | AB020986 | gccttaccctcagggaccttgcattccagatggtaaaaatgccaca caccagtatgcaaaggctggcctcgcaccatggcaactgagcagct gaaccagcgcactcctcagcaggcggaaatgctgaactgagaatgt cagtgctcaggggcccacaggctaaccctgctcccacttcgtagca tttttgcttttcagggcacggcagcamattactgtgtagccacatc cctctgaagcagcagcatagctgacaatttaaaaataagaactaag aacatacctaagaccataacggcagacaagtagcagggccgagact agagttcaggacctctgactcccagagtgtcccgggagccaggtaa tgctccctggaggtgcaaataggggtttgggcagggggagaccagaagt gcttacagggagagaggacttggaggtgattttgcaggaggtgagg gatgtgaattgcctgaatggcggaggctgttttgtcatgc | (SEQ ID NO: 156) |
| C43 | prostaglandin D synthase | AB026988 | aggtgtccctgcagcccaacttccaacaggataagttcctggggcg ctggttcacctcgggcctgcctccaactcgagctggttccgggag aagaagaacgtgctgtccatgtgtatgtcagtggtggccccgaccg cagacgcgaggcctcaacctcacctccaccttcctcaggaaagacca gtgtgagactcgaaccctgctcctacggccggcgggaaccccgggc tgctacagctacacgagtccccactggggcagtaccccacgacgtgt gggtggtagccaccaactacgaggagtacgcgcttctctacaccgc aggcagcaaaggcctcggccaggacttccacatggccactctctac agccgcacccagaccccaaaggccgagataaaggagaaattcagca cctttgccaagacccagggcttcacagaggatgccattgtcttcct gccacagactgataaatgcatggaggagaacaagtaggtgaccgcc gccc | (SEQ ID NO: 157) |
| C44 | paraoxonase2 (PON2) | L48515 | caggactccacagcttttcccagataagcctggagggatattaat gatggatctaaaaaaggaaaacccgagggcactggaattaagaatc agccgtgggttcaatttggcttcgttcaatccacatggtatcagca ccttcatagacagcgacgacacagtttatctctttgttgtaaacca tccagaattcaagaatacagtggaaattttttaaatttgaagaagaa gaaaattctcttctgcatctaaaaacaatcaaacatgaacttcttc caagtgtgaatgatatcatagctggtggaccagcacatttctatgc caccaatgaccactatttctctgatcctttcttaaagtatttggaa acatacttgaadttacactgggcaaatgttgtttactacagtccag | (SEQ ID NO: 158) |

TABLE 2-continued

TARGET SEQUENCES FOR CANINE ARRAY

| ID# | Gene Name | Accession Number | Target Sequence | |
|---|---|---|---|---|
| | | | atgaagttaaagtggtagcagaagggtttgatgcagcaaatgggat caatatttcacc | |
| C45 | beta-glucuronidase | AF019759 | cgccgtatgtggacgtcatctgtgtcaacagttactactcttggta tcacgactatgggcacatggaggtgattcagctgcagctggccacc gagtttgagaactggtataggacctaccagaaaccaataatccaga gcgagtacggggcagagacaattgcaggcttccaccaggatccacc tctgatgttcagtgaggagtaccagaaaggtctgctcgagcagtat cacttggtgctggatcagaaacgcaaagaatatgtggttggagagc tcatctggaattttgctgattttatgactgaccagtcaccacagag agcagtagggaacagaaagggcatcttcactcgccagagacaaccc aaagcggcggccttccttttgcgagagaggtactggaaacttgcca atgaaaccgggcaccaccggtccgcggccaagtcccagtgtttgga aaacagcccgttcgccctctgaagcctctgtct | (SEQ ID NO: 159) |
| C46 | caveolin-2 | AF039223 | ctccaggtgggcttcgaggacgtgatcgcggacgccgtgtctacgc actcctttgacaaagtgtggatttgcagccatgccctgtttgaggt cagcaagtacgtgatctacaagttcctgacgttgctcctggcgatg cccatggccttcgcggcaggggttctcttcgccaccctcagctgcc tgcacatctggattataatgcctttcgtgaagacctgcctcatggt cctgccttcggtgcagaccatatgaagagtgtaacagatgctgtc attgccccgtttgtgttcaagtgtaggacgcagcttctcttctgtca gcttgcaagtgagtcacgactgagcacttggaccca | (SEQ ID NO: 160) |
| C47 | matrix metalloproteinase-14 | AF032025 | ttcttcaaaggagacaagcactgggtgtttgatgaagcttctctgg aacctggctaccccaagcacatcaaggagctgggccgaggactgcc tactgacaaaatcgatgctgctctcttctggatgcccaatggaaag acctacttcttccggggaaacaagtattaccgtttcaacgaggaac tcaggcagtggacagcgagtaccccaaaaacatcaaggtctggga aggaatccctgagtctcccagagggtcattcatgggcagtgatgaa gtcttcacttacttctacaaggggaacaaatactggaaattcaaca accagaagctgaaggtagagccaggcta | (SEQ ID NO: 161) |
| C48 | matrix metalloproteinase-9 | AB006421 | gattctccaaggggcaagggacgccgggtgcagggccccttcttatc accgagcacgtggcctgcgctgccccgcaagctggactccgcctttt gaggacgggctcaccaagaagactttcttcttctctggcgccaag tgtgggtgtacacaggcacgtcggtggtaggcccgaggcgtctgga caagctgggcctgggccggaggttacccaagtcaccggcgccctc ccgcaagcgggggtaaggtgctgctgttcagcaggcagcgcttct ggagtttcgacgtgaagacgcagaccgtggatcccaggagcgccgg ctcggtggaacagatgtaccccgggggtgcccttgaacacgcatgac atcttccagtaccaagagaaagcctacttctgccaggaccgcttct actggcgtgtgaattctcggaatgaggtgaaccaggtggacgaagt gggctacgtga | (SEQ ID NO: 162) |
| C49 | IL-8 | U10308 | gtggcccacattgtgaaaactcagaaatcattgtaaagcttttcaa tggaaatgaggtgtgcctggacccaaggaaaaatgggtacaaaag gttgtgcagatatttctaaagaaggctgagaaacaagatccgtgaa acaacaaacacattctctgtggttccaagaattcctcaggaaaga tgccaatgagacttcaaaaaaatctatttcagtacttcatgtcccg tgtagacctggtgtaggattgccagataaaaatacagtatgcccag ttagatttgaatattaagtaaaacaatgaatagttttttttctaaag tctcatatatgttgccctattcaatgtctaggcacacttacattaa acatattattcattgtttgctgtaaattcaaatgtagctggaaatc ctggatatattttgttgttgttacatctttccacctcacctacagg ccaggatgcatgagtcccttttcaaccttgccttgtc | (SEQ ID NO: 163) |
| C50 | keratinocyte growth factor | U80800 | caatgacatgactccagagcaaatggctacaaatgtgaactgttcc agccctgagcgacataacaagaagttatgattacatggagagggg atataagagtgagaagactcttctgtcgaacacagtggtatctgag gattgataaacgaggcaaagtcaaagggacccaagagatgaagaac agttacaatatcatggaaatcaggacagtggcagttggaatagtgg caatcaaaggggtgaaagtgaatattatcttgcaatgaataagga aggaaagctctatgcaaagaaagaatgcaatgaagattgcaacttc aaagaattaattctggaaaaccattacaacacatatgcatcagcta aatggacacacagcggaggagaaatgtttgttgctttaaatcaaaa ggggggttcctgtaaggggaaaaaaacgaagaaagaacaaaaaaaca gcccactttcttcctatggcaa | (SEQ ID NO: 164) |
| C51 | decorin | U83141 | gattgaaaatggagccttccagggaatgaagaagctctcctatatc cgcattgctgataccaatataactaccatccctcaaggtcttcctc cttccctactgaattacatcttgaaggcaacaaaatcaccaaggt tgatgcatctagcctgaaaggactgaataatttggctaagttggga ctgagttttaacagcatctccgctgttgacaatggcactctagcca acactcctcatctgagggagcttcacttggacaacaataagctcat cagagtaccggtgggctggcggagcataagtacatccaggttgtc taccttcataacaacaatatatctgcagtcggatctaatgacttct gcccacctggatacaacaccaaaaaggcttcttattcaggtgtgag ccttttcagcaaccagtcagtactgggagatccagccatccacc ttccggtgtgtctacgtgcgctctgccatccagcttggaaattat | (SEQ ID NO: 165) |
| C52 | glucose-6-phosphatase | U91844 | ctggggatctcagctgcaggattttctacctgtcccatccttacaa | (SEQ ID NO: 166) |

TABLE 2-continued

TARGET SEQUENCES FOR CANINE ARRAY

| ID# | Gene Name | Accession Number | Target Sequence | |
|---|---|---|---|---|
| | | | gaaaagggaaaggagcagtggcatttgatagagaagaagaatggat<br>taaggaaagacttcttcgtatcctgcatatcatgcaaattcatgtt<br>acacaaaatctaaatcgctttgattatatttgaattttaggtaag<br>gaactctcaatagtggggaccaacttaaagcataactaataggta<br>gttaatggggtaattctgcttcttctatgtttctactatgtattca<br>gtgacctagatttgtgctgggtcagagcattcagatatagtcagct<br>tctctatcacactacatcttcctccttgtcagcctagctcagcttt<br>ccctagaactttccactgctctacatcgtgctgacacagagatgcc<br>taaaggcagctctagggtagtgcttttgtatggtttagtcaagctc<br>tgaaatcttgggcaaaaggtgaggagagggcaaggagaggaaagg<br>at | |
| C53 | TGFB1 | L34956 | gaccccttcctgctcctcatggccaccccactggagagggcccagca<br>cctgcacagctcccggcagcgccgggccctggacaccaactactgc<br>ttcagctccacggagaagaactgctgcgtccggcagctctacattg<br>acttccgcaaggatctgggctggaagtggatccatgagcccaaggg<br>ttaccgctaacttctgcctgggccctgcccctacatttggagc<br>ctggacacgcagtacagcaaggtcctggccctgtacaaccagcaca<br>acccgggcgcgtcggcggcgccgtgctgcgtgccgcaggcgctgga<br>gccactgccatcgtgtactacgtgggccgcaagcccaaggtggag<br>cagctgtcgaacatgatcgtgcgctcctgcaagtgcagctgaggcc<br>ccgccccgtccggcaggcccgcccaccggcaggnccggccccgcc<br>cccgcccgctgcgccgggctgtatttaag | (SEQ ID NO: 167) |
| C54 | ZAP36/annexin IV | D38223 | gacacgtccttcatgttccagagggtgctggtgtcgctgtcggccg<br>gtggcagggatgaaggaaattttctggacgatgctctcatgagaca<br>ggatgctcaggacctgtatgaggctggagagaagaaatggggaaca<br>gatgaggtgaaattctgactgttctctgctcccggaaccgaaatc<br>acctgttgcatgtgtttgatgaatacaaaaggatatcacagaagga<br>tattgagcagggtattaaatctgaaacatccggtagctttgaagat<br>gctctgctggccatagtaaagtgcatgaggaacaaatctgcatact<br>ttgctgaaaggctttataaatctatgaagggcttgggaacagatga<br>taacaccctcatcagggttatggtgtctcgagcggagatcgatatg<br>atggacatccgggagagcttcaagaggctttacggaaagtctctgt<br>actccttcatcaagggtgacacatctgg | (SEQ ID NO: 168) |
| C55 | N-ras | U62093 | gttggagcaggtggtgttgggaaaagcgcactgacaatccagctaa<br>tccagaaccactttgtagatgaatatgatcccaccatagaggattc<br>ttaccgaaaacaggtggttatagacggtgaaacctgtctgttgac<br>atactggatacagctggtcaagaagagtacagtgccatgagagacc<br>aatacatgaggacaggcgaaggcttcctctgtgtatttgc | (SEQ ID NO: 169) |
| C56 | K-ras | U62094 | gtagttggagctggtggcgtaggcaagagtgccttgacgatacagc<br>taattcagaatcactttgtggatgaatatgatcctacaatagagga<br>ttcctacaggaaacaagtagtaattgatgagaaacctgtctcttg<br>gatattctcgacacagcaggtcaagaggagtacagtgcaatgaggg<br>accagtacatgaggactggggagggctttcttttgtgtatttgc | (SEQ ID NO: 170) |
| C57 | p38 MAPK | AF003597 | ctggtgacccatcttatgggagcagatctgaacaacattgtgaaat<br>gtcagaagcttacggatgaccatgttcagttccttatctaccaaat<br>tctccgaggtctcaagtatatacattcagctgacataattcacagg<br>gacctaaaacctagcaatctagctgtgaatgaagactgtgagctga<br>agatcctggactttggactggccccgacatacagatgatgaaatgac<br>aggctatgtggctaccaggtggtacagggctcctgagataatgctg<br>aactggatgcattacaaccagacagttgatatttggtcagtgggat<br>gcataatggccgaactgttgactggaagaacgttgtttcctggtac<br>agaccatattgatcagttgaagctcattttaagactcgttggaacc<br>ccaggggctgatcttttgaagaaaatctcctcagagtctgcaagaa<br>actacattcagtctttgacccagatgccgaagatgaactttgcaaa | (SEQ ID NO: 171) |

TABLE 3

50-mer target sequence for canine arrays

| ID# | Gene Name | GenBank Accession Number | 50-mer sequence | |
|---|---|---|---|---|
| C58 | Cytochrome P450 2D | D17397 | ccggctcctcagcaggggcccgaggtacaat<br>aaaccagtttggtggctcc | (SEQ ID NO: 172) |
| C59 | Cytochrome P450 2B | M92447 | aactcaaataaacatcaaaagcctgacatcc<br>cctggtcaggtggtgagcc | (SEQ ID NO: 173) |
| C60 | Cytochrome P450 2C41 | AF016248 | ccagtgaacatccaacctccattaaaggaaa<br>gtctccagaattttctttgc | (SEQ ID NO: 174) |

TABLE 3-continued 50-mer target sequence for canine arrays

| ID# | Gene Name | GenBank Accession Number | 50-mer sequence |
|---|---|---|---|
| C61 | Cytochrome P450 2C21 | AF049909 | tatctctgcctctctctgtgtgtgtctctcatgaa taaataaaatctt (SEQ ID NO: 175) |
| C62 | Cytochrome P450 3A | X54915 | gtgacacagaatgagaaactcttaactctggg aaatgtacaagggatagt (SEQ ID NO: 176) |

TABLE 4

| ID # | Gene Name | Accession Number |
|---|---|---|
| C2 | c-erb B-2 | ABOO8451 |
| C3 | Catalase | ABO12918 |
| C4 | p53 | AF080514 |
| C7 | Metallothionein 1 | D84397 |
| C9 | Multidrug resistant protein-1 | AF045016 |
| C11 | Tumor necrosis factor-alpha | S74068 |
| C13 | BRCA-1 | U50709 |
| C17 | CD40 ligand | AF086711 |
| C18 | Cubilin | AF137068 |
| C19 | Alkaline phosphatase | AF149417 |
| C23 | Tissue inhibitor of metalloproteinases-1 | AF077817 |
| C24 | Ubiquitin | AB032025 |
| C27 | Vascular cell adhesion molecule 1 (VCAM- 1) | U32085 |
| C28 | Phenol sulfotransferase | D29807 |
| C29 | GRP94 | U01153 |
| C33 | IL-10 | U33843 |
| C36 | Rab2 | M35521 |
| C37 | Rab5 | M35520 |
| C38 | Rab7 | M35522 |
| C41 | FGFR2 | AF211257 |
| C43 | Prostaglandin D synthase | AB026988 |
| C44 | Paraoxonase2 (PON2) | L48515 |
| C45 | Beta-gluouroniclase | AF019759 |
| C46 | Caveolin-2 | AF039223 |
| C49 | IL-8 | U10308 |
| C50 | Keratinocyte growth factor | U80800 |
| C51 | Decorin | U83141 |
| C52 | Glucose-6-phosphatase | U91844 |
| C54 | ZAP36/annexin IV | D38223 |
| C57 | p38 MAPK | AF003597 |

TABLE 5

Canine Genes from Differential Display

| Differential Display | BLAST Search | Accession Number | BLAST Score |
|---|---|---|---|
| DD9 | *Homo sapiens* angiopoietin-like 3 | | 159 |
| DD13 | (1) *Canis famillaris* mitochondrion | AF028213 | 874 |
| | (2) *Canis lupus* cytochrome c oxidase subunit II | | 835 |
| DD17 | *Homo sapiens* cytochrome-c oxidase subunit VIIaL | AF134406 | 76 |
| DD18 | *Homo sapiens* cytochrome-c oxidase subunit VIIaL | | 76 |
| DD21 | *Homo sapiens* histidine ammonia-lyase | D83077 | 172 |
| DD22 | *Homo sapiens* mRNA for TPRD (tetratricopeptide repeat domain from the Down syndrome region of chromosome 21) | | 218 |

TABLE 6

| ID# | Gene Name | Left PCR primer sequence | Right PCR primer sequence | Target Sequence on canine array |
|---|---|---|---|---|
| C64 | Gadd45 | AACTGAACCAAATTGC ACTGAA (SEQ ID NO: 177) | CCATGTAGCGACTTTC CCG (SEQ ID NO: 178) | CGCGTCTAGAAACTGAACCAAATTGCACTGAAGTTTT GAAATACCTTTGTAGTTACTCAAGCAGTTACTCCCCA CACTGATGCAAGGATTACAGAAACTGATGTCAAGGGG CTGAGTGAGTTCAACTACAGATTCCGGGGGCCCGAG CTAGATGACTTTGCAGATGGAAAGAGGTGAAAATGAA GAAGGAAGCTATGTTGAAACAAATACAAGTCAAAAGG AACAAAAATTACAAAGAACCATGCAGGAAGAAGCTTG GCC (SEQ ID NO: 179) |
| C65 | Super-oxide dismu-tase Mn | AACAACCTGAACGTCA CCGA (SEQ ID NO: 180) | TCTCCCAGTTGATTAC ATTCCAAA (SEQ ID NO: 181) | GCGCGAATTCAACAACCTGAACGTCACCGAGGAGAAG TATCTGGAGGCGCTGGAGAAGGGTGACATTACAGCTC AGATAGCTCTTCAGCCTGGGCTCAAGTTCAATGGAGG AGGTCATATCAATCATTCCATCTTCTGGACAAACCTG AGCCCTAAGGGTGGTGAGAACCAAAAGGGGAATTGC TGGAAGCCATCAAACGTGATTTTGGTTCCTTCGACAA ATTTAAGGAGAAGTTGACCACTATATCCGTCGGTGTC CAAGGCTCAGGTTGGGGTTGGCTTGGTTTCAATAAGG AGCAGGGACGCTTGCAGATTGCTGCTTGTTTTAACCA GGATCCCCTGCAAGGAACAACAGGTCTTATTCCACTA (SEQ ID NO: 182) |

TABLE 6-continued

| ID# | Gene Name | Left PCR primer sequence | Right PCR primer sequence | Target Sequence on canine array | |
|---|---|---|---|---|---|
| C66 | UV Excision repair protein RAD23 (XP-C) | GAAAGTCAGGCTGTGG TTGA (SEQ ID NO: 183) | TGGCAGCCAAATTCTC ATTC (SEQ ID NO: 184) | CTGGGGATCGATGTGTGGGAGCATGCTTATTACCTTC AGTATAAAAATGTCAGACCGGATTATCTAAAAGCTAT TTGGAATGTAATCAACTGGGAGAAAGCTTGGCC CGCGGGATCCGAAAGTCAGGCTGTGGTTGACACCCCT CCCGCAGTCAGCACTGGGGCTCCTCCATCTTCGGTGG CAGCTGCTGCAGCAACTACAACAGCGTCAACAACCAC AGCGAGTCCTGGAGGACATCCCCTTGAATTTTTACGG AATCAGCCTCAATTTCAACAGATGAGACAAATTATTC AACAGAATCCTTCCCTGCTCCCAGCATTGCTACAACA GATAGGTCGAGAAAATCCTCAATTACTGCAGCAAATT AGCCAGCACCAGGAGCATTTTATTCAGATGTTAAATG AACCAGTTCAAGAAGCTGGTGGTCAAGGAGGAGGGGG TGGAGGTGGCAGTGGAGGAATTGCAGAAGCCGGAAGT GGTCATATGAACTACATTCAAGTAACACCTCAGGAAA AAGAAGCTATAGAAAGGTTAAAGGCACTAGGATTTCC TGAAGGACTTGTGATACAAGCGTATATTGCTTGTGAG AAGAATGAGAATTTGGCTGCCAAAGCTTGGCC | (SEQ ID NO: 185) |
| C67 | Proliferating cell nuclear antigen gene | GATAACGCGGATACCT TGGC (SEQ ID NO: 186) | AGTGTCCCATATCCGC AATTTT (SEQ ID NO: 187) | GCGCGGATCCGATAACGCGGATACCTTGGCGCTGGTA TTTGAAGCACCAAGAACAGGAGTACAGCTGTGTAGTA AAGATGCCTTCTGCTGTGAATTTGCACGTATATGCCGAG ATCTCAGCCATATTGGAGATGCTGTTGTAATTTCCTG TGCAAAAGACGGAGTGAAATTTTCTGCGAGTGGAGAA CTTGGAAATGGAAACATTAAATTGTCACGGACAAGTA ATGTCGATAAAGAGGAGGAAGCTGTTACCATAGAGAT GAATGAACCAGTTCAACTAACTTTTGCACTGAGGTAC CTGAACTTCTTTACAAAAGCCACTCCACTCTCTTCAA CGGTGACACTCAGTATGTCTGCAGATGTACCCCTTGT TGTAGAGTATAAAATTGCGGATATGGGACACTAAGCT TGGCC | (SEQ ID NO: 188) |
| C68 | Glucose-regulated protein 94 | CTGTGGTGTCTCTGCG CCT (SEQ ID NO: 189) | TTTCAGCTGTAGATTC CTTTGCTG (SEQ ID NO: 190) | CGCGGGATCCCTGTGGTGTCTCAGCGCCTGACAGAGT CTCCGTGTGCTCTGGTGGCCAGCCAGTATGGATGGTC TGGCAACATGGAGAGAATCATGAAAGCTCAAGCATAC CAGACGGGCAAAGACATCTCTACAAATTACTATGCCA GCCAAAAGAAAACATTTGAAATTAATCCCAGACATCC CCTGATCAAAGACATGCTTCGACGAGTTAAGGAAGAT GAGGATGACAAAACGGTATCGGATCTTGCTGTGGTTT TGTTTGAGACAGCAACGCTGAGATCAGGCTATCTGCT ACCAGACACTAAAGCATATGGAGATCGAATAGAAAGA ATGCTTCGCCTCAGTTTAAACATTGACCCTGATGCAA AGGTGGAAGAAGAACCAGAAGAAGAACCCGAAGAGAC AACCGAGGACACCACAGAAGACACAGAGCAGGACGAT GAAGAAGAAATGGATGCAGGAACAGACGACGAAGAAC AAGAAACAGCAAAGGAATCTACAGCTGAAAAAGCTTG GCC | (SEQ ID NO: 191) |
| C69 | Glutathione S-transferase alpha subunit | CAGAGAAGCCCAAGCT CCAC (SEQ ID NO: 192) | ACCAGATGAATGTCAG CCCG (SEQ ID NO: 193) | CGCGGGATCCCAGAGAAGCCCAAGCTCCACTACTTCA ATGGACGAGGCAGAATGGAGTCCATCCGGTGGCTCCT GGCTTCAGCTGGAGTAGAGTTTGAAGAGAAATTTATA AATGCTCCAGAAGACTTGGATAAATTAAAAAATGAT GGAAGTCTGATGTTCCAGCAAGTGCCAATGGTGGAAA TTGATGGAATGAAGCTGGTACAGACCAGAGCCATTCT CAACTACATTGCCACCAAATACAACCTCTATGGGAAA GACATAAAGGAGAGAGCTCTGATAGATATGTACACAG AAGGTATAGTAGATTTGAATGAAATGATCATGGTTTT GCCTCTATGCCCACCTGATCAAAAAGATGCCAAGATT ACTCTGATCAGAGAGAACAACAGATCGTTATCTCC CCGTGTTTGAAAAAGTGTTAAAGAGCCATGGACAAGA CTACCTTGTTGGCAACAAGCTGAGCCGGGCTGACATT CATCTGGTCTCGAGGGCC | (SEQ ID NO: 194) |
| C70 | BR-cadherin | GTCCGTGGCAGAGTCC CTCAGCTCTAT (SEQ ID NO: 192) | CACCGTGATGCCACAT AGCTATCTTCG (SEQ ID NO: 196) | GTCCGTGGCAGAGTCCCTCAGCTCTATAGACTCTCTC ACCACAGAGGCTGACCAGGACTACGACTATCTGCAG ACTGGAACCCCGCTTTAAAGTCTTGGCAGACATGTT TGGGAAGAAGAGAGTTATAACCCTGATAAAGTCACT TAGGGCAGAAGCCAAGGATAAAACACAACCAAAAGGA GAAATTTAAAATAAACACAAATAGAAATCTCTCTCTC TCACACACACACATGCATACATGCACGTGCACACA CAGACACACAGACACACACACCAGGCTTTGTAGGACA CAATCATTTGATGATCTGGTTTCTAGCAAGTTGCTGT AGTTATCATATTGTCAAGTTTTGTTTTACTCTGCCAA CACAAGATAAATCCTATTACATGTACTTGCTTGGTTT TGTTTTTGTTCTTTTGGATACACACTGAGACAAGCTCA GGCCTATTAAATACAATTTACTGACATGACAACATAG AACGAAGATAGCTATTGGCATCACGGTG | (SEQ ID NO: 197) |
| C71 | N-cadherin | GGAGCCTGATGCCATC AAGCCTG | GGTTTGCAGCCTATGC CAAAGCC | GGAGCCTGATGCCATCAAGCCTGTAGGAATCCGACGA TTGGATGAGAGACCCATCCACGCCGAACCCCAGTACC | (SEQ ID NO: 200) |

TABLE 6-continued

| ID# | Gene Name | Left PCR primer sequence | Right PCR primer sequence | Target Sequence on canine array |
|---|---|---|---|---|
| | | (SEQ ID NO: 198) | (SEQ ID NO: 199) | CGGNCCGATCTGCAGCCCCGCACCCTGGGGACATCGG GGACTTCATTAATGAGGGCCTTAAAGCTGCTGACAAT GATCCCACAGCTCCACCATATGACTCCCTCTTAGTCT TTGACTACGAAGGCAGTGGCTCTACCGCTGGGTCTTT CTCCCTTAATTCTTCAAGTAGTGGTGGCGAGCAGGAC TATGACTACCTGAACGACTGGGGGCCACGGTTCAAGA AACTTGCTGACATGTATGGTGGAGGTGATGACTGAAC TTCAGGGTGAACTTGGTCTTTTGGACAAGTACAAACA ATTTCAACTGATATTCCCAAAAAGCATTCAGAAGCTA GGCTTTAACTTTGTAGTCTACTAGCACAGTGCTTGCT GGAGGCTTTGGCATAGGCTGCAAACC |
| C72 | Mek5 | TCATGGATGGGGGATC TTTGGATG (SEQ ID NO: 201) | GGGTGGCCCATCAATT CTTCAGGT (SEQ ID NO: 202) | GGGTGGCCCATCAATTCTTCAGGTGCTGGTCTTTCTT TCGGTTGTTTTCGCATGCACTGAGTGATGAAATGTAC AAATGGCTCGGAGAACTCTCCAACCGGAAGGACGGGC GAATCCTCATCAACAATGCACTGCAGAAGCTGGAGAG GCTCCATGAAAGAGATTCCTAAACTCCGGACATCAGA ATGGATTCCATACTGCTCCCCTGAAATTCTTTCAGGC GCCATATAAGCATTTGTTCCAACATACGTCTTGGCTA TAGAATTCACCAGCTGAGTGCTAACTCCAAAATCGCA CAGCTTGACCTGTCCTCTTGTGTTTACTAGCGTATTG GAGGGCTTCACATCTCTATGTAAAATCTTTAAACTCC ACAAGTAGGTAAGGCCTTTAACAACTGCTATTGCAAT TCTTCCAAGGACATGCTCTGGAATTTTTCTATATACA TCCAAAGATCCCCCATCCATGA (SEQ ID NO: 203) |
| C73 | Glucose trans- porter | GCAGCAGCCTGTGTAT GCCACC (SEQ ID NO: 204) | AAGCCGGAAGCGATCT CATCGAA (SEQ ID NO: 205) | AAGCCGGAAGCGATCTCATCGAAGGTCCGGCCTTTGG TCTCAGGAACTTTGAAGTAGGTGAAGATGAAGAACAG AACCAGGAGCACGGTGAAGATGATGAAGACGTACGGA CCACACAGTTGCTCTACATACTGGAAGCACATGCCCA CAATGAAATTTGAGGTCCAGTTGGAGAAGCCAGCAAC AGCAATGGCAGCTGGGCGAGGACCCTGGCTGAGGAGT TCAGCCACAATGAACCATGGGATGGGGCCAGGGCCCA CTTCAAAGAAGGCCACAAAGCCAAAGATGGCCACGAT GCTGAGATACGACATCCAGGGCAGTTGTTCCAGCAGC GCCAGCGCGATGGTCATGAGCACGGCACAGCCCGCCA TGCCAGCCAGGCCTATGAGGTGCAGGGTCCGCCGGCC GGCGCGTTCCACCACGAACAGCGACACCACGGTGAAG GCCGTGTTCACGATGCCGGAGCCGATGGTGGCATACA CAGGCTGCTGC (SEQ ID NO: 206) |
| C74 | SHB (Src homology 2 protein) | CGCCGATGAGTACGAC CAGCCTT (SEQ ID NO: 207) | GCTCAGCCCCCTTTGAT GGGTAGC (SEQ ID NO: 208) | CGCCGATGAGTACGACCAGCCTTGGGAGTGGAACCGG GTCACCATCCCAGCTCTGGCAGCCCAGTTTAATGGCA ACGAGAAACGGCAATCATCCCCCTCTCCTTCCCGGGA CCGGCGGCGCCAGCTTCGAGCTCCTGGAGGGGGCTTC AAGCCCATTAAGCATGGGAGCCCTGAGTTCTGTGGGA TCTTGGGAGAAAGAGTGGATCCTGCTGTCCCGCTGGA AAAAGCAAATCTGGTATCACGGAGCCATCAGCAGAGGA GATGCTGAGAACCTTCTGCGGCTCTGCAAGGAGTGCA GCTACCTTGTCCGGAACAGCCAGACAAGCAAGCACGA CTATTCCCTCTCTTTGAAGAGCAACCAGGGCTTTATG CACATGAAACTGGCCAAAACCAAAGAGAAGTATGTTC TGGGTCAGAACAGCCCCCCGTTCGACAGTGTCCCAGA AGTCATCCACTACTATACCACCAGAAAGCTACCCATC AAAGGGGCTGAGC (SEQ ID NO: 209) |
| C75 | Ear-3 (verbA related) or Apolipo- protein AI regulatory protein (ARP-1) | TGCAGATCACCGACCA GGTGTCC (SEQ ID NO: 210) | CATATCGCGGATGAGA GTTTCGATGG (SEQ ID NO: 211) | TGCAGATCACCCGACCAGGTGTCCCTGCTTCGCCTCA CCTGGAGCGAGCTGTTTGTGCTGAATGCAGCACAGTG CTCCATGCCCCTCCACGTCGCCCCGCTCCTGGCCGCC GCAGGCCTACACGCCTCACCCATGTCCGCCGACCGAG TGGTCGCCTTTATGGACCACATACGGATCTTCCAAGA GCAAGTGGAGAAGCTCAAAGCGCTGCACGTCGACTCC GCCGAGTACAGCTGTCTCAAGGCCATAGTCCTGGTTC ACCTCAGATGCCTGTGGTCTCTCTGATGTAGCCCATG TGGAAAGCTTGCAGGAAAAGTCCCAGTGTGCTTTGGA AGAATACGTTAGGAGCCAGTACCCCAACCAACCAACA CGATTCGGAAAGCTTTTACTTCGCCTCCCTTCCCTCC GCACGGTCTCCTCCTCAGTCATAGAGCAATTGTTTTT CGTCCGTTTGGTAGGTAAAACCCCCATCGAAACTCTC ATCCGCGATATG (SEQ ID NO: 212) |

TABLE 7

| Band # | Genbank Gene Name | Accession | Sequence | |
|---|---|---|---|---|
| CTP1D | No significant match | | GACTGAGACCATTTATTCNAGACACGCAGCTGACC AAGGAGTGAGGGAGGGACCAGGTGTGCAAGCTAAT AAATAGAGGAGGGGGAGACTTCCTGGAGCTGTAGC CATTCAGTCTTCATTCTTCTCAGGCATGAAGGCAT CTCTTTTCTGACCAAAGCTT | (SEQ ID NO: 213) |
| CTP1G | No significant match | | AAGCTTTGGTCAGCAATTATATTAGTTTGCATTTT AGTGACAGGTGTAAGAGAAAGGCCCCTTCTTCCCT TACTGGGACAAATCTAGAAATCTTACACAGATGTG CAAATAAAGCTCGCGTGGTGTTC | (SEQ ID NO: 214) |
| CTP3B | *Homo Sapien* N-myc downstream regulated (NDRG1) | BC003175 | GCAAAGTTACAAATTTATTGGTCTGGAAATAAATA CAAATATCTGATTAAGAACTTCTCTGAAAGACTT GTACACAACAGTTTTCCTGTCTCGATTCAGCCACT CCTGCCCTGACCAAAGCTT | (SEQ ID NO: 215) |
| CTP4B | No significant match | | GAGCAGCAGTGAGCAAAACCCACGAAGTTGTTTTA AGGTTACAGCTATGAATAAACATTGTCCAAACAAT GAAGATTTAGGGCTGAAGAACGAGCGTATGTCTAC AGTCGAAGCTT | (SEQ ID NO: 216) |
| CTP7B | No significant match | | CAGGTGCAAGAGGTTTGTTTGGGAGGTAATCCTAG AAACCACAGAAGGGGGTGGGGATAGGAGGGATGGC AGGAAAACCAGTAAGAACTGTGTTATTGAGAAGGT TATCACTGTGGACAACTGGCACAGAATACACTTCA GAGCTGTCGCCCTGAGGGACAATGACGCCAAGGTC TTTTTCTCTAAGTCCTGTTTCTTATAGGCCGAGGG TGGCTCCTGGGAGCAGTAACTGCCAACAGTCGAAG CTT | (SEQ ID NO: 217) |
| CTP8A | No significant match | | AAGCTTGATTGCCCATACCTGAGCCATTGATATAT TTGAAAATTATGGCACAATGGAAGAGAACCACATT TGAAAAGCTTCCAGCCTTTCAACAGAAGATAACTC TTCTTGTTTTGCAGATTGAGCAGATAATTTCTTTT GAAGGTGATAGTTTCCTAAATTGGATAAAACCGTG GCTGCCATTATATTCACAGAAAATAAAATGAAAAC TTCAGTTAATTGTGGATTTG | (SEQ ID NO: 218) |
| CTP8C | Human DNA sequence from clone RP4-734P14 on chromosome 20 | HSJ734P14 | CAATATTCTTAAGAGTTTATTATAAACTAGTTTCA CAGGCTACAAGGAAGTATTTAGGACTATGTACAGC CTGACGGGAAACAGGCAGGGAGCTGAGGAGGGCCA AGATGAGTCTAGGGCCTTGGTGGGCGCATTCCCGG GGGAGGGGCCCTGAAAGGGAAACCAGACAATCCT GTGAGACTCCAAGAACAACGGCATAACAAACAAAC ACGTCTGTGGCAATCAAGCTT | (SEQ ID NO: 219) |
| CTP10Y | Canis familiaris mitochondrion | CFU96639 | AGTATATGGGACCGAGAATAATTTTAGGGTTAAGG GATAGGAGGAGTAGGGGCAGTAGGTGCAAGGTCAT TAGGGCATTTTCTCGTGTGAATGATGGTTTGATAT TTTTGATGGTGGGAATATTTACCACGTTGTGTGGT GATTAATATATAAAGTGAGTATAGGGCGGTAAAAG CTT | (SEQ ID NO: 220) |
| CTP11A | cyclin-dependent kinase inhibitor 1A (p21, Cip1), | BC001935 | ACTAAGAAATATTTATTGAGCACCTGCTGTGTACC CAGCACTGCGGGAGGGGCTGTGAGGAGACCCAGGG AGTACAGGACTTGTTCTTGCCCTTCAGAGGGCTTAT AGTCTAGGTGGAAACAGGAGAACCAGGACACATGA GGAGCCAGGAGAAAACAGTACAGGCCAGGATGTTA CAGGAGCTTACAGTGTTTGGGGTCAGACCCACTAA GTGCTTCAGTACCTCTAGGGGCTCAATGTTCAGGG CCAGAAGAGACAATAACTCACAACTAGCCCATGTA GCATGCCCTATCCACAGCGTCTACCTCTGCTATCT TAAAACATCTGACTCCTCGTTAAGCTT | (SEQ ID NO: 221) |
| CTP16B | *Homo sapiens* cDNA FLJ20541 fis, clone KAT11364 | AK000548 | CAAAGAATTTTGTTTTATTATAGTACATGAGCTGG ACTGATGGGAAAGGGTAGGTGTATGGGCAACCACT GCCCAGATTAGCATCGGATGCCCATCCCGATGGCC ATGAATGTGCCAAATGTGCCGCCACTCTGCATCAT GGTTTTCCCGATGCCGCCCATCAGCTCCCGACCCC GCATTCCGATCCTGAGACAGGAAAAGGTGCCGAAG AGCGCCCCGGCCGCCATGCCCACTGCACAACCCAT CACAAAGCCCATCTTCACGCGGTAAAAGCTT | (SEQ ID NO: 222) |
| CTP17G | No significant match | | CATATATATTCTTTTTTATTTCTTGTTATACCTTC CCAAAACAGAGACATTCAACAGTAGTTAGAATGGC CATCTCCCAACATTTTAAAAAAACTGCACCCCCCA ATGGGTGAACAAAGTAAAGAGTAGTGAACCTAGAG TTCAGCTGAGTAAGCCACTGTGGAGCCTTAAGTGG TGAGGTCTTCCAATTTCAGAGTGATGTGTCTTCAA CTTGTATCATCATTTTAGCGGTAAAAGCTT | (SEQ ID NO: 223) |
| CTP18B | No significant match | | CCAAAGAAGTGTTTATTAACATTTGGGGCCTCAGC GGGGCCAGAGAGGAAGTGGGTGCTAGAGGGCTCCTG AGGCTCAGGGCAAGGCCTGCAAGACAGATCCCATT GCTCAGGAGGCAGCCCAGATTGCAAATGGAGACAG G | (SEQ ID NO: 224) |
| CTP19F | *Homo sapiens* chromosome 5 clone CTB-187A7 | AC008651 | AAGCTTTTACCGCAATGAGGGATTTATACATGAAA AATGGACAAGGCTTTGCATTAGTTTACTCCATCAC | (SEQ ID NO: 225) |

TABLE 7-continued

| Band # | Genbank Gene Name | Accession | Sequence | |
|---|---|---|---|---|
| | | | AGCACAGTCTACATTTAATGATTTACAAGATCTGA<br>GAGAGCAGATTCTTCGAGTTAAAGACACTGATGAT<br>GTAAGCTGACTTCCTAATAAATATATTTTACTTG | |
| CTP20B | Bos taurus ribosomal protein L30 mRNA | AF063243 | AAGCTTAACGAGGACAGGCCATCAGGGCTGCCAAG<br>GAAGCAAAAAAGGCTAAACAAGCATCTAAAAAGAC<br>AGCAATGGCTGCTGCTAAGGCTCCCACAAAGGCAG<br>CACATAAGCAAAAGATTGTGAAGCCTGTGAAGGTT<br>TCCGCACCCCGAGTTGGTGAAAAACGCTAAGTTTT<br>AGTGGATCAGATTTTTAAATAAACATCTGACTCTA<br>ACT | (SEQ ID NO: 226) |
| CTP21A | Rattus norvegicus ribosomal protein L31 (Rpl31), | NM_022506 | CATGGAGCNGTTTTATACCCTTTATTTGACAATCAG<br>CGATTAGTTCTCATCCACATTAACAGTCTGTAGAT<br>TTTTGAAAGTGGTGACAGGTACGTAGGTAACCAGC<br>GTGTAGAGCTTGTTTGGTGAATCTTCATCCTCGTT<br>AAGCTT | (SEQ ID NO: 227) |
| CTP22C | Canis familiaris mRNA for ubiquitin-ribosomal protein L40, fusion | AJ388512 | CAATGGTGTCACTGGGCTCGACCTCAAGGGTGATA<br>GTTTTGCCCGTCAGGGTCTTCACAAAGATCTGCAT<br>CTCTGCGTCTGCTGGAGCGAACTCGCAAGGCCGCC<br>GCCACCCAAACCGCTCGCCCACCTCGTTAAGCTT | (SEQ ID NO: 228) |
| CTP25D | No significant match | | AAGCTTGCACCATATATATAACTCTTGGGCAGAGG<br>GTCTGGCATACATAAGTAGATACTCAGAAATATCT<br>GTTGGATTGTGTTGATTTAATTATTTTTGTGTTGC<br>TTCTTTTAAAGATGAGCACTTTCTATTAGATATTT<br>TTTTGATCAAAAAAAAGATATTTTTTTGATCATAC<br>AGATTTAAGCAGGATTTTTATTAATTCGTTTCTCT<br>TCCTGGTTGG | (SEQ ID NO: 229) |
| CTP26A | Canis familiaris chymase gene | U89607 | CATGAGAGAGACGGAAAGAGAGGCAGAGACACAGG<br>CAGAGAGAGAAGCAGGCTCCATGCAGGGAGCCTGA<br>CGAGGGACTCGATCCCAAGACTCCAAGATCGTACC<br>CTGGGCCAAAGGCAGGAGCTTAACCGCTGAGCCAC<br>CCAGGTGTCCCAACTGTCAGGGTTTTAAAAGAGTG<br>AGTGAAATTTGGGGAAATATCAAGGCACAGTCATA<br>TTCATAAACATAATACGTTGAGAAGCTT | (SEQ ID NO: 230) |
| CTP26B | H.sapiens cycA gene for cyclin A | X68303 | AAGCTTCTCAACGTATATGGTGTACAGTTTTTGTA<br>AGGTTTTAATTTTACAATCATTCTGAATAGTTATG<br>GTCAAGTACAAATTATGGTATCTATTACTTTTTAA<br>ATGGTTTTAATTTGTATATCTTTTGTACATGTAAC<br>TATCTTAGTTAATTTGGCTAATTTTAAGTGGTTTT<br>GTTAAAGTATTAATGATGCCACCTGTCAGCACAAT<br>AAGAGTAAGAACTAATAAATGGATTTGG | (SEQ ID NO: 231) |
| CTP27C | Homo sapiens CTCL tumor antigen se20-10 mRNA | AF177227 | AAGCTTCTCAACGTATTCAAGAGAAAACTTCTAAA<br>TTGCCAGATATGTTAAAAGACCATTATCCATGTGT<br>GTCTTCACTGGAGCAGTTAACAGAGTTGGGAGGTG<br>AAACTGATGTTTTTGTATGCCGTCCTAACACAGCC<br>CTATGCCCGATGTACTCAGAGACTGGAACAGCACA<br>AGAGAAATAAAGCAACAATCAGTAATGGG | (SEQ ID NO: 232) |
| CTP28D | Homo sapiens upstream binding protein 1 (LBP-1a) (UBP1 | NM_014517 | AAGCTTTGGTCAGGCAGGAATAGGAATGAGTAATT<br>TGGGCTTTGAAATCTCTCCCAGAAGACAAACTACT<br>TCGATGGGAAAAAGCTTTGACATTTTGTGTTTTAT<br>TTGTAGAGGGGGTTATTGGATACAGAGGAGCCTGG<br>TCTCATACATTTTCATCTTCAGTCTGAAAAGATCT<br>GTAATTCTGTAGACCCTGAAGCGGGGGAACTTTTC<br>TTTCTGCCATCTCCCTTTGCTTTCATATGAACACC<br>TCTTCTGTACCATCATTTGAAAAGAAGTGAGCAT<br>ATCTCTTGTTTTAAAAGTTTTGCTTGNCTGGTTAG<br>CATTCCTTTTGAGCTCAACATATATGGAACAATAA<br>ATGTCATTTAATGCTGNGNGCTATTTTGAATTCCT<br>CATCAGGTTTTAGAAGTGGGGTCAAGAACACTTAA<br>AAGCTCATTGGACTTTGAAATTATNCCAGCCGCCN<br>TTGACCATTATCTGGCCCANCAAAGCAGGTTAAAT<br>TATGGCNCCNGCAAATTTGCTTTTTTTTTTAATAG<br>NNGGANGNNTACNTTTCAGNTTAATAAATGTTTTC<br>CGATGGTTTGC | (SEQ ID NO: 233) |
| CTP30E | Homo sapiens BAC clone CTB-60N22 from 7q21 | AC003083 | GGTCAAAGTGTATAGTTTTGACTTACCCCTCCCAG<br>ATCCTGAATGTCCTTTTGGAGTTTTCAGATACGGT<br>GACAGAAGGTAAGTCAATGTAAAATATTTTTCCCC<br>AGAGTGGCTTATATTTGTATTTTTCTGGTTTGTTA<br>TCAGTTTTCATAGATTTCATAGATCTGTTTTTTTC<br>ATTTTTGACTTGGATTCCACCTGTTGTTTAAAAAA<br>AGTAGAATCAGATCATGATTTATGTGGACAGAAAA<br>TTTCTCTTTTAAAAATACTTTTTATACAGTCATCA<br>TTTCATAGAGGGGAAAAAATCTTTATAATACCAC<br>CAATTAAACACTCAATAGCATTTTACTGTATTTCT<br>TCGTAGTATCACTTAGGATAAAACCAGAATACCAT<br>ATTTGTTTTAACAGATCCCATACTGTAAAATAATC<br>ATCGTTCACAGCCTACAGTCGAAGCTT | (SEQ ID NO: 234) |
| CTP31A | No significant match | | GGGGCAGATAAAAACACTTAATGTAAAATTTACCC | (SEQ ID NO: 235) |

TABLE 7-continued

| Band # | Genbank Gene Name | Accession | Sequence | |
|---|---|---|---|---|
| | | | TCTCAGAAAAATTTCCAGTATGCTATACGGTATCA<br>CTAACTATAGTCACTATAGTATACAGTAGATCCCT<br>AGGGATTTATTCATGATGTACAGTCGAAGCTT | |
| CTP32D | cDNA FLJ14795 fis, clone NT2RP4001219 | AK027701 | AAGCTTGATTGCCAGAGTTACGAAAAGCATCAAAG<br>CATCTTTATGGTCAGCTTAAATTTGGTACACTAGA<br>TTGTACAATTCATGAGGGACTCTGTAACATGTATA<br>ACATTCAGGCTTATCCAACAATAGTGGTGTTCAAC<br>CAGTCCAACGTTCATGAATACGAAGGCCATCACTC<br>TGCTGAACAGATCTTGGAATTCATAGAGGACCTTA<br>TGAATCCTTCAGTGATCTCCCTGACACCCACCACT<br>TTCAATGAACTGGTTAAACAGAGAAAACATGACCA<br>AGTCTGGATGGTTGATTCTATTCTCCATGGTGTC<br>ATCCATGTCAAGTCCTAATGCCAGAATGGAAAAGA<br>ATGGCCCGGACATTAACTGGACTGATCAATGTGGG<br>CAGCGTAGACTGCCAACAGTATCATTCTTTTTGTG<br>CCCAAGAAATGTTCGGAGATCCCTGAGATAAGAA<br>TTTACCCCCC | (SEQ ID NO: 236) |
| CTP34A | *Homo sapiens* ribosomal protein S29 | NM_001032 | AAGCTTTGGTCAGGGCTCTCGTTCTTGCCGCGTCT<br>GTTCAAACCGGCACGGTCTGATCCCGGAAATACGG<br>CCTCAACATGTGCCGGCCAGTGTTTCCGTCAGTAC<br>GCCAAGGATATAGGCTTCATTAAGTTGGATTAAGT<br>GAACTTCCTTGAATGGGTCATCCAAGATACCTACC<br>TTAACTGCAGATGTCCAAGATACCTACTTTGATGC<br>CAACTCATTGTATATAAAATAAAAATACTCCAATT<br>ATGAGTGTTTTAATGTG | (SEQ ID NO: 237) |
| CTP36A | No significant match | | CAAGTTTTACCATTGTTTTAATTATTGAAACAAAA<br>TTAACGTAAGTAGAATCATGTGCAACAGTGTCTCT<br>AACATATGGAAGAGGTAAATATGAAATTTTATACA<br>ATAAGGTATATTATCCACTGTAACAAATTTCCAAT<br>AATTTGGCATTTATCTTTCACAAAATGTCTCCCAA<br>ATTCTAAGCAAAGTATGCAAATTGGAGATTAACTC<br>TAAACAGGCATAATTATCTTCTTATCCAGTTTTTC<br>TGAAGAGACTGAAGAGTTCAGGTCTGACCAAAGCT<br>T | (SEQ ID NO: 238) |
| CTP37A | *Homo sapiens* nuclear factor associated with dsRNA NFAR-1 | AF167569<br>AF167569 | CAGATGTGATAAAATCGTTTTCATTACTGTCAAAG<br>GCATCAACCAGATTTGGGAATTTGTTAAAAGGTTA<br>AAAATTCATACAAAACCTGCTGTAAATTAAGACAA<br>AGGTAGATTAAAATGCATCATTATCTGTCTCTTAA<br>ATAAGTAATGCTTTCATAAAAAGCAAAGGTGGGC<br>TTTTGCCTTGATGCTGACCAAAGCTT | (SEQ ID NO: 239) |
| CTP41B | *Homo sapiens* mRNA for KIAA1392 protein | AB037813 | GGGAAGTGTCAAGGATCAGTTCCGTGGCACCCTCT<br>GACCACAGACTGGGAGCAACACGCATCTGTGGCAT<br>TTAAAAATGGAATTGGCAACTTCATGACATTGGAA<br>TGCATATCACACTTACAGTGTCTAGACTTTCCTAT<br>GTGTGCTCAGTTACAAGTAGTGAAGCAAAAGTATA<br>CATATCACCCCTACTGCTATTCGGTTGCTACAGAG<br>CCATAAATGTGAAAAGCAATACTCTGAAATAAAGA<br>TTTTTGTTTTTTGCCCTAGCCTACTAAGCTT | (SEQ ID NO: 240) |
| CTP47G | No significant match | | AAGCTTGCACCATACTCCTCCTCTACATATGCTCC<br>CAAATTACCTTCTAAAAAGGCTGTATTAATTTACT<br>TTCACCAGTAGTATTATGAGAGTGCCCATGTCCCT<br>TAGCCTTTTAAAATTCACTATGAGCAATCTTTAAA<br>TCATGTACTAAATCTTATAGGCAAAGAATAGGGCC<br>TTGCCCCTGCCCCTGTT | (SEQ ID NO: 241) |
| CTP50A | No significant match | | ATTCCTTTTCCAAGGACCTCTCTTCTATGTGATCA<br>CTGAGTAAGTTCAGTCACTCCCATCATCTCTAGAT<br>TGGAGATTTCCAAATTTATGGCCTTTCCTAACTTT<br>GAAGTCCTTATTTCTAACTGCCTACTAAGCTT | (SEQ ID NO: 242) |
| CTP51A | *Homo sapiens* intestinal N-acetylglucosamine-6-O-sulfotransferase | AF219991 | ATAAATAGAGATGGGGGTCTTGCTATGTTGCCAGG<br>CTGGTCTTGAACTTCTGGGATCAAGCAATCTGCCT<br>GCCTTGGCCTCCTAAAGTGCTGGGATTACAGGTGT<br>GAGTCACTGTGCCTGGCCTCATATAGTCACTATAA<br>CAGCCTACTAAGCTT | (SEQ ID NO: 243) |
| CTP52B | No significant match | | AAGCTTAGTAGGCAATAATAGAGAAGTAGAAATTG<br>AATGTGGAACATTAACCATTAAAAATCATACTTTT<br>GAATGTGCTGAGGTCATGAATTGTTTTTACCTTCT<br>TTGTAATTTGTGTTTTTCAGATTTTCTGTAGTTAG<br>CATATATTCTATAATCAGAAAAAGATGCTTCAAGT<br>TTTTTGCAGATTTCACAGAATTTTGTTT | (SEQ ID NO: 244) |
| CTP53A | No significant match | | AAACAAAATTCTGTGAAATCTGCAAAAAACTTGAA<br>GCATCTTTTTCTGATTATAGAATATCTGCTAACTA<br>CAGAAAATCTGAAAAACACAAATTACAAAGAAGAT<br>AAAAACAATTCATGACCTCAGCACATTCAAAAGTA<br>TGATTTTTAATGGTTAATGTTCCACATTCAATTTC<br>TACTTCTCTATTATTGCCTACTAAGCTT | (SEQ ID NO: 245) |
| CTP58A | No significant match | | AATTGTCACGAACAGGGCTGACTGACACTGCAGTG<br>TGTCCTTGTTTGTTGATCCCTGATCTAGGCCTCGG | (SEQ ID NO: 246) |

TABLE 7-continued

| Band # | Genbank Gene Name | Accession | Sequence | |
|---|---|---|---|---|
| | | | CTTTTCAAACTGCAGTTGATCAAACTGGGATATGC<br>TTCGCTGAATCTGCTCTCTGGTGCTTCTCTTTAAT<br>CGTTTTCTCCTTAAATGGGTTACTTTCTTACTAGG<br>AAAAAAAAAATGTTCCACCTCTGGAATTAACGTTG<br>AGAAGCTT | |
| CTP59A | *Homo sapiens* cyclin D2 (CCND2) | XM_012143 | AGGTCAAGGTGAGTTTATTGTCCAAATAGCATAAC<br>CTAATTGCATTCAAAACCATTTTCAAATCCATCTT<br>TAAACTAGTCAGAAAACAGGTTATTATTTTTTTAA<br>ATCACTTAACACTGAACAGATAAGACCTCTTAAAA<br>GGCAGCTGACTATATCATGTCACCATCATAGCCAA<br>TACAACATTTTTGCCATACTTCCTAAAAACCTTTT<br>CGCATACACTGATCATGCTACTTATCAGCACTTTT<br>TAACATCCTGACCAAAGCTT | (SEQ ID NO: 247) |
| CTP60B | *Homo sapiens* RNA binding motif, single stranded interacting protein 1 (RBMS1) | XM_016120 | ACTAAATAAACCTGTTCGGGGGGAACAGCTACTAG<br>ATGAATTTAAGGGTTTTATGCACCTTATAGAACTT<br>ATAGCAAAAATAGTTTTAGTTGATTTCATTATAAA<br>TAACGTTTTCAAGAACCTGTGCAAAACTGTCAATA<br>ATTTCCTAAAGCACAATTGATCAGAAAAATCCATG<br>ATTGTTCAGCCTTCACACCCTTCTTCATGTAAGAA<br>CACCCTTCTGTACATCTCACAGTTACTTATTAGGT<br>TGAAAGGTATATGGTGAATGGTCATTAGACGTCTC<br>GACAGCCACCTGCTGCTGACCAAAGCTT | (SEQ ID NO: 248) |
| CTP61D | prion protein [mink, Genomic, 2446 nt] | S46825 | ACATTAAATGCCCAGTGCAAGCCAGGAACATTGCA<br>GAATGCTAAATTTATCTGCTAGGTGATGATATTGA<br>ACGATCTAGACAATAATTTCACCTTACTTAAATAA<br>CAATGAACAGAATTCCTTTTTTTTCCACTCTGAGTG<br>GATATTCTGTCATCTCTGACCAAAGCTT | (SEQ ID NO: 249) |
| CTP62A | No significant match | | AAGCTTCGACTGTCGCATCAATGAATGTTTTAAGT<br>AATAACTTTGCTGGTTATCAGCTTGATGGTGCATT<br>AATTTTATGGCTCATTTCCTTTATTTTGACCATTG<br>TCGGATTCTTCATTTTATATTGGACGATCCCCAAT<br>CGAACGGTACCAATTTTTTCAGCTGTGATTGCGGC<br>ATGTTTCAACGCGACCGTTTTTGAAATTTTAAAAC<br>ATTTATTTGGCTGGGTCATGAGTAATTTCACCAGC<br>TATGAAATCGTTTATGGTGCTTTTGCAGCAGTTCC<br>TATTTTTCTACTTTGGATCTATCTGTCTTGGAATA<br>TCATTTTATTGGGTGTAGAAGTGAGTTATGCACTC<br>ACCGCCTTCCATTCTGGT | (SEQ ID NO: 250) |
| CTP63A | No significant match | | AGAATCAAGCCACCAGGTGTTTATTTTTGCACTAT<br>AAATAGAGTTCCCTAGTCCCATTTTGTTACATAAT<br>ATATGAGATAACAGAGAACCTAAAATTCATTTGGT<br>GAAAATCAAGTGTGTAGTATACCTAAATACCAATG<br>AGCTAGTAAGACTTGTAAGGCACTGAAGCTAAGGC<br>TAACAGCAACAGAGTCCTTTATGAAAATAATTTCA<br>GAACCACAACGCATTCTCTGATGGTGCATTCCCCT<br>GGGACAGTCGAAGCTT | (SEQ ID NO: 251) |
| CTP64B | No significant match | | CATCGCAGACATTTATTTTAGTTTTGTTAATTTCA<br>AATATTCATTAACCTCTTGTATCAGATTTAAGGCA<br>GAGAAAAGATACACGCCCCTGGTTAACTGAACCGG<br>GGTTTAGATAGTGTAGTCCACCCTGGGTTCCACCA<br>GGGAGACCTCACCCGAGATGACAGGTCCGGTTGCT<br>GGTGCACAGTCGAAGCTT | (SEQ ID NO: 252) |
| CTP65A | Pig mRNA for endoplasmic-reticulum Ca(2+)-transport ATPase (class 3 non muscle transcript) | X16951 | CCATTTAAAATGTTTTATTTTCCTTTTTAAACTAG<br>ATTGTGAAGTGCCACTGAAATAGGCAATGTTGGCA<br>AAACAATGTCTGTTACAATAAAATACATTAGACAT<br>TTAAATAAATAACCTTAAAAACTACATGGGGGGAC<br>ATGAACCCAGTCGATTGAATCTGGAACAATGTTTT<br>CTGCACAAGCGAGAACAGGCATACCTCTTGTTAAG<br>ACTGATGTAAACAGAACCATCGGAACCCTACAGTC<br>GAAGCTT | (SEQ ID NO: 253) |
| CTP67A | cloneRP5-1071L10 on chromosome 20 | AL133228 | CACGTTTTAAAACTTTATTTGCATATTAAAAAAAT<br>TGTGCATTCCAATAATTAAAATCATTTGAACAAAA<br>AAATGGCACTCTGATTAAACTGCATTTTAACAGCC<br>TGCAAGATACCTTGGGCCAGCTTGGTTTTTTACTC<br>TAGATCTCACTGTCCTCCCACCCAGCTTCTTCCTT<br>CACCAACATGCAAGTTCTTTTCCTTCCCTGCCAGC<br>CAGCCAGACAGGCAGATGGGAAAGGCAGGCGCCTT<br>CGTTGTCAGTAGTTCTCCCATTCTTTGATGTGAAAA<br>GGGGCAGCACAGTCATTTAAACTCGATCCAACCGC<br>TTTGCATCTTACAAAGTTAAACAGCTAAAAGAAGT<br>AAAATAAGAAGGCAATGCTTGTGGAATGTACAGTG<br>CATATTGGCGGCGCACGCCTCATTACGATTCGGCT<br>ACTAAGCTT | (SEQ ID NO: 254) |
| CTP68F | *Oryctolagus cuniculus* New Zealand white elongation factor 1 alpha Rabefla2) | U09823 | CTCATTAAACTTTTGTTTTAATGGGTCTCAAAATT<br>CTGTGACAGATTTTTGGTCAAGTTGTTTCCATTAA<br>AAAGTACTGATTTTAAAAACTAATAACTTAAAACT<br>GCCACACACGCACAAAAAAAAAAAAAAAAACAAAT | (SEQ ID NO: 255) |

TABLE 7-continued

| Band # | Genbank Gene Name | Accession | Sequence | |
|---|---|---|---|---|
| | | | GGTCCACAAAACATTCTCCTTTCCTTCTGAAGGTT<br>TTACGATGCATTGTTATCATTAGCCAGTCTTTTAC<br>TATTAAACTTAAATGGCCAATTGACACAAACAGTT<br>CTGAGACCGTTCTTCCACCACTGATTAAGACTGGG<br>GTGGCAGGTATTAGGGATAATATTCATTTAGCCTA<br>CTAAGCTT | |
| CTP70A | No significant match | | AAGCTTAGTAGGCACGCAATAAATAGGAGAATGAA<br>TCAGAGTCCTCCAACGCGTCCTCCCTAATGTCCCT<br>TTGAGCTGCCTCCTCTTCCACTCTGCCTCAGCTTG<br>TCCATGTCACTTCGCTCCAGAGCAGCCGCAAGAGC<br>ATCTTAACACCTTGTGGCCTGAACTCTCTCCCATC<br>CTCCACTGTACAGTGATATGACTGAAACCTCATTT<br>AACCTTTTAGAACTACCAGGAGGAGGTTCCCAAGG<br>ATCCCAGG | (SEQ ID NO: 256) |
| CTP71A | Canis familiaris caveolin-1 mRNA | U47060 | CACTGAATCTCAATCAGGAAACTCTTAATGCACGG<br>CACAACTGCCCAGATGTGCAGGAAAGAAAGAATGG<br>CAAAGTAAATGCCCCATATGAGTGCCATTGGGATG<br>CCAAAGAGGGCAGACAGCAAGCGGTAAAACCAGTA<br>TTTTGTCACAGTGAAGGTGGTGAAGCTGGCCTTCC<br>AGATGCCATCAAAACTGTGTGTTCCTTCTGGTTCT<br>GCAATCACATCTTCAAAATCAATCTTGACCACGTC<br>GTCGTTGAGAAGCTT | (SEQ ID NO: 257) |
| CTP72B | No significant match | | CCATTTTTGCTCTTAAAGAGCATCTTAAGTGAGAG<br>ATCATGACAATCTTTGGCCACTCCAGGTTTTCTCA<br>TCTACTACATGATCTGTTCCCAACAATAAGCCATT<br>GAAATTAAAGGTCTCCAGAAGTTTTATCTGGGGTC<br>TGTGATTGAAAAGAAGGAAAATGAGATGAGAGACT<br>GCCTACTAAGCTT | (SEQ ID NO: 258) |
| CTP73A | Homo sapiens chromosome 11 clone RP11-546N8 map 11q | AC026201 | CAAGCCCATCAATTAGTGTTCTTTTTATAGACATT<br>ACACACAACACATATATAGTGACACAAACACAAGA<br>TTCAACACTTGTAAGATTTTTTATTTGCCAGTTTC<br>TTAATTGGATTACTGGCATCAGGGTGGAAACTTTA<br>GAGGAAGAGAGCCAGGTAGCATGCATTTCTAGGGC<br>CTACTAAGCTT | (SEQ ID NO: 259) |
| CTP73B | No significant match | | CCCATAAGAAACATCTTTAAAACATTCAGAATACT<br>CAGGATAATCAAGGCTAATATTCCTATAAATTCCT<br>TACGTGTATTATGTACATTCAGAAAAGTGTAAATT<br>ACTCAAATATTATACTCAAAACCCCTTATAGTCTG<br>CTAACTTGCATGTAGAAACATCTGAAGTAACATGC<br>TGCCTACTAAGCTT | (SEQ ID NO: 260) |
| CTP74A | No significant match | | AAGCTTAGTAGGCATCAATTGGATCCTTTCCTATG<br>TTGAAATGGAAGAATTAATGAGCTTACATTAATTA<br>GTATTGTAATGTGTAAAGGAAGCCCAGCAAAATTT<br>TTTGAAAACTTGATGATCCCAACGTATTTACCATT<br>GTATGTTAAAGCAAAATAATCACCATTTTTTTA | (SEQ ID NO: 261) |
| CTP75C | No significant match | | AAGCTTCTCAACGGCCTCCACCTCCTTTCTGCCCT<br>CACAGCCTCCTGGCTCTGGCCCAAAAAGTGATTCA<br>TTTGTAAATTATCATGGTTTTCTGCATTAAAATGG<br>CCATTTCTGG | (SEQ ID NO: 262) |
| CTP76B | No significant match | | AAGCTTTTACCGCCATCTTGGCTCCTGTGGAGGCC<br>TGCTGGGACCAGGACTCCTAAAGCGACGANTTTTT<br>NTGGAAGGCTTTGGTCCAAGGCCATTTTTGCCGGC<br>TATAAACGGGGTCTFCCGGAACCAAAGGGAGCACA<br>CAGCTCTTCTTAAAATTGAAGGTGTTTACGCCCGA<br>GATGAAACAGAATTCTATTTGGGCAAGAGATGCGC<br>TTATGTATATAAAGCAAAAGAACAACACAGTCACT<br>CCTGGCGGCAAAACCAAACAAAACCAGNAGTCATCT<br>GGGGAAAAGTAACTCTGGGCCCATGGAAACAAGTG<br>GCATGNGTTCCGTGCCAAATTCCGAAGCAATNTTC<br>CTGCTAATGCCATTGGACACAGAATCCGAGTGATG<br>CTGTACCCCTCANAGGATTAAAACTAACGAANAA<br>NCAATAAATAAATGTGGATTTGCGNTCTTNGG | (SEQ ID NO: 263) |
| CTP77D | No significant match | | CAATTGGTTTAGTTTTATTTCAAAATTGTACAAAA<br>TGGCCATAAGCGGCTATAAAAAATTTCGTTTTCGG<br>AACACGTGGAAATTCAGAAAGAACAACAAAGCAGG<br>TTATCATTTCACAGTGTAATGAAAAGCTCTCTCT<br>GAGGCAGGAATCACAACTCTTCCTTCTTCTTCCCC<br>AGTCTCTCGTGGTCTCCTTCCCGGAGCGCTCGAAT<br>GAAACTGGTAAACCCCGATTCCGTCCGATCGC | (SEQ ID NO: 264) |
| CTP78B | Homo sapiens SON DNA binding protein (SON | XM_009738 | CGATGTTGAGATCCAGATGACACAGGAAATTCTTT<br>TGTTAATGTTACCTGGCTTTTTGGTGGAGTTGGCT<br>TTGCTGCAGCAATATTCAGATTGAAAAAAAATGGG<br>TTTGGGTTCACTGAGTTTAAAGGGATGATGATAAA<br>AAGGAGGTTCTTCTTCCTCTTCATCCCGAAACATG<br>AGGCTTATTCACTATTACATCATCATCTTCTTTAC<br>TCTGTGCGATCTGTTTGCATTTCTCAAGTTAGTTC<br>TTCTATAGTNGCTCCTCCTGATTTTTTAGCAACTT | (SEQ ID NO: 265) |

TABLE 7-continued

| Band # | Genbank Gene Name | Accession | Sequence |
|---|---|---|---|
| CTP79B | No significant match | | TCTCTTCTATTGTGGGTGGAGGTGCACGCTTTTAG<br>GTTTGGCGGGTAAAAGCTT<br>CATATATATTCTTTTTTATTTCTTGTTATACCTTC (SEQ ID NO: 266)<br>CCAAAACAGAGACATTCAACAGTAGTTAGAATGGC<br>CATCTCCCAACATTTTAAAAAAACTGCACCCCCCA<br>ATGGGTGAACAAAGTAAAGAGTAGTAACCTAGAGT<br>TCAGCTGAGTAAGCCACTGTGGAGCCTTAAGTGGT<br>GAGGTCTTCCAATTTCAGAGTGATGTGTCTTCAAC<br>TTGTATCATCATTTTAGCGGTAAAAGCTT |
| CTP80A | *Homo sapiens* WDR4 gene for WD repeat protein | AB039887 | CGCCGGCCAGAAAGCGTAATATTCTTTAAAGGAAC (SEQ ID NO: 267)<br>CTTAACAAAACTTTACACTTAATAATGTAAATCTC<br>ACCATGTTCCTAGTCAAAATTTACTACACAGACTC<br>AGTAGCGGTAAAAGCTT |
| CTP81A | No significant match | | CCAAAGAAGTGTTTATTAACATTTGGGGCCTCAGC (SEQ ID NO: 268)<br>GGGGCCAGAGAGGAAGTGGGTGCTAGAGGCTCCTG<br>AGGCTCAGGGCAAGGCCTGCAAGACAGATCCCATT<br>GCTCAGGAGGCAGCCCAGATTGCAAATGGAAGACA<br>GGCCATGGTAGCGGTAAAAGCTT |
| CTP85D | *Homo sapiens* Rho-associated, coiled-coil containing protein kinase 1 (ROCK 1) | XM_008814 | AAGCTTAACGAGGAGACAGAGGTCATGATTCTGAG (SEQ ID NO: 269)<br>ATGATTGGAGACCTTCAAGCTCGAATTACATCCTT<br>ACAAGAGGAGGTGAAGCATCTCAAACATAATCTTG<br>AAAGAGTGGAGGGAGAAAGGAAAGAAGCTCAGGAC<br>TTGCTTAATCACTCGGAAAAGGAAAAGAATAATTT<br>AGAGATAGATTTAAACTATAAGCTTAAATCATTAC<br>AACAACGGCTAGAACAAGAGGTGAATGAACATAAA<br>GTAACCAAAGCTCGTTTAACTGACAAACATCAATC<br>TATTGAAGAAGCAAAGTCTGTTGCAATGTGTG |
| CTP86F | *Homo sapiens* chromodomain helicase DNA binding protein 3 (CHD3 | NM_001272 | AAGCTTAACGAGGACCCAAGAAGCAGAAGGAGAAC (SEQ ID NO: 270)<br>AAGCCAGGAAAACCCCGAAAACGCAAGAAGCTTGA<br>CAGTGAGGAGGAATTTGGCTCTGAGCGAGATGAGT<br>ACCGGGAGAAGTCAGAGAGTGGAGGCAGCGAATAT<br>GGAACTGGACCGGTCGGAAACGGAGGCGGAAGCAC<br>AGGG |
| CTP87B | *Homo sapiens* tetratricopeptide repeat domain 3 (TTC3 | XM_009760 | AAGCTTAACGAGGCATGTGAAAATTATGAGCAGAG (SEQ ID NO: 271)<br>AAAACTGAGGCTCAGAAGAGACCAGGGATCTGG<br>AAGAAAAATTGAAAAGGAACTTAGAGAAAACAAG<br>ATCTCAAAGACAGAATTAGATTGGTTCCTTGAAGA<br>CTTGAAAAGGAAATCAAGAAATGGCAACAGGAG |
| CTP88A | *Rattus norvegicus* ribosomal protein L31 (Rpl31 | NM_022506 | AAGCTTAACGAGGATGAAGATTCACCAAACAAGCT (SEQ ID NO: 272)<br>CTACACGCTGGTTACCTACGTACCTGTCACCACTC<br>TCAAAAATCTACAGACTGTTAATGTGGATGAGAAC<br>TAATCGCTGATTGTCAAATAAAGGTATAAAACTGC<br>TCCATG |
| CTP89B | *Homo sapiens* genomic DNA, chromosome 8q23, clone: KB1935H12 | AP003473 | CTAAAGGGCCAGATAGTAGCTGTGGGCTGGGGTCT (SEQ ID NO: 273)<br>CAAACTGTGTTGCCCACTACTCAACTCTGCCATTG<br>TAATGTGAAAGTAGTCACAGACAAAATATAAAGAA<br>ATGAGTGTGACTGTGTTCCAATAAAACTTTATTTA<br>CAAAAGCATTCAGTGGGCTGGATTTGGCTTTTGGG<br>CCATAATTAAATCCCCTCTGGTAAAATAATCACTA<br>TTTTAGCTGGATCATGAGTACGTGGAAGCTT |
| CTP90A | *Homo sapiens* clone 24800 | AF070622 | ACAGGTTTCATCTGAATACATATTTATTAGATAAA (SEQ ID NO: 274)<br>TATTAGAGGTTGTCACATCATCTAACTACATACAG<br>CTTTGCAAGACTAGAAATCACAATTAGTTTTTTGA<br>CCAGTTTAAAGTATGAAATGATTGCATTGTACATA<br>CGATGTACAAAGACGATGATGGTTTCTGTGGGAGT<br>TACTTCAGGCTGCCACTGGTGGGTGTGTTTATGTGT<br>GTACGTGGAAGCCT |
| CTP92A | No significant match | | GCACTAAATTCAAACCAATGACCTCCCATGTTCTA (SEQ ID NO: 275)<br>ATTCTGATTGTTTAATCCAACTGGGAGGGTAAACG<br>GGAGACTCTTTGGCCTGTCAGTGACAAAATGGTTT<br>GTAAAAAAGAAAAAATAAATACGATATACAAGTAA<br>GTATAACTAGCACTCAAGCTT |
| CTP92C | Human DNA sequence from clone RP4-580N22 on chromosome 1q42.2-44 | AL133286 | GGGGTGTTGAAGAGCCTTGTTTTGTCATATTACCA (SEQ ID NO: 276)<br>GAGTTTTTCTTGGTTCCTTCTCATTTGGGTAGG<br>CTCTGTCAGAGAGAAGGTCTAGGGCTGAAGGCTGT<br>TGTTCAGATTCTTTTGTCCCAAGTGGTGTTCCCTT<br>GATGTAGCACTCAAGCTT |
| CTP93F | clone RP1-211D12 on chromosome 20a12-13.2 | Z93016 | AAGCTTGAGTGCTGTTGCTGATGTACAACTTAAAA (SEQ ID NO: 277)<br>ATGTGAAGTTTGTAGCTTTAACTTTTTGTAATAAA<br>AACTAATAACACTGGCTTAAGTGCTGACTTGAAAT<br>GCTATTTTATAAAGTTTGGATGTAAATAATCAATC<br>GAGGTCAGCAGTTTGTATATGTAGGAGACATAGCT<br>TCCTCCCTGCACCCCCATTTTTTTAAAATTTGAG<br>GTGCTTCCTGTGTGTTTTTATGTTAGAATTGTTCT<br>CCCTCCTTCCTACACGTGGTCACCTTTGTTTTAAA<br>TAAACTGTCCTTTGG |
| CTP94B | *Homo sapiens* clathrin, | NM_008305 | AAGCTTGAGTGCTGTATCCTGTGCTTTTTCTGTGG (SEQ ID NO: 278) |

TABLE 7-continued

| Band # | Genbank Gene Name | Accession | Sequence | |
|---|---|---|---|---|
| | heavy polypeptide (Hc) (CLTC) | | GACCATTCCATTCAGGAGCAAAGAGCACCATGATT CCAATCTTGTGTGTGTTTACTAACCCTTCCCTGAG GTTTGTGTATGTTGGATATTGTGGTGTTTTAGATC ACTGAGTGTACAGAAGAGAGAAATTCAAACAAAAT ATTGCTGTTCTTCAGTTTTGTTTGTGGAATTTGAA ATTACTCAAATTTAAAATAAATTACTGGACTGTGG | |
| CTP99A | No significant match | | AGCATATGTAAGATCTCTGGCTTGTAGAAGACAAG TTTATATAGCACTTAAAAAACCATTTGTTACATTA AATGTCGAACTCAAACTTTTAAAGAGTATAGAGAA CTACAAAATGGAAAAAGGAGCAGATATACGCTTTA TGAGGAAATTGTGTTAATGATCTCTCCTCTAAAAA AGGACTCTTCCCTATTATCATAATGACCACACTGC CCGTCCTTAAAACCACTGGTCGCTGACATTATGCC GAAGCTT | (SEQ ID NO: 279) |
| CTP100A | COX15 (yeast) homolog cytochrome c oxidase assembly protein, clone MGC:8634 | BC002382 | AACATATAAAAACATTTATTCACTAGGAATAATTG TGGCAGACACAATCCAGTGAAAGCAGCTCAATCCT GCTCAGTTAGGCTAGTTGAAGAACCATACTTTAAA AAAAGAAAGGAAGACAGGCAAACAAGTGTTTTACA GGAGCAACAGACTTCAAGGTCACCCCCACAAGACA CCCTGCACAGCAGGGACGGGGACAGGGAGGATGAC CTCTTAGGGCCTGTGCCTTCGCAGAGGTGCTCGGC GGATGGGTGTGGTCTTCTTGGGTGTCTCCTCTTCT GTCATCTATGCCGAAGCTT | (SEQ ID NO: 280) |
| CTP103JJ | No significant match | | AAGCTTCGGCATAGTTACTGTTTGATTTTAAGTTT TTATATAGTTCTTAGTTTTGAAGAAATCCTTCAAG AACAGTTTCTCTAAAGAGCATGTTTTAATTAAATG CTAATTAATTACCTTTCTTAGTTTTTCCAATTTAGT AGGCCACTTTCAATGTCTATTAAAGTGAAATAAAC CTTCTGAACTTAAACATTTTTAAATCGATTAAAAA TTGTGTCAAAAT | (SEQ ID NO: 281) |
| CTP104I | No significant match | | AAGCTTTTTTTTTTCAAAACGGATTTGTAAAAAC TGTATTTCTTACACTGTGCACAAACCTTTTATACT AAATAAATATCAAACTACATTCTTCAGAAAGATGT TTCTAGTATTTTTCTTAGGTCACTTCCATATGTAG TATGTACAGTGAGACCACTTTTTAAAAAGCAATGA CTTAGGCAAACCAACCCTAATGGTTTGTTAGACCA TTTCCCTGTTTTTAATTAAAAATCATAGGGTTGTG CTTCTGTATAAAGTTTGTACATTTCACAATGTAAA ATACTGACATT | (SEQ ID NO: 282) |
| CTP109P | No significant match | | ATGCAACCACACGGAATTTATTGAACATTTTCACA AGTGATTTCATTAAAGGAAGGCTTTTTCGTGCCTA TATTGGTTACCATCACTTTTGCCCCTATCACAATC TCATGGTGTAGTCCTTGCATGTAGCAGGAACTCAA CAAATGTCTGCTAAATTGACAGATGGAGCCCCAGA CGACCTAAAACTTGCACTTTAGAAGCACTTACTTC ATCCTGAGCTATTATGAATAAGGAACTCAAGTGAC TGTTAAAAGCATTCTACTGATGAGTTGGTAATGTT CTAAAGCAACATATCTCAAAGGAAAGGATATTGAG TTTGTCTCCACCATAAAATCCTATTTTTAAACAAA GGTACTACTTAAAAATGGTCTTCCAAAGGCCTCAG CAGAGGTTCTAAAGAGATGTGACAATATGCCGAAG CTT | (SEQ ID NO: 283) |
| CTP110A | No significant match | | AACATATAAAAACATTTATTCACTAGGAATAATTG TGGCAGACACAATCAGTGAAAGCAGCTCAATCCTG CTCAGTTAGGCTAGTTGAAGAACCATACTTTAAA AAAAGAAAGGAAGACAGGCAAACAAGTGTTTTACAG GAGCAACAGACTTCAAGGTCACCCCCACAAGACAC CCTGCACAGCAGGGACGGGGACAGGGAGGATGACC TCTTAGGGCCTGTGCCTTCGCAGAGGTGCTCGGCG GATGGGTGTGGTCTTCTTGGGTGTCTCCTCTTCTG TCATCTATGCCGAAGCTT | (SEQ ID NO: 284) |
| CTP111A | No significant match | | AAGCTTCGGCATAAACGATCCATTCTCCTCGGCCT CCCAAAGTGCTAAGGTTCCAGGCGTGAACCACCAT GCCCAGCCTGTTCTTTTTTTTTATCTCTAGGTGGTG CTCTCCAGCTGTAGTAGAAATAGCATTTGTATTGG ATCTATTTTTTTAAATAGGGACTAAATACAGACCA TTTTGTTAGAGTGAAATGCCAAACAAGAACGAGAT TTTTCTCTTGGCT | (SEQ ID NO: 285) |
| CTP112B | *Bos taurus* peroxiredoxin 1 mRNA | AF305561 | CTCAGTTCAAGTTTAATAGAAACAACAAAAGATCA AAAGTGATGCCTTGCTACTACTGTACATATCAGTT GGCCTGCCCCATAGCACACCTCAGACCATCCTCTC CAGAGGAAGAAAGGCTGGCCTCCCCAACCCCTGCA GGAAAGGGCGGTCTTGTCCCATACCACATACCACA TCTGCAGAGTCTAAGTCTTGTTATAAGCATGACAA TAGTACAAAAAAAGATTCTGTTTTCATGGATCCCC CACTACAGCCCGGACCTAAAATGGCGAGGCGCTCA CTTCTGCTTAGAGAAATATTCTTTGCTCTTCTGGA | (SEQ ID NO: 286) |

TABLE 7-continued

| Band # | Genbank Gene Name | Accession | Sequence | |
|---|---|---|---|---|
| | | | CATCAGGCTTGATGGTATCACTGCCAGGCTTCCAG<br>CCAGCTGGGCACACTTCCCCATGCTTGTCAGTAAA<br>CTGGAAGGCCTGAACCAGTCGCAGTGTCTCATCCA<br>CAGAGCGACCAACAGGAAGGTCGTTTACAGTGATA<br>TGCCGAAGCTT | |
| CTP113A | Bos taurus ribosomal protein L30 mRNA | AF063243 | CTAGTTAGAGTCAGATGTTTATTTAAAAATCTGAT<br>CCACTAAAACTTAGCGTTTTCCACCAACTCGGGGT<br>GCGGAAACCTTCACAGGCTTCACAATCTTTTGCTT<br>AGGTGCTGCCTTTGTGGGAGCCTTAGCAGCAGCCA<br>TTGCTGTCTTTTTAGATGCTTGCTTAGCCTTTTTT<br>GCTTCCTTGGCAGCCCTGATGGCCTGTTCTCGTTG<br>AGCCTTCCTAACTTCAGGTTTCTGATTCCTCTTAG<br>CCATTATATCAGCAAGAGATGCCCCAGTGATGGCC<br>CTCTGGAATTTGACTGCACGGCGGGTTCTTTTCTT<br>CTGAATTTCTTCCGACTGTCCCTTTTTGTGCTTTC<br>TTCTGTAGAGGACAGTCCAGTTGATATGCCGAAGC<br>TT | (SEQ ID NO: 287) |
| CTP115B | Homo sapiens chromosome 17, clone hRPK.227_G_15 | AO005899 | CTAAGGTGATATAGAAGTGGACTAAGGGAGAGCCA<br>AAGTGGCAATCCCATTAATCTTACAACTTCCTAAA<br>TTATGGCAATCACAATGCCTGCCTGAATGAATATA<br>GCAAGTCCTAAAGGATGTCTTCTGTGAGGGCAGAT<br>GGAAGTTTACTTCAACTCAACTCCATCTACTATTT<br>AAGGGAAGGATAAGTCAAAGTAAGAGTTAATTATT<br>TCAACATGGTTTGTTCCATTCATGATTTAACCACA<br>CTATGGACCCCAGAAGCAGTTAGGTAAAAGGGATT<br>TTCTAGAAGCTTAATTATGCCGAAGCTT | (SEQ ID NO: 288) |
| CTP116A | No significant match | | AAAAGAGCATACTTATCAGTTGAATGGGATAGAG<br>GTTTTAGATATTTTCCAAAATATTTATAAAACACT<br>TCATTGTTGAGAAATCACTTACAGAATGGTGGCTA<br>TCAAACAAATAATTATAAATTTTTAAAGCACAAGT<br>CACATGTTTTGTAACTCCTGTGTGAATTTATTTTA<br>GCTGTGACATTTAATTGAAAACATCAGATATGTTT<br>TGGAAAAGTCTTAATTTGAGAACAACTGAAGGAAG<br>TTAATCCAGAATCTATATGTAGTTAGCTATTAATG<br>ATGATGCTTTATTGACAGTATATTGCTAATATATT<br>TCTTCATGAAATCTGAAGTTAAACCAGCTTTGCCA<br>TAAAAAAAAAAGCTT | (SEQ ID NO: 289) |
| CTP117B | Homo sapiens similar to J KAPPA-RECOMBINATION SIGNAL BINDING PROTEIN (RBP-J KAPPA) (M. musculus) (LOC82995), | XM_017740 | AAGCTTTTTTTTTTAAGCTGATGTCTTATGACTT<br>TTTATGAGTCGAAATTGTTTTGATTTCAGCAAGTC<br>AAATCTTGTAAAGGCCCGCGTATTTTTTTTAAGAT<br>TATATGAAGTCTGTGCAAAAGCTTTAAAAAGAAAT<br>GCCTCTGCCTTGCCTGCAATACATGCAATGTACGT<br>TAACTCGTCTCTGTCCTCAGACACTGTCCGTATT<br>TACTTCCTTGTTTTCCTTTTTCTTAAT | (SEQ ID NO: 290) |
| CTP119J | Homo sapiens SPR-2 mRNA for GT box binding protein | X68560<br>S52144 | CAAAAGAAAAAAAATAGTGTTTTATTAACTACCAC<br>ACTGTTATAATACACTTTAAACGTACAATAAGGTA<br>GCCTTTAAATTTGAGGTGGTCTTAAGAATAACAAA<br>TGAACAGAATTCCAAATTTTTGAAATAGGTGAACT<br>GCTGTAGTTATAGGTATACATTTAGGAAAATTGTA<br>TAGCTTTTACAAGACCAGCAATGAAACTTATTTTT<br>GTACATTTTTTTAATAATTGAAAATATAAACAATA<br>ATTAAAAAATAAAAGAAAATACAGCATAATAAAA<br>ACATACATTTCTCAATTAAATGTACTGGATACATA<br>TAAATTTAAAGGGAAGAAGCAAAAAAGGAAAATGG<br>TTGATATTTAAGTGCAGACTGACTACCTAGACGAA<br>AAAAAAAAAGCTT | (SEQ ID NO: 291) |
| CTP121D | Human ribosomal protein L23a | U43701 | AAGCTTCATTCCGACGACCCAAGACCCTGCGTCTC<br>CGAAGGCAGCCNAAATATCCTCGAAAGAGCGCCCC<br>CAGGAGAAACAAGCTTGATCACTATGCCATCATCA<br>AGTTCCCCTTAACTACTGAGTCAGCCATGAAGAAA<br>ATAGAAGACAACAACACACTTGTGTTCATTGTGGA<br>TGTCAAGGCCAATAAGCACCAGATCAAACAGGCTG<br>TGAAGAAGCTCTATGACATTGATGTGGCCAAGGTC<br>AACACCTTGATCAGGCCTGATGGAGAGAAGAAAGC<br>ATATGTTCGACTGGCTCCTGACTATGATGCTTTGG<br>ATGTTGCCAACAAAATTGGGATCATCTAAACTGAG<br>TCCAGCCGGCTATAAATCTAAATATAAATTTTTTC<br>ACCAT | (SEQ ID NO: 292) |
| CTP122I | Human mRNA for KIAA0033 gene | D26067 | AAGCTTTTTTTTTGGGACTGCTTTGATTAATG<br>CAGTTATCCAATTTAAGTGTTTTTACTTTAACTCA<br>AAGTAAAAGAAATTCTCACATGGTAACTACTCTA<br>TTTAAATGGTCCTGGAAACATTAAACAGCTTTCTG<br>CTGCTTGCTTAATGGTAATACCTTTGATTTCTTGA<br>TTCTAGGACATAGCTGATTATTAGGTAAAGTACT<br>CTGTCAATTTTACCTTCACCCAAGACTGTCATGTT<br>TAAAATACTTTAGCTGTGGGAGAAATCCTTGTCTG<br>TTTTTATTGTGAGAGGAATGGTCATCCTCAAAGTC |  (SEQ ID NO: 293) |

TABLE 7-continued

| Band # | Genbank Gene Name | Accession | Sequence | |
|---|---|---|---|---|
| CTP124B | No significant match | | TGTTTCTACTACATAATGTGGACTAATTATTTTTT CTATCACAGTATTAACAAATGGATTTATTGTAAAT ACAAAGAAGATATTAATATACTATTCTTATGTC ATGGCAAAGCTGGTTTATTGAACTTCGTAAGGGAA ATGTTACAGTGACACTATTCCACAACGAAATTATT TAACTTCAGATTTCATGAAGAAATATATTAGCAAT ATACTGTCAATAAAGCATCATCATTAATAGCTAAC TACATATAGATTCTGGATTAACTTCCTTCAGTTGT TCTCAAATTAAGACTTTTCCAAAACATATCTGATG TTTTCAATTAAATGTCACAGCTAAAATAAATTCAC ACAGGAGTTACAAAACATGTGACTTGTGCTTTAAA AATTTATAATTATTTGTTTGATAGCCACCATTCTG TAAGTGATTTCTCAACAATGAAGTGTTTTATAAAT ATTTTGGAAAATATCTAAAACCTCTATCCCCATTC AACTGATAAGTATGCTCTTTTAAAAAAAAAAAGCT T | (SEQ ID NO: 294) |
| CTP126A | No significant match | | AAAGAAAGTAATTATGGAACTAGATTTTTAACATT GTAAAATACTAAATGATCCTTCAGTTGTAAGTTGA TATATATTTGTAACCTTTGTGAAATTGTATCCTTA TGAAAATACCACTTTTGTGGAAGAGAGAATCCAAC TATGTAATATTTAATTAAAACAATCCATGTTTACC CTATCCCTGCTCAATTAAACAGTGTATATAGGTCT AATAATAGCTCTGGAGCAACTTTTATCATGAGTCA AATATATTAAACACATTGATGTCTTCTTGGTATAT CTGAAAACAAGAGGTAGAAGTCCTGTTGAGAGTCT TTAAAATAAACTATTTTTACAAATGTAAAAAAAAA AAGCTT | (SEQ ID NO: 295) |
| CTP129A | *Homo sapiens* Similar to cadherin 1, type 1, E-cadherin (epithelial), clone MGC:1151 | BC007583 | AAGCTTCATTCCGACGACCCAAGACCCTGCGTCTC CGAAGGCAGCCGAAATATCCTCGAAAGAGCGCCCC CAGGAGAAACAAGCTTGATCACTATGCCATCATCA AGTTCCCCTTAACTACTGAGTCAGCCATGAAGAAA ATAGAAGACAACAACACACTTGTGTTCATTGTGGA TGTCAAGGCCAATAAGCACCAGATCAAACAGGCTG TGAAGAAGCTCTATGACATTGATGTGGCCAAGGTC AACACCTTGATCAGGCCTGATGGAGAGAAGAAAGC ATATGTTCGACTGGCTCCTGACTATGATGCTTTGG ATGTTGCCAACAAAATTGGGATCATCTAAACTGAG TCCAGCCGGCTATAAATCTAAATATAAATTTTTTC ACCAT | (SEQ ID NO: 296) |
| CTP131B | *Homo sapiens* similar to sperm autoantigenic protein 17 | XM_006087 | AAGCTTCATTCCGGGGACACATAGCCAGAGAGGAG GCAAAGAAAATGAAAACAAATAGTCTTCAAAATGA GGAAAAAGAGGAAAACAAGTGAGGACACTGGTTTT ACCTCCAGGAAACATGAAAAATAATCCAAATCCAT CAACCTTCTTATTAATGTCATTTCTTCCTGAGGAA GGAAGATTTGATGTTGTGAAATAACATTCGTTACT GTTGTG | (SEQ ID NO: 297) |
| CTP133B | No significant match | | CCAAAAAGAGCCATGCCCAGAGGGAAAGTTGGAAA CGAAAGCCAAGTTTTCATTTAAAAGGAAACANTAA AGAGGTTAGCCAGAGAAACTTGAACCAAAGAAAAG ACAGCACGCTGTTCAGAATGGTCAATAAGAGCCTA AAACGGTACCCTCGGAATGAAGCTT | (SEQ ID NO: 298) |
| CTP134A | No significant match | | CCAAAAAGAGCCATGCCCAGAGGGAAAGTTGGAAA CGAAAGCCAAGTTTTCATTTAAAAGGAAACATTAA AGAGGTTAGCCAGAGAAACTTGAACCAAAGAAAAG ACAGCACGCTGTTCAGAATGGTCAATAAGAGCCTA AAACGGTACCCTCGGAATGAAGCTT | (SEQ ID NO: 299) |
| CTP | 135A*Homo sapiens* cDNA FLJ11508 fis, clone HEMBA1002162 | AK021570 | CCATCAAATGTAATTTATTTAAATAACAATTCAAT TGCATGTTAAGTAAACCAGTTGTAGCAATATAAAA ATACAGAATTTTGAGAAAATCTGCCAAATTAAACC TGTATCTAAATGCAGCATATTCTGTGATACTACGG AATGAAGCTT | (SEQ ID NO: 300) |
| CTP143B | No significant match | | AAGATTTCAAAGAGTGAGCAAGTGCATTAGCAGGG CAGAGAGAGAGGCAGCAGCAGACTCCCTGCTGAGC TGGGAGCCAACTTGGGACTCGATGCCGGGACCCCA GGATCATTACCCGAAGCTT | (SEQ ID NO: 301) |
| CTP144B | No significant match | | GGGTAAATCCGTCCAGTTTACTGTAAATATGCCTT TGACAAACTGGTAACTCATGTCCCATCCCAGTCCC GAGTACTGGACCAGGGAAACTCCAGCCACAGTTGA GGGAAGGCCACCTGTTGGCTCTGGGGCAGCAGGTC ATCCAGTGGGCTTCAGGAGTCACCAGGCCTCTGAC CAGTTCCTCCCCACCAAGCAGTTTCAGAGTTGTCC GCCAAGTCTATTTCACACCTCTCGTGTATGCCGAA GCTT | (SEQ ID NO: 302) |
| CTP145B | No significant match | | GGACTGATAATAATAGGATTTTATTTCTAAAATTT ATCTTAGAGCTTTCAAAGAGTATAACACACAGATC TTTACCACCACACCCCCCTTGCCTATACAGGAAAC AACCAAGTTGTGAGAACATTTATCATGCACAGACA | (SEQ ID NO: 303) |

TABLE 7-continued

| Band # | Genbank Gene Name | Accession | Sequence | |
|---|---|---|---|---|
| | | | CATCAGGGCTTGCAGGTGCTACACAGGAATCACAA ATGCTGTTCCACATCATGTCTTCTGTTATGCCGAA GCTT | |
| CTP148B | *Homo sapiens* serine-threonine protein kinase (MNBH) | AF108830 | AGCATATGTAAGATCTCTGGCTTGTAGAAGACAAG TTTATATAGCACTTAAAAAACCATTTGTTACATTA AATGTCGAACTCAAACTTTTAAAGAGTATAGAGAA CTACAAAATGGAAAAGGAAGCAGATATACGCTTT ATGAGGAAATTGTGTTAATGATCTCTCCTCTAAAA AAGGACTCTTCCCTATTATCATAATGACCACACTG CCCGTCCTTAAAACCACTGGTCGCTGACATTATGC CGAAGCTT | (SEQ ID NO: 304) |
| CTP149B | No significant match | | AGGAAGAATAAAAACATATAAAAACATTTATTCAC TAGGAATAATTGTGGCAGACACAATCCAGTGAAAG CAGCTCAATCCTGCTCAGTTAGGCTAGTTGAAGAA CCATACTTTAAAAAAAGAAAGGAAGACAGGCAAAC AAGTGTTTTACAGGAGCAACAGACTTCAAGGTCAC CCCCACAAGACACCCTGCACAGCAGGGACGGGGAC AGGGAGGATGACCTCTTAGGGCCTGTGCCTTCGCA GAGGTGCTCGGCGGATGGGTGTGGTCTTCTTGGGT GTCTCCTCTTCTGTCATCTATGCCGAAGCTT | (SEQ ID NO: 305) |
| CTP150A | No significant match | | AGCATATGTAAGATCTCTGGCTTGTAGAAGACAAG TTTACATAGCACTTAAAAAACCATTTGTTACATTA AATGTCGAACTCAAACTTTTAAAGAGTATAGAGAA CTACAAAATGGAAAAGGAAGCAGATATACGCTTT ATGAGGAAATTGTGTTAATGATCTCTCCTCTAAAA AAGGACTCTTCCCTATTATCATAATGACCACACTG CCCGTCCTTAAAACCACTGGTCGCTGACATTATGC CGAAGCTT | (SEQ ID NO: 306) |
| CTP150C | Canis familiaris mitochondrion | CFU96639 | AGGATCCTCATCAATAAATAGATACATACAAGAAT AGCCAGACTACATCAACAAAGTGTCAATATCATGC AGCGGCTTCAAATCCGAAGTGGTGGTTTGATGTGA AGTGGTAGTATAGCTGTCGGAGGAAGCACACGATG AGGAATGTAGAGCCAATAATTACGTGTAATCCGTG AAATCCAGTGGCTATAAAAAAGGTAGATCCGTATA CCCCATCGGAGATTGTAAAAGATGTCTCATAGTAT GCCGAAGCTT | (SEQ ID NO: 307) |
| CTP154A | No significant match | | AGCATATGTAAGATCTCTGGCTTGTAGAAGACAAG TTTATATAGCACTTAAAAAACCATTTGTTACATTA AATGTCGAACTCAAACTTTTAAAGAGTATAGAGAA CTACAAAATGGAAAAGGAAGCAGATATACGCTTT ATGAGGAAATTGTGTTAATGATCTCTCCTCTAAAA AAGGACTCTTCCCTATTATCATAATGACCACACTG CCCGTCCTTAAAACCACTGGTCGCTGACATTATGC CGAAGCTT | (SEQ ID NO: 308) |
| CTP156J | Human DNA sequence from clone RP5-975D15 on chromosome 1p31.3-32.2 | AL136120 | AAGCTTCGGGTAACCACTGCTAATAACTAAAATAC TCTAACTTGGAATAATCGACTCCGACGTCTTTATT TTTCCAAGTTGCCTTTTCTTTAAAACACCTTTTTC TGATTTAATACGGAATAACGGTCTTCTTTTCCACT CGATAACTATGGTGTCCTCTTGGGTTACTGCTTAA GAAAAGTTGGTTTGGGCCATTTCG | (SEQ ID NO: 309) |
| CTP161B | Canis familiaris TCTA gene, AMT gene, DAG1 gene and BSN gene | AJ012166 | AAGCTTTTTTTTTTGAAGATACAAGTTAGAGTTC AATCAGTACCAAAGGTAAGGAAAAATTAACTCTAT GTACACAGTCGAGTTTTATCCTGCTTAAAATTGTC AAGTAGAGAAAATTCTGAAAATATTTATGAAAAAG CTATTCTCATGCTGGCAGCAATGGTTAAAATAAAG ATATTTCCTTTATTAAAAAAGAAAAAGCCTAAAAA ACAACTTTAAATAATCAAGTTGCTGTGAAGTGAAA GGGTTTGAAAGTGATGAAACTGAAGTTAAAAGTTC TCTATATGTGTGTTTTACTTTAAGCAAATTAGACA TAGTGAATAAAATTTGAATTTTCAGACAAATTATT TGCTTTTTTTTTATTTTATTTATTTATTCATGAGA GACACAGAGAGAGAGGCAGAGACACAGGCAGAG GGAGAAGCAGGCTCCACGCAGGGAGCCCAATGTGG GACTCGATCTGGGAACTCCGGGATCAAGCCCTGAG CTGAAGGTAGACACTCAACCGCTGAGCCACCCAGG TGCCCTGATTTGCTTTTTAAAGAAGTCTCCCCCTT CC | (SEQ ID NO: 310) |
| CTP164A | No significant match | | AAGCTTCGGCATACGTGTGAGGTTACAGTTCCAGT TTTGTGTGCTTTACTACACGGTTTGGTTACAGGAC TTCTGTGCATTGTAAAACATAAACAGCATGGAAAA GGTTAAATACCTGTGTGCAGATTGTAAGATCTGGT CCGGACTTGCTGTGTATATTGTAACGTTAAGTGAA AAAGAACCCCCCTTTGTATATAGTCATGCGGTCT TATGTATGATAAACAGTTGAATAATTTGTCCTCAG ACTCTTTACTATGCTTTTTTAAAATTAAGAAAAAT GTAAATATAGTAAAAATCTTCCTATGCAATTAACC TGG | (SEQ ID NO: 311) |

TABLE 7-continued

| Band # | Genbank Gene Name | Accession | Sequence | |
|---|---|---|---|---|
| CTP178B | *Homo sapiens* mRNA for KIAA1524 protein | AB040957 | AATAAGGCTTCATCTAGATTTTTTTCTGTGAACTG<br>AAGTTGGTCAAGGATTGTAGGCAGCAGAAGGCTCA<br>CAAAACGGTCAGTTGAGGAACAGTTAGCAGTATCT<br>GCAACATCCTCAAATATTTCCTTGAACAACTCTAA<br>GGCTAGAAGAGAACAGTTTTCTGATCTGTCCAGAG<br>GTTGGTTTGACCAACGCAGTAGAGCCACAGTAGGT<br>TCTAAACATTTAGAACGGCTTCCCAGAATGGTGTT<br>GCCAGATGGAGACTGTTCAAATATCATCTGAGTGA<br>GCACGTGGCGCAGCTGAGTCACTGAACAGAAGGCA<br>AGAAGTAATTCTAAAACCTTTGAAGAAGAATCAGG<br>ATCCTTTCCATTGAGAAGACCTAATACTTGACTAA<br>GACATGAAGAAAAGTGCTCATACCTGGTAAGCTT | (SEQ ID NO: 312) |
| CTP179K | No significant match | | AAGCTTACCAGGTAGAGGGACTGTTGGAGGTATGG<br>ACGCACACAGGAGGGCCAGGCCAAGGCACGAGTTT<br>TTCAGTGAAGGGGGTAAAGCATCACAATTTAAAAT<br>GTTTGCAATTAAACTGGTTTGTTAAATATC | (SEQ ID NO: 313) |
| CTP185C | No significant match | | CAGCGAAGAGGCATTAAAGATTCATGCCATAAGTT<br>TATTTACAAACATGTTGTGTATGTTGAATTCAAGA<br>GATTGATCCATTTTTCAGAGACTGCACCTCTTAAA<br>ATGTTCCTTTTCACATCTGTTTAGTGGATCAAAAG<br>CTT | (SEQ ID NO: 314) |
| CTP197A | No significant match | | ATGGTGTGTGTGTGGGTTCAAATAGTTTATTCACC<br>TCTGTAGTGGAAAAACAAGGAGAAATAAAATCTGC<br>TTACAATGGCCAAAATTTATGGAGAAGCCCTAAAG<br>TTGCTTTCCCCAAATCACAAATCTGATTCAAGAGA<br>AGGAAAAAAATGATGAAAAACATCTCATCACACAA<br>AACTCAGTGTGGTGTCTCTGATAGTCATCAGCCAG<br>CAGAAGCTT | (SEQ ID NO: 315) |
| CTP201B | *Homo sapiens* exostoses (multiple) 1, clone MGC:2129 | BC001174 | ATCATTTCAAAAATAATCATTTAATGTTCCATAAT<br>TAAAACTGTACACGACCTAGTCTTGGGACATAGAAG<br>CCAGTGAGGTGAGTTTGGAGCAGTCCCAGGAGCCA<br>GGAGTCGAGTTTTCATTGGCCTTTTTTTTCTTTTT<br>TCTTTTTGTCATTCTGTTCATCTAAGATTATTTGG<br>ATACTTGGCACAATCTGGCTCTGCTGCTAAGCTT | (SEQ ID NO: 316) |
| CTP202C | No significant match | | AGAAAAAAAATTGATAATTAGGTGCAGATAGAAAA<br>TATGAATTAGAAGAGGTTAATTCAAGTGATCAGCC<br>TGAAAGTTCAGCTTCATTAGCTTTGTGGTAAATCC<br>ACCACTTCAGATAGTAACTAAAGTAAATTTTAAAT<br>TTCATAAGAATAAAGTAATCCCTGAAAAGAATTCA<br>CTTTTTTCCCAGAAGAAGCTTATAATTAAAAAAAA<br>AAAGCTT | (SEQ ID NO: 317) |
| CTP205D | *Homo sapiens* similar to J KAPPA-RECOMBINATION SIGNAL BINDING PROTEIN | XM_011187 | ATTAAGAAAAAGGAAAGCAAGGAAGTAAATACGGA<br>CAGTGTCTGAGAACAGAGACGAAGTTAACGTACAT<br>TGCATGTATTGCAGGCAAGGCAGAGGCATTTCTTT<br>TTAAAGCTTTTGCACAGACTTCATATAATCTTAAA<br>AAAAATACGCGGGCCTTTACAAGATTTGACTTGCT<br>GAAATCAAAACAATTTCCACTCATAAAAAGTCATA<br>AGACATCAGCTT | (SEQ ID NO: 318) |
| CTP206A | *Homo sapiens* fatty acid desaturase 1 (FADS1) | NM_013402 | CAGGCTGGTGTTATAGGTGAAGATAGGCATCTCTT<br>ACAGATGGGGGTGGGGGCTGTTGTTACTGGTGAAG<br>ATAGGCATCTAGCCAGAGCTGCCCAGACTCCTTCA<br>GTGAGTAGATAATGTCGGCGAAGGCTGAGAGCAGG<br>GGCTTGGACTGGTACTCTATGCCATGCTTGGCACA<br>CAGGGACTGCACCAGGGGAGCCACTTTATGGTAAT<br>TGTGTCGAGGCATCGTAAGCTT | (SEQ ID NO: 319) |
| CTP208B | No significant match | | CTAGAGGAAGTGCTTTTTATTTTTAGATCAACCAA<br>ACATATTTAATATAAAAACCTTTTAATATACAAAC<br>TGTAATCACAATTGCATCCACGTAGCAGCGAGGGA<br>ATGGGGTGTTGCAGGAAGCTT | (SEQ ID NO: 320) |
| CTP215B | No significant match | | AAGCTTAGAGGCAGTAAACAGGAGCGTCCCCAAGA<br>AAAAGAGGAAATTCTCTTCTAAGGAGGAGCCACTT<br>AGCAGTGGACCTGAAGAGGCTGCTGGCAACAAGAG<br>CGGCAGCTCCAAGAAAAGAAAAAGCTCCAGAAGC<br>TATCCCAGGAAGATTAGAATGGACATTTTACCAGG<br>TGGGGCAAACCCACATGATTCCAAACCCACCCTTA<br>TATCCCAATAAAAACAAATTCACAGG | (SEQ ID NO: 321) |
| CTP216A | Canis familiaris heat-shock protein (HSP27) | U19368 | AGGCAGTTGCTTTGAACTTTATTTGAGAAAAACAA<br>AAGGTAAATGTATCAAAAGAGCATACAGGTTAGTG<br>TGCAGGGACGGTCAGTGATGGCTACTGAGGTGAGG<br>ATGTGGGCTAAGCAGGGCTAAGGCCTTTACTTGGC<br>TCCAGACTGCTCCGACTTTCCAGCTTCTGGGCCCC<br>CAATCTGGGCACGTGCCTCTAAGCTT | (SEQ ID NO: 322) |
| CTP222D | No significant match | | AAGCTTACCAGGTGAAGAGTGGGGTTGTCATGACC<br>TTGGCTATGACGCCCAGCATTTCGAGGTGGCTCCC<br>TCTATTCTTTACTTTGGGCATCATAGAAAACGTGT<br>CTCTGGGGGATTAATCCTTAGAGAAAAATAAAGCCT<br>TTCTGCTG | (SEQ ID NO: 323) |

TABLE 7-continued

| Band # | Genbank Gene Name | Accession | Sequence | |
|---|---|---|---|---|
| CTP300B | *Homo sapiens* utrophin (homologous to dystrophin) (UTRN), | NM_007124 | CCAAGGTTCACCAAGCTTTCAACAAGCACTGTTCT<br>TCTAATAATTCCTGCCACAATATATTAATTTCTTG<br>TAGCCTACTCCAACGTTCCTCTGTCCAACGGCACA<br>CTGCTGTCCAGCGTTCACCAAGCTT | (SEQ ID NO: 324) |
| CTP304B | *Homo sapiens* unknown mRNA | XM_002211 | AAGCTTAGCAGCACAGCACACCAACATATACAAAC<br>ACCGAGTGACTACAGTACATGCCGAGGTAAGAAAA<br>GTACATTCGGGGAGACTATCACTGACACTCAAGCC<br>ATTTTTATTTCCAATATGTTTTGCTTTCACCTTTC<br>CCAGTGCCAAAAAAAAAAAAACCTAGTCACAAATT<br>GGAGTAAATAAGAATCGGTGCCAGTTGACCT | (SEQ ID NO: 325) |
| CTP306B | No significant match | | AAGCTTCTGCTGGTATGGAAAGCCTTCAAGGAAGA<br>GGGTAATGAGGGGGAAGAAGTGCTGTGCCAAAGTG<br>ACAGCATTCAGTGAGGAATAAAGAAAGGAGCTCAG<br>TGGTAGCAGGATGTTGAGCTTCCAAGAAAATCTGG<br>TGGTGGTGAGAAAGTGGCTGCTGTGCACTGCAAGG<br>AAACAGAGCGATTAAAGAAAGAGATGTGACAGGGT<br>AGGTGGAAGAGATAGCCAGAAGTTAGAAATGGGTT<br>ACACTGAAGAAGTAAATTATTTGATTAAACAATAA<br>GTAAATATACTGGGGATAACAAAAGCCTGATTTCT<br>CCACTGTCTCAGAAGGGATTTGCAAGTATGG | (SEQ ID NO: 326) |
| CTP308KK | No significant match | | AAGCTTTCTCTGGATGAACAGTTAAATGGAACCTG<br>TTCCTTAAGCAAGGCAGTGTCAAAGGCAACCCTCC<br>CAGCAAGACTTCAGAAAACAGCTGGCAGAACTACA<br>GGATCTGGTGTCTGGTGTGTAAAATACTCTCCTCC<br>CTGTTCAAATGATTCAGAACATGTGCAAAGTGTGC<br>TAGCTTTCATCACATATACATAACAGCATTATGTA<br>TCAAGTTACCCTGTTCAAACAAGGAGCAGGCTTCC<br>TCTTTTTGACTTAAATGACATGAAGTGAGAAAAAA<br>AATGAGAATAACCNTCNNGGGAATTATAGAGGGTT<br>ATAATTCTATCCCNACTATTTCAATAAAAGCCATC<br>ACGGG | (SEQ ID NO: 327) |
| CTP309A | No significant match | | AAGCTTTCTCTGGCTTTCCGAAGGTAAAACTGTTG<br>CCGAAGTTGCTGCGTTACAAGAGCGTATCCCAGAA<br>ACCATAAGGCTACAACGCCGAAATTGGGAGCTACA<br>TCAGTTTGAATCGATTCAAGAAGGTCATCGCTCAG<br>GCCGTCCCAATACACTGACCTCAAACTATCAGGCT<br>CAAATCTTAGAGTGGGTCAACACAAGCCCACTCAA<br>TGCAGAACAAATCCGAGTCAAACTGCATGAAAAAC<br>ACGGTGTGTCCGTGTCTGTTGAAACTCTTCGCAAG<br>TTTTTGCGAGATTCAGGCATGGTCTTCAAACGCAC<br>CCGCCACAGCTTG | (SEQ ID NO: 328) |

TABLE 8

| Band # | Genbank Gene Name | Accession | Sequence | |
|---|---|---|---|---|
| CTP1D | No significant match | | GACTGAGACCATTTATTCNAGACACGCAGCTGACCAAGGAGTGAGG<br>GAGGGACGAGGTGTGCAAGCTAATAAATAGAGGAGGGGGAGACTTC<br>CTGGAGCTGTAGCCATTCAGTCTTCATTCTTCTCAGGCATGAAGGC<br>ATCTCTTTTCTGACCAAAGCTT | (SEQ ID NO: 329) |
| CTP1G | No significant match | | AAGCTTTGGTCAGCAATTATATTAGTTTGCATTTTAGTGACAGGTG<br>TAAGAGAAAGGCCCCTTCTTCCCTTACTGGGACAAATCTAGAAATC<br>TTACACAGATGTGCAAATAAAGCTCGCTGTGGTTC | (SEQ ID NO: 330) |
| CTP4B | No significant match | | GAGCAGCAGTGAGCAAAACCCACGAAGTTGTTTTAAGGTTACAGCT<br>ATGAATAAACATTGTCCAAACAATGAAGATTTAGGGCTGAAGAACG<br>AGCGTATGTCTACAGTCGAAGCTT | (SEQ ID NO: 331) |
| CTP7B | No significant match | | CAGGTGCAAGAGGTTTGTTTGGGAGGTAATCCTAGAAACCACAGAA<br>GGGGTGGGGATAGGAGGGATGGCAGGAAAACCAGTAAGAACTGTG<br>TTATTGAGAAGGTTATCACTGTGGACAACTGGCACAGAATACACTT<br>CAGAGCTGTCGCCCTGAGGGACAATGACGCCAAGGTCTTTTTCTCT<br>AAGTCCTGTTTCTTATAGGCCGAGGGTGGCTCCTGGGAGCAGTAAC<br>TGCCAACAGTCGAAGCTT | (SEQ ID NO: 332) |
| CTP8A | No significant match | | AAGCTTGATTGCCCATACCTGAGCCATTGATATATTTGAAAATTAT<br>GGCACAAATGGAAGAGAACCACATTTGAAAAGCTTCCAGCCTTTCA<br>ACAGAAGATAACTCTTCTTGTTTTGCAGATTGAGCAGATAATTTCT<br>TTTGAAGGTGATAGTTTCCTAAATTGGATAAAAACCGTGGCTGCCAT<br>TATATTCACAGAAAATAAAATGAAAACTTCAGTTAATTGTGGATTT<br>G | (SEQ ID NO: 333) |
| CTP17G | No significant match | | CATATATATTCTTTTTTATTTCTTGTTATACCTTCCCAAAACAGAG<br>ACATTCAACAGTAGTTAGAATGGCCATCTCCCAACATTTTAAAAAA<br>ACTGCACCCCCAATGGGTGAACAAAGTAAAGAGTAGTAACCTAGA<br>GTTCAGCTGAGTAAGCCACTGTGGAGCCTTAAGTGGTGAGGTCTTC<br>CAATTTCAGAGTGATGTGTCTTCAACTTGTATCATCATTTTAGCGG<br>TAAAAGCTT | (SEQ ID NO: 334) |

TABLE 8-continued

| Band # | Genbank Gene Name | Accession | Sequence | |
|---|---|---|---|---|
| CTP18B | No significant match | | CCAAAGAAGTGTTTATTAACATTTGGGGCCTCAGCGGGGCCAGAGA<br>GGAAGTGGGTGCTAGAGGCTCCTGAGGCTCAGGGCAAGGCCTGCAA<br>GACAGATCCCATTGCTCAGGAGGCAGCCCAGATTGCAAATGGAAGA<br>CAGG | (SEQ ID NO: 335) |
| CTP25D | No significant match | | AAGCTTGCACCATATATATAACTCTTGGGCAGAGGGTCTGGCATAC<br>ATAAGTAGATACTCAGAAATATCTGTTGGATTGTGTTGATTTAATT<br>ATTTTTTGTGTTGCTTCTTTTAAAGATGAGCACTTTCTATTAGATAT<br>TTTTTTGATCAAAAAAAAGATATTTTTTTGATCATACAGATTTAAG<br>CAGGATTTTTATTAATTCGTTTCTCTTCCTGGTTGG | (SEQ ID NO: 336) |
| CTP31A | No significant match | | GGGGCAGATAAAAACACTTAATGTAAAATTTACCCTCTCAGAAAAA<br>TTTCCAGTATGCTATACGGTATCACTAACTATAGTCACTATAGTAT<br>ACAGTAGATCCCTAGGATTTATTCATGATGTACAGTCGAAGCTT | (SEQ ID NO: 337) |
| CTP36A | No significant match | | CAAGTTTTACCATTGTTTTAATTATTGAAACAAAATTAACGTAAGT<br>AGAATCATGTGCAACAGTGTCTCTAACATATGGAAGAGGTAAATAT<br>GAATTTTATACAATAAGGTATATTATCCACTGTAACAAATTTCCAA<br>TAATTTGGCATTTATCTTTCACAAAATGTCTCCCAAATTCTAAGCA<br>AAGTATGCAAATTGGAGATTAACTCTAAACAGGCATAATTATCTTC<br>TTATCCAGTTTTTCTGAAGAGACTGAAGAGTTCAGGTCTGACCAAA<br>GCTT | (SEQ ID NO: 338) |
| CTP47G | No significant match | | AAGCTTGCACCATACTCCTCCTCTACATATGCTCCCAAATTACCTT<br>CTAAAAAGGCTGTATTAATTTACTTTCACCAGTAGTATTATGAGAG<br>TGCCCATGTCCCTTAGCCTTTTAAAATTCACTATGAGCAATCTTTA<br>AATCATGTACTAAATCTTATAGGCAAAGAATAGGGCCTTGCCCCTG<br>CCCCTGTT | (SEQ ID NO: 339) |
| CTP50A | No significant match | | ATTCCTTTTCCAAGGACCTCTCTTCTATGTGATCACTGAGTAAGTT<br>CAGTCACTCCCATCATCTCTAGATTGGAGATTTCCAAATTTATGGC<br>CTTTCCTAACTTTGAAGTCCTTATTTCTAACTGCCTACTAAGCTT | (SEQ ID NO: 340) |
| CTP52B | No significant match | | AAGCTTAGTAGGCAATAATAGAGAAGTAGAAATTGAATGTGGAACA<br>TTAACCATTAAAAATCATACTTTTGAATGTGCTGAGGTCATGAATT<br>GTTTTTACCTTCTTTGTAATTTGTGTTTTTCAGATTTTCTGTAGTT<br>AGCATATATTCTATAATCAGAAAAAAGATGCTTCAAGTTTTTTGCAG<br>ATTTCACAGAATTTTGTTT | (SEQ ID NO: 341) |
| CTP53A | No significant match | | AAACAAAATTCTGTGAAATCTGCAAAAAACTTGAAGCATCTTTTTC<br>TGATTATAGAATATCTGCTAACTACAGAAAATCTGAAAAACACAAA<br>TTACAAAGAAGATAAAAACAATTCATGACCTCAGCACATTCAAAAG<br>TATGATTTTTAATGGTTAATGTTCCACATTCAATTTCTACTTCTCT<br>ATTATTGCCTACTAAGCTT | (SEQ ID NO: 342) |
| CTP58A | No significant match | | AATTGTCACGAACAGGGCTGACTGACACTGCAGTGTGTCCTTGTTT<br>GTTGATCCCTGATCTAGGCCTCGGCTTTTCAAACTGCAGTTGATCA<br>AACTGGGATATGCTTCGGCTGAATCTGCTCTCTGGTGCTTCTCTTT<br>AATCGTTTTCTCCTTAAATGGGTTACTTTCTTACTAGGAAAAAAAA<br>AATGTTCCACCTCTGGAATTAACGTTGAGAAGCTT | (SEQ ID NO: 343) |
| CTP62A | No significant match | | AAGCTTGACTGTCGCATCAATGAATGTTTTAAGTAATAACTTTGC<br>TGGTTATCAGCTTGATGGTGCATTAATTTTTATGGCTCATTTCCTTT<br>ATTTTGACCATTGTCGGATTCTTCATTTTATATTGGACGATCCCCA<br>ATCGAACGGTACCAATTTTTTCAGCTGTGATTGCGGCATGTTTCAA<br>CGCGACCGTTTTTGAAATTTTAAAACATTTATTTGGCTGGGTCATG<br>AGTAATTTCACCAGCTATGAAATCGTTTATGGTGCTTTTGCAGCAG<br>TTCCTATTTTTCTACTTTGGATCTATCTGTCTTGGAATATCATTTT<br>ATTGGGTGTAGAAGTGAGTTATGCACTCACCGCCTTCCATTCTGGT | (SEQ ID NO: 344) |
| CTP63A | No significant match | | AGAATCAAGCCACCAGGTGTTTATTTTTGCACTATAAATAGAGTTC<br>CCTAGTCCCATTTTGTTACATAATATATGAGATAACAGAGAACCTA<br>AAATTCATTTGGTGAAAATCAAGTGTGTAGTATACCTAAATACCAA<br>TGAGCTAGTAAGACTTGTAAGGCACTGAAGCTAAGGCTAACAGCAA<br>CAGAGTCCTTTATGAAAATAATTTCAGAACCACAACGCATTCTCTG<br>ATGGTGCATTCCCCTGGGACAGTCGAAGCTT | (SEQ ID NO: 345) |
| CTP64B | No significant match | | CATCGCAGACATTTATTTTAGTTTTGTTAATTTCAAATATTCATTA<br>ACCTCTTGTATCAGATTTAAGGCAGAGAAAAGATACACGCCCCTGG<br>TTAACTGAACCGGGGTTTAGATAGTGTAGTCCACCCTGGGTTCCAC<br>CAGGGAGACCTCACCCGAGATGACAGGTCCGGTTGCTGGTGCACAG<br>TCGAAGCTT | (SEQ ID NO: 346) |
| CTP70A | No significant match | | AAGCTTAGTAGGCACGCAATAAATAGGAGAATGAATCAGAGTCCTC<br>CAACGCGTCCTCCCTAATGTCCCTTTGAGCTGCCTCCTCTTCCACT<br>CTGCCTCAGCTTGTCCATGTCACTTCGCTCCAGAGCAGCCGCAAGA<br>GCATCTTAACACCTTGTGGCCTGAACTCTCTCCCATCCTCCACTGT<br>ACAGTGATATGACTGAAACCTCATTTAACCTTTTAGAACTACCAGG<br>AGGAGGTTCCCAAGGATCCCAGG | (SEQ ID NO: 347) |
| CTP72B | No significant match | | CCATTTTTGCTCTTAAAGAGCATCTTAAGTGAGAGATCATGACAAT<br>CTTTGGCCACTCCAGGTTTTCTCATCTACTACATGATCTGTTCCCA<br>ACAATAAGCCATTGAAATTAAAGGTCTCCAGAAGTTTTATCTGGGG<br>TCTGTGATTGAAAAGAAGGAAAATGAGATGAGAGACTGCCTACTAA<br>GCTT | (SEQ ID NO: 348) |
| CTP73B | No significant match | | CCCATAAGAAACATCTTTAAAACATTCAGAATACTCAGGATAATCA<br>AGGCTAATATTCCTATAAATTCCTTACGTGTATTATGTACATTCAG<br>AAAAGTGTAAATTACTCAAATATTATACTCAAAACCCCTTATAGTC<br>TGCTAACTTGCATGTAGAAACATCTGAAGTAACATGCTGCCTACTA<br>AGCTT | (SEQ ID NO: 349) |

TABLE 8-continued

| Band # | Genbank Gene Name | Accession | Sequence | |
|---|---|---|---|---|
| CTP74A | No significant match | | AAGCTTAGTAGGCATCAATTGGATCCTTTCCTATGTTGAAATGGAA<br>GAATTAATGAGCTTACATTAATTAGTATTGTAATGTGTAAAGGAAG<br>CCCAGCAAAATTTTTTGAAAACTTGATGATCCCAACGTATTTACCA<br>TTGTATGTTAAAGCAAAATAAATCACCATTTTTTTA | (SEQ ID NO: 350) |
| CTP75C | No significant match | | AAGCTTCTCAACGGCCTCCACCTCCTTTCTGCCCTCACAGCCTCCT<br>GGCTCTGGCCCAAAAAGTGATTCATTTGTAAATTATCATGGTTTTC<br>TGCATTAAAATGGCCATTTCTGG | (SEQ ID NO: 351) |
| CTP76B | No significant match | | AAGCTTTTACCGCCATCTTGGCTCCTGTGGAGGCCTGCTGGGACCA<br>GGACTCCTAAAGCGACGANTTTTTNTGGAAGGCTTTGGTCCAAGGC<br>CATTTTTGCCGGCTATAAACGGGGTCTCCGGAACCAAAGGGAGCAC<br>ACAGCTCTTCTTAAAATTGAAGGTGTTTACGCCCGAGATGAAACAG<br>AATTCTATTTGGGCAAGAGATGCGCTTATGTATATAAAGCAAAAGA<br>ACAACACAGTCACTCCTGGCGGCAAACCAAACAAAACCAGNAGTCA<br>TCTGGGGAAAAGTAACTCTGGGCCCATGGAAACAAGTGGCATGNGT<br>TCCGTGCCAAATTCCGAAGCAATNTTCCTGCTAATGCCATTGGACA<br>CAGAATCCGAGTGATGCTGTACCCCTCANAGGATTTAAAACTAACG<br>AANAANCAATAAATAAATGTGGATTTGCGNTCTTNGG | (SEQ ID NO: 352) |
| CTP77D | No significant match | | CAATTGGTTTAGTTTTATTTCAAAATTGTACAAAATGGCCATAAGC<br>GGCTATAAAAAATTTCGTTTTCGGAACACGTGGAAATTCAGAAAGA<br>ACAACAAAGCAGGTTATCATTTCACAGTGTAATGGAAAAGCTCTCT<br>CTGAGGCAGGAATCACAACTCTTCCTTCTTCTTCCCCAGTCTCTCG<br>TGGTCTCCTTCCCGGAGCGCTCGAATGAAACTGGTAAACCCCGATT<br>CCGTCCGATCGC | (SEQ ID NO: 353) |
| CTP79B | No significant match | | CATATATATTCTTTTTTATTTCTTGTTATACCTTCCCAAAACAGAG<br>ACATTCAACAGTAGTTAGAATGGCCATCTCCCAACATTTTAAAAAA<br>ACTGCACCCCCCAATGGGTGAACAAAGTAAAGAGTAGTAACCTAGA<br>GTTCAGCTGAGTAAGCCACTGTGGAGCCTTAAGTGGTGAGGTCTTC<br>CAATTTCAGAGTGATGTGTCTTCAACTTGTATCATCATTTTAGCGG<br>TAAAAGCTT | (SEQ ID NO: 354) |
| CTP81A | No significant match | | CCAAAGAAGTGTTTATTAACATTTGGGGCCTCAGCGGGGCCAGAGA<br>GGAAGTGGGTGCTAGAGGCTCCTGAGGCTCAGGGCAAGGCCTGCAA<br>GACAGATCCCATTGCTCAGGAGGCAGCCCAGATTGCAAATGGAAGA<br>CAGGCCATGGTAGCGGTAAAAGCTT | (SEQ ID NO: 355) |
| CTP92A | No significant match | | GCACTAAATTCAAACCAATGACCTCCCATGTTCTAATTCTGATTGT<br>TTAATCCAACTGGGAGGGTAAACGGGAGACTCTTTGGCCTGTCAGT<br>GACAAAATGGTTTGTAAAAAAGAAAAAATAAATACGATATACAAGT<br>AAGTATAACTAGCACTCAAGCTT | (SEQ ID NO: 356) |
| CTP99A | No significant match | | AGCATATGTAAGATCTCTGGCTTGTAGAAGACAAGTTTATATAGCA<br>CTTAAAAAAACCATTTGTTACATTAAATGTCGAACTCAAACTTTTAA<br>AGAGTATAGAGAACTACAAAATGGAAAAAGGAAGCAGATATACGCT<br>TTATGAGGAAATTGTGTTAATGATCTCTCCTCTAAAAAAGGACTCT<br>TCCCTATTATCATAATGACCACACTGCCCGTCCTTAAAACCACTGG<br>TCGCTGACATTATGCCGAAGCTT | (SEQ ID NO: 357) |
| CTP103JJ | No significant match | | AAGCTTCGGCATAGTTACTGTTTGATTTTAAGTTTTTATATAGTTC<br>TTAGTTTTGAAGAAATCCTTCAAGAACAGTTTCTCTAAAGAGCATG<br>TTTTTAATTAAATGCTAATTAATTACCTTTCTTAGTTTTCCAATTTA<br>GTAGGCCACTTTCAATGTCTATTAAAGTGAAATAAACCTTCTGAAC<br>TTAAACATTTTTAAATCGATTAAAAATTGTGTCAAAAT | (SEQ ID NO: 358) |
| CTP104I | No significant match | | AAGCTTTTTTTTTTCAAAACGGATTTGTAAAAACTGTATTTCTTA<br>CACTGTGCACAAACCTTTTATACTAAATAAATATCAAACTACATTC<br>TTCAGAAAGATGTTTCTAGTATTTTTCTTAGGTCACTTCCATATGT<br>AGTATGTACAGTGAGACCACTTTTTAAAAAGCAATGACTTAGGCAA<br>ACCAACCCTAATGGTTTGTTAGACCATTTCCCTGTTTTTAATTAAA<br>AATCATAGGGTTGTGCTTCTGTATAAAGTTTGTACATTTCACAATG<br>TAAAATACTGACATT | (SEQ ID NO: 359) |
| CTP109P | No significant match | | ATGCAACCACACGGAATTTATTGAACATTTTCACAAGTGATTTCAT<br>TAAAGGAAGGCTTTTTCGTGCCTATATTGGTTACCATCACTTTTGC<br>CCCTATCACAATCTCATGGTGTAGTCCTTGCATGTAGCAGGAACTC<br>AACAAATGTCTGCTAAATTGACAGATGGAGCCCCAGACGACCTAAA<br>ACTTGCACTTTAGAAGCACTTACTTCATCCTGAGCTATTATGAATA<br>AGGAACTCAAGTGACTGTTAAAAGCATTCTACTGATGAGTTGGTAA<br>TGTTCTAAAGCAACATATCTCAAAGGAAAGGATATTGAGTTTGTCT<br>CCACCATAAAATCCTATTTTTAAACAAAGGTACTACTTAAAAATGG<br>TCTTCCAAAGGCCTCAGCAGAGGTTCTAAAGAGATGTGACAATATG<br>CCGAAGCTT | (SEQ ID NO: 360) |
| CTP110A | No significant match | | AACATATAAAAACATTTATTCACTAGGAATAATTGTGGCAGACACA<br>ATCCAGTCAAAGCAGCTCAATCCTGCTCAGTTAGGCTAGTTGAAGA<br>ACCATACTTTAAAAAAAGAAAGGAAGACAGGCAAACAAGTGTTTTA<br>CAGGAGCAACAGACTTCAAGGTCACCCCCACAAGACACCCTGCACA<br>GCAGGGACGGGGACAGGGAGGATGACCTCTTAGGGCCTGTGCCTTC<br>GCAGAGGTGCTCGGCGGATGGGTGTGGTCTTCTTGGGTGTCTCCTC<br>TTCTGTCATCTATGCCGAAGCTT | (SEQ ID NO: 361) |
| CTP111A | No significant match | | AAGCTTCGGCATAAACGATCCATTCTCCTCGGCCTCCCAAAGTGCT<br>AAGGTTCCAGGCGTGAACCACCATGCCCAGCCTGTTCTTTTTTTTA<br>TCTCTAGGTGGTGCTCTCCAGCTGTAGTAGAAATAGCATTTGTATT<br>GGATCTATTTTTTTAAATAGGGACTAAATACAGACCATTTTGTTAG<br>AGTGAAATGCCAAACAAGAACGAGATTTTTCTCTTGGCT | (SEQ ID NO: 362) |

TABLE 8-continued

| Band # | Genbank Gene Name | Accession | Sequence | |
|---|---|---|---|---|
| CTP116A | No significant match | | AAAAGAGCATACTTATCAGTTGAATGGGATAGAGGTTTTAGATAT<br>TTTCCAAAATATTTATAAAACACTTCATTGTTGAGAAATCACTTAC<br>AGAATGGTGGCTATCAAACAAATAATTATAAATTTTTAAAGCACAA<br>GTCACATGTTTTGTAACTCCTGTGTGAATTTATTTTAGCTGTGACA<br>TTTAATTGAAAACATCAGATATGTTTTGGAAAAGTCTTAATTTGAG<br>AACAACTGAAGGAAGTTAATCCAGAATCTATATGTAGTTAGCTATT<br>AATGATGATGCTTTATTGACAGTATATTGCTAATATATTTCTTCAT<br>GAAATCTGAAGTTAAATAGTTTCGTTGTGGAAATAGTGTCACTGTAA<br>CATTTCCCTTACGAAGTTCAATAAACCAGCTTTGCCATAAAAAAAA<br>AAGCTT | (SEQ ID NO: 363) |
| CTP124B | No significant match | | ATGGCAAAGCTGGTTTATTGAACTTCGTAAGGGAAATGTTACAGTG<br>ACACTATTCCACAACGAAATTATTTAACTTCAGATTTCATGAAGAA<br>ATATATTAGCAATATACTGTCAATAAAGCATCATCATTAATAGCTA<br>ACTACATATAGATTCTGGATTAACTTCCTTCAGTTGTTCTCAAATT<br>AAGACTTTTCCAAAACATATCTGATGTTTTCAATTAAATGTCACAG<br>CTAAAATAAATTCACACAGGAGTTACAAAACATGTGACTTGTGCTT<br>TAAAAATTTATAATTATTTGTTTGATAGCCACCATTCTGTAAGTGA<br>TTTCTCAACAATGAAGTGTTTTATAAATATTTTGGAAAATATCTAA<br>AACCTCTATCCCCATTCAACTGATAAGTATGCTCTTTTAAAAAAAA<br>AAAGCTT | (SEQ ID NO: 364) |
| CTP126A | No significant match | | AAAGAAAGTAATTATGGAACTAGATTTTTAACATTGTAAAATACTA<br>AATGATCCTTCAGTTGTAAGTTGATATATATTTGTAACCTTTGTGA<br>AATTGTATCCTTATGAAAATACCACTTTTGTGGAAGAGAGAATCCA<br>ACTATGTAATATTTAATTAAAACAATCCATGTTTACCCTATCCCTG<br>CTCAATTAAACAGTGTATATAGGTCTAATAATAGCTCTGGAGCAAC<br>TTTTATCATGAGTCAAATATATTAAACACATTGATGTCTTCTTGGT<br>ATATCTGAAAACAAGAGGTAGAAGTCCTGTTGAGAGTCTTTAAAAT<br>AAACTATTTTTACAAATGTAAAAAAAAAAAGCTT | (SEQ ID NO: 365) |
| CTP133B | No significant match | | CCAAAAAGAGCCATGCCCAGAGGGAAAGTTGGAAACGAAAGCCAAG<br>TTTTCATTTAAAAGGAAACANTAAAGAGGTTAGCCAGAGAAACTTG<br>AACCAAAGAAAAGACAGCACGCTGTTCAGAATGGTCAATAAGAGCC<br>TAAAACGGTACCCTCGGAATGAAGCTT | (SEQ ID NO: 366) |
| CTP134A | No significant match | | CCAAAAAGAGCCATGCCCAGAGGGAAAGTTGGAAACGAAAGCCAAG<br>TTTTCATTTAAAAGGAAACATTAAAGAGGTTAGCCAGAGAAACTTG<br>AACCAAAGAAAAGACAGCACGCTGTTCAGAATGGTCAATAAGAGCC<br>TAAAACGGTACCCTCGGAATGAAGCTT | (SEQ ID NO: 367) |
| CTP143B | No significant match | | AAGATTTCAAAGAGTGAGCAAGTGCATTAGCAGGGCAGAGAGAGAG<br>GCAGCAGCAGACTCCCTGCTGAGCTGGGAGCCAACTTGGGACTCGA<br>TGCCGGGACCCCAGGATCATTACCCGAAGCTT | (SEQ ID NO: 368) |
| CTP144B | No significant match | | GGGTAAATCCGTCCAGTTTACTGTAAATATGCCTTTGACAAACTGG<br>TAACTCATGTCCCATCCCAGTCCCGAGTACTGGACCAGGGAAACTC<br>CAGCCACAGTTGAGGGAAGGCCACCTGTTGGCTCTGGGGCAGCAGG<br>TCATCCAGTGGGCTTCAGGAGTCACCAGGCCTCTGACCAGTTCCTC<br>CCCACCAAGCAGTTTCAGATTGTCCGCCAAGTCTATTTCACACCT<br>CTCGTGTATGCCGAAGCTT | (SEQ ID NO: 369) |
| CTP145B | No significant match | | GGACTGATAATAATAGGATTTTATTTCTAAAATTTATCTTAGAGCT<br>TTCAAAGAGTATAACACACAGATCTTTACCACCACACCCCCCTTGC<br>CTATACAGGAAACAACCAAGTTGTGAGAACATTTATCATGCACAGA<br>CACATCAGGGCTTGCAGGTGCTACACAGGAATCACAAATGCTGTTC<br>CACATCATGTCTTCTGTTATGCCGAAGCTT | (SEQ ID NO: 370) |
| CTP149B | No significant match | | AGGAAGAATAAAAACATATAAAAACATTTATTCACTAGGAATAATT<br>GTGGCAGACACAATCCAGTGAAAGCAGCTCAATCCTGCTCAGTTAG<br>GCTAGTTGAAGAACCATACTTTAAAAAAAGAAAGGAAGACAGGCAA<br>ACAAGTGTTTTACAGGAGCAACAGACTTCAAGGTCACCCCCACAAG<br>ACACCCTGCACAGCAGGGACGGGGACAGGGAGGATGACCTCTTAGG<br>GCCTGTGCCTTCGCAGAGGTGCTCGGCGGATGGGTGTGGTCTTCTT<br>GGGTGTCTCCTCTTCTGTCATCTATGCCGAAGCTT | (SEQ ID NO: 371) |
| CTP150A | No significant match | | AGCATATGTAAGATCTCTGGCTTGTAGAAGACAAGTTTACATAGCA<br>CTTAAAAAACCATTTGTTACATTAAATGTCGAACTCAAACTTTTAA<br>AGAGTATAGAGAACTACAAAATGGAAAAAGGAAGCAGATATACGCT<br>TTATGAGGAAATTGTGTTAATGATCTCTCCTCTAAAAAAGGACTCT<br>TCCCTATTATCATAATGACCACACTGCCCGTCCTTAAAACCACTGG<br>TCGCTGACATTATGCCGAAGCTT | (SEQ ID NO: 372) |
| CTP154A | No significant match | | AGCATATGTAAGATCTCTGGCTTGTAGAAGACAAGTTTATATAGCA<br>CTTAAAAAACCATTTGTTACATTAAATGTCGAACTCAAACTTTTAA<br>AGAGTATAGAGAACTACAAAATGGAAAAAGGAAGCAGATATACGCT<br>TTATGAGGAAATTGTGTTAATGATCTCTCCTCTAAAAAAGGACTCT<br>TCCCTATTATCATAATGACCACACTGCCCGTCCTTAAAACCACTGG<br>TCGCTGACATTATGCCGAAGCTT | (SEQ ID NO: 373) |
| CTP164A | No significant match | | AAGCTTCGGCATACGGTGTGAGGTTACAGTCCAGTTTTGTGTGCTT<br>TACTACACGGTTTGGTTACAGGACTTCTGTGCATTGTAAAACATAA<br>ACAGCATGGAAAAGGTTAAATACCTGTGTGCAGATTGTAAGATCTG<br>GTCCGGACTTGCTGTGTATATTGTAACGTTAAGTGAAAAAGAACCC<br>CCCTTTGTATCATAGTCATGCGGTCTTATGTATGATAAACAGTTGA<br>ATAATTTGTCCTCGACTCTTTACTATGCTTTTTTAAAATTAAGAA<br>AAATGTAAATATAGTAAAAAATCTTCCTATGCAATTAACCTGG | (SEQ ID NO: 374) |

TABLE 8-continued

| Band # | Genbank Gene Name | Accession | Sequence | |
|---|---|---|---|---|
| CTP179K | No significant match | | AAGCTTACCAGGTAGAGGGACTGTTGGAGGTATGGACGCACACAGG<br>AGGGCCAGGCCAAGGCACGAGTTTTTCACTGAAGGGGGTAAAGCAT<br>CACAATTTAAAATGTTTGCAATTAAACTGGTTTGTTAAATATC | (SEQ ID NO: 375) |
| CTP185C | No significant match | | CAGCGAAGAGGCATTAAAGATTCATGCCATAAGTTTATTTACAAAC<br>ATGTTGTGTATGTTGAATTCAAGAGATTGATCCATTTTTCAGAGAC<br>TGCACCTCTTAAAATGTTCCTTTTCACATCTGTTTAGTGGATCAAA<br>AGCTT | (SEQ ID NO: 376) |
| CTP197A | No significant match | | ATGGTGTGTGTGTGGGTTCAAATAGTTTATTCACCTCTGTAGTGGA<br>AAAACAAGGAGAAATAAAATCTGCTTACAATGGCCAAAATTTATGG<br>AGAAGCCCTAAAGTTGCTTTCCCCAAATCACAAATCTGATTCAAGA<br>GAAGGAAAAAAATGATGAAAACATCTCATCACACAAAACTCAGTG<br>TGGTGTCTCTGATAGTCATCAGCCAGCAGAAGCTT | (SEQ ID NO: 377) |
| CTP202C | No significant match | | AGAAAAAAAATTGATAATTAGGTGCAGATAGAAAATATGAATTAGA<br>AGAGGTTAATTCAAGTGATCAGCCTGAAAGTTCAGCTTCATTAGCT<br>TTGTGGTAAATCCACCACTTCAGATAGTAACTAAAGTAAATTTTAA<br>ATTTCATAAGAATAAAGTAATCCCTGAAAAGAATTCACTTTTTTCC<br>CAGAAGAAGCTTATAATTAAAAAAAAAAAGCTT | (SEQ ID NO: 378) |
| CTP208B | No significant match | | CTAGAGGAAGTGCTTTTTATTTTTAGATCAACCAAACATATTTAAT<br>ATAAAAACCTTTTAATATACAAACTGTAATCACAATTGCATCCACG<br>TAGCAGCGAGGGAATGGGGTGTTGCAGGAAGCTT | (SEQ ID NO: 379) |
| CTP215B | No significant match | | AAGCTTAGAGGCAGTAAACAGGAGCGTCCCCAAGAAAAAGAGGAAA<br>TTCTCTTCTAAGGAGGAGCCACTTAGCAGTGGACCTGAAGAGGCTG<br>CTGGCAACAAGAGCGGCAGCTCCAAGAAAAAGAAAAAGCTCCAGAA<br>GCTATCCCAGGAAGATTAGAATGGACATTTTACCAGGTGGGCAAA<br>CCCACATGATTCCAAACCCACCCTTATATCCCAATAAAAACAAATT<br>CACAGG | (SEQ ID NO: 380) |
| CTP222D | No significant match | | AAGCTTACCAGGTGAAGAGTGGGGTTGTCATGACCTTGGCTATGAC<br>GCCCAGCATTTCGAGGTGGCTCCCTCTATTCTTTACTTTGGGCATC<br>ATAGAAAACGTGTCTCTGGGGATTAATCTTAGAGAAAAATAAAGC<br>CTTTCTGCTG | (SEQ ID NO: 381) |
| CTP306B | No significant match | | AAGCTTCTGCTGGTATGGAAAGCCTTCAAGGAAGAGGGTAATGAGG<br>GGGAAGAAGTGCTGTGCCAAAGTGACAGCATTCAGTGAGGAATAAA<br>GAAAGGAGCTCAGTGGTAGCAGGATGTTGAGCTTCCAAGAAAATCT<br>GGTGGTGGTGAGAAAGTGGCTGCTGTGCACTGCAAGGAAACAGAGC<br>GATTAAAGAAAGAGATGTGACAGGGTAGGTGGAAGAGATAGCCAGA<br>AGTTAGAAATGGGTTACACTGAAGAAGTAAATTATTTGATTAAACA<br>ATAAGTAAATATACTGGGGATAACAAAAGCCTGATTTCTCCACTGT<br>CTCAGAAGGGATTTGCAAGTATGG | (SEQ ID NO: 382) |
| CTP308KK | No significant match | | AAGCTTTCTCTGGATGAACAGTTAAATGGAACCTGGAAACCTCTTC<br>CTGGGATTATTCCTTAAGCAAGGCAGTGTCAAAGGCAACCCTCCCA<br>GCAAGACTTCAGAAAACAGCTGGCAGAACTACAGGATCTGGTGTCT<br>GGTGTGTAAAATACTCTCCTCCCTGTTCAAATGATTCAGAACATGT<br>GCAAAGTGTGCTAGCTTTCATCACATATACATAACAGCATTATGTA<br>TCAAGTTACCCTGTTCAAACAAGGAGCAGGCTTCCTCTTTTTGACT<br>TAAATGACATGAAGTGAGAAAAAAAATGAGAATAACCNTCNNGGGA<br>ATTATAGAGGGTTATAATTCTATCCCNACTATTTCAATAAAAGCCA<br>TCACGGG | (SEQ ID NO: 383) |
| CTP309A | No significant match | | AAGCTTTCTCTGGCTTTCCGAAGGTAAAACTGTTGCCGAAGTTGCT<br>GCGTTACAAGAGCGTATCCCAGAAACCATAAGGCTACAACGCCGAA<br>ATTGGGAGCTACATCAGTTTGAATCGATTCAAGAAGGTCATCGCTC<br>AGGCCGTCCCAATACACTGACCTCAAACTATCAGGCTCAAATCTTA<br>GAGTGGGTCAACACAAGCCCACTCAATGCAGAACAAATCCGAGTCA<br>AACTGCATGAAAAACACGGTGTGTCCGTGTCTGTTGAAACTCTTCG<br>CAAGTTTTTGCGAGATTCAGGCATGGTCTTCAAACGCACCCGCCAC<br>AGCTTG | (SEQ ID NO: 384) |

TABLE 9

| Band # | Genbank Gene Name | Expression Pattern |
| --- | --- | --- |
| CTP1D | No significant match | upregulated with Etoposide, caffeine and aspirin |
| CTP1G | No significant match | upregulated with Etoposide, caffeine and aspirin |
| CTP3B | *Homo Sapien* N-myc dow BC003175 | doublet-larger band is upregulated etoposide, caffeine and aspirin, the smaller band is upregul |
| CTP4B | No significant match | upregulated in Caffeine treated |
| CTP7B | No significant match | upregulated in Etoposide treated |
| CTP8A | No significant match | repressed in Etoposide treated |
| CTP8C | Human DNA sequence fn HSJ734P14 | repressed in Etoposide treated |
| CTP10Y | *Canis familiaris* mitochon CFU96639 | upregulated in Etoposide treated |
| CTP11A | cyclin-dependent kinase i BC001935 | upregulated in Etoposide treated |
| CTP16B | *Homo sapiens* cDNA FLJAK000548 | repressed in Etoposide treated |
| CTP17G | No significant match | repressed in Etoposide treated |
| CTP18B | No significant match | upregulated in Etoposide treated |
| CTP19F | *Homo sapiens* chromosor AC008651 | upregulated in Etoposide treated |
| CTP20B | *Bos taurus* ribosomal prol AF063243 | upregulated in Caffeine treated |
| CTP21A | *Rattus norvegicus* ribosor NM_022506 | upregulated in Caffeine treated |
| CTP22C | *Canis familiaris* mRNA for AJ388512 | upregulated in Caffeine treated |
| CTP25D | No significant match | repressed with caffeine and aspirin |
| CTP26A | *Canis familiaris* chymase U89607 | repressed with caffeine and aspirin |
| CTP26B | *H. sapiens* cycA gene for X68303 | repressed with caffeine and aspirin |
| CTP27C | *Homo sapiens* CTCL turn AF177227 | repressed with etoposide and aspirin |
| CTP28D | *Homo sapiens* upstream INM_014517 | repressed in carboplatin |
| CTP30E | *Homo sapiens* BAC clone AC003083 | repressed in carboplatin |
| CTP31A | No significant match | upregulated in cisplatin |
| CTP32D | cDNA FLJ14795 fls, clone AK027701 | repressed with caffeine and aspirin |
| CTP34A | *Homo sapiens* ribosomal NM_001032 | repressed in Etoposide |
| CTP36A | No significant match | upregulated in Caffeine |
| CTP37A | *Homo sapiens* nuclear fax AF167569 | repressed with etoposide |
| CTP41B | *Homo sapiens* mRNA for AB037813 | repressed in cisplatin |
| CTP47G | No significant match | induced with cisplatin |
| CTP50A | No significant match | induced with cisplatin |
| CTP51A | *Homo sapiens* intestinal 1 AF219991 | induced with cisplatin |
| CTP52B | No significant match | induced with cisplatin |
| CTP53A | No significant match | induced with cisplatin |
| CTP58A | No significant match | repressed with carboplatin |
| CTP59A | *Homo sapiens* cyclin D2 (XM_012143 | induced with cisplatin |
| CTP60B | *Homo sapiens* RNA bindii XM_016120 | repressed with carbo and trans platin |
| CTP61D | prion protein [mink, Geno S46825 | repressed with carbo and trans platin |
| CTP62A | No significant match | induced with cisplatin |
| CTP63A | No significant match | induced with cisplatin |
| CTP64B | No significant match | induced with cisplatin |
| CTP65A | Pig mRNA for endoplasm X16951 | repressed with carbo and trans platin |
| CTP67A | clone RP5-1071L10 on cl AL133228 | repressed with cisplatin |
| CTP68F | *Oryctolagus cuniculus* Ne U09823 | repressed with cisplatin |
| CTP70A | No significant match | repressed with cisplatin |
| CTP71A | *Canis familiaris* caveolin- U47060 | induced with carboplatin |
| CTP72B | No significant match | repressed with cisplatin |
| CTP73A | *Homo sapiens* chromosor AC026201 | repressed with cisplatin |
| CTP73B | No significant match | repressed with cisplatin |
| CTP74A | No significant match | repressed with carbo, trans and cisplatin |
| CTP75C | No significant match | repressed with carbo, trans and cisplatin |
| CTP76B | No significant match | induced with cisplatin |
| CTP77D | No significant match | repressed with cisplatin |
| CTP78B | *Homo sapiens* SON DNA XM_009738 | induced with cisplatin |
| CTP79B | No significant match | induced with cisplatin |
| CTP80A | *Homo sapiens* WDR4 ger AB039887 | repressed with cisplatin |
| CTP81A | No significant match | induced with cisplatin |
| CTP85D | *Homo sapiens* Rho-assoc XM_008814 | repressed with carbo, trans and cisplatin |
| CTP86F | *Homo sapiens* chromodoi NM_001272 | induced with cisplatin |
| CTP87B | *Homo sapiens* tetratricopi XM_009760 | induced with cisplatin |
| CTP88A | *Rattus norvegicus* ribosor NM_022506 | repressed with cisplatin |
| CTP89B | *Homo sapiens* genomic [AP003473 | induced with cisplatin |
| CTP90A | *Homo sapiens* clone 248(AF070622 | induced with cisplatin |
| CTP92A | No significant match | induced with cisplatin |
| CTP92C | Human DNA sequence fn AL133286 | induced with cisplatin |
| CTP93F | clone RP1-211D12 on ch Z93016 | induced with cisplatin |

TABLE 9-continued

| Band # | Genbank Gene Name | Expression Pattern |
|---|---|---|
| CTP94B | *Homo sapiens* clathrin, h NM_008305 | induced with cisplatin |
| CTP99A | No significant match | repressed with cisplatin |
| CTP100A | COX15 (yeast) homolog, BC002382 | induced with cisplatin |
| CTP103JJ | No significant match | induced with cisplatin |
| CTP104I | No significant match | repressed with cisplatin |
| CTP109P | No significant match | induced with cisplatin |
| CTP110A | No significant match | induced with cisplatin |
| CTP111A | No significant match | induced with cisplatin |
| CTP112B | *Bos taurus* peroxiredoxin AF305561 | induced with cisplatin |
| CTP113A | *Box taurus* ribosomal proi AF063243 | induced with cisplatin |
| CTP115B | *Homo sapiens* chromosoi AC005899 | induced with cisplatin |
| CTP116A | No significant match | induced with cisplatin |
| CTP117B | *Homo sapiens* similar to XM_017740 | induced with cisplatin |
| CTP119J | *H. sapiens* SPR-2 mRNA 1X68560 S52 | induced with cisplatin |
| CTP121D | Human ribosomal protein U43701 | induced with cisplatin |
| CTP122I | Human mRNA for KIAA0(D26067 | repressed with carbo and transplatin |
| CTP124B | No significant match | induced with cisplatin |
| CTP126A | No significant match | induced with cisplatin |
| CTP129A | *Homo sapiens,* Similar to BC007583 | induced with transplatin |
| CTP131B | *Homo sapiens* similar to s XM_006087 | induced with cisplatin |
| CTP133B | No significant match | induced with cisplatin |
| CTP134A | No significant match | induced with cisplatin |
| CTP135A | *Homo sapiens* cDNA FLJAK021570 | induced with cisplatin |
| CTP143B | No significant match | induced with etoposide and caffeine |
| CTP144B | No significant match | repressed with caffeine and aspirin |
| CTP145B | No significant match | repressed with aspirin |
| CTP148B | *Homo sapiens* serine-thre AF108830 | induced with aspirin |
| CTP149B | No significant match | induced with caffeine |
| CTP150A | No significant match | repressed with etoposide |
| CTP150C | *Canis familiaris* mitochon CFU96639 | repressed with etoposide |
| CTP154A | No significant match | induced with caffeine |
| CTP156J | Human DNA sequence fn AL136120 | induced with etoposide and caffeine |
| CTP161B | *Canis familiaris* TCTA ger AJ012166 | induced with aspirin |
| CTP164A | No significant match | induced with aspirin |
| CTP178B | *Homo sapiens* mRNA for AB040957 | induced with carboplatin |
| CTP179K | No significant match | induced with carboplatin |
| CTP185C | No significant match | induced with carbo and trans platin |
| CTP197A | No significant match | induced with carboplatin |
| CTP201B | *Homo sapiens,* exostoses BC001174 | induced with carboplatin |
| CTP202C | No significant match | induced with carboplatin |
| CTP205D | *Homo sapiens* similar to XM_011187 | induced with carboplatin |
| CTP206A | *Homo sapiens* fatty acid c NM_013402 | repressed with carbo and transplatin |
| CTP208B | No significant match | induced with transplatin |
| CTP215B | No significant match | induced with aspirin |
| CTP216A | *Canis familiaris* heat-shoc U19368 | repressed with etoposide |
| CTP222D | No significant match | induced with aspirin |
| CTP300B | *Homo sapiens* utrophin (I-NM_007124 | repressed with cisplatin |
| CTP304B | *Homo sapiens* unknov XM_002211 | induced with cisplatin |
| CTP306B | No significant match | induced with cisplatin |
| CTP308KK | No significant match | induced with cisplatin |
| CTP309A | No significant match | repressed with cisplatin |

TABLE 10

| | | | |
|---|---|---|---|
| 1-chloro-2-nitrobenzene | chloroquine | guanine | progesterone |
| 1-naphthylisothiocyanate | chlorpromazine | haloperidol | puromycin |
| 2,4-dinitrophenol | cimetidine | hexobarbital | quinidine |
| 2-acetylaminofluorene | cisplatin | hydroxyurea | reserpine |
| 2-azido-2-deoxycytidine | clenbuterol | indomethacin | rezulin |
| 2-azido-2-deoxyuridine | clofibrate | iodoacetamide | rifampicin |
| 4-acetamidofluorene | clozapine | isoniazid | rifampin |
| 5-azacytidine | colchicine | isonicotinic acid | rosiglitazone |
| 5-chlorouracil | cycloheximide | ketoconazole | Simvastatin |
| 5-fluorouracil | cyclophosphamide | lipopolysaccharide | sodium azide |
| 6-mercaptopurine | cyclosporin A | Lovastatin | streptozotocin |
| 6-thioguanine | cyclosporin G | mechlorethamine | sulfamethoxazole |
| acetamidofluorene | Cyclosporin H | melatonin | sulfisoxazole |
| acetaminophen | cytosine arabinoside | melphalan | tacrine |
| acetylsalicylic acid | dacarbazine | merbarone | tamoxifen |
| acridine | DEHP | methapyriline | TCDD |
| actinomycin | dexamethasone | methocel | tetracyclin |
| aflatoxin B1 | dieldrin | methotrexate | thalidomide |
| allyl alcohol | diethylhexylpthalate | methyl methanesulfonate | theophylline |
| aminopterin | diethylstilbestrol | mitomycin C | thioguanine |
| aminotriazole | diflunisal | mitoxantrone | transplatin |
| amphotericin B | diflunisol | naloxone | triamcinolone |
| ampicillin | digitoxin | naproxen | triethylenemelamine |
| amsacrine | dimethylhydrazine | nicotine | triethylenethiophosphoramide (S-TEPA) |
| ANIT | dimethylnitrosamine | nifedipine | troglitazone |
| antimycin A | DL-ethionine | nitrofurantoin | trovan |
| antipyrine | D-Mannitol | N-nitroso-N-ethylurea | Valproic Acid |
| Aspirin | DMBA | N-nitroso-N-methylurea | verapamil |
| Atorvastatin | DMSO | oligomycin | Wy-14643 |
| azathioprine | doxorubicin | o-toluidine | |
| Benz[a]pyrene | endotoxin | oxymetholone | |
| benzene | erythromycin | paclitaxel | |
| benzo(a)pyrene | erythromycin estolate | paracetamol | |
| bleomycin | estradiol | PEG 300 | |
| bromobenzene | ethanol | Penicillin | |
| busulfan | ethinyl estradiol | phenobarbital | |
| cadmium chloride | ethionine | phenylhydrazine | |
| caffeine | ethyl methanesulfonate | phenytoin | |
| camptothecin | etomoxir | phorbol 12-myristate 13-acetate diester | |
| carbamazepine | etoposide | pioglitazone | |
| carbon tetrachloride | fenofibrate | polyethylene glycol | |
| carboplatin | flufenamic acid | prednisolone | |
| carmustine | ganciclovir | prednisone | |
| chlorambucil | gemfibrozil | pregnenolone-16-alpha-carbonitrile | |
| chloroform | gentamicin | proflavin | |

TABLE 11

| Genes | Acetaminophen, 10198, Canine Liver, 300 mg/kg, 10 days | Acetaminophen, 10188, Canine kidney, 300 mg/kg, 2 days | Acetaminophen, 10318, Canine liver, 300 mg/kg, 10 day | Acetaminophen, 10185, Canine kidney, 300 mg/kg, 2 days | Amphoteracin B, 10190, Canine kidney, 0.8 mg/kg, 2 days | Amphoteracin B, 10197, Canine Liver, 0.8 mg/kg, 2 days | Amphoteracin B, 10317, Canine liver, 0.8 mg/kg, 2 day | Amphoteracin-B, 10187, Canine kidney, 0.8 mg/kg, 2 days | Erythromycin estolate, 10080, canine kidney, 100 mg/kg, 10 days |
|---|---|---|---|---|---|---|---|---|---|
| Alkaline phosphatase | 1.4 | 1.2 | -1.4 | 1.4 | 1.5 | 1.4 | -1.1 | 1.2 | -1.0 |
| Angiopoietin-related protein 3 (ANGPTL3) | -1.1 | -1.0 | -1.4 | 1.4 | -1.1 | 1.0 | -1.8 | 1.2 | 1.0 |
| Beta-glucuronidase | 1.1 | 1.1 | -1.4 | 1.1 | 1.3 | 1.6 | -1.1 | 1.1 | 1.1 |
| BR-cadherin | 1.4 | -2.0 | 1.1 | -1.0 | -1.0 | 1.2 | -1.0 | 1.2 | -1.1 |
| BRCA1 | 1.2 | -1.5 | -1.0 | -1.2 | 1.1 | 1.4 | -1.1 | 1.0 | 1.2 |
| c-erb B-2 | 1.3 | 2.0 | -1.1 | 1.0 | 1.3 | 1.3 | 1.0 | -1.1 | 1.4 |
| Canis familiaris mitochondrion, complete genome | 1.2 | -5.7 | 1.3 | -1.8 | -1.4 | -1.2 | -1.2 | -1.5 | -1.4 |
| Catalase | 1.2 | 1.2 | -1.2 | 1.5 | 1.1 | 1.2 | -1.3 | 1.6 | -1.1 |
| Caveolin-1 | -1.3 | 1.4 | -1.1 | 1.2 | 1.0 | -1.1 | -1.1 | 1.2 | 1.3 |
| Caveolin-2 | 1.0 | -2.0 | -1.0 | 1.9 | 1.0 | -1.2 | -1.2 | 2.1 | -1.4 |
| CD40 ligand | 1.1 | 1.1 | -1.0 | 2.4 | 1.4 | 1.2 | 1.1 | 2.2 | -1.1 |
| Cubilin | 1.1 | 1.0 | 1.0 | -1.3 | -1.2 | 1.1 | 1.1 | -1.1 | -1.3 |
| Cytochrome c oxidase subunit II | 1.2 | -4.0 | 1.5 | -1.5 | -1.5 | -1.3 | -1.1 | -1.3 | -1.2 |
| Cytochrome c oxidase subunit VIIaL | 1.1 | -2.0 | -1.0 | -1.4 | -1.1 | 1.0 | -1.1 | -1.3 | -1.2 |
| Cytochrome P450 2B | -1.4 | 1.3 | -2.3 | 1.1 | 1.2 | -3.0 | -2.5 | 1.1 | -1.0 |
| Cytochrome P450 2C21 | 1.2 | -1.1 | -1.2 | -1.3 | -1.1 | 1.2 | 1.0 | -1.2 | 1.1 |
| Cytochrome P450 2C41 | -1.9 | 1.4 | 1.6 | 1.4 | 1.2 | -1.6 | 1.6 | 1.6 | 1.2 |
| Cytochrome P450 2D | -1.4 | 1.0 | -2.0 | 1.4 | -1.2 | -1.4 | -1.2 | 1.2 | 1.5 |
| Cytochrome P450 3A | 1.7 | 1.6 | 1.1 | 1.5 | 1.3 | 1.3 | -1.2 | 1.2 | 1.3 |
| Decorin | -1.1 | -1.0 | -1.6 | -1.1 | -1.0 | -1.1 | -1.4 | -1.1 | 1.1 |
| FGFR2 | 1.0 | 1.0 | -1.0 | -1.2 | -1.1 | -1.0 | 1.1 | -1.3 | -1.2 |
| Gadd45 | 1.6 | 1.7 | 1.6 | -1.3 | 1.2 | 2.0 | 1.9 | -1.2 | 1.0 |
| Glucose transporter | 1.3 | 1.6 | -1.1 | 1.4 | 2.0 | 1.3 | -1.0 | 1.3 | 1.1 |
| Glucose-6-phosphatase | -1.1 | -1.5 | -1.1 | -1.2 | 1.3 | -1.1 | -1.1 | -1.2 | -1.2 |
| Glucose-regulated protein 94 #1 | 1.1 | -1.0 | -1.4 | 1.1 | -1.2 | -1.3 | -1.0 | 1.2 | 1.4 |
| Glucose-regulated protein 94 #2 | 1.7 | -1.8 | 1.0 | -1.0 | 1.5 | 1.5 | 1.2 | 1.1 | -1.1 |
| Glutathione S-transferase alpha subunit | 1.9 | 1.0 | 1.1 | 1.9 | 1.9 | 1.4 | -1.1 | 1.8 | 1.1 |
| GRP94 | 1.4 | 2.0 | 2.0 | -1.0 | 1.1 | -1.0 | -1.3 | 1.2 | -1.0 |
| Heat shock protein 27 | -1.5 | 3.3 | 1.0 | 1.1 | -1.2 | -1.5 | 1.4 | 1.2 | -1.1 |
| Histidine ammonia-lyase | -1.4 | 1.1 | -2.0 | 1.2 | -1.3 | -1.5 | -1.0 | -1.0 | -1.0 |
| Interleukin-10 | 1.4 | 1.7 | -1.1 | 5.3 | 1.1 | 1.2 | -1.1 | 5.9 | -1.0 |
| Interleukin-8 | -1.1 | -1.3 | -1.5 | 1.2 | 1.2 | -1.0 | -1.4 | 1.2 | -1.0 |
| Keratinocyte growth factor | -1.1 | -1.4 | -1.1 | 1.6 | -1.0 | -1.1 | -1.2 | 1.6 | -1.1 |
| Mek5 | 1.1 | -1.4 | 1.2 | 1.1 | 1.2 | 1.7 | 1.1 | -1.2 | -1.1 |
| Metallothionein 1 | 1.4 | -2.1 | 1.0 | 2.5 | 2.1 | 1.4 | -1.0 | 3.1 | -1.1 |
| Multidrug resistant protein-1 | 1.4 | 1.4 | -1.1 | -1.2 | 1.2 | 1.0 | 1.1 | -1.2 | 1.2 |
| N-cadherin | 1.6 | 1.3 | 1.2 | -1.3 | -1.0 | 1.1 | 1.0 | -1.1 | 1.1 |
| p38 MAPK | -1.3 | -2.4 | -1.4 | -1.1 | 1.2 | -1.1 | 1.1 | -1.0 | 1.4 |
| p53 | 1.6 | 1.3 | 1.0 | 1.2 | 1.4 | 1.5 | -1.1 | 1.2 | -1.6 |
| Paraoxonase2 (PON2) | 1.3 | -1.4 | 1.1 | 1.9 | -1.0 | 1.2 | -1.3 | 2.1 | -1.2 |
| Phase-1 CCT-1 | 1.1 | -2.8 | 1.2 | -1.2 | -1.3 | -1.3 | 1.0 | -1.1 | -1.2 |
| Phase-1 CCT-10 | 1.1 | -2.2 | -1.0 | -1.0 | 1.0 | 1.0 | -1.2 | -1.3 | -1.3 |
| Phase-1 CCT-11 | 1.1 | -1.7 | 1.2 | 1.1 | 1.3 | 1.2 | 1.1 | 1.1 | -1.0 |

TABLE 11-continued

| | | | | | | | | |
|---|---|---|---|---|---|---|---|---|
| Phase-1 CCT-12 | -1.3 | 1.3 | -1.0 | 1.4 | -1.1 | -1.3 | 1.1 | 1.3 | 1.1 |
| Phase-1 CCT-13 | -1.1 | 1.7 | 1.0 | 2.4 | 1.0 | -1.1 | 1.0 | 2.3 | 1.0 |
| Phase-1 CCT-14 | -1.2 | -1.7 | 1.1 | 1.0 | 1.2 | -1.0 | 1.1 | 1.1 | 1.0 |
| Phase-1 CCT-15 | -1.1 | 1.2 | -1.0 | 1.4 | -1.0 | -1.2 | 1.0 | 1.2 | -1.0 |
| Phase-1 CCT-16 | -1.2 | 1.2 | -1.0 | -1.1 | 1.1 | 1.0 | 1.0 | -1.1 | 1.0 |
| Phase-1 CCT-17 | -1.0 | 1.1 | -1.0 | -1.0 | 1.1 | 1.0 | 1.0 | 1.0 | 1.0 |
| Phase-1 CCT-18 | -1.6 | 1.2 | 1.1 | 1.2 | 1.1 | -1.4 | 1.0 | 1.2 | 1.2 |
| Phase-1 CCT-19 | -1.5 | 1.5 | -1.0 | 1.0 | -1.0 | 1.0 | -1.2 | -1.1 | 1.2 |
| Phase-1 CCT-2 | -1.1 | -1.3 | 1.2 | -1.2 | -1.0 | -1.1 | 1.0 | -1.3 | -1.0 |
| Phase-1 CCT-20 | 1.0 | 1.9 | 1.1 | -1.2 | -1.4 | 1.0 | -1.2 | -1.3 | -1.2 |
| Phase-1 CCT-21 | -1.0 | -1.0 | 1.1 | -1.0 | -1.0 | 1.4 | 1.0 | 1.0 | -1.0 |
| Phase-1 CCT-22 | -1.3 | -1.1 | 1.1 | -1.1 | -1.0 | 1.9 | 1.0 | -1.2 | -1.5 |
| Phase-1 CCT-24 | -1.1 | -1.7 | 1.0 | -1.7 | -1.1 | 1.0 | 1.6 | -1.7 | -1.3 |
| Phase-1 CCT-25 | 1.2 | 2.0 | 1.2 | -1.9 | 1.0 | 1.9 | 1.2 | -1.2 | 1.4 |
| Phase-1 CCT-26 | 1.2 | -1.8 | -1.4 | -1.0 | -1.1 | 1.0 | 1.5 | 1.1 | -1.3 |
| Phase-1 CCT-27 | -1.7 | 1.9 | 1.0 | 1.4 | 1.0 | -1.5 | 1.1 | 1.1 | -1.2 |
| Phase-1 CCT-28 | -1.1 | -1.9 | 1.2 | -1.3 | 1.2 | 1.3 | -1.0 | -1.3 | 1.3 |
| Phase-1 CCT-29 | 1.2 | -1.9 | -1.1 | -1.3 | 1.5 | 1.2 | -1.2 | -1.2 | -1.2 |
| Phase-1 CCT-3 | -1.1 | -5.4 | 1.1 | -1.4 | 1.1 | -1.2 | 1.1 | -1.4 | -2.3 |
| Phase-1 CCT-30 | -1.1 | 1.4 | 1.0 | -1.0 | 1.0 | -1.1 | 1.0 | 1.0 | 1.3 |
| Phase-1 CCT-31 | -1.5 | 1.0 | -1.0 | 1.1 | -1.0 | -1.3 | 1.1 | 1.1 | 1.1 |
| Phase-1 CCT-32 | -1.7 | 1.3 | -1.1 | 1.2 | -1.0 | -1.5 | -1.0 | 1.1 | 1.1 |
| Phase-1 CCT-33 | -1.3 | -1.1 | -1.0 | 1.0 | -1.1 | -1.3 | 1.2 | 1.1 | 1.1 |
| Phase-1 CCT-34 | -1.5 | 1.5 | -1.0 | 1.1 | 1.0 | -1.5 | 1.1 | -1.1 | -1.0 |
| Phase-1 CCT-35 | 1.1 | -1.6 | -1.3 | -1.2 | 1.0 | -1.6 | -1.2 | -1.2 | -1.2 |
| Phase-1 CCT-36 | -1.2 | 1.0 | 1.0 | -1.1 | -1.0 | 1.1 | -1.1 | -1.1 | 1.0 |
| Phase-1 CCT-37 | -1.3 | 1.4 | -1.0 | 1.0 | -1.0 | -1.3 | -1.0 | -1.0 | 1.1 |
| Phase-1 CCT-4 | -1.2 | -1.1 | -1.2 | -1.1 | 1.1 | -1.2 | -1.0 | -1.0 | 1.2 |
| Phase-1 CCT-40 | 1.1 | -1.1 | 1.1 | 1.1 | 1.1 | 1.1 | -1.0 | -1.0 | -1.2 |
| Phase-1 CCT-41 | -1.2 | 1.5 | -1.1 | -1.2 | -1.0 | -1.5 | -1.1 | -1.0 | 1.2 |
| Phase-1 CCT-42 | -1.5 | 1.6 | 1.0 | 1.2 | -1.0 | -1.1 | -1.1 | -1.0 | 1.1 |
| Phase-1 CCT-43 | -1.7 | 1.5 | 1.1 | 1.1 | -1.0 | -1.5 | 1.0 | -1.0 | -1.0 |
| Phase-1 CCT-44 | -1.5 | 1.7 | -1.0 | 1.1 | -1.2 | -1.6 | 1.2 | -1.0 | -1.0 |
| Phase-1 CCT-45 | 1.1 | 1.6 | -1.3 | 1.8 | 1.1 | 1.1 | -1.0 | 1.7 | -1.6 |
| Phase-1 CCT-46 | 1.0 | -1.1 | 1.2 | -1.1 | 1.0 | 1.2 | -1.0 | -1.0 | 1.1 |
| Phase-1 CCT-47 | 1.2 | -1.2 | 1.0 | -1.1 | 1.0 | 1.0 | -1.1 | -1.0 | 1.1 |
| Phase-1 CCT-49 | 1.1 | 1.9 | 1.1 | 1.5 | 1.1 | 1.2 | -1.1 | 1.4 | -1.0 |
| Phase-1 CCT-5 | -1.1 | -3.7 | -1.1 | -1.1 | -1.0 | -1.2 | 1.2 | -1.1 | -1.6 |
| Phase-1 CCT-50 | -1.1 | 1.0 | -1.0 | -1.4 | -1.0 | -1.1 | -1.1 | -1.4 | 1.1 |
| Phase-1 CCT-51 | -1.8 | 1.0 | -1.0 | -1.1 | 1.0 | -1.5 | -1.0 | -1.0 | 1.1 |
| Phase-1 CCT-52 | -1.0 | 1.1 | 1.1 | 1.2 | 1.2 | -1.1 | 1.2 | 1.2 | 1.2 |
| Phase-1 CCT-53 | -1.1 | -1.9 | -1.3 | -1.2 | -1.3 | -1.1 | 1.1 | -1.0 | 1.0 |
| Phase-1 CCT-54 | -1.2 | -1.4 | -1.0 | -1.2 | -1.1 | -1.2 | -1.2 | -1.3 | -1.3 |
| Phase-1 CCT-55 | -1.7 | 1.9 | -1.0 | 1.3 | -1.0 | -1.5 | 1.0 | 1.2 | 1.1 |
| Phase-1 CCT-56 | -1.2 | 1.0 | 1.0 | 1.3 | 1.0 | -1.2 | 1.0 | 1.0 | 1.5 |
| Phase-1 CCT-57 | -1.2 | -1.3 | -1.1 | -1.3 | -1.0 | -1.4 | -1.0 | -1.2 | -1.0 |
| Phase-1 CCT-58 | -1.6 | 1.3 | -1.0 | -1.4 | -1.0 | -1.1 | -1.0 | -1.0 | -1.0 |
| Phase-1 CCT-59 | -1.8 | 1.1 | -1.0 | -1.1 | -1.1 | -1.6 | 1.1 | 1.1 | 1.5 |
| Phase-1 CCT-6 | -1.1 | -1.4 | 1.1 | 1.0 | -1.1 | -1.2 | 1.0 | -1.0 | 1.0 |
| Phase-1 CCT-60 | -1.6 | 1.1 | 1.0 | 1.1 | -1.1 | -1.6 | 1.0 | 1.3 | -1.1 |
| Phase-1 CCT-61 | 1.2 | 1.2 | 1.1 | -1.4 | -1.1 | 1.1 | 1.0 | -1.0 | -1.2 |
| Phase-1 CCT-62 | -1.8 | 1.4 | 1.0 | 1.0 | -1.2 | -1.6 | 1.1 | -1.1 | 1.1 |

TABLE 11-continued

| | | | | | | | |
|---|---|---|---|---|---|---|---|
| Phase-1 CCT-63 | 1.0 | -1.4 | -1.0 | -1.2 | -1.1 | 1.1 | -1.1 |
| Phase-1 CCT-65 | -1.3 | 1.7 | 1.0 | 1.1 | -1.2 | 1.1 | 1.1 |
| Phase-1 CCT-66 | -1.7 | 1.5 | 1.0 | 1.2 | -1.6 | 1.1 | 1.1 |
| Phase-1 CCT-67 | 2.3 | 1.4 | 1.8 | -1.3 | 1.6 | -1.2 | -1.3 |
| Phase-1 CCT-68 | -1.0 | 1.1 | 1.0 | 1.0 | 1.1 | 1.1 | -1.0 |
| Phase-1 CCT-7 | -1.1 | 1.0 | -1.1 | 1.0 | -1.1 | -1.1 | -1.1 |
| Phase-1 CCT-70 | 1.0 | -2.2 | 1.2 | -1.3 | -1.2 | -1.0 | -1.1 |
| Phase-1 CCT-71 | -1.1 | -1.4 | -1.0 | -1.0 | -1.3 | -1.3 | -1.1 |
| Phase-1 CCT-72 | 1.0 | -1.8 | 1.1 | -1.0 | -1.0 | -1.0 | -1.1 |
| Phase-1 CCT-73 | -1.7 | 1.4 | 1.0 | -1.2 | -1.2 | 1.1 | -1.0 |
| Phase-1 CCT-74 | 1.0 | -1.8 | 1.1 | -1.1 | -1.7 | 1.1 | -1.1 |
| Phase-1 CCT-75 | -1.3 | -1.2 | -1.1 | -1.1 | 1.0 | -1.1 | -1.1 |
| Phase-1 CCT-76 | -1.0 | -1.3 | -1.1 | -1.2 | -1.4 | -1.2 | 1.0 |
| Phase-1 CCT-78 | -1.0 | -1.4 | 1.0 | -1.0 | -1.1 | 1.1 | -1.0 |
| Phase-1 CCT-79 | -1.2 | -1.6 | -1.1 | -1.0 | -1.3 | 1.0 | -1.0 |
| Phase-1 CCT-8 | -1.1 | -1.1 | -1.1 | -1.1 | 1.1 | 1.1 | 1.1 |
| Phase-1 CCT-80 | 1.3 | -1.9 | -1.3 | -1.3 | 1.2 | -1.3 | -1.0 |
| Phase-1 CCT-81 | -1.3 | -1.3 | -1.3 | 1.3 | 1.1 | -1.1 | 1.1 |
| Phase-1 CCT-82 | 1.2 | -1.9 | -1.2 | -1.1 | 1.9 | 1.5 | 1.2 |
| Phase-1 CCT-83 | -1.1 | 1.1 | 1.1 | 1.0 | 1.0 | 1.0 | 1.0 |
| Phase-1 CCT-84 | 1.2 | -1.6 | -1.1 | -1.4 | -1.2 | -1.2 | -1.0 |
| Phase-1 CCT-87 | -1.3 | 1.3 | -1.2 | 1.3 | 1.0 | 1.5 | 1.1 |
| Phase-1 CCT-88 | -1.2 | 1.4 | -1.2 | -1.2 | -1.2 | 1.0 | -1.0 |
| Phase-1 CCT-89 | -1.1 | 1.2 | 1.1 | -1.1 | 1.4 | -1.0 | -1.1 |
| Phase-1 CCT-9 | 1.2 | 1.4 | -1.0 | 1.0 | -1.0 | -1.1 | 1.1 |
| Phase-1 CCT-91 | 1.0 | -4.4 | 1.2 | -1.6 | -1.2 | -1.4 | -1.4 |
| Phase-1 CCT-92 | -1.2 | -1.0 | 1.0 | 1.3 | -1.3 | 1.5 | -1.1 |
| Phase-1 CCT-93 | -1.0 | 1.6 | 1.0 | 1.4 | 1.2 | 1.4 | -1.2 |
| Phase-1 CCT-94 | -1.2 | -1.7 | 1.0 | -1.1 | -1.0 | -1.0 | 1.0 |
| Phase-1 CCT-97 | 1.2 | 1.2 | -1.0 | 1.1 | -1.0 | 1.1 | -1.0 |
| Phenol sulfotransferase | 1.2 | -2.1 | 1.1 | -1.9 | 1.8 | -1.9 | -2.0 |
| Proliferating cell nuclear antigen gene | 1.4 | -1.1 | 1.1 | 4.1 | -1.1 | 5.3 | -1.2 |
| Prostaglandin D synthase | 1.1 | -2.2 | 1.2 | -1.3 | 1.1 | -1.2 | 1.1 |
| Rab2 | 1.2 | -1.5 | -1.4 | 1.4 | 1.3 | 1.4 | 1.2 |
| Rab5 | 1.1 | 1.4 | 1.0 | 1.0 | 1.6 | 1.1 | 1.2 |
| Rab7 | 1.3 | 1.5 | 1.1 | 1.1 | 1.2 | 1.1 | 1.2 |
| SHB (Src homology 2 protein) | 1.1 | -1.3 | -1.4 | 2.2 | 2.2 | 1.1 | 1.4 |
| Superoxide dismutase Mn | 1.0 | 1.5 | -1.3 | 1.1 | -1.1 | 1.2 | -1.0 |
| TFCOUP-related (probable steroid hormone receptor) | 1.3 | -1.2 | 1.1 | -1.3 | -1.0 | 1.1 | 1.1 |
| Tissue inhibitor of metalloproteinases-1 | 1.1 | -5.3 | -1.3 | -1.2 | 2.5 | -1.1 | -1.2 |
| TPRD | -1.3 | -1.0 | 1.0 | 1.3 | -1.1 | -1.3 | 1.1 |
| Tumor necrosis factor-alpha | 1.5 | -1.4 | 1.2 | 3.3 | 2.0 | 3.5 | -1.3 |
| Ubiquitin | 1.2 | -1.6 | -1.0 | 1.2 | 1.0 | 1.3 | -1.0 |
| UV excision repair protein RAD 23 (XP-C) | 1.4 | -2.1 | -1.1 | -1.0 | 1.6 | 1.1 | 1.2 |
| Vascular cell adhesion molecule 1 (VCAM-1) | -1.0 | -2.1 | -1.0 | -1.1 | 1.1 | -1.1 | -1.2 |
| ZAP36/annexin IV | 1.5 | 1.1 | -1.1 | 1.0 | 1.4 | 1.1 | 1.6 |

TABLE 11-continued

| Genes | Erythromycin estolate, 10083, canine kidney, 100 mg/kg, 10 days | Erythromycin estolate, 10084, canine kidney, 100 mg/kg, 10 days | Erythromycin estolate, 10086, canine kidney, 100 mg/kg, 10 days | Erythromycin estolate, 10088, canine kidney, 100 mg/kg, 10 days | Erythromycin Estolate, 10195, Canine Liver, 100 mg/kg, 10 days | Erythromycin Estolate, 10315, Canine liver, 100 mg/kg, 10 day | Estradiol, 10081, canine kidney, 0.3 mg/kg, 10 days | Estradiol, 10082, canine kidney, 0.3 mg/kg, 10 days | Estradiol, 10085, canine kidney, 0.3 mg/kg, 10 days |
|---|---|---|---|---|---|---|---|---|---|
| Alkaline phosphatase | 1.6 | 1.6 | 1.6 | 1.3 | 1.5 | −1.0 | 1.4 | 1.6 | 1.6 |
| Angiopoietin-related protein 3 (ANGPTL3) | −1.1 | −1.1 | −1.1 | −1.0 | 1.5 | −1.2 | 1.1 | −1.1 | −1.1 |
| Beta-glucuronidase | 1.4 | 1.4 | 1.4 | 1.3 | 1.5 | −1.0 | 1.3 | 1.4 | 1.4 |
| BR-cadherin | −1.1 | −1.1 | −1.1 | 1.2 | 1.2 | −1.0 | −1.5 | −1.1 | −1.1 |
| BRCA1 | 1.4 | 1.4 | 1.4 | −1.3 | 1.5 | −1.1 | 1.1 | 1.4 | 1.4 |
| c-erb B-2 | 1.4 | 1.4 | 1.4 | 1.6 | 1.3 | 1.1 | 1.3 | 1.4 | 1.4 |
| Canis familiaris mitochondrion, complete genome | −1.1 | −1.1 | −1.1 | 1.2 | 1.1 | 1.0 | −1.8 | −1.1 | −1.1 |
| Catalase | 1.2 | 1.2 | 1.2 | −1.4 | 1.4 | −1.1 | −1.0 | 1.2 | 1.2 |
| Caveolin-1 | 1.0 | 1.0 | 1.0 | −1.0 | −1.3 | −1.1 | 1.4 | 1.0 | 1.0 |
| Caveolin-2 | 1.6 | 1.6 | 1.6 | −1.5 | 1.2 | −1.0 | 1.7 | 1.6 | 1.6 |
| CD40 ligand | −1.0 | −1.0 | −1.0 | −1.0 | −1.1 | −1.1 | 1.2 | −1.0 | −1.0 |
| Cubilin | 1.1 | 1.1 | 1.1 | −2.6 | 1.1 | 1.0 | 1.1 | 1.1 | 1.1 |
| Cytochrome c oxidase subunit II | −1.3 | −1.3 | −1.3 | −1.0 | −1.1 | 1.6 | −1.0 | −1.3 | −1.3 |
| Cytochrome c oxidase subunit VIIaL | 1.0 | 1.0 | 1.0 | 1.2 | 1.0 | −1.0 | −1.4 | 1.0 | 1.0 |
| Cytochrome P450 2B | −1.0 | −1.0 | −1.0 | −1.3 | 1.9 | 1.5 | 1.2 | −1.0 | −1.0 |
| Cytochrome P450 2C21 | −1.1 | −1.1 | −1.1 | 1.1 | 1.3 | −1.1 | −1.9 | −1.1 | −1.1 |
| Cytochrome P450 2C41 | −1.1 | −1.1 | −1.1 | −1.3 | 4.5 | 18.8 | 1.7 | −1.1 | −1.1 |
| Cytochrome P450 2D | 1.1 | 1.1 | 1.1 | 1.5 | −1.2 | 1.1 | 1.2 | 1.1 | 1.1 |
| Cytochrome P450 3A | −1.1 | −1.1 | −1.1 | 1.3 | 7.0 | 4.1 | 1.0 | −1.1 | −1.1 |
| Decorin | 1.3 | 1.3 | 1.3 | 1.2 | −1.0 | −1.4 | 1.1 | 1.3 | 1.3 |
| FGFR2 | −1.0 | −1.0 | −1.0 | 1.4 | 1.2 | −1.0 | −1.2 | −1.0 | −1.0 |
| Gadd45 | −1.1 | −1.1 | −1.1 | 1.4 | 1.2 | 1.4 | 1.1 | −1.1 | −1.1 |
| Glucose transporter | 1.3 | 1.3 | 1.3 | −1.6 | 1.3 | 1.0 | 1.2 | 1.3 | 1.3 |
| Glucose-6-phosphatase | 1.0 | 1.0 | 1.0 | −1.1 | 1.4 | 1.1 | 1.2 | 1.0 | 1.0 |
| Glucose-regulated protein 94 #1 | 1.0 | 1.0 | 1.0 | −1.1 | 1.5 | 1.1 | −1.2 | 1.0 | 1.0 |
| Glucose-regulated protein 94 #2 | 1.2 | 1.2 | 1.2 | 1.3 | 1.5 | −1.1 | −1.2 | 1.2 | 1.2 |
| Glutathione S-transferase alpha subunit | 1.0 | 1.0 | 1.0 | 1.5 | 1.6 | 1.5 | −1.1 | 1.0 | 1.0 |
| GRP94 | 1.3 | 1.4 | 1.4 | −1.3 | 1.6 | 1.0 | −1.0 | 1.3 | 1.3 |
| Heat shock protein 27 | 1.0 | 1.0 | 1.0 | −1.2 | −1.9 | 1.3 | 1.5 | 1.0 | 1.0 |
| Histidine ammonia-lyase | −1.3 | −1.2 | −1.2 | −1.2 | −1.4 | 1.0 | 1.0 | −1.3 | −1.2 |
| Interleukin-10 | 1.3 | 1.3 | 1.3 | 1.3 | 1.1 | 1.0 | 1.2 | 1.3 | 1.3 |
| Interleukin-8 | 1.1 | 1.1 | 1.1 | 1.1 | 1.1 | −1.2 | −1.1 | 1.1 | 1.1 |
| Keratinocyte growth factor | 1.1 | 1.1 | 1.1 | −1.3 | 1.2 | −1.0 | 1.2 | 1.1 | 1.1 |
| Mek5 | 1.2 | 1.2 | 1.2 | 1.1 | 1.1 | −1.3 | −1.0 | 1.2 | 1.2 |
| Metallothionein 1 | 1.2 | 1.2 | 1.2 | −1.1 | 1.6 | 1.1 | 1.3 | 1.2 | 1.2 |
| Multidrug resistant protein-1 | 1.5 | 1.5 | 1.5 | −1.3 | 1.3 | 1.1 | 1.3 | 1.5 | 1.5 |
| N-cadherin | 1.1 | 1.1 | 1.1 | −1.5 | 1.1 | −1.1 | −1.0 | 1.1 | 1.1 |
| p38 MAPK | −1.0 | −1.0 | −1.0 | 1.6 | 1.1 | 1.2 | 1.2 | −1.0 | −1.0 |
| p53 | 1.4 | 1.4 | 1.4 | −1.4 | 1.2 | 1.1 | 1.2 | 1.4 | 1.4 |
| Paraoxonase2 (PON2) | 1.5 | 1.5 | 1.5 | −1.1 | 1.5 | 1.3 | 1.6 | 1.5 | 1.5 |
| Phase-1 CCT-1 | −1.1 | −1.1 | −1.1 | −1.1 | 1.0 | 1.3 | −1.2 | −1.1 | −1.1 |
| Phase-1 CCT-10 | −1.1 | −1.1 | −1.1 | −1.1 | 1.0 | 1.1 | −1.5 | −1.1 | −1.1 |
| Phase-1 CCT-11 | 1.2 | 1.2 | 1.2 | 1.4 | 1.1 | 1.1 | 1.2 | 1.2 | 1.2 |

TABLE 11-continued

| | | | | | | | | |
|---|---|---|---|---|---|---|---|---|
| Phase-1 CCT-12 | -1.1 | -1.1 | 1.0 | -1.6 | -1.0 | -1.0 | -1.1 | -1.1 |
| Phase-1 CCT-13 | -1.1 | -1.1 | 1.1 | -1.3 | 1.1 | -1.2 | -1.1 | -1.1 |
| Phase-1 CCT-14 | 1.2 | 1.2 | 1.1 | -1.2 | 1.0 | 1.3 | 1.2 | 1.2 |
| Phase-1 CCT-15 | -1.1 | -1.1 | -1.0 | -1.4 | -1.1 | -1.1 | -1.1 | -1.1 |
| Phase-1 CCT-16 | 1.2 | 1.2 | -1.1 | -1.2 | 1.1 | 1.1 | 1.2 | 1.2 |
| Phase-1 CCT-17 | 1.0 | 1.0 | 1.3 | -1.1 | 1.0 | 1.0 | 1.0 | 1.0 |
| Phase-1 CCT-18 | 1.2 | 1.2 | -1.1 | -1.8 | 1.1 | 1.2 | 1.2 | 1.2 |
| Phase-1 CCT-19 | -1.1 | -1.1 | 1.0 | -1.5 | 1.1 | 1.5 | -1.1 | -1.1 |
| Phase-1 CCT-2 | -1.0 | -1.0 | -1.3 | -1.3 | -1.0 | -1.2 | -1.0 | -1.0 |
| Phase-1 CCT-20 | 1.0 | 1.0 | -1.3 | 1.0 | 1.0 | -1.4 | 1.0 | 1.0 |
| Phase-1 CCT-21 | -1.1 | -1.1 | 1.0 | -1.1 | -1.0 | -1.5 | -1.1 | -1.1 |
| Phase-1 CCT-22 | 1.2 | 1.2 | -1.2 | -1.4 | 1.1 | 1.3 | 1.2 | 1.2 |
| Phase-1 CCT-24 | -1.1 | -1.1 | 1.1 | -1.2 | -1.1 | -1.3 | -1.1 | -1.1 |
| Phase-1 CCT-25 | 1.0 | 1.0 | -1.3 | 1.1 | 1.1 | 1.1 | 1.0 | 1.0 |
| Phase-1 CCT-26 | -1.6 | -1.6 | -1.5 | -1.1 | -1.0 | -1.9 | -1.6 | -1.6 |
| Phase-1 CCT-27 | 1.3 | 1.3 | -1.1 | -2.4 | 1.2 | 1.4 | 1.3 | 1.3 |
| Phase-1 CCT-28 | 1.1 | 1.1 | -1.4 | -1.3 | 1.1 | -1.4 | 1.1 | 1.1 |
| Phase-1 CCT-29 | -1.0 | -1.0 | -1.1 | -1.0 | -1.0 | -1.4 | -1.0 | -1.0 |
| Phase-1 CCT-3 | -1.1 | -1.1 | -1.1 | -1.2 | -1.1 | -1.8 | -1.1 | -1.1 |
| Phase-1 CCT-30 | 1.3 | 1.3 | 1.5 | -1.1 | -1.0 | 1.1 | 1.3 | 1.3 |
| Phase-1 CCT-31 | 1.0 | 1.0 | 1.4 | -1.4 | 1.1 | 1.0 | 1.0 | 1.0 |
| Phase-1 CCT-32 | 1.2 | 1.2 | -1.3 | -1.9 | 1.0 | 1.2 | 1.2 | 1.2 |
| Phase-1 CCT-33 | -1.1 | -1.1 | 1.0 | -1.7 | 1.1 | 1.0 | -1.1 | -1.1 |
| Phase-1 CCT-34 | -1.1 | -1.1 | -1.1 | -1.7 | 1.1 | 1.4 | -1.1 | -1.1 |
| Phase-1 CCT-35 | -1.0 | -1.0 | -1.1 | -1.1 | -1.2 | -1.3 | -1.0 | -1.0 |
| Phase-1 CCT-36 | -1.1 | -1.1 | 1.0 | -1.1 | -1.0 | 1.2 | -1.1 | -1.1 |
| Phase-1 CCT-37 | -1.1 | -1.1 | -1.1 | -1.5 | -1.0 | 1.4 | -1.1 | -1.1 |
| Phase-1 CCT-4 | -1.0 | -1.0 | -1.0 | -1.6 | -1.1 | -1.0 | -1.0 | -1.0 |
| Phase-1 CCT-40 | 1.1 | 1.1 | 1.3 | 1.5 | 1.1 | -1.0 | 1.1 | 1.1 |
| Phase-1 CCT-41 | 1.0 | 1.0 | 1.1 | 1.0 | -1.0 | 1.5 | 1.0 | 1.0 |
| Phase-1 CCT-42 | -1.1 | -1.1 | -1.2 | -1.7 | 1.0 | 1.7 | -1.1 | -1.1 |
| Phase-1 CCT-43 | -1.1 | -1.1 | -1.2 | -1.9 | 1.0 | -1.0 | -1.1 | -1.1 |
| Phase-1 CCT-44 | 1.1 | 1.1 | 1.1 | -1.6 | -1.1 | -1.4 | 1.1 | 1.1 |
| Phase-1 CCT-45 | 1.0 | 1.0 | -1.4 | -1.1 | -1.1 | 1.3 | 1.0 | 1.0 |
| Phase-1 CCT-46 | -1.1 | -1.1 | 1.2 | 1.1 | -1.1 | -1.3 | -1.1 | -1.1 |
| Phase-1 CCT-47 | -1.1 | -1.1 | -1.1 | 1.0 | -1.2 | 1.0 | -1.1 | -1.1 |
| Phase-1 CCT-49 | 1.3 | 1.3 | -1.0 | 1.2 | -1.1 | 1.1 | 1.3 | 1.3 |
| Phase-1 CCT-5 | 1.0 | 1.0 | -1.5 | -1.2 | -1.0 | -1.6 | 1.0 | 1.0 |
| Phase-1 CCT-50 | -1.1 | -1.1 | 1.1 | -1.0 | -1.1 | -1.3 | -1.1 | -1.1 |
| Phase-1 CCT-51 | 1.3 | 1.3 | -1.1 | -2.0 | 1.1 | 1.7 | 1.3 | 1.3 |
| Phase-1 CCT-52 | -1.1 | -1.1 | -1.1 | -1.2 | 1.1 | -1.0 | -1.1 | -1.1 |
| Phase-1 CCT-53 | 1.1 | 1.1 | 1.1 | 1.1 | -1.2 | -1.4 | 1.1 | 1.1 |
| Phase-1 CCT-54 | -1.1 | -1.1 | -1.1 | -1.5 | -1.1 | -1.3 | -1.1 | -1.1 |
| Phase-1 CCT-55 | -1.1 | -1.1 | -1.3 | -2.0 | -1.0 | 1.5 | -1.1 | -1.1 |
| Phase-1 CCT-56 | 1.0 | 1.0 | 1.2 | 1.0 | 1.1 | 1.3 | 1.0 | 1.0 |
| Phase-1 CCT-57 | -1.1 | -1.1 | 1.1 | -1.2 | 1.0 | 1.0 | -1.1 | -1.1 |
| Phase-1 CCT-58 | -1.1 | -1.1 | 1.5 | -1.9 | 1.0 | -1.3 | -1.1 | -1.1 |
| Phase-1 CCT-59 | -1.2 | -1.2 | 1.0 | -2.2 | -1.0 | 1.3 | -1.2 | -1.2 |
| Phase-1 CCT-6 | -1.0 | -1.0 | -1.1 | -1.3 | -1.0 | -1.2 | -1.0 | -1.0 |
| Phase-1 CCT-60 | -1.1 | -1.1 | 1.1 | -1.9 | -1.0 | -1.0 | -1.1 | -1.1 |
| Phase-1 CCT-61 | -1.0 | -1.0 | -1.1 | -1.0 | 1.0 | -1.2 | -1.0 | -1.0 |
| Phase-1 CCT-62 | -1.1 | -1.1 | -1.3 | -1.9 | 1.1 | 1.3 | -1.1 | -1.1 |

TABLE 11-continued

| | | | | | | | |
|---|---|---|---|---|---|---|---|
| Phase-1 CCT-63 | -1.1 | -1.1 | -1.1 | -1.0 | -1.0 | -1.1 | -1.1 |
| Phase-1 CCT-65 | -1.1 | -1.1 | -1.1 | 1.0 | -1.0 | 1.1 | -1.1 |
| Phase-1 CCT-66 | -1.2 | -1.2 | -1.2 | -1.2 | 1.1 | 1.7 | -1.2 |
| Phase-1 CCT-67 | 1.0 | 1.0 | 1.0 | -1.3 | 1.0 | -1.2 | 1.0 |
| Phase-1 CCT-68 | -1.1 | -1.1 | -1.1 | -1.1 | 1.0 | -1.3 | -1.1 |
| Phase-1 CCT-7 | -1.1 | -1.1 | -1.1 | -1.1 | 1.1 | -1.4 | -1.1 |
| Phase-1 CCT-70 | -1.1 | -1.1 | -1.1 | -1.1 | -1.0 | -1.3 | -1.1 |
| Phase-1 CCT-71 | 1.0 | 1.0 | 1.0 | -1.1 | 1.0 | 1.0 | 1.0 |
| Phase-1 CCT-72 | -1.1 | -1.1 | -1.1 | 1.2 | -1.1 | -1.6 | -1.1 |
| Phase-1 CCT-73 | -1.1 | -1.1 | -1.1 | -1.8 | -1.2 | 1.2 | -1.1 |
| Phase-1 CCT-74 | -1.0 | -1.0 | -1.0 | 1.0 | 1.0 | -1.6 | -1.0 |
| Phase-1 CCT-75 | -1.1 | -1.1 | -1.1 | -1.7 | -1.2 | -1.2 | -1.1 |
| Phase-1 CCT-76 | -1.0 | -1.0 | -1.0 | -1.0 | -1.2 | -1.1 | -1.0 |
| Phase-1 CCT-78 | 1.0 | 1.0 | 1.0 | -1.1 | 1.0 | -1.5 | 1.0 |
| Phase-1 CCT-79 | -1.1 | -1.1 | -1.1 | -1.4 | -1.1 | 1.0 | -1.1 |
| Phase-1 CCT-8 | 1.3 | 1.3 | 1.3 | 1.2 | 1.1 | 1.0 | 1.3 |
| Phase-1 CCT-80 | -1.3 | -1.3 | -1.3 | -1.2 | -1.3 | -1.3 | -1.3 |
| Phase-1 CCT-81 | -1.3 | -1.3 | -1.3 | 1.2 | -1.1 | -2.5 | -1.3 |
| Phase-1 CCT-82 | -1.2 | -1.2 | -1.2 | 1.0 | -1.0 | -1.2 | -1.2 |
| Phase-1 CCT-83 | 1.0 | 1.0 | 1.0 | 1.2 | 1.0 | -1.5 | 1.0 |
| Phase-1 CCT-84 | -1.1 | -1.1 | -1.1 | -1.4 | -1.1 | -2.3 | -1.1 |
| Phase-1 CCT-87 | 1.2 | 1.2 | 1.2 | 1.5 | 1.1 | -1.1 | 1.2 |
| Phase-1 CCT-88 | 1.3 | 1.3 | 1.3 | -1.5 | -1.2 | 1.2 | 1.3 |
| Phase-1 CCT-89 | -1.1 | -1.1 | -1.1 | -1.1 | 1.1 | -1.0 | -1.1 |
| Phase-1 CCT-9 | -1.1 | -1.1 | -1.1 | -1.4 | -1.1 | -1.8 | -1.1 |
| Phase-1 CCT-91 | -1.0 | -1.0 | -1.0 | -1.4 | -1.1 | -1.3 | -1.0 |
| Phase-1 CCT-92 | 1.1 | 1.1 | 1.1 | -1.3 | -1.1 | 1.1 | 1.1 |
| Phase-1 CCT-93 | -1.0 | -1.0 | -1.0 | 1.1 | -1.0 | -1.2 | -1.0 |
| Phase-1 CCT-94 | -1.2 | -1.2 | -1.2 | -1.1 | -1.0 | -1.5 | -1.2 |
| Phase-1 CCT-97 | 1.0 | 1.0 | 1.0 | 1.2 | 1.4 | -1.1 | 1.0 |
| Phenol sulfotransferase | -1.0 | -1.0 | -1.0 | -1.0 | 1.0 | 1.3 | -1.0 |
| Proliferating cell nuclear antigen gene | 1.5 | 1.5 | 1.5 | 1.5 | 1.0 | 1.3 | 1.5 |
| Prostaglandin D synthase | 1.2 | 1.2 | 1.2 | 1.1 | -1.1 | 1.3 | 1.2 |
| Rab2 | 1.2 | 1.2 | 1.2 | 1.4 | -1.1 | 1.2 | 1.2 |
| Rab5 | 1.4 | 1.4 | 1.4 | 1.2 | -1.1 | 1.4 | 1.4 |
| Rab7 | 1.2 | 1.2 | 1.2 | 1.2 | -1.0 | 1.0 | 1.2 |
| SHB (Src homology 2 protein) | 1.1 | 1.1 | 1.1 | 1.2 | -1.0 | -1.0 | 1.1 |
| Superoxide dismutase Mn | 1.2 | 1.2 | 1.2 | 1.3 | 1.0 | 1.1 | 1.2 |
| TFCOUP-related (probable steroid hormone receptor) | | | | | | | |
| Tissue inhibitor of metalloproteinases-1 | 1.1 | 1.1 | 1.1 | 1.2 | -1.3 | 1.0 | 1.1 |
| TPRD | -1.1 | -1.1 | -1.1 | -1.7 | -1.1 | -1.1 | -1.1 |
| Tumor necrosis factor-alpha | -1.1 | -1.1 | -1.1 | 1.2 | -1.1 | -1.2 | -1.1 |
| Ubiquitin | 1.1 | 1.1 | 1.1 | 1.1 | -1.1 | -1.3 | 1.1 |
| UV excision repair protein RAD 23 (XP-C) | 1.4 | 1.4 | 1.4 | 1.5 | -1.0 | 1.1 | 1.4 |
| Vascular cell adhesion molecule 1 (VCAM-1) | -1.0 | -1.0 | -1.0 | 1.1 | -1.1 | -1.1 | -1.0 |
| ZAP36/annexin IV | 1.2 | 1.2 | 1.2 | 1.4 | -1.1 | 1.0 | 1.2 |

TABLE 11-continued

| Genes | Estradiol, 10087, canine kidney, 0.3 mg/kg, 10 days | Estradiol, 10089, canine kidney, 0.3 mg/kg, 10 days | Estradiol, 10196, Canine Liver, 0.3 mg/kg, 10 days | Estradiol, 10316, Canine liver, 0.3 mg/kg, 10 day | Methotrexate, 10186, Canine kidney, 2 mg/kg, 2 days | Methotrexate, 10189, Canine kidney, 2 mg/kg, 2 days | Methotrexate, 10199, Canine Liver, 2 mg/kg, 3 days | Methotrexate, 10319, Canine liver, 2 mg/kg, 3 day |
|---|---|---|---|---|---|---|---|---|
| Alkaline phosphatase | 1.6 | 1.0 | 1.0 | -1.1 | 1.0 | 1.1 | 2.1 | -1.1 |
| Angiopoietin-related protein 3 (ANGPTL3) | -1.1 | -1.1 | -1.3 | -1.5 | 1.3 | -1.0 | 1.1 | -1.5 |
| Beta-glucuronidase | 1.4 | 1.1 | -1.2 | -1.2 | 1.1 | 1.2 | 2.6 | -1.1 |
| BR-cadherin | -1.1 | -1.2 | 1.3 | -1.0 | -1.0 | -1.2 | 1.3 | 1.1 |
| BRCA1 | 1.4 | 1.8 | -1.2 | -1.2 | -1.2 | 1.1 | 1.9 | 1.0 |
| c-erb B-2 | 1.4 | 1.1 | 1.1 | -1.1 | 1.2 | 1.3 | 1.6 | 1.0 |
| Canis familiaris mitochondrion, complete genome | -1.1 | -1.2 | -1.1 | -1.6 | -1.7 | -1.5 | 1.3 | 1.5 |
| Catalase | 1.2 | -1.6 | -1.1 | -1.6 | 1.4 | -1.0 | 1.6 | -1.1 |
| Caveolin-1 | 1.0 | 1.2 | 1.3 | 1.2 | 1.2 | 1.2 | -1.1 | -1.0 |
| Caveolin-2 | 1.6 | -1.3 | -1.2 | -1.2 | 1.9 | 1.4 | 1.2 | -1.1 |
| CD40 ligand | -1.0 | -1.3 | 1.0 | 1.1 | 2.2 | -1.2 | 1.4 | 1.2 |
| Cubilin | 1.1 | -1.9 | 1.2 | -1.0 | -1.3 | 1.2 | 1.4 | 1.2 |
| Cytochrome c oxidase subunit II | -1.3 | -1.2 | -1.2 | -1.2 | -1.5 | -1.4 | 1.1 | 1.5 |
| Cytochrome c oxidase subunit VIIaL | 1.0 | 1.1 | -1.0 | -1.3 | -1.4 | -1.1 | 1.1 | 1.0 |
| Cytochrome P450 2B | -1.0 | -1.1 | 1.3 | -1.2 | 1.1 | 1.3 | -1.4 | -1.7 |
| Cytochrome P450 2C21 | -1.1 | -1.3 | -1.4 | 1.9 | -1.4 | 1.2 | 1.2 | -1.1 |
| Cytochrome P450 2C41 | -1.1 | 1.5 | 1.0 | -1.3 | 1.4 | 1.1 | -1.6 | -1.2 |
| Cytochrome P450 2D | 1.1 | 1.0 | 1.6 | -1.3 | 1.6 | 1.0 | -1.4 | -1.9 |
| Cytochrome P450 3A | -1.1 | 1.2 | -1.2 | -1.5 | 1.5 | -1.1 | 1.7 | -1.0 |
| Decorin | 1.3 | -1.1 | 1.2 | 1.0 | -1.1 | -1.1 | -1.2 | -1.5 |
| FGFR2 | -1.0 | 1.1 | 1.1 | 1.1 | -1.4 | -1.4 | 1.7 | 1.4 |
| Gadd45 | -1.1 | -1.2 | -1.1 | -1.1 | -1.2 | -1.0 | 1.7 | 1.5 |
| Glucose transporter | 1.3 | -1.2 | -1.2 | -1.4 | 1.5 | -1.0 | 1.5 | -1.1 |
| Glucose-6-phosphatase | 1.0 | -1.6 | -1.0 | 1.1 | -1.2 | 1.5 | 1.9 | 1.3 |
| Glucose-regulated protein 94 #1 | 1.0 | 1.2 | 1.0 | -1.1 | 1.1 | -1.2 | 1.5 | 1.2 |
| Glucose-regulated protein 94 #2 | 1.2 | -1.2 | 1.1 | -1.2 | 1.0 | 1.3 | 1.8 | 1.2 |
| Glutathione S-transferase alpha subunit | 1.0 | 1.1 | 1.2 | -1.5 | 2.6 | -1.2 | 1.1 | -1.0 |
| GRP94 | 1.3 | 1.8 | 1.2 | -1.2 | 1.1 | -1.1 | 1.9 | 1.1 |
| Heat shock protein 27 | 1.0 | 1.5 | -1.5 | 1.2 | 1.1 | -1.1 | -1.1 | 1.2 |
| Histidine ammonia-lyase | -1.3 | 1.3 | -1.4 | 1.3 | 1.1 | -1.0 | -1.2 | 1.2 |
| Interleukin-10 | 1.3 | -1.1 | 1.3 | -1.0 | 6.4 | -1.1 | 1.6 | -1.0 |
| Interleukin-8 | 1.1 | -1.2 | -1.2 | -1.2 | 1.2 | 1.3 | 1.3 | -1.2 |
| Keratinocyte growth factor | -1.1 | -1.6 | -1.0 | -1.0 | 1.6 | 1.3 | 1.1 | -1.2 |
| Mek5 | 1.2 | 1.2 | 1.0 | 1.1 | 1.2 | 1.0 | 1.1 | 1.0 |
| Metallothionein 1 | 1.2 | -1.3 | -1.0 | -1.5 | 2.7 | -1.5 | 2.0 | 1.5 |
| Multidrug resistant protein-1 | 1.5 | 1.9 | -1.1 | -1.1 | -1.5 | 1.1 | 1.8 | 1.1 |
| N-cadherin | 1.1 | -1.0 | -1.0 | -1.2 | -1.2 | 1.0 | 1.3 | 1.0 |
| p38 MAPK | -1.0 | -1.6 | -1.2 | -1.2 | 1.0 | 1.3 | 1.5 | 1.5 |
| p53 | 1.4 | 1.1 | 1.4 | 1.1 | 1.3 | 1.2 | 2.1 | -1.1 |
| Paraoxonase2 (PON2) | 1.5 | -1.1 | -1.1 | -1.4 | 2.0 | 1.3 | 1.4 | 1.4 |
| Phase-1 CCT-1 | -1.1 | -1.0 | -1.1 | -1.2 | -1.3 | -1.3 | 1.1 | -1.0 |
| Phase-1 CCT-10 | -1.1 | -1.1 | -1.0 | -1.5 | -1.1 | -1.1 | 1.0 | -1.0 |
| Phase-1 CCT-11 | 1.2 | -1.1 | 1.3 | -1.1 | 1.1 | -1.2 | 1.5 | 1.4 |
| Phase-1 CCT-12 | -1.1 | 1.1 | -1.1 | 1.2 | 1.4 | -1.0 | -1.3 | -1.1 |

TABLE 11-continued

| | | | | | | | | |
|---|---|---|---|---|---|---|---|---|
| Phase-1 CCT-13 | -1.1 | 1.2 | -1.1 | 1.2 | 2.2 | -1.1 | -1.2 | 1.0 |
| Phase-1 CCT-14 | 1.2 | 1.1 | 1.1 | 1.2 | 1.1 | -1.0 | 1.0 | 1.2 |
| Phase-1 CCT-15 | -1.1 | -1.0 | -1.0 | 1.1 | 1.3 | 1.0 | -1.3 | -1.1 |
| Phase-1 CCT-16 | 1.2 | 1.2 | 1.0 | 1.1 | -1.2 | 1.0 | -1.1 | 1.0 |
| Phase-1 CCT-17 | 1.0 | -1.0 | 1.0 | 1.1 | -1.1 | 1.1 | 1.2 | 1.1 |
| Phase-1 CCT-18 | 1.2 | 1.6 | 1.3 | 1.6 | -1.1 | 1.0 | -1.3 | -1.0 |
| Phase-1 CCT-19 | -1.1 | 1.2 | -1.3 | 1.5 | 1.2 | -1.1 | -1.1 | 1.0 |
| Phase-1 CCT-2 | -1.0 | 1.1 | -1.2 | 1.0 | -1.4 | -1.1 | 1.0 | 1.3 |
| Phase-1 CCT-20 | 1.0 | 1.9 | -1.2 | -1.2 | 1.1 | -1.3 | -1.0 | -1.0 |
| Phase-1 CCT-21 | -1.1 | -1.2 | -1.2 | -1.0 | -1.1 | -1.4 | -1.0 | -1.1 |
| Phase-1 CCT-22 | 1.2 | 1.0 | -1.1 | 1.5 | 1.1 | 1.1 | -1.2 | -1.2 |
| Phase-1 CCT-24 | -1.1 | -1.2 | 1.1 | 1.0 | -1.1 | -1.3 | -1.1 | 1.0 |
| Phase-1 CCT-25 | 1.0 | 1.8 | 1.3 | 1.0 | -1.8 | -1.1 | -1.5 | -1.1 |
| Phase-1 CCT-26 | -1.7 | -1.2 | 1.5 | 1.1 | -1.0 | -1.0 | -1.7 | -1.2 |
| Phase-1 CCT-27 | 1.3 | 1.7 | -1.6 | 2.2 | 1.3 | 1.1 | -1.2 | 1.0 |
| Phase-1 CCT-28 | 1.1 | 1.8 | -1.0 | 1.2 | -1.1 | 1.2 | 1.2 | -1.0 |
| Phase-1 CCT-29 | -1.0 | -1.1 | 1.2 | -1.0 | -1.2 | -1.0 | -1.1 | -1.1 |
| Phase-1 CCT-3 | 1.1 | -1.6 | -1.2 | 1.0 | -1.4 | -1.4 | -1.1 | -1.0 |
| Phase-1 CCT-30 | 1.3 | 1.4 | -1.1 | 1.4 | -1.1 | -1.3 | 1.4 | 1.2 |
| Phase-1 CCT-31 | 1.0 | 1.4 | 1.1 | 1.8 | 1.5 | 1.0 | -1.2 | 1.1 |
| Phase-1 CCT-32 | 1.2 | 1.8 | -1.5 | 1.5 | 1.0 | 1.1 | -1.4 | -1.0 |
| Phase-1 CCT-33 | -1.1 | -1.2 | -1.3 | 1.4 | 1.1 | -1.0 | -1.2 | -1.1 |
| Phase-1 CCT-34 | -1.1 | 1.3 | 1.2 | 1.4 | 1.1 | 1.1 | -1.3 | -1.0 |
| Phase-1 CCT-35 | -1.0 | -1.1 | 1.0 | -1.4 | -1.3 | 1.1 | -1.0 | -1.1 |
| Phase-1 CCT-36 | 1.1 | 1.4 | -1.0 | 1.0 | -1.2 | 1.2 | -1.2 | -1.0 |
| Phase-1 CCT-37 | -1.1 | 1.1 | -1.1 | 1.5 | -1.1 | -1.0 | -1.2 | -1.1 |
| Phase-1 CCT-4 | -1.1 | 1.2 | -1.3 | 1.3 | -1.1 | 1.1 | -1.3 | -1.1 |
| Phase-1 CCT-40 | 1.1 | -1.1 | 1.1 | 1.1 | 1.1 | 1.1 | 1.4 | 1.0 |
| Phase-1 CCT-41 | 1.0 | 1.3 | 1.0 | 1.3 | 1.8 | -1.0 | -1.0 | 1.0 |
| Phase-1 CCT-42 | -1.1 | 1.2 | -1.3 | 1.5 | -1.1 | 1.2 | -1.4 | -1.1 |
| Phase-1 CCT-43 | -1.1 | 1.5 | -1.3 | 1.9 | 1.5 | -1.0 | -1.4 | -1.0 |
| Phase-1 CCT-44 | -1.1 | 1.1 | -1.3 | 1.4 | -1.2 | 1.1 | -1.3 | -1.1 |
| Phase-1 CCT-45 | 1.0 | 1.2 | 1.2 | 1.1 | 1.8 | 1.0 | -1.1 | 1.0 |
| Phase-1 CCT-46 | -1.1 | -1.1 | 1.1 | -1.3 | -1.1 | -1.3 | -1.0 | 1.0 |
| Phase-1 CCT-47 | -1.1 | 1.4 | 2.5 | 1.1 | 1.5 | 1.2 | 1.1 | 1.1 |
| Phase-1 CCT-49 | 1.3 | 1.1 | 1.2 | 1.0 | -1.2 | -1.0 | 1.2 | -1.0 |
| Phase-1 CCT-5 | 1.0 | -1.5 | -1.1 | 1.1 | -1.3 | -1.1 | -1.2 | -1.0 |
| Phase-1 CCT-50 | -1.1 | -1.2 | 1.2 | 1.1 | -1.2 | -1.1 | 1.0 | -1.1 |
| Phase-1 CCT-51 | 1.3 | 1.6 | 1.0 | 2.0 | 1.4 | 1.1 | -1.4 | -1.0 |
| Phase-1 CCT-52 | -1.1 | 1.0 | -1.0 | 1.3 | 1.0 | 1.0 | -1.1 | -1.0 |
| Phase-1 CCT-53 | 1.1 | -1.1 | 1.1 | -1.2 | -1.2 | -1.1 | 1.2 | -1.3 |
| Phase-1 CCT-54 | -1.1 | -1.3 | -1.1 | 1.2 | 1.4 | -1.3 | -1.3 | 1.1 |
| Phase-1 CCT-55 | -1.1 | 1.8 | 1.2 | 1.6 | 1.0 | 1.1 | 1.1 | -1.0 |
| Phase-1 CCT-56 | 1.0 | 1.0 | 1.2 | 1.1 | 1.0 | 1.0 | -1.4 | -1.2 |
| Phase-1 CCT-57 | -1.1 | 1.0 | -1.0 | 1.2 | -1.3 | -1.0 | -1.2 | -1.1 |
| Phase-1 CCT-58 | -1.1 | 1.0 | -1.4 | 1.5 | -1.3 | 1.2 | -1.5 | -1.1 |
| Phase-1 CCT-59 | -1.2 | 1.2 | -1.6 | 1.6 | -1.0 | -1.1 | -1.6 | -1.0 |
| Phase-1 CCT-6 | -1.0 | 1.2 | -1.2 | 1.2 | -1.1 | 1.1 | 1.1 | 1.0 |
| Phase-1 CCT-60 | -1.1 | -1.2 | -1.1 | 1.4 | 1.2 | -1.1 | -1.1 | -1.2 |
| Phase-1 CCT-61 | -1.0 | -1.1 | -1.1 | -1.1 | -1.3 | 1.0 | -1.6 | 1.1 |
| Phase-1 CCT-62 | -1.1 | 1.4 | -1.6 | 1.6 | -1.2 | -1.2 | -1.7 | -1.2 |
| Phase-1 CCT-63 | -1.1 | -1.2 | 1.2 | -1.1 | -1.0 | -1.1 | -1.0 | -1.1 |

TABLE 11-continued

| | | | | | | | |
|---|---|---|---|---|---|---|---|
| Phase-1 CCT-65 | -1.1 | 1.2 | 1.0 | 1.2 | 1.2 | 1.1 | -1.1 | 1.0 |
| Phase-1 CCT-66 | -1.2 | 1.2 | -1.5 | 1.6 | 1.6 | 1.1 | -1.5 | -1.1 |
| Phase-1 CCT-67 | 1.0 | -1.5 | 1.2 | -1.2 | -1.2 | -1.5 | 1.5 | 1.0 |
| Phase-1 CCT-68 | -1.1 | -1.1 | 1.1 | -1.1 | -1.0 | -1.3 | -1.0 | 1.1 |
| Phase-1 CCT-7 | -1.1 | -1.2 | 1.2 | 1.0 | -1.0 | 1.0 | -1.2 | 1.0 |
| Phase-1 CCT-70 | -1.1 | -1.1 | -1.1 | -1.0 | -1.0 | -1.1 | -1.1 | 1.2 |
| Phase-1 CCT-71 | -1.1 | 1.1 | -1.3 | -1.0 | -1.0 | -1.3 | -1.4 | -1.1 |
| Phase-1 CCT-72 | 1.0 | 1.2 | 1.2 | -1.3 | 1.0 | 1.1 | 1.0 | 1.1 |
| Phase-1 CCT-73 | -1.1 | 1.2 | -1.4 | 1.6 | 1.2 | 1.1 | -1.5 | 1.0 |
| Phase-1 CCT-74 | -1.0 | -1.1 | 1.2 | -1.2 | -1.0 | -1.3 | 1.0 | -1.1 |
| Phase-1 CCT-75 | -1.1 | 1.1 | -1.4 | 1.1 | -1.1 | -1.1 | -1.3 | 1.0 |
| Phase-1 CCT-76 | -1.0 | -1.0 | 1.0 | -1.2 | -1.4 | -1.2 | -1.0 | -1.1 |
| Phase-1 CCT-78 | 1.0 | 1.0 | -1.0 | -1.0 | 1.1 | -1.1 | -1.1 | -1.1 |
| Phase-1 CCT-79 | -1.1 | -1.1 | -1.1 | 1.1 | -1.1 | -1.1 | -1.3 | -1.2 |
| Phase-1 CCT-8 | 1.3 | -1.1 | 1.1 | 1.0 | -1.2 | -1.2 | 1.4 | -1.1 |
| Phase-1 CCT-80 | -1.3 | -1.0 | -1.2 | -1.2 | -1.4 | 1.0 | -1.2 | 1.0 |
| Phase-1 CCT-81 | -1.3 | -1.4 | 1.5 | -1.1 | -1.1 | -1.1 | 1.1 | -1.1 |
| Phase-1 CCT-82 | 1.0 | -1.0 | -1.1 | -1.0 | 1.0 | 1.0 | -1.1 | -1.2 |
| Phase-1 CCT-83 | -1.1 | -1.3 | 1.5 | -1.0 | -1.3 | 1.2 | 1.1 | -1.1 |
| Phase-1 CCT-84 | -1.1 | 1.1 | 1.1 | 1.2 | 1.5 | -1.0 | -1.3 | -1.0 |
| Phase-1 CCT-87 | 1.2 | -1.1 | -1.1 | -1.2 | -1.1 | 1.1 | 1.9 | -1.1 |
| Phase-1 CCT-88 | 1.3 | 1.2 | 1.2 | 1.3 | 1.2 | -1.1 | -1.1 | -1.1 |
| Phase-1 CCT-89 | -1.1 | -1.1 | 1.1 | 1.1 | -1.0 | -1.0 | -1.1 | 1.0 |
| Phase-1 CCT-9 | -1.1 | -1.2 | -1.2 | -1.5 | -1.5 | -1.3 | 1.2 | 1.4 |
| Phase-1 CCT-91 | -1.1 | 1.2 | 1.0 | 1.2 | 1.4 | 1.2 | -1.1 | 1.0 |
| Phase-1 CCT-92 | 1.1 | 1.2 | 1.2 | 1.2 | 1.3 | -1.0 | -1.2 | -1.0 |
| Phase-1 CCT-93 | -1.0 | -1.0 | -1.0 | -1.0 | -1.1 | -1.1 | -1.1 | -1.1 |
| Phase-1 CCT-94 | -1.0 | -1.0 | -1.1 | 1.0 | 1.1 | -1.1 | 1.1 | -1.2 |
| Phase-1 CCT-97 | -1.2 | 1.8 | 1.5 | 1.1 | -2.0 | -1.1 | -1.2 | 1.0 |
| Phenol sulfotransferase | 1.0 | -1.3 | 1.4 | 1.1 | 5.2 | -1.1 | 1.2 | 2.3 |
| Proliferating cell nuclear antigen gene | -1.0 | -1.1 | -1.2 | -1.1 | -1.3 | -1.1 | 2.2 | 2.3 |
| Prostaglandin D synthase | 1.5 | 1.1 | -1.1 | -1.2 | 1.4 | 1.1 | 2.6 | -1.1 |
| Rab2 | 1.2 | 1.0 | 1.3 | -1.2 | 1.0 | 1.2 | 1.4 | 1.2 |
| Rab5 | 1.4 | 1.1 | 1.2 | -1.1 | 1.1 | 1.1 | 1.7 | 1.2 |
| Rab7 | 1.2 | 1.0 | -1.0 | -1.3 | 1.0 | 1.2 | 1.8 | -1.1 |
| SHB (Src homology 2 protein) | 1.2 | -1.1 | 1.1 | -1.1 | 1.1 | 1.0 | 1.3 | -1.1 |
| Superoxide dismutase Mn | 1.1 | -1.2 | -1.4 | -1.1 | -1.1 | -1.1 | 2.2 | 2.4 |
| TFCOUP-related (probable steroid hormone receptor) | 1.2 | -1.1 | 1.0 | -1.0 | -1.2 | 1.1 | 1.8 | 1.1 |
| Tissue inhibitor of metalloproteinases-1 | 1.1 | -1.4 | 1.1 | -1.3 | -1.2 | 1.2 | 1.5 | -1.1 |
| TPRD | -1.1 | 1.2 | -1.4 | 1.4 | -1.1 | -1.0 | -1.5 | -1.1 |
| Tumor necrosis factor-alpha | -1.1 | -1.6 | 1.0 | -1.5 | 3.3 | -1.6 | 2.0 | 1.5 |
| Ubiquitin | 1.1 | -1.3 | 1.1 | -1.2 | 1.2 | -1.1 | 1.4 | 1.2 |
| UV excision repair protein RAD 23 (XP-C) | -1.4 | -1.0 | 1.0 | -1.4 | 1.0 | 1.1 | 1.8 | -1.0 |
| Vascular cell adhesion molecule 1 (VCAM-1) | -1.0 | -1.5 | 1.1 | -1.0 | -1.2 | 1.2 | 1.2 | 1.0 |
| ZAP36/annexin IV | 1.2 | -1.1 | 1.2 | -1.1 | 1.0 | -1.0 | 1.7 | -1.1 |

What is claimed is:

1. An array comprising a combination of canine nucleic acid molecules comprising SEQ ID Nos.: 116–118, 121 and 123 and the complements thereof, and consisting of SEQ ID No. 329 and the complements thereof.

2. The array according to claim 1 wherein the array contains a substrate for attaching nucleic acid molecules thereto.

3. The array according to claim 2 wherein the substrate is glass.

4. An array as described in claim 1 wherein the array further comprises SEQ ID Nos.: 115, 119, 120, 124–171, 179, 182, 185, 188, 191, 194, 197, 200, 203, 206, 209, 212, 213–328 and the complements thereof and SEQ ID Nos.: 329–384 and the complements thereof.

5. A method for detection of a nucleic acid in a canine sample, said method comprising:

a) obtaining nucleic acids from a canine sample;

b) contacting the nucleic acids of the canine sample with the array of claim 1 or 4 under conditions to form one or more hybridization complexes; and c) detecting said hybridization complexes.

* * * * *

SEQUENCE LISTING

<160> NUMBER OF SEQ ID NOS: 386

<210> SEQ ID NO 1
<211> LENGTH: 27
<212> TYPE: DNA
<213> ORGANISM: Canis familiaris

<400> SEQUENCE: 1
caagaggacg aagaagaaat tgatgtt                27

<210> SEQ ID NO 2
<211> LENGTH: 21
<212> TYPE: DNA
<213> ORGANISM: Canis familiaris

<400> SEQUENCE: 2
cgcttccgca acaagtcctt t                21

<210> SEQ ID NO 3
<211> LENGTH: 24
<212> TYPE: DNA
<213> ORGANISM: Canis familiaris

<400> SEQUENCE: 3
gtgtttgatg gtgacttggg aatg                24

<210> SEQ ID NO 4
<211> LENGTH: 24
<212> TYPE: DNA
<213> ORGANISM: Canis familiaris

<400> SEQUENCE: 4
gtactccggg ttctctgctg tagg                24

<210> SEQ ID NO 5
<211> LENGTH: 24
<212> TYPE: DNA
<213> ORGANISM: Canis familiaris

<400> SEQUENCE: 5
gacaaaatgc ttcagggtcg tctt                24

<210> SEQ ID NO 6
<211> LENGTH: 24
<212> TYPE: DNA
<213> ORGANISM: Canis familiaris

<400> SEQUENCE: 6
ccatgctgca taaaggtgtg aatc                24

<210> SEQ ID NO 7
<211> LENGTH: 24
<212> TYPE: DNA
<213> ORGANISM: Canis familiaris

<400> SEQUENCE: 7
acttttcgac acagtgtggt ggtg                24

<210> SEQ ID NO 8
<211> LENGTH: 24
<212> TYPE: DNA
<213> ORGANISM: Canis familiaris

```
<400> SEQUENCE: 8
cgagaggtag attgccccct cttt                                              24

<210> SEQ ID NO 9
<211> LENGTH: 19
<212> TYPE: DNA
<213> ORGANISM: Canis familiaris

<400> SEQUENCE: 9
gactccagcc gccccttct                                                    19

<210> SEQ ID NO 10
<211> LENGTH: 24
<212> TYPE: DNA
<213> ORGANISM: Canis familiaris

<400> SEQUENCE: 10
aggaatgtag tagcaaacgg gtca                                              24

<210> SEQ ID NO 11
<211> LENGTH: 24
<212> TYPE: DNA
<213> ORGANISM: Canis familiaris

<400> SEQUENCE: 11
tcacagtaac ctcaactcct gcca                                              24

<210> SEQ ID NO 12
<211> LENGTH: 26
<212> TYPE: DNA
<213> ORGANISM: Canis familiaris

<400> SEQUENCE: 12
gtcagtgttg agaagatgct ttgaca                                            26

<210> SEQ ID NO 13
<211> LENGTH: 23
<212> TYPE: DNA
<213> ORGANISM: Canis familiaris

<400> SEQUENCE: 13
gctctgactc tccctgtggt ctg                                               23

<210> SEQ ID NO 14
<211> LENGTH: 26
<212> TYPE: DNA
<213> ORGANISM: Canis familiaris

<400> SEQUENCE: 14
caaacgggaa tgtagaaaac aagtca                                            26

<210> SEQ ID NO 15
<211> LENGTH: 24
<212> TYPE: DNA
<213> ORGANISM: Canis familiaris

<400> SEQUENCE: 15
caagtcagag ctggaatttc ccat                                              24

<210> SEQ ID NO 16
<211> LENGTH: 24
<212> TYPE: DNA
```

<213> ORGANISM: Canis familiaris

<400> SEQUENCE: 16
tggaaagaac tcccaactgg acat  24

<210> SEQ ID NO 17
<211> LENGTH: 25
<212> TYPE: DNA
<213> ORGANISM: Canis familiaris

<400> SEQUENCE: 17
ggcaaagaga taaagcacct gaatg  25

<210> SEQ ID NO 18
<211> LENGTH: 24
<212> TYPE: DNA
<213> ORGANISM: Canis familiaris

<400> SEQUENCE: 18
atagatgcct ttctgagcca gcag  24

<210> SEQ ID NO 19
<211> LENGTH: 24
<212> TYPE: DNA
<213> ORGANISM: Canis familiaris

<400> SEQUENCE: 19
aagtattctg tgtggatcgg aggc  24

<210> SEQ ID NO 20
<211> LENGTH: 24
<212> TYPE: DNA
<213> ORGANISM: Canis familiaris

<400> SEQUENCE: 20
caacttcaag gcaattaacc accc  24

<210> SEQ ID NO 21
<211> LENGTH: 24
<212> TYPE: DNA
<213> ORGANISM: Canis familiaris

<400> SEQUENCE: 21
caaattgcct ccaactaatc agcc  24

<210> SEQ ID NO 22
<211> LENGTH: 24
<212> TYPE: DNA
<213> ORGANISM: Canis familiaris

<400> SEQUENCE: 22
acagggcaat gatcccaaag taga  24

<210> SEQ ID NO 23
<211> LENGTH: 23
<212> TYPE: DNA
<213> ORGANISM: Canis familiaris

<400> SEQUENCE: 23
gtccttgcat cctcattgga cct  23

<210> SEQ ID NO 24
<211> LENGTH: 24

```
<212> TYPE: DNA
<213> ORGANISM: Canis familiaris

<400> SEQUENCE: 24
gctgttttgc tgcaccatct tttt                                             24

<210> SEQ ID NO 25
<211> LENGTH: 24
<212> TYPE: DNA
<213> ORGANISM: Canis familiaris

<400> SEQUENCE: 25
tttctgggta ttgcaggagg aaaa                                             24

<210> SEQ ID NO 26
<211> LENGTH: 24
<212> TYPE: DNA
<213> ORGANISM: Canis familiaris

<400> SEQUENCE: 26
agtctgcagc agttctggga atct                                             24

<210> SEQ ID NO 27
<211> LENGTH: 24
<212> TYPE: DNA
<213> ORGANISM: Canis familiaris

<400> SEQUENCE: 27
ctgtgacagc attggagctt cttg                                             24

<210> SEQ ID NO 28
<211> LENGTH: 24
<212> TYPE: DNA
<213> ORGANISM: Canis familiaris

<400> SEQUENCE: 28
tttacatgag tgtcaccacc acca                                             24

<210> SEQ ID NO 29
<211> LENGTH: 25
<212> TYPE: DNA
<213> ORGANISM: Canis familiaris

<400> SEQUENCE: 29
ggctctgttg ttggaaatat acccc                                            25

<210> SEQ ID NO 30
<211> LENGTH: 24
<212> TYPE: DNA
<213> ORGANISM: Canis familiaris

<400> SEQUENCE: 30
cagttcacac aagagacgca ttca                                             24

<210> SEQ ID NO 31
<211> LENGTH: 27
<212> TYPE: DNA
<213> ORGANISM: Canis familiaris

<400> SEQUENCE: 31
gagacttggc tgctagaaat atcctcc                                          27

<210> SEQ ID NO 32
```

```
<211> LENGTH: 21
<212> TYPE: DNA
<213> ORGANISM: Canis familiaris

<400> SEQUENCE: 32
aattgatccg cacggaatgg t                                              21

<210> SEQ ID NO 33
<211> LENGTH: 24
<212> TYPE: DNA
<213> ORGANISM: Canis familiaris

<400> SEQUENCE: 33
ccaatttgaa gcctttctca agga                                           24

<210> SEQ ID NO 34
<211> LENGTH: 24
<212> TYPE: DNA
<213> ORGANISM: Canis familiaris

<400> SEQUENCE: 34
gagtaagcca aaagacgtga agcc                                           24

<210> SEQ ID NO 35
<211> LENGTH: 24
<212> TYPE: DNA
<213> ORGANISM: Canis familiaris

<400> SEQUENCE: 35
tgaatgcaca catgacttct tgga                                           24

<210> SEQ ID NO 36
<211> LENGTH: 25
<212> TYPE: DNA
<213> ORGANISM: Canis familiaris

<400> SEQUENCE: 36
tgatggatac actgcatact ctgcg                                          25

<210> SEQ ID NO 37
<211> LENGTH: 25
<212> TYPE: DNA
<213> ORGANISM: Canis familiaris

<400> SEQUENCE: 37
cagatgtgga gtatgagatg gacga                                          25

<210> SEQ ID NO 38
<211> LENGTH: 23
<212> TYPE: DNA
<213> ORGANISM: Canis familiaris

<400> SEQUENCE: 38
agaccaaaga tagagttgcc ccg                                            23

<210> SEQ ID NO 39
<211> LENGTH: 24
<212> TYPE: DNA
<213> ORGANISM: Canis familiaris

<400> SEQUENCE: 39
actcagagag catcctcaac cctg                                           24
```

```
<210> SEQ ID NO 40
<211> LENGTH: 25
<212> TYPE: DNA
<213> ORGANISM: Canis familiaris

<400> SEQUENCE: 40
cagaagctgt gcactgttttt ctcct                                    25

<210> SEQ ID NO 41
<211> LENGTH: 23
<212> TYPE: DNA
<213> ORGANISM: Canis familiaris

<400> SEQUENCE: 41
agccctggag gaagaggacc cct                                       23

<210> SEQ ID NO 42
<211> LENGTH: 23
<212> TYPE: DNA
<213> ORGANISM: Canis familiaris

<400> SEQUENCE: 42
cagaggctgg agttggtttg gcc                                       23

<210> SEQ ID NO 43
<211> LENGTH: 27
<212> TYPE: DNA
<213> ORGANISM: Canis familiaris

<400> SEQUENCE: 43
tcacctccca actgattcca actctgg                                   27

<210> SEQ ID NO 44
<211> LENGTH: 27
<212> TYPE: DNA
<213> ORGANISM: Canis familiaris

<400> SEQUENCE: 44
gtcttgtttg ccatgctgct gaggttc                                   27

<210> SEQ ID NO 45
<211> LENGTH: 26
<212> TYPE: DNA
<213> ORGANISM: Canis familiaris

<400> SEQUENCE: 45
cttgtgcaac tcccaaatcg tcatca                                    26

<210> SEQ ID NO 46
<211> LENGTH: 26
<212> TYPE: DNA
<213> ORGANISM: Canis familiaris

<400> SEQUENCE: 46
gtgcatatcc ctggctctct tggcag                                    26

<210> SEQ ID NO 47
<211> LENGTH: 27
<212> TYPE: DNA
<213> ORGANISM: Canis familiaris

<400> SEQUENCE: 47
gcagattttt gtaaagaccc tgacggg                                   27
```

```
<210> SEQ ID NO 48
<211> LENGTH: 27
<212> TYPE: DNA
<213> ORGANISM: Canis familiaris

<400> SEQUENCE: 48
acttcttctt gcggcagttg acagcac                                    27

<210> SEQ ID NO 49
<211> LENGTH: 23
<212> TYPE: DNA
<213> ORGANISM: Canis familiaris

<400> SEQUENCE: 49
agcggtcagt gtgaaggagg tgg                                        23

<210> SEQ ID NO 50
<211> LENGTH: 23
<212> TYPE: DNA
<213> ORGANISM: Canis familiaris

<400> SEQUENCE: 50
tgtcccaggg cacgatgaag tca                                        23

<210> SEQ ID NO 51
<211> LENGTH: 27
<212> TYPE: DNA
<213> ORGANISM: Canis familiaris

<400> SEQUENCE: 51
cctggtccag atgctaaaga gcaaggt                                    27

<210> SEQ ID NO 52
<211> LENGTH: 27
<212> TYPE: DNA
<213> ORGANISM: Canis familiaris

<400> SEQUENCE: 52
acctggctcc gaaacatcga ggatatt                                    27

<210> SEQ ID NO 53
<211> LENGTH: 25
<212> TYPE: DNA
<213> ORGANISM: Canis familiaris

<400> SEQUENCE: 53
tggaatttga acccaaacaa aggca                                      25

<210> SEQ ID NO 54
<211> LENGTH: 25
<212> TYPE: DNA
<213> ORGANISM: Canis familiaris

<400> SEQUENCE: 54
cccgcatcct ctaactggac cttgt                                      25

<210> SEQ ID NO 55
<211> LENGTH: 23
<212> TYPE: DNA
<213> ORGANISM: Canis familiaris

<400> SEQUENCE: 55
gctcccccag accttgttgg atc                                        23
```

<210> SEQ ID NO 56
<211> LENGTH: 23
<212> TYPE: DNA
<213> ORGANISM: Canis familiaris

<400> SEQUENCE: 56
gcatcaaagc gctcattctg ggc                                    23

<210> SEQ ID NO 57
<211> LENGTH: 27
<212> TYPE: DNA
<213> ORGANISM: Canis familiaris

<400> SEQUENCE: 57
aatcccagac atcccctgat caaagac                                27

<210> SEQ ID NO 58
<211> LENGTH: 27
<212> TYPE: DNA
<213> ORGANISM: Canis familiaris

<400> SEQUENCE: 58
cacttctttc tgtgacccac aatccca                                27

<210> SEQ ID NO 59
<211> LENGTH: 27
<212> TYPE: DNA
<213> ORGANISM: Canis familiaris

<400> SEQUENCE: 59
ttacacggtt gctgtcactg gatgaaa                                27

<210> SEQ ID NO 60
<211> LENGTH: 27
<212> TYPE: DNA
<213> ORGANISM: Canis familiaris

<400> SEQUENCE: 60
cacccaggtg ccccactatt catgttt                                27

<210> SEQ ID NO 61
<211> LENGTH: 27
<212> TYPE: DNA
<213> ORGANISM: Canis familiaris

<400> SEQUENCE: 61
tgcactatca tcagagcatg cctccct                                27

<210> SEQ ID NO 62
<211> LENGTH: 27
<212> TYPE: DNA
<213> ORGANISM: Canis familiaris

<400> SEQUENCE: 62
tccatcctag gaccccgaga tcatgac                                27

<210> SEQ ID NO 63
<211> LENGTH: 23
<212> TYPE: DNA
<213> ORGANISM: Canis familiaris

<400> SEQUENCE: 63

```
ggacccttc cgcgactggt acc                                           23
```

<210> SEQ ID NO 64
<211> LENGTH: 23
<212> TYPE: DNA
<213> ORGANISM: Canis familiaris

<400> SEQUENCE: 64

```
tgatttctgc cgactgggtg gct                                          23
```

<210> SEQ ID NO 65
<211> LENGTH: 26
<212> TYPE: DNA
<213> ORGANISM: Canis familiaris

<400> SEQUENCE: 65

```
cgggtccctg ctggaggact ttaaga                                       26
```

<210> SEQ ID NO 66
<211> LENGTH: 26
<212> TYPE: DNA
<213> ORGANISM: Canis familiaris

<400> SEQUENCE: 66

```
ggtatgacgg ggttctccaa gcagtt                                       26
```

<210> SEQ ID NO 67
<211> LENGTH: 23
<212> TYPE: DNA
<213> ORGANISM: Canis familiaris

<400> SEQUENCE: 67

```
tccgaggggc acctctacac cgt                                          23
```

<210> SEQ ID NO 68
<211> LENGTH: 23
<212> TYPE: DNA
<213> ORGANISM: Canis familiaris

<400> SEQUENCE: 68

```
ttgccaacag cctcaaagaa cgg                                          23
```

<210> SEQ ID NO 69
<211> LENGTH: 27
<212> TYPE: DNA
<213> ORGANISM: Canis familiaris

<400> SEQUENCE: 69

```
accatccagc tcatccagaa ccacttc                                      27
```

<210> SEQ ID NO 70
<211> LENGTH: 27
<212> TYPE: DNA
<213> ORGANISM: Canis familiaris

<400> SEQUENCE: 70

```
tggcaaatac acagagaaag ccctccc                                      27
```

<210> SEQ ID NO 71
<211> LENGTH: 27
<212> TYPE: DNA
<213> ORGANISM: Canis familiaris

<400> SEQUENCE: 71
agacaagagg tttcagccag tgcatga                                    27

<210> SEQ ID NO 72
<211> LENGTH: 27
<212> TYPE: DNA
<213> ORGANISM: Canis familiaris

<400> SEQUENCE: 72
gtgtgtggca ttagtagcag cgtgctg                                    27

<210> SEQ ID NO 73
<211> LENGTH: 27
<212> TYPE: DNA
<213> ORGANISM: Canis familiaris

<400> SEQUENCE: 73
aagcctagtg cttcgttttg tgaaggg                                    27

<210> SEQ ID NO 74
<211> LENGTH: 27
<212> TYPE: DNA
<213> ORGANISM: Canis familiaris

<400> SEQUENCE: 74
ttggctgcgt gggttcagta aggtcta                                    27

<210> SEQ ID NO 75
<211> LENGTH: 26
<212> TYPE: DNA
<213> ORGANISM: Canis familiaris

<400> SEQUENCE: 75
ccccaacaca ttcaaaaccc tcgata                                     26

<210> SEQ ID NO 76
<211> LENGTH: 26
<212> TYPE: DNA
<213> ORGANISM: Canis familiaris

<400> SEQUENCE: 76
tgtgtgtgtc agggtgaagt gtttgg                                     26

<210> SEQ ID NO 77
<211> LENGTH: 27
<212> TYPE: DNA
<213> ORGANISM: Canis familiaris

<400> SEQUENCE: 77
ctggttctgt tgcttgtcct cctggta                                    27

<210> SEQ ID NO 78
<211> LENGTH: 27
<212> TYPE: DNA
<213> ORGANISM: Canis familiaris

<400> SEQUENCE: 78
ggtcagtgaa aatccctgcg taagtgc                                    27

<210> SEQ ID NO 79
<211> LENGTH: 23
<212> TYPE: DNA
<213> ORGANISM: Canis familiaris

```
<400> SEQUENCE: 79
ctgtccgcct ctgtccccct gtt                                            23

<210> SEQ ID NO 80
<211> LENGTH: 23
<212> TYPE: DNA
<213> ORGANISM: Canis familiaris

<400> SEQUENCE: 80
ggagtaggga caacacccag ccg                                            23

<210> SEQ ID NO 81
<211> LENGTH: 27
<212> TYPE: DNA
<213> ORGANISM: Canis familiaris

<400> SEQUENCE: 81
tgattgttct tctgccacca aaatgcc                                        27

<210> SEQ ID NO 82
<211> LENGTH: 27
<212> TYPE: DNA
<213> ORGANISM: Canis familiaris

<400> SEQUENCE: 82
taaatacaga acgcacaaca cggcgac                                        27

<210> SEQ ID NO 83
<211> LENGTH: 23
<212> TYPE: DNA
<213> ORGANISM: Canis familiaris

<400> SEQUENCE: 83
gccttaccct cagggacctt gca                                            23

<210> SEQ ID NO 84
<211> LENGTH: 23
<212> TYPE: DNA
<213> ORGANISM: Canis familiaris

<400> SEQUENCE: 84
gcatgaacaa aacagcctcc gcc                                            23

<210> SEQ ID NO 85
<211> LENGTH: 23
<212> TYPE: DNA
<213> ORGANISM: Canis familiaris

<400> SEQUENCE: 85
aggtgtccct gcagcccaac ttc                                            23

<210> SEQ ID NO 86
<211> LENGTH: 23
<212> TYPE: DNA
<213> ORGANISM: Canis familiaris

<400> SEQUENCE: 86
gggcggcggt cacctacttg ttc                                            23

<210> SEQ ID NO 87
<211> LENGTH: 27
<212> TYPE: DNA
<213> ORGANISM: Canis familiaris
```

-continued

```
<400> SEQUENCE: 87
caggactcca cagcttttcc ccagata                                         27

<210> SEQ ID NO 88
<211> LENGTH: 27
<212> TYPE: DNA
<213> ORGANISM: Canis familiaris

<400> SEQUENCE: 88
ggtgaaatat tgatcccatt tgctgca                                         27

<210> SEQ ID NO 89
<211> LENGTH: 25
<212> TYPE: DNA
<213> ORGANISM: Canis familiaris

<400> SEQUENCE: 89
cgccgtatgt ggacgtcatc tgtgt                                           25

<210> SEQ ID NO 90
<211> LENGTH: 25
<212> TYPE: DNA
<213> ORGANISM: Canis familiaris

<400> SEQUENCE: 90
agacagaggc ttcagagggc gaacg                                           25

<210> SEQ ID NO 91
<211> LENGTH: 23
<212> TYPE: DNA
<213> ORGANISM: Canis familiaris

<400> SEQUENCE: 91
ctccaggtgg gcttcgagga cgt                                             23

<210> SEQ ID NO 92
<211> LENGTH: 23
<212> TYPE: DNA
<213> ORGANISM: Canis familiaris

<400> SEQUENCE: 92
tggggtccaa gtgctcagtc gtg                                             23

<210> SEQ ID NO 93
<211> LENGTH: 27
<212> TYPE: DNA
<213> ORGANISM: Canis familiaris

<400> SEQUENCE: 93
ttcttcaaag gagacaagca ctgggtg                                         27

<210> SEQ ID NO 94
<211> LENGTH: 27
<212> TYPE: DNA
<213> ORGANISM: Canis familiaris

<400> SEQUENCE: 94
tagcctggct ctaccttcag cttctgg                                         27

<210> SEQ ID NO 95
<211> LENGTH: 23
<212> TYPE: DNA
```

<213> ORGANISM: Canis familiaris

<400> SEQUENCE: 95
gattctccaa gggcaaggga cgc                                              23

<210> SEQ ID NO 96
<211> LENGTH: 23
<212> TYPE: DNA
<213> ORGANISM: Canis familiaris

<400> SEQUENCE: 96
tcacgtagcc cacttcgtcc acc                                              23

<210> SEQ ID NO 97
<211> LENGTH: 27
<212> TYPE: DNA
<213> ORGANISM: Canis familiaris

<400> SEQUENCE: 97
gtggcccaca ttgtgaaaac tcagaaa                                          27

<210> SEQ ID NO 98
<211> LENGTH: 27
<212> TYPE: DNA
<213> ORGANISM: Canis familiaris

<400> SEQUENCE: 98
gaccaaggca aggttgaaaa gggactc                                          27

<210> SEQ ID NO 99
<211> LENGTH: 27
<212> TYPE: DNA
<213> ORGANISM: Canis familiaris

<400> SEQUENCE: 99
caatgacatg actccagagc aaatggc                                          27

<210> SEQ ID NO 100
<211> LENGTH: 27
<212> TYPE: DNA
<213> ORGANISM: Canis familiaris

<400> SEQUENCE: 100
ttgccatagg aagaaagtgg gctgttt                                          27

<210> SEQ ID NO 101
<211> LENGTH: 27
<212> TYPE: DNA
<213> ORGANISM: Canis familiaris

<400> SEQUENCE: 101
gattgaaaat ggagccttcc agggaat                                          27

<210> SEQ ID NO 102
<211> LENGTH: 27
<212> TYPE: DNA
<213> ORGANISM: Canis familiaris

<400> SEQUENCE: 102
ataatttcca agctggatgg cagagcg                                          27

<210> SEQ ID NO 103
<211> LENGTH: 27

```
<212> TYPE: DNA
<213> ORGANISM: Canis familiaris

<400> SEQUENCE: 103
ctggggatct cagctgcagg attttct                                              27

<210> SEQ ID NO 104
<211> LENGTH: 27
<212> TYPE: DNA
<213> ORGANISM: Canis familiaris

<400> SEQUENCE: 104
atcctttcct ctccttgccc tctcctc                                              27

<210> SEQ ID NO 105
<211> LENGTH: 23
<212> TYPE: DNA
<213> ORGANISM: Canis familiaris

<400> SEQUENCE: 105
gacccttcct gctcctcatg gcc                                                  23

<210> SEQ ID NO 106
<211> LENGTH: 23
<212> TYPE: DNA
<213> ORGANISM: Canis familiaris

<400> SEQUENCE: 106
cttaaataca gcccggcgca gcg                                                  23

<210> SEQ ID NO 107
<211> LENGTH: 27
<212> TYPE: DNA
<213> ORGANISM: Canis familiaris

<400> SEQUENCE: 107
gacacgtcct tcatgttcca gagggtg                                              27

<210> SEQ ID NO 108
<211> LENGTH: 27
<212> TYPE: DNA
<213> ORGANISM: Canis familiaris

<400> SEQUENCE: 108
ccagatgtgt caccttgat gaaggag                                               27

<210> SEQ ID NO 109
<211> LENGTH: 26
<212> TYPE: DNA
<213> ORGANISM: Canis familiaris

<400> SEQUENCE: 109
gttggagcag gtggtgttgg gaaaag                                               26

<210> SEQ ID NO 110
<211> LENGTH: 26
<212> TYPE: DNA
<213> ORGANISM: Canis familiaris

<400> SEQUENCE: 110
gcaaatacac agaggaagcc ttcgcc                                               26

<210> SEQ ID NO 111
```

```
<211> LENGTH: 26
<212> TYPE: DNA
<213> ORGANISM: Canis familiaris

<400> SEQUENCE: 111
gtagttggag ctggtggcgt aggcaa                                        26

<210> SEQ ID NO 112
<211> LENGTH: 26
<212> TYPE: DNA
<213> ORGANISM: Canis familiaris

<400> SEQUENCE: 112
ggcaaataca caaagaaagc cctccc                                        26

<210> SEQ ID NO 113
<211> LENGTH: 27
<212> TYPE: DNA
<213> ORGANISM: Canis familiaris

<400> SEQUENCE: 113
ctggtgaccc atcttatggg agcagat                                       27

<210> SEQ ID NO 114
<211> LENGTH: 27
<212> TYPE: DNA
<213> ORGANISM: Canis familiaris

<400> SEQUENCE: 114
tttgcaaagt tcatcttcgg catctgg                                       27

<210> SEQ ID NO 115
<211> LENGTH: 503
<212> TYPE: DNA
<213> ORGANISM: Canis familiaris

<400> SEQUENCE: 115
caagaggacg aagaagaaat tgatgttgtt tctgtggaaa aaaggcaggc cctgccaaa    60
aggtccgaat cggggtcccc ctctgctgga ggccacagca aacctcctca cagcccactg  120
gtccttaaga gatgccatgt gtccacccat cagcacaact acgcggcacc ccctccacc   180
aggaaggact atcccgccgc caagagggcg aggttggaca gtggtagagt cctgaaacag  240
atcagcaaca accgcaaatg tgccagcccc aggtcttcgg acacggagga gaatgacaag  300
aggcgaacac acaacgtctt ggagcgccag aggaggaaca agctgaaacg gagcttcttt  360
gccctgcgtg atcagatccc ggagttggaa acaatgaaa aggcccccaa ggtagtgatc  420
cttaaaaaag ccaccgcgta catcctgtcc gtccaagccg aggagcaaaa gctcctttcc  480
gaaaaggact tgttgcggaa gcg                                          503

<210> SEQ ID NO 116
<211> LENGTH: 507
<212> TYPE: DNA
<213> ORGANISM: Canis familiaris

<400> SEQUENCE: 116
gtgtttgatg gtgacttggg aatgggggca gccaaggggc tgcagagcct tccctcacag   60
gaccccagcc ctctccagcg gtacagtgag gaccctacgg tacccttgcc ccctgagact  120
gatggtaagg ttgcccccct gacctgcagc cccagcctg aatatgtgaa ccagccagaa   180
gtttggccgc agccccccct tgccctagaa ggccctttgc ctccttcccg accggctggt  240
```

```
gccactctgg aaaggcccaa gactctgtcc cccaagactc tctccctgg caagaatggg      300 gttgtcaaag acgttttgc ctttgggagt gctgtggaga atccggagta cctggcaccc      360
cggggcagag ctgcccctca gccccaccct cctccagcct tcagcccagc ctttgacaac      420
ctgtattact gggaccagga tccatcagag cggggctctc acccagcac ctttgaaggg       480 accctacag cagagaaccc ggagtac                                           507

<210> SEQ ID NO 117
<211> LENGTH: 506
<212> TYPE: DNA
<213> ORGANISM: Canis familiaris

<400> SEQUENCE: 117
gacaaaatgc ttcagggtcg tcttttttgcc tatcctgaca ctcaccgcca ccgcctggga    60
cccaactatc ttcagatacc tgtgaactgt cctttccggg ctcgagtggc caactaccaa    120
cgggatggcc ccatgtgcat gctcgacaat cagggtggtc ctccaaatta ctaccccaat    180
agctttagtg ctcctgaaca acagcgttgt gtcctagagc atagcagcca atgttcgcca    240
gatgtgcagc gcttcaacag tgccaatgaa gataatgtca ctcaggtgcg gaccttctat    300
ttgaaggtac ttggtgaaga ggagaggaaa cgcctgtgcg agaacattgc tggccatctg    360
aaggacgcac aacttttcat ccagaagaaa gcggtcaaga acttcagtga tgtccaccct    420 gactacggg cccgcattca ggctcttttg gacaaataca atgctgagaa acctaagaac     480
gcgattcaca cctttatgca gcatgg                                         506

<210> SEQ ID NO 118
<211> LENGTH: 506
<212> TYPE: DNA
<213> ORGANISM: Canis familiaris

<400> SEQUENCE: 118
acttttcgac acagtgtggt ggtgccttat gagccacccg aggttggctc tgactatacc     60
accatccact acaactacat gtgtaacagt tcctgcatgg gaggcatgaa ccggcggccc    120
atcctcacta tcatcaccct ggaagactcc agtgaaacg tgctgggacg caacagcttt     180
gaggtacgcg tttgtgcctg tcccgggaga gaccgccgga ctgaggagga gaatttccac    240 aagaagggg agccttgtcc tgagccaccc ccggggagta ccaagcgagc actgcctccc    300
agcaccagct cctctccccc gcaaaagaag aagccactag atggagaata tttcacccctt    360 cagatccgtg gcgtgaacg ctatgagatg ttcaggaatc tgaatgaagc cttggagctg     420
aaggatgccc agagtggaaa ggagccaggg ggaagcaggg ctcactccag ccacctgaag    480
gcaaagaagg ggcaatctac ctctcg                                        506

<210> SEQ ID NO 119
<211> LENGTH: 330
<212> TYPE: DNA
<213> ORGANISM: Canis familiaris

<400> SEQUENCE: 119
gactccagcc gccccttctc gcatggatc ccaactgctc ctgcgccgcg gggggctcct      60
gcacgtgcgc cggctcctgc aaatgcaaag agtgcagatg cacctcctgc aagaagagct    120
gctgctcctg ctgccccgtg ggctgtgcca agtgtgccca gggctgcatc tgcaagggcg    180
catcggacaa gtgcagctgc tgtgcctgat gtggggaga gcctattcct gatgtaaata    240
```

```
gagcgacgtg tacaaaccta cagtttgtgg ggggtttttt ggtgctttt gttttgggtc      300 caactctgac ccgtttgcta ctacattcct                                      330

<210> SEQ ID NO 120
<211> LENGTH: 490
<212> TYPE: DNA
<213> ORGANISM: Canis familiaris

<400> SEQUENCE: 120
tcacagtaac ctcaactcct gccacaatgt acaaaatgca actcttgtct tgcatcgcac      60
tgacgcttgt acttgtcgca aacagtgcac ctattacttc aagctctaca aggaaacag      120 agcaacagat ggagcaatta ctgctggatt tacagttgct tttgaatgga gttaataatt     180
atgagaaccc ccaactctcc aggatgctca catttaagtt ttacacgccc aagaaggcca     240
cagaatttac acccttcaa tgtctagcag aagaactcaa aaacctggag gaagtgctag      300
gtttacctca aagcaaaaac gttcacttga cagacaccaa ggaattaatc agcaatatga     360
atgtaacact tctgaaacta aagggatctg aaacaagtta caactgtgaa tatgatgacg     420
agacagcaac cattacagaa tttctgaaca aatggattac cttttgtcaa agcatcttct     480
caacactgac                                                           490

<210> SEQ ID NO 121
<211> LENGTH: 376
<212> TYPE: DNA
<213> ORGANISM: Canis familiaris

<400> SEQUENCE: 121
gctctgactc tccctgtggt ctgcctggga cctccgtcct cgcctcgcct cgcctcgcct      60
cgcctcgcct gggctcgaga tggaccccga ctgctcctgc tccaccggtg gctcctgcac     120
gtgcgctggc tcctgcaaat gcaaggagtg caaatgcacc tcctgcaaga agagttgctg     180
ctcctgctgc cccgtgggct gtgccaagtg tgcccagggc tgcatctgca agggtgcgtc     240
ggacaagtgc agctgctgtg cctgatgtgt gagaacacct gttcctgatg tatatagagc     300
aagcaacatg tacaaacctg cagttttaaa gcattttttt catatcactc tgacttgttt     360
tctacattcc cgtttg                                                    376

<210> SEQ ID NO 122
<211> LENGTH: 507
<212> TYPE: DNA
<213> ORGANISM: Canis familiaris

<400> SEQUENCE: 122
caagtcagag ctggaatttc ccattccatt ggctaagctg ctttcctcca gaggaggact      60
ggcaatggtg atacagttta gttggcgaca tgcccaggga caacccactg agccccatac     120
tcctccccgt cactgacact gacctctgtt agccgtctct ctccccatac gcatctctgc     180
tagtgctcac gatgacatcg ctgcatgcct gaacacgaat gaccactcac tggcagctaa     240
actgtggagt cccatgaaac tgcccaaccc ctatgtgtcc ctgcctggtc ctgtttccat     300
ctcggtggca ccatacaagg acacagcact ctggcagccc aaattcctgc agagacgagg     360
gccctgcagg cagttggcag aagaggccgg cgaggattcc tgtcccagct ccggaagctt     420
ctctcttgta gtaataaagc ttgtctgtgg gcgcttgtct tgtgtgagtg gagggaggt      480 gtcatgtcca gttgggagtt ctttcca                                        507
```

```
<210> SEQ ID NO 123
<211> LENGTH: 510
<212> TYPE: DNA
<213> ORGANISM: Canis familiaris

<400> SEQUENCE: 123
ggcaaagaga taaagcacct gaatgtccag tggctccgag cacacctggg catcgtgtct      60
caggagccca tcctgtttga ctgcagcatt gccgagaaca ttgcctatgg agacaacagc     120
cgggtcgtat cacatgaaga gattatgcag gcagccaagg aggccaacat acaccacttc     180
atcgagacac tccctgagaa atacaacacc agagtaggac acaaaggaac ccagctctct     240
ggtggccaga acagcgcat tgccatagct cgcgctcttg ttagacagcc tcatattttg      300
cttttggatg aagctacatc agctctggat acagaaagtg aaaaggttgt ccaagaagcc     360
ctggacaaag ccagagaagg ccgcacctgc attgtgatcg cccaccgctt gtccaccatc     420
cagaatgcag atttaatagt ggtgtttcag aatggcaaag tcaaggagca tggcacacat     480
caacagctgc tggctcagaa aggcatctat                                     510

<210> SEQ ID NO 124
<211> LENGTH: 509
<212> TYPE: DNA
<213> ORGANISM: Canis familiaris
<220> FEATURE:
<221> NAME/KEY: misc_feature
<222> LOCATION: (1)...(509)
<223> OTHER INFORMATION: n = A, T, C or G

<400> SEQUENCE: 124
aagtattctg tgtggatcgg aggctccatc ctggcctcgc tgtccacctt ccagcagatg      60
tggatcagca gcaggagta cgacgagtcg ggccccctcca tcgtccatcg caaatgcttc     120
tagatcgact gcgagcagat gcgtagcatt tgctgcatga gtgaattccg aagtataaat     180
tggccctggc aaatggctag cctcatgaaa ctggaataag cgctttgaaa agaaatttgt     240
ccttgaagct ngtatctgat atatcagcan tggattgtag aacttgttgc tgatcttgac     300
nttgtatcca agttaactgt tcccttggta tatgtttaat accgcctatt ccaggattct     360
ctagaggctg gcaagagtct gaaccagttg tcatttctgt cttgccggtc taacagggtt     420
gggaaggtcc gagccttagg acccactttc ctgtcttacc caatgttttc ctgccagaac     480
accgtgggtg gttaattgcc ttgaagttg                                      509

<210> SEQ ID NO 125
<211> LENGTH: 510
<212> TYPE: DNA
<213> ORGANISM: Canis familiaris

<400> SEQUENCE: 125
caaattgcct ccaactaatc agccctcttg cccagacagt caaatcatct tctcgaaccc      60
caagtgacaa gccagtagct catgttgtag caaaccccga agctgagggg cagctccagt     120
ggctgagccg acgtgccaat gacctcctgg ccaatgacgt ggagctgaca gacaaccagc     180
tgatagtgcc gtcagatggg ttgtacctcg atagctccca ggtcctcttc aagggccaag     240
ggtgcccttc cacccatgtg ctcctcaccc acaccatcag ccgcttcgcc gtctcctacc     300
agacaaaggt caacctactc tctgccatca agagcccttg ccaaagggag accccagagg     360
ggaccgaggc caagccctgg tacgagccca tctacctggg aggggtcttc caactggaga     420
agggtgatcg actcagcgct gagatcaatc tgcctaacta tctggacttt gccgagtctg     480
```

```
ggcaggtcta ctttgggatc attgccctgt                                    510

<210> SEQ ID NO 126
<211> LENGTH: 510
<212> TYPE: DNA
<213> ORGANISM: Canis familiaris

<400> SEQUENCE: 126
gtccttgcat cctcattgga cctggcacag gcatcgcccc cttccgcagt ttctggcagc    60
agcggctcca tgacatcaag cacaaagggc tccggggcag ccgcatgacc ctggtgtttg   120
ggtgccgccg cccagatgag gaccacctgt atcgggagga gatgttggag atggcccaga   180
gtggggtgct gcatgaggtg cacacagcct attctcgcct gcctggccag cccaaggtct   240
atgttcaaga catcctgcgg cagcagctgg ccagccaggt gctccgcatg ctccatgagg   300
agcagggcca cctttatgtc tgtggggatg tgcgtatggc ccgggatgtg cccataccc    360 tgaagcacct ggtggctgcc aagctgagcc tgagtgaaga gcaagttgag gactattttt   420
tccagcttaa gagccagaag cgctatcatg aagatatctt tggtgctgtg tttccctatg   480
aggtgaaaaa agatggtgca gcaaaacagc                                    510

<210> SEQ ID NO 127
<211> LENGTH: 499
<212> TYPE: DNA
<213> ORGANISM: Canis familiaris

<400> SEQUENCE: 127
tttctgggta ttgcaggagg aaaatgggta gttagctatt tctgggtaac ccagtctatt    60
aaagaaagaa agatactaga tgagcatgat tttgaagtca gaggagatgt tgtgaatgga   120
agaaatcacc agggtccgaa gcgagcaaga gaatcccagg acagagaatc ccaagacaga   180
aagatcttca ggggcctaga atctgttgc tatggacccct ttaccaacat gcccacagat   240
caattagagt ggatggtgca cctctgtggg gcttctgtgg tgaaggagcc ttcgttattc   300
accctcagca aggcactca tccagtggta gtcgtgcagc cggacgcctg gacagaggac   360
agtggcttcc atgcgattgg gcagatgtgt gaggcacctg tggtgacccg agagtgggta   420
ctggacagtg tagccctcta ccagtgccag gagctggaca cctacctgat cccgcagatt   480
cccagaactg ctgcagact                                                499

<210> SEQ ID NO 128
<211> LENGTH: 385
<212> TYPE: DNA
<213> ORGANISM: Canis familiaris

<400> SEQUENCE: 128
ctgtgacagc attggagctt cttggacacc tggacatgga ccccgggaa tgcacctgca    60 tgtctggagg aatctgtatc tgtggagaca attgcaaatg tacaacctgc aactgtaaaa   120
catgtcgaaa aagctgctgt ccttgctgcc ccccggctg tgccaagtgt gcccagggct   180
gcatctgcaa aggaggctcg gacaagtgca gctgctgtgc ctgaaccgca tccgtggtgc   240
tggggctggc gggggcgggg gttgtggatg ccacagcccc ggaaatgtct gtacagtgca   300
ttagttgaga aactgaaatt attgtaccat aggttatgct tttatatat ttgctcagag    360 gtggtggtgg tgacactcat gtaaa                                         385

<210> SEQ ID NO 129
<211> LENGTH: 507
```

```
<212> TYPE: DNA
<213> ORGANISM: Canis familiaris

<400> SEQUENCE: 129
ggctctgttg ttggaaatat accccataag cgttactgca cttgttcctc accccggaa      60 cagggtgaag agagctattc tgtgtcccca gggaaaatat attcaccctc aagacgattc    120
catttgctgt acgaagtgcc acaaagggac ctacctgtac aatgactgtc caggcccagg    180
gctggacaca gactgcaggg aatgtgaaaa cggaactttt acagcttcag agaaccacct    240
cagacaatgt cttagctgct ccaaatgccg aaaagaaatg aaccaggtgg agatttctcc    300
ttgtactgtg taccgggaca cggtgtgtgg ctgcaggaag aaccagtacc ggttttattg    360
gagtgaaacc cttttccagt gcaataactg cagcctctgc ctcaatggca cggtgcagat    420
ctcctgccaa gagaagcaga acaccatatg cacctgccac gcggggttct ttctaagaga    480
gcatgaatgc gtctcttgtg tgaactg                                        507

<210> SEQ ID NO 130
<211> LENGTH: 504
<212> TYPE: DNA
<213> ORGANISM: Canis familiaris

<400> SEQUENCE: 130
gagacttggc tgctagaaat atcctcctta ctcatggtcg aatcacaaag atttgtgatt      60
ttggtctagc cagagacatc aagaatgatt ctaattatgt ggtcaaagga aacgctcggc    120
tacctgtgaa gtggatggcc cctgagagca ttttcaactg tgtgtacaca tttgaaagtg    180
atgtctggtc ctatgggatt tttctgtggg agctcttctc tttaggaagc agccctacc     240 ctgggatgcc agtcgattca aagttctaca agatgatcaa ggaaggcttc cggatgctca    300
gccctgagca tgcacctgct gaaatgtatg acatcatgaa acgtgctgg gatgctgatc     360 ccctgaaaag gccgacgtcc aagcagatcg tgcagctaat tgagaagcag atttcagata    420
gcaccaatca tatttattcc aacctcgcga actgcagccc caacccagag cgccccgtgg    480
tggaccattc cgtgcggatc aatt                                           504

<210> SEQ ID NO 131
<211> LENGTH: 508
<212> TYPE: DNA
<213> ORGANISM: Canis familiaris

<400> SEQUENCE: 131
ccaatttgaa gcctttctca aggagataat gctaaacaac gaaatgaaga aagaagaaaa      60
cattgcaatg caaaaaggtg atcaggatcc tcgaattgca gcccatgtca taagtgaggc    120
tagtagtaac ccagcgtccg ttctgcggtg ggcgccaaaa gggtactaca ccataagcag    180
caacctggtg agcctcgaga atgggaaaca gttggccgtg aaaagacaag gactctatta    240
cgtctatgcc caagtcacct tctgctccaa tcgggcagct tcgagtcaag ctccgttcgt    300
cgccagccta tgcctccatt ccccgagtgg aacggagaga gtcttactcc cgccgcgag     360 ctcccgcggc tcgtccaaac cttgcggcca acagtccatc cacttgggag gagtatttga    420
attgcatcca ggtgcttcgg tgttcgtcaa cgtgactgat ccaagccaag tgagccacgg    480
gaccggcttc acgtctttg gcttactc                                        508

<210> SEQ ID NO 132
<211> LENGTH: 508
<212> TYPE: DNA
```

<213> ORGANISM: Canis familiaris

<400> SEQUENCE: 132

| | | | | | |
|---|---|---|---|---|---|
| tgaatgcaca | catgacttct | tggaggtaag | aaatggaagt | gatagcagtt | caccattatt | 60 |
| tggcacatac | tgtggaactc | tgttgccaga | tcctatcttc | tctcgaaaca | acaaactata | 120 |
| cctacggttt | aagaccgata | gcgcaacttc | caatcgtggg | tatgaaattg | tctggacctc | 180 |
| atcaccctct | ggctgtggtg | gaacccttta | tggagacagt | ggttccttca | ccagcccgg | 240 |
| ctatcccggc | acttaccca | acaacactga | ctgtgaatgg | gccatcatcg | ctcctgctgg | 300 |
| aagacctgtc | accgtcacct | tttactttat | cagcatcgat | gatcccggag | actgtgtcca | 360 |
| gaactatctc | atactctacg | atggaccgga | tgctaattct | ccatcctttg | gaccatactg | 420 |
| tggggcagac | accaacatag | ctccctttgt | ggcctcttca | catcgtgtct | tcataaaatt | 480 |
| tcacgcagag | tatgcagtgt | atccatca | | | | 508 |

<210> SEQ ID NO 133
<211> LENGTH: 499
<212> TYPE: DNA
<213> ORGANISM: Canis familiaris

<400> SEQUENCE: 133

| | | | | | |
|---|---|---|---|---|---|
| cagatgtgga | gtatgagatg | gacgagaagt | ccaggggcac | gaggctggat | ggcctgaacc | 60 |
| tcatcgacat | ctggaagaac | ttcaaaccga | gacacaagca | ctctcactac | gtctggaacc | 120 |
| gcacggaact | cctggccctc | gaccctaca | ccgtggacta | cctcttgggt | ctctttgagc | 180 |
| cgggggacat | gcagtacgag | ctgaacagga | acaacgtgac | tgacccgtca | ctctccgaga | 240 |
| tggtggaaat | agccatcaag | attctgagca | agaaccccag | aggcttcttc | ttgctggtgg | 300 |
| aaggaggcag | gattgaccac | gggcatcacg | agggcaaggc | caagcaggcg | ctgcacgagg | 360 |
| cagtggagat | ggaccgggca | attgggaagg | caggcgtcat | gacctccttg | gaagacacgc | 420 |
| tgaccgtcgt | cactgcggac | cactcccacg | tcttcacctt | tggcgggtac | acccccgggg | 480 |
| gcaactctat | ctttggtct | | | | | 499 |

<210> SEQ ID NO 134
<211> LENGTH: 490
<212> TYPE: DNA
<213> ORGANISM: Canis familiaris

<400> SEQUENCE: 134

| | | | | | |
|---|---|---|---|---|---|
| actcagagag | catcctcaac | cctgatggat | ttgcttccta | cccctgtgct | tcctacaggg | 60 |
| cctttgaatc | taacaagtgc | ttcccctgcc | cagatcaagg | gtgcccacag | atgggtcact | 120 |
| atgctgataa | atttgctgtc | aagacaagtg | atgagacaca | gaaatacttc | ctgaacaccg | 180 |
| gagattccag | caattttgct | cgctggagat | acggggtttc | tataacattg | tctgggaaaa | 240 |
| gagccactgg | tcaggctaaa | gttgcttttgt | ttggaagtaa | gggaaatact | catcaattca | 300 |
| atatcttcaa | ggggattctc | aaaccaggct | ctactcattc | caatgagttt | gatgcaaagc | 360 |
| ttgatgttgg | aacaattgag | aaagtcaagt | ttctttggaa | taacaacgtg | gtaaacccaa | 420 |
| cctttcccaa | agtgggtgca | gccaagatca | ccgtgcaaaa | gggagaggag | aaaacagtgc | 480 |
| acagcttctg | | | | | | 490 |

<210> SEQ ID NO 135
<211> LENGTH: 236
<212> TYPE: DNA
<213> ORGANISM: Canis familiaris

<400> SEQUENCE: 135

```
agccctggag gaagaggacc cctccctcct gggccttatg cagggttaca tgcagcacgc      60
caccaagacg gcccaggaca cgctgaccag cgttcaggag tcccaggtgg cgcagcgggc     120
caggggctgg atgaccgata gcttcagttc cctgaaagac tactgcagca cgtttaaggg    180
caagttcact gggttctggg attcagcctc tgaggccaaa ccaactccag cctctg         236
```

<210> SEQ ID NO 136
<211> LENGTH: 301
<212> TYPE: DNA
<213> ORGANISM: Canis familiaris

<400> SEQUENCE: 136

```
tcacctccca actgattcca actctggtct gcttactagc actcaccagc acctttgtcc      60
acggacataa cttcaatatt actattaaag agatcatcaa aatgttgaac atcctcacag    120
cgagaaacga ctcgtgcatg gagctgactg tcaaggacgt cttcactgct ccaaagaaca    180
caagcgataa ggaaatcttc tgcagagctg ctactgtact gcggcagatc tatacacaca    240
actgctccaa cagatatctc agaggactct acaggaacct cagcagcatg gcaaacaaga    300
c                                                                    301
```

<210> SEQ ID NO 137
<211> LENGTH: 492
<212> TYPE: DNA
<213> ORGANISM: Canis familiaris

<400> SEQUENCE: 137

```
cttgtgcaac tcccaaatcg tcatcagggc caagttcgtg gggaccgcag aagtcaacca      60
gaccgactta aaccggcgtt atgagatcaa gatgaccaag atgttcaagg gtttcagcgc    120
cttggggaat gcctcggaca tccgcttcgt cgacaccccc gccctggaaa gcgtctgcgg    180
atacttgcac aggtcccaga accgcagcga ggagtttctg gtcgccggaa acctgcggga    240
cggacacttg cagatcaaca cctgcagttt cgtggcccg tggagcagcc tgagtaccgc     300
tcagcgccgg ggcttcacca agacctatgc tgctggctgt gagggtgca cagtgtttac      360
ctgttcatcc atcccctgca aactgcagag tgacactcac tgcttgtgga cggaccactt    420
cctcacaggc tctgacaagg gtttccagag ccgccacctg gcctgcctgc aagagagcc     480
agggatatgc ac                                                         492
```

<210> SEQ ID NO 138
<211> LENGTH: 341
<212> TYPE: DNA
<213> ORGANISM: Canis familiaris

<400> SEQUENCE: 138

```
gcagattttt gtaaagaccc tgacgggcaa aactatcacc cttgaggtcg agcccagtga      60
caccattgaa aatgtcaaag ccaaaatcca agacaaggag ggcatcccgc ctgaccagca    120
gcgtctgatt tttgcgggca aacagctaga agatggccga actctgtcag actacaatat    180
ccagaaagag tccaccttgc acttggtgct tcgcctgcga ggtggcatca ttgagccttc    240
actccgccag ctgcccagaa aatacaactg cgacaagatg atctgccgca agtgttatgc    300
tcgcctgcac ccccgtgctg tcaactgccg caagaagaag t                         341
```

<210> SEQ ID NO 139

```
<211> LENGTH: 260
<212> TYPE: DNA
<213> ORGANISM: Canis familiaris

<400> SEQUENCE: 139
agcggtcagt gtgaaggagg tggactctgg gaatgacatc tacggcaacc ccatcaagcg      60
gattcagtat gagatcaagc agataaagat gttcaaagga ccagacaagg acatagagtt     120
tatctacacg gctccttcct ccgccgtatg cggggtctcc ctggacatcg aggaaagaa      180 ggagtatctc attgcgggaa aggccgaggg gaacggcaag atgcacatca cccttttgtga    240 cttcatcgtg ccctgggaca                                                 260

<210> SEQ ID NO 140
<211> LENGTH: 493
<212> TYPE: DNA
<213> ORGANISM: Canis familiaris

<400> SEQUENCE: 140
cctggtccag atgctaaaga gcaaggtaaa gaatcaggat gaagtgacca ctcctgaccc      60
aaccacagac gccagcctgc aggctatctt gcagtcgcag gatgagtgcg tgaagcacac     120
aacaattcac ctcatcctgc ggagtctgga ggatttcctg cagttcagtc tgagggctgt    180
tcggataatg tagcctgggc atctaagatt gctgtagttc atgggcattc ctttctccag    240
tcagaaacct gtgcagtggg cacaaaactt atgttgttct ctgtgaggaa ctaaaagtat    300
gagcgttagg acactatttt aattattttt aatttattga tatttaaata tgtgatatgg    360
agttaattta tataagtaat agatatttat attttttatg aagtgccact tgaaatattt    420
tatgtattca ttttgaaaaa gttaacgtaa aatgctatgc ggcttgaata tcctcgatgt    480
ttcggagcca ggt                                                        493

<210> SEQ ID NO 141
<211> LENGTH: 517
<212> TYPE: DNA
<213> ORGANISM: Canis familiaris

<400> SEQUENCE: 141
tggaatttga acccaaacaa aggcagagta cacagacact ttatgttaat gttgccccca      60
gggatacaac cgtcgtggtc agcccctcct ccatcgtgga ggaaggtagt cctgtgaaca     120
tgacctgctc tagcgatggc cttccagctc cgaacatcct gtggagcagg cggctaagta    180
atgggcgcct gcagtctctt tctgaggatc caattctcac cttaacttct gcaaaaatgg    240
aagattctgg tatttatgtg tgtgaaggga ttaaccaggc tggaataagc agaaaagaag    300
tagaattaat tatccaagtt gctccgaaag acatacagct tatagctttt ccttctgaga    360
gtgtcaagga aggagacact gtcattatct cctgtacatg tggaaatgtt ccaaaaactt    420
ggataatcct gaagaaaaaa gcagagacgg gagacacagt gctaaagtcc agagatggtg    480
catataccat ccacaaggtc cagttagagg atgcggg                              517

<210> SEQ ID NO 142
<211> LENGTH: 495
<212> TYPE: DNA
<213> ORGANISM: Canis familiaris

<400> SEQUENCE: 142
gctcccccag accttgttgg atcagaaggt caaggtggtc tacgtcgccc gcaacgcaaa      60
agatgtagct gtctcctatt accacttcta ccgcatggcc aaggtgcacc ctgaccctga    120
```

```
cacctgggac agcttcctgg agaagttcat ggctggggaa gtgtcctatg ggtcctggta      180
tcagcatgtg caggaatggt gggagctgag tcacactcac cctgttctct acctcttcta      240
tgaggacatg aaagagaacc ccaaaaggga gattcagaag atcctgaagt tgtggggcg       300 ctccctgcca gaggagactg tggatctcat tgtccagcac acgtctttca aggagatgaa      360
gaacaactcc atggctaact acaccacctt atctcctgac atcatggacc acagcatttc      420
tgccttcatg aggaaaggca ctcgggggga ctggaagacc accttcactg tggcccagaa      480
tgagcgcttt gatgc                                                       495

<210> SEQ ID NO 143
<211> LENGTH: 503
<212> TYPE: DNA
<213> ORGANISM: Canis familiaris

<400> SEQUENCE: 143
aatcccagac atccctgat caaagacatg ctgcgacgag ttaaggaaga tgaagatgac       60
aaaacggtat cggatcttgc tgtggttttg tttgagacag caacgctgag atcaggctat     120
ctgctaccag acactaaagc atatggagat cgaatagaaa gaatgcttcg cctcagttta     180
aacattgacc ctgatgcaaa ggtggaagaa gaaccagaag aagaacccga agagacaacc     240
gaggacacca cagaagacac agagcaggac gatgaagaag aaatggatgc aggaacagac     300
gacgaagaac aagaaacagt aaagaaatct acagctgaaa aagatgaatt ataaattata     360
ctctcaccat ttggaacctg tgtggagagg gaatgtgaaa tttaagtcat ttctttcgag     420
agagacttgt tttggatgct ccccgcagcc cccttctccc ctgcactgta aaatgttggg     480
attgtgggtc acagaaagaa gtg                                             503

<210> SEQ ID NO 144
<211> LENGTH: 506
<212> TYPE: DNA
<213> ORGANISM: Canis familiaris

<400> SEQUENCE: 144
ttacacggtt gctgtcactg gatgaaataa ttgccaagga gtttagggga acaacttgg       60 tcaaagtatt ctatcaccaa catgcaaaaa aatattttaa atgcccacag gcgagtacat     120
ggggaaatcc tgcttaatac tttgtgcaag gattgctaaa cacagtccta atcccttta      180 cccctgtggg attcagtgca ttttaaagtg ttccttagaa ttttaaagtg ttcttttatt     240
tgcattggct aaagtacaat tttccctaat tcttaattca gtgtaagtgt ttagagactt     300
taaaatatat gcatgttaga gctatgatag ggtaaaagtt acttatcagg gatctttgtt     360
tatgaaggga ctctaatgtt atatctgtag taaattcatt ttaaaggggg caaatgctgt     420
ccccagtatt acgtgaatca gtgtaaagtt gtgaatgttt ttactatagt tgcttttaaa     480
aacatgaata gtgggcacc tgggtg                                           506

<210> SEQ ID NO 145
<211> LENGTH: 501
<212> TYPE: DNA
<213> ORGANISM: Canis familiaris

<400> SEQUENCE: 145
tgcactatca tcagagcatg cctccctact acaacctgac agacatgcat gtgccaatcg      60
cagtgtggaa cggtggcaac gacttgctgg ccgaccctca cgatgttgac ctttgctttt     120
```

```
ccaagctccc caatctcatt taccacagga agattcctcc ttacaatcac ttggacttta      180
tctgggccat ggatgcccct caagcggttt acaatgaaat tgtttccatg atgggaacag      240
ataataagta gttctagatt taaggaatta ttcttttatt gttccaaaat acgttcttct      300
ctcacacgtg gttttctatc atgtttgaga cacggtgatt gttcccatgg ttttgatttc      360
agaaatgtgt tagcatcaac aatcttttcca ttggtaattt ttgaatttaa aatgattttt      420
aaatttgggg catctgggtg gctcagtcgg ctaagtcgtc tgccttcggc ttaagtcatg      480
atctcggggt cctaggatgg a                                                501

<210> SEQ ID NO 146
<211> LENGTH: 503
<212> TYPE: DNA
<213> ORGANISM: Canis familiaris

<400> SEQUENCE: 146 ggacccttc cgcgactggt acccggccca cagccgcctc ttcgaccagg ccttcgggct       60
gccccggctg ccggaggagt gggcgcagtg gttcggccac agcggctggc cgggctacgt     120
gcgcccgatc ccccccgcgg tcgagggccc cgccgcggcc gccgcggccg ccgcgcccgc     180
ctacagccgc gcgctcagcc ggcagctcag cagcggcgtg tcggagatcc ggcagacggc     240
cgaccgctgg cgcgtgtccc tggacgtcaa ccacttcgcc cccgaggagc tgacggtcaa     300
gacgaaggac ggcgtggtgg agataactgg caagcacgaa gagaggcagg atgagcatgg     360
ctacatctcc cgccgcctca ctcccaaata caccctgccc cctggtgtgg atcctaccct     420
ggtctcctcc tccctgtccc ctgagggcac tctcacggtg gaggctccca tgcccaagcc     480
agccacccag tcggcagaaa tca                                              503

<210> SEQ ID NO 147
<211> LENGTH: 472
<212> TYPE: DNA
<213> ORGANISM: Canis familiaris

<400> SEQUENCE: 147
cgggtccctg ctggaggact ttaagagtta cctgggttgc caagccctgt cggagatgat       60 ccagtttttac ttggaggagg tgatgccccg ggctgagaac cacgacccag acatcaagaa     120
ccacgtgaac tccctgggag agaagctcaa gaccctcagg ctgagactga ggctgcgacg     180
ctgtcaccga tttcttccct gtgagaataa gagcaaggcg gtggagcagg tgaagagcgc     240
atttagtaag ctccaggaga aggtgtctca caaagccatg agtgagtttg acatcttcat     300
caactacata gaaacctaca tgacaatgag gatgaaaatc tgaaacgtgc tggagaacaa     360
aacacccagg atggcaactc ttctcgactc taggacatga attggagatc tgcaaaatac     420
catcccgaga tgtaggagag ccgaccaact gcttggagaa ccccgtcata cc              472

<210> SEQ ID NO 148
<211> LENGTH: 470
<212> TYPE: DNA
<213> ORGANISM: Canis familiaris

<400> SEQUENCE: 148
tccgaggggc acctctacac cgttcccatc cgggagcagg gcaacatcta caagcccaac       60
aacaaggcca tggcggagga gatgagcgag aagcaggtgt acgacgcgca caccaaggaa     120
atcgacctgg tcaaccgcga ccccaagcat ctcaacgacg acgtggtcaa gattgatttt     180
gaagatgtga ttgcagaacc agaaggaaca cacagttttg atggcatctg gaaggccagc     240
```

-continued

```
ttcaccacct tcactgtgac aaaatactgg ttttaccgct tgctgtctgc cctctttggc      300
atcccaatgg cactcatatg gggcatttac tttgccattc tttctttcct gcacatctgg      360
gcagttgtgc cgtgcattaa gagtttcctg attgagattc agtgcatcag ccgtgtctat      420
tccatctacg tccacaccct ctgtgacccg ttctttgagg ctgttggcaa                 470

<210> SEQ ID NO 149
<211> LENGTH: 193
<212> TYPE: DNA
<213> ORGANISM: Canis familiaris

<400> SEQUENCE: 149
accatccagc tcatccagaa ccacttcgtg gatgagtacg accccaccat cgaggactcc       60
tatcggaagc aagtggtcat tgacggggag acgtgcctgc tggacatcct ggacacagcg      120
ggccaggagg agtacagcgc catgcgggac cagtacatgc gcacggggga gggcttcctc      180
tgtgtatttg cca                                                         193

<210> SEQ ID NO 150
<211> LENGTH: 514
<212> TYPE: DNA
<213> ORGANISM: Canis familiaris

<400> SEQUENCE: 150
agacaagagg tttcagccag tgcatgacct gactatcggt gtagagtttg gtgctcgaat       60
gataactatt gatgggaaac agataaaact tcagatatgg gatacggcag ggcaagagtc      120
ctttcgttcc atcacaaggt catattacag aggtgcagca ggggctttac tagtgtatga      180
tattacaagg agagatacat tcaaccactt gacaacctgg ttagaagatg cccgccagca      240
ttccaattcc aacatggtca ttatgcttat tggaaataaa agtgatttag aatcaagaag      300
agaagtaaaa aaagaagaag gtgaagcttt tgcacgagaa catggactta tcttcatgga      360
aacttctgct aagactgctt ccaatgtaga agaggcattt attaatacag caaaagaaat      420
ttatgagaaa atccaagaag gagtctttga cattaatat gaggcaaacg gcattaaaat       480
tggccctcag cacgctgcta ctaatgccac acac                                  514

<210> SEQ ID NO 151
<211> LENGTH: 521
<212> TYPE: DNA
<213> ORGANISM: Canis familiaris

<400> SEQUENCE: 151
aagcctagtg cttcgttttg tgaagggcca atttcatgaa tttcaagaga gtaccatagg       60
ggctgctttt ctaacccaaa ctgtgtgtct tgatgataca acagtaaagt ttgaaatatg      120
ggatacagct ggtcaagaac gataccatag cttagcacca atgtactaca gaggagcaca      180
agcagccata gttgtatatg atatcacaaa tgaggagtcc tttgccagag ccaaaaactg      240
ggttaaagaa cttcagaggc aagccagtcc taacattgta atagctttat caggaaacaa      300
ggctgatctt gcaaataaaa gagctgtcga tttccaggaa gcacagtcct atgcagatga      360
caacagttta ttattcatgg agacatcagc taaaacatcg atgaacgtaa atgaaatatt      420
catggcaata gctaaaaagt tgccaaagaa cgaaccacag aatccaggag caaattctgc      480
cagaggaaga ggagtagacc ttactgaacc cacgcagcca a                          521

<210> SEQ ID NO 152
```

<210> SEQ ID NO 152
<211> LENGTH: 508
<212> TYPE: DNA
<213> ORGANISM: Canis familiaris

<400> SEQUENCE: 152

| | | | | | |
|---|---|---|---|---|---|
| ccccaacaca | ttcaaaaccc | tcgatagctg | gagagatgag | tttctcatcc | aggccagtcc | 60 |
| ccgggatcct | gaaaacttcc | ctttcgttgt | gttgggaaac | aagattgacc | tcgaaaacag | 120 |
| acaagtggcc | acaaagcggg | cacaggcctg | gtgctacagc | aaaaacaaca | ttccctactt | 180 |
| cgagaccagt | gccaaggagg | ccatcaatgt | ggagcaggcg | ttccagacga | ttgcaaggaa | 240 |
| tgcacttaaa | caggaaacag | aggtggagct | gtacaatgaa | ttccctgaac | ccatcaaact | 300 |
| ggacaagaac | gaccgggcca | agacctcagc | ggaaagctgc | agttgctgaa | ggggcagtga | 360 |
| gagcagagca | cagagtcctt | cacaaacaaa | gaacacactt | aggccttcca | acacgagccc | 420 |
| ccttcttctc | ttccaaacaa | aacataaagt | catctctcga | atccagctgc | aaaagaccc  | 480 |
| taccaaacac | ttcaccctga | cacacaca   |            |            |            | 508 |

<210> SEQ ID NO 153
<211> LENGTH: 256
<212> TYPE: DNA
<213> ORGANISM: Canis familiaris

<400> SEQUENCE: 153

| | | | | | |
|---|---|---|---|---|---|
| ctggttctgt | tgcttgtcct | cctggtattg | ggatttgagg | tccaggggc  | ccatgagtcc | 60 |
| cagcaagatg | aaaccaccag | ctccgccctg | ctcacccaga | tgcaggaatc | actctacagt | 120 |
| tactggggca | cagccagatc | ggctgccgag | gacctgtaca | agaaggcata | cccaactacc | 180 |
| atggatgaga | aaatcaggga | catatacagc | aaaagcacag | cagctgtgag | cacttacgca | 240 |
| gggattttca | ctgacc     |            |            |            |            | 256 |

<210> SEQ ID NO 154
<211> LENGTH: 330
<212> TYPE: DNA
<213> ORGANISM: Canis familiaris

<400> SEQUENCE: 154

| | | | | | |
|---|---|---|---|---|---|
| ctgtccgcct | ctgtccccct | gttgcgcacg | caggcaaggg | ccaggtggcc | gctgccccgg | 60 |
| agcatccagc | accctcagcc | cgggcccgag | gctcccacct | gcggcctcgg | cgttgctcct | 120 |
| gcagctcctg | gctcgacaag | gagtgcgtct | acttctgcca | cctggacatc | atctgggtga | 180 |
| acactcccgg | gtgagctccc | gcggggaccc | aggcggggct | gctagaggcg | ggcaggggg  | 240 |
| tggggaacct | gtagctagca | cagctctccc | tgggcctcca | gacggatcgc | tgagctgaca | 300 |
| tgaagagcgg | ctgggtgttg | tccctactcc |            |            |            | 330 |

<210> SEQ ID NO 155
<211> LENGTH: 498
<212> TYPE: DNA
<213> ORGANISM: Canis familiaris

<400> SEQUENCE: 155

| | | | | | |
|---|---|---|---|---|---|
| tgattgttct | tctgccacca | aaatgccagt | agtaaacaaa | cccatcgata | ggaaagtatt | 60 |
| ttgttttgct | gtgcagctct | gtcattgggc | ccatggagcg | cggaactgga | cttcccaaga | 120 |
| caaatggtac | cagcgttctc | ttaaaaagat | gccttaatcc | attcctcgag | ggtggacctt | 180 |
| agttgagatg | atagcagact | gtactcccct | ccggcagctg | gccttctgcc | ctgagttgca | 240 |
| cgttaatcag | attagcctgt | attctcttca | gtggattttg | ataatggctt | ccagattcat | 300 |

```
tggcgttagg gaagcctttt agaatcttca cgtgtcatcg tcgaaattga aacactgagt      360
tgttctgctg atggttttgg agatacttcc atcttttaa gggtttgctt ctgtctaatt      420
ctggcaggac ctcaccaaaa gatcgggcct cgtaccaacg tcagacacga tgtcgccgtg     480
ttgtgcgttc tgtattta                                                   498

<210> SEQ ID NO 156
<211> LENGTH: 503
<212> TYPE: DNA
<213> ORGANISM: Canis familiaris

<400> SEQUENCE: 156
gccttaccct cagggacctt gcattccaga tggtaaaaat gccacacacc agtatgcaaa      60
ggctggcctc gcaccatggc aactgagcag ctgaaccagc gcactcctca gcaggcggaa     120
atgctgaact gagaatgtca gtgctcaggg gcccacaggc taaccctgct cccacttcgt     180 agcattttg cttttcaggg cacggcagca tttattactg tgtagccaca tccctctgaa     240
gcagcagcat agctgacaat ttaaaaataa gaactaagaa catacctaag accataacgg     300
cagacaagta gcagggccga gactagagtt caggacctct gactcccaga gtgtcccggg     360
agccaggtaa tgctccctgg aggtgcaaat agggttgggc aggggagacc agaagtgctt     420
acagggagag aggacttgga ggtgattttg caggaggtga gggatgtgaa ttgcctgaat     480
ggcggaggct gttttgttca tgc                                             503

<210> SEQ ID NO 157
<211> LENGTH: 510
<212> TYPE: DNA
<213> ORGANISM: Canis familiaris

<400> SEQUENCE: 157
aggtgtccct gcagcccaac ttccaacagg ataagttcct ggggcgctgg ttcacctcgg      60
gcctcgcctc caactcgagc tggttccggg agaagaagaa cgtgctgtcc atgtgtatgt     120
cagtggtggc cccgaccgca gacggaggcc tcaacctcac ctccaccttc ctcaggaaag     180
accagtgtga gactcgaacc ctgctcctac ggccggcggg aaccccgggc tgctacagct     240
acacgagtcc ccactggggc agtacccacg acgtgtgggt ggtagccacc aactacgagg     300
agtacgcgct tctctacacc gcaggcagca aaggcctcgg ccaggacttc cacatggcca     360
ctctctacag ccgcacccag accccaaagg ccgagataaa ggagaaattc agcacctttg     420
ccaagaccca gggcttcaca gaggatgcca ttgtcttcct gccacagact gataaatgca     480
tggaggagaa caagtaggtg accgccgccc                                      510

<210> SEQ ID NO 158
<211> LENGTH: 472
<212> TYPE: DNA
<213> ORGANISM: Canis familiaris

<400> SEQUENCE: 158
caggactcca cagcttttcc ccagataagc ctggagggat attaatgatg gatctaaaaa      60
aggaaaaccc gagggcactg gaattaagaa tcagccgtgg gttcaatttg gcttcgttca     120
atccacatgg tatcagcacc ttcatagaca gcgacgacac agtttatctc tttgttgtaa     180
accatccaga attcaagaat acagtggaaa tttttaaatt tgaagaagaa gaaaattctc     240
ttctgcatct aaaaacaatc aaacatgaac ttcttccaag tgtgaatgat atcatagctg     300
```

```
ttggaccagc acatttctat gccaccaatg accactattt ctctgatcct ttcttaaagt      360
atttggaaac atacttgaac ttacactggg caaatgttgt ttactacagt ccagatgaag      420
ttaaagtggt agcagaaggg tttgatgcag caaatgggat caatatttca cc              472

<210> SEQ ID NO 159
<211> LENGTH: 493
<212> TYPE: DNA
<213> ORGANISM: Canis familiaris

<400> SEQUENCE: 159
cgccgtatgt ggacgtcatc tgtgtcaaca gttactactc ttggtatcac gactatgggc       60
acatggaggt gattcagctg cagctggcca ccgagtttga aactggtat aggacctacc      120 agaaaccaat aatccagagc gagtacgggg cagagacaat tgcaggcttc caccaggatc      180
cacctctgat gttcagtgag gagtaccaga aggtctgct cgagcagtat cacttggtgc      240
tggatcagaa acgcaaagaa tatgtggttg gagagctcat ctggaatttt gctgattta      300 tgactgacca gtcaccacag agagcagtag ggaacagaaa gggcatcttc actcgccaga      360
gacaacccaa agcggcggcc ttccttttgc gagagagta ctggaaactt gccaatgaaa      420
ccgggcacca ccggtccgcg gccaagtccc agtgtttgga aaacagcccg ttcgccctct      480
gaagcctctg tct                                                        493

<210> SEQ ID NO 160
<211> LENGTH: 359
<212> TYPE: DNA
<213> ORGANISM: Canis familiaris

<400> SEQUENCE: 160
ctccaggtgg gcttcgagga cgtgatcgcg gacgccgtgt ctacgcactc ctttgacaaa       60
gtgtggattt gcagccatgc cctgtttgag gtcagcaagt acgtgatcta caagttcctg      120
acgttgctcc tggcgatgcc catggccttc gcggcagggg ttctcttcgc caccctcagc      180
tgcctgcaca tctggattat aatgcctttc gtgaagacct gcctcatggt cctgccttcg      240
gtgcagacca tatggaagag tgtaacagat gctgtcattg ccccgttgtg ttcaagtgta      300
ggacgcagct tctcttctgt cagcttgcaa gtgagtcacg actgagcact tggaccca       359

<210> SEQ ID NO 161
<211> LENGTH: 350
<212> TYPE: DNA
<213> ORGANISM: Canis familiaris

<400> SEQUENCE: 161
ttcttcaaag gagacaagca ctgggtgttt gatgaagctt ctctggaacc tggctacccc       60
aagcacatca aggagctggg ccgaggactg cctactgaca aaatcgatgc tgctctcttc      120
tggatgccca atgaaagac ctacttcttc cggggaaaca gtattaccg tttcaacgag      180 gaactcaggg cagtggacag cgagtacccc aaaaacatca aggtctggga aggaatccct      240
gagtctccca gagggtcatt catgggcagt gatgaagtct tcacttactt ctacaagggg      300
aacaaatact ggaaattcaa caaccagaag ctgaaggtag agccaggcta                350

<210> SEQ ID NO 162
<211> LENGTH: 471
<212> TYPE: DNA
<213> ORGANISM: Canis familiaris

<400> SEQUENCE: 162
```

```
gattctccaa gggcaaggga cgccgggtgc agggccccctt cttatcaccg agcacgtggc      60
ctgcgctgcc ccgcaagctg gactccgcct ttgaggacgg gctcaccaag aagactttct     120
tcttctctgg gcgccaagtg tgggtgtaca caggcacgtc ggtggtaggc ccgaggcgtc     180
tggacaagct gggcctgggc ccggaggtta cccaagtcac cggcgccctc ccgcaagcgg     240
ggggtaaggt gctgctgttc agcaggcagc gcttctggag tttcgacgtg aagacgcaga     300
ccgtggatcc caggagcgcc ggctcggtgg aacagatgta ccccggggtg cccttgaaca     360
cgcatgacat cttccagtac caagagaaag cctacttctg ccaggaccgc ttctactggc     420
gtgtgaattc tcggaatgag gtgaaccagg tggacgaagt gggctacgtg a             471

<210> SEQ ID NO 163
<211> LENGTH: 498
<212> TYPE: DNA
<213> ORGANISM: Canis familiaris

<400> SEQUENCE: 163
gtggcccaca ttgtgaaaac tcagaaatca ttgtaaagct tttcaatgga aatgaggtgt      60
gcctggaccc caaggaaaaa tgggtacaaa aggttgtgca gatatttcta aagaaggctg     120
agaaacaaga tccgtgaaac aacaaacaca ttctctgtgg tttccaagaa ttcctcagga     180
aagatgccaa tgagacttca aaaaaatcta tttcagtact tcatgtcccg tgtagacctg     240
gtgtaggatt gccagataaa aatacagtat gcccagttag atttgaatat taagtaaaac     300
aatgaatagt tttttttctaa agtctcatat atgttgccct attcaatgtc taggcacact     360
tacattaaac atattattca ttgtttgctg taaattcaaa tgtagctgga atcctggat     420 atattttgtt gttgttacat cttttccacct cacctacagg ccaggatgca tgagtccctt     480
ttcaaccttg ccttggtc                                                  498

<210> SEQ ID NO 164
<211> LENGTH: 482
<212> TYPE: DNA
<213> ORGANISM: Canis familiaris

<400> SEQUENCE: 164
caatgacatg actccagagc aaatggctac aaatgtgaac tgttccagcc ctgagcgaca      60
tacaagaagt tatgattaca tggaaggagg ggatataaga gtgagaagac tcttctgtcg     120
aacacagtgg tatctgagga ttgataaacg aggcaaagtc aaaggaccc aagagatgaa     180 gaacagttac aatatcatgg aaatcaggac agtggcagtt ggaatagtgg caatcaaagg     240
ggtggaaagt gaatattatc ttgcaatgaa taaggaagga aagctctatg caaagaaga     300 atgcaatgaa gattgcaact tcaaagaatt aattctggaa accattaca acacatatgc     360 atcagctaaa tggacacaca gcggaggaga atgtttgtt gctttaaatc aaaagggggt     420
tcctgtaagg gggaaaaaaa cgaagaaaga acaaaaaaca gcccactttc ttcctatggc     480
aa                                                                    482

<210> SEQ ID NO 165
<211> LENGTH: 505
<212> TYPE: DNA
<213> ORGANISM: Canis familiaris

<400> SEQUENCE: 165
gattgaaaat ggagccttcc agggaatgaa gaagctctcc tatatccgca ttgctgatac      60
```

```
caatataact accatccctc aaggtcttcc tccttccctt actgaattac atcttgaagg    120
caacaaaatc accaaggttg atgcatctag cctgaaagga ctgaataatt tggctaagtt    180
gggactgagt tttaacagca tctccgctgt tgacaatggc actctagcca acactcctca    240
tctgagggag cttcacttgg acaacaataa gctcatcaga gtacccggtg ggctggcgga    300
gcataagtac atccaggttg tctaccttca taacaacaat atatctgcag tcggatctaa    360
tgacttctgc ccacctggat acaacaccaa aaaggcttct tattcaggtg tgagccttt     420 cagcaaccca gtgcagtact gggagatcca gccatccacc ttccggtgtg tctacgtgcg    480
ctctgccatc cagcttggaa attat                                         505
```

<210> SEQ ID NO 166
<211> LENGTH: 508
<212> TYPE: DNA
<213> ORGANISM: Canis familiaris

<400> SEQUENCE: 166

```
ctggggatct cagctgcagg attttctacc tgtcccatcc ttacaagaaa agggaaagga    60
gcagtggcat ttgatagaga agaagaatgg attaaggaaa gacttcttcg tatcctgcat    120
atcatgcaaa ttcatgttac acaaaatcta aatcgctttg attatatttg aattttagg    180 taaggaactc tcaatagtgg gggaccaact taaagcataa ctaataggta gttaatgggg   240
taattctgct tcttctatgt ttctactatg tattcagtga cctagatttg tgctgggtca    300
gagcattcag atatagtcag cttctctatc acactacatc ttcctccttg tcagcctagc    360
tcagctttcc ctagaacttt ccactgctct acatcgtgct gacacagaga tgcctaaagg    420
cagctctagg gtagtgcttt tgtatggttt agtcaagctc tgaaatcttg ggcaaaaagg    480
tgaggagagg gcaaggagag gaaaggat                                      508
```

<210> SEQ ID NO 167
<211> LENGTH: 489
<212> TYPE: DNA
<213> ORGANISM: Canis familiaris
<220> FEATURE:
<221> NAME/KEY: misc_feature
<222> LOCATION: (1)...(489)
<223> OTHER INFORMATION: n = A, T, C or G

<400> SEQUENCE: 167

```
gacccttcct gctcctcatg gccacccac tggagagggc ccagcacctg cacagctccc     60
ggcagcgccg ggccctggac accaactact gcttcagctc cacggagaag aactgctgcg    120
tccggcagct ctacattgac ttccgcaagg atctgggctg gaagtggatc catgagccca    180
agggttacca cgctaacttc tgcctggggc cctgccccta catttggagc ctggacacgc    240
agtacagcaa ggtcctggcc ctgtacaacc agcacaaccc gggcgcgtcg gcggcgccgt    300
gctgcgtgcc gcaggcgctg gagccactgc ccatcgtgta ctacgtgggc cgcaagccca    360
aggtggagca gctgtcgaac atgatcgtgc gctcctgcaa gtgcagctga ggccccgccc    420
cgtccggcag gccccgccca ccggcaggnc cggccccgcc ccgcccgct gcgccgggct     480 gtatttaag                                                           489
```

<210> SEQ ID NO 168
<211> LENGTH: 488
<212> TYPE: DNA
<213> ORGANISM: Canis familiaris

<400> SEQUENCE: 168

```
gacacgtcct tcatgttcca gagggtgctg gtgtcgctgt cggccggtgg cagggatgaa      60
ggaaattttc tggacgatgc tctcatgaga caggatgctc aggacctgta tgaggctgga     120
gagaagaaat ggggaacaga tgaggtgaaa tttctgactg ttctctgctc ccggaaccga     180
aatcacctgt tgcatgtgtt tgatgaatac aaaaggatat cacagaagga tattgagcag     240
ggtattaaat ctgaaacatc cggtagcttt gaagatgctc tgctggccat agtaaagtgc     300
atgaggaaca atctgcata ctttgctgaa aggctttata atctatgaa gggcttggga      360 acagatgata cacccctcat cagggttatg tgtctcgag cggagatcga tatgatggac      420
atccgggaga gcttcaagag gctttacgga aagtctctgt actccttcat caagggtgac     480
acatctgg                                                              488
```

<210> SEQ ID NO 169
<211> LENGTH: 224
<212> TYPE: DNA
<213> ORGANISM: Canis familiaris

<400> SEQUENCE: 169

```
gttggagcag gtggtgttgg gaaaagcgca ctgacaatcc agctaatcca gaaccacttt      60
gtagatgaat atgatcccac catagaggat tcttaccgaa acaggtggt tatagacggt      120 gaaacctgtc tgttggacat actggataca gctggtcaag aagagtacag tgccatgaga     180
gaccaataca tgaggacagg cgaaggcttc ctctgtgtat ttgc                      224
```

<210> SEQ ID NO 170
<211> LENGTH: 228
<212> TYPE: DNA
<213> ORGANISM: Canis familiaris

<400> SEQUENCE: 170

```
gtagttggag ctggtggcgt aggcaagagt gccttgacga tacagctaat tcagaatcac      60
tttgtggatg aatatgatcc tacaatagag gattcctaca ggaaacaagt agtaattgat     120
ggagaaacct gtctcttgga tattctcgac acagcaggtc aagaggagta cagtgcaatg     180
agggaccagt acatgaggac tggggagggc tttctttgtg tatttgcc                  228
```

<210> SEQ ID NO 171
<211> LENGTH: 506
<212> TYPE: DNA
<213> ORGANISM: Canis familiaris

<400> SEQUENCE: 171

```
ctggtgaccc atcttatggg agcagatctg aacaacattg tgaaatgtca gaagcttacg      60
gatgaccatg ttcagttcct tatctaccaa attctccgag gtctcaagta tatacattca     120
gctgacataa ttcacaggga cctaaaacct agcaatctag ctgtgaatga agactgtgag     180
ctgaagatcc tggactttgg actggcccga catacagatg atgaaatgac aggctatgtg     240
gctaccaggt ggtacagggc tcctgagata atgctgaact ggatgcatta caaccagaca     300
gttgatattt ggtcagtggg atgcataatg gccgaactgt tgactggaag aacgttgttt     360
cctggtacag accatattga tcagttgaag ctcattttaa gactcgttgg aaccccaggg     420
gctgatcttt tgaagaaaat ctcctcagag tctgcaagaa actacattca gtctttgacc     480
cagatgccga agatgaactt tgcaaa                                          506
```

<210> SEQ ID NO 172

```
<211> LENGTH: 50
<212> TYPE: DNA
<213> ORGANISM: Canis familiaris

<400> SEQUENCE: 172
ccggctcctc agcaggggcc cgaggtacaa taaaccagtt tggtggctcc            50

<210> SEQ ID NO 173
<211> LENGTH: 50
<212> TYPE: DNA
<213> ORGANISM: Canis familiaris

<400> SEQUENCE: 173
aactcaaata aacatcaaaa gcctgacatc ccctggtcag gtggtgagcc            50

<210> SEQ ID NO 174
<211> LENGTH: 50
<212> TYPE: DNA
<213> ORGANISM: Canis familiaris

<400> SEQUENCE: 174
ccagtgaaca tccaacctcc attaaaggaa agtctccaga atttctttgc            50

<210> SEQ ID NO 175
<211> LENGTH: 50
<212> TYPE: DNA
<213> ORGANISM: Canis familiaris

<400> SEQUENCE: 175
tatctctgcc tctctctgtg tgtgtgtctc tcatgaataa ataaaatctt            50

<210> SEQ ID NO 176
<211> LENGTH: 50
<212> TYPE: DNA
<213> ORGANISM: Canis familiaris

<400> SEQUENCE: 176
gtgacacaga atgagaaact cttaactctg ggaaatgtac aagggatagt            50

<210> SEQ ID NO 177
<211> LENGTH: 22
<212> TYPE: DNA
<213> ORGANISM: Canis familiaris

<400> SEQUENCE: 177
aactgaacca aattgcactg aa                                          22

<210> SEQ ID NO 178
<211> LENGTH: 19
<212> TYPE: DNA
<213> ORGANISM: Canis familiaris

<400> SEQUENCE: 178
ccatgtagcg actttcccg                                              19

<210> SEQ ID NO 179
<211> LENGTH: 262
<212> TYPE: DNA
<213> ORGANISM: Canis familiaris

<400> SEQUENCE: 179
cgcgtctaga aactgaacca aattgcactg aagtttttgaa atacctttgt agttactcaa   60
gcagttactc cccacactga tgcaaggatt acagaaactg atgtcaaggg gctgagtgag  120
```

-continued

```
ttcaactaca gattccgggg gcccggagct agatgacttt gcagatggaa agaggtgaaa       180
atgaagaagg aagctatgtt gaaacaaata caagtcaaaa ggaacaaaaa ttacaaagaa       240
ccatgcagga agaagcttgg cc                                                262
```

```
<210> SEQ ID NO 180
<211> LENGTH: 20
<212> TYPE: DNA
<213> ORGANISM: Canis familiaris

<400> SEQUENCE: 180
```

```
aacaacctga acgtcaccga                                                    20
```

```
<210> SEQ ID NO 181
<211> LENGTH: 24
<212> TYPE: DNA
<213> ORGANISM: Canis familiaris

<400> SEQUENCE: 181
```

```
tctcccagtt gattacattc caaa                                               24
```

```
<210> SEQ ID NO 182
<211> LENGTH: 477
<212> TYPE: DNA
<213> ORGANISM: Canis familiaris

<400> SEQUENCE: 182
```

```
gcgcgaattc aacaacctga acgtcaccga ggagaagtat ctggaggcgc tggagaaggg        60
tgacattaca gctcagatag ctcttcagcc tgggctcaag ttcaatggag gaggtcatat       120
caatcattcc atcttctgga caaacctgag ccctaagggt ggtggagaac caaaagggga       180
attgctggaa gccatcaaac gtgattttgg ttccttcgac aaatttaagg agaagttgac       240
cactatatcc gtcggtgtcc aaggctcagg ttggggttgg cttggtttca ataaggagca       300
gggacgcttg cagattgctg cttgttttaa ccaggatccc ctgcaaggaa caacaggtct       360
tattccacta ctggggatcg atgtgtggga gcatgcttat taccttcagt ataaaaatgt       420
cagaccggat tatctaaaag ctatttggaa tgtaatcaac tgggagaaag cttggcc         477
```

```
<210> SEQ ID NO 183
<211> LENGTH: 20
<212> TYPE: DNA
<213> ORGANISM: Canis familiaris

<400> SEQUENCE: 183
```

```
gaaagtcagg ctgtggttga                                                    20
```

```
<210> SEQ ID NO 184
<211> LENGTH: 20
<212> TYPE: DNA
<213> ORGANISM: Canis familiaris

<400> SEQUENCE: 184
```

```
tggcagccaa attctcattc                                                    20
```

```
<210> SEQ ID NO 185
<211> LENGTH: 513
<212> TYPE: DNA
<213> ORGANISM: Canis familiaris

<400> SEQUENCE: 185
```

```
cgcgggatcc gaaagtcagg ctgtggttga caccccctccc gcagtcagca ctggggctcc      60
tccatcttcg gtggcagctg ctgcagcaac tacaacagcg tcaacaacca cagcgagtcc     120
tggaggacat ccccttgaat ttttacggaa tcagcctcaa tttcaacaga tgagacaaat     180
tattcaacag aatccttccc tgctcccagc attgctacaa cagataggtc gagaaaatcc     240
tcaattactg cagcaaatta gccagcacca ggagcatttt attcagatgt aaatgaacc      300 agttcaagaa gctggtggtc aaggaggagg gggtggaggt ggcagtggag gaattgcaga     360
agccggaagt ggtcatatga actacattca agtaacacct caggaaaaag aagctataga     420
aaggttaaag gcactaggat ttcctgaagg acttgtgata caagcgtata ttgcttgtga     480
gaagaatgag aatttggctg ccaaagcttg gcc                                  513
```

<210> SEQ ID NO 186
<211> LENGTH: 20
<212> TYPE: DNA
<213> ORGANISM: Canis familiaris

<400> SEQUENCE: 186

```
gataacgcgg ataccttggc                                                  20
```

<210> SEQ ID NO 187
<211> LENGTH: 22
<212> TYPE: DNA
<213> ORGANISM: Canis familiaris

<400> SEQUENCE: 187

```
agtgtcccat atccgcaatt tt                                               22
```

<210> SEQ ID NO 188
<211> LENGTH: 412
<212> TYPE: DNA
<213> ORGANISM: Canis familiaris

<400> SEQUENCE: 188

```
gcgcggatcc gataacgcgg ataccttggc gctggtattt gaagcaccaa gaacaggagt      60
acagctgtgt agtaaagatg ccttctggtg aatttgcacg tatatgccga gatctcagcc     120
atattggaga tgctgttgta atttcctgtg caaaagacgg agtgaaattt tctgcgagtg     180
gagaacttgg aaatggaaac attaaattgt cacggacaag taatgtcgat aaagaggagg     240
aagctgttac catagagatg aatgaaccag ttcaactaac ttttgcactg aggtacctga     300
acttctttac aaaagccact ccactctctt caacggtgac actcagtatg tctgcagatg     360
taccccttgt tgtagagtat aaaattgcgg atatgggaca ctaagcttgg cc             412
```

<210> SEQ ID NO 189
<211> LENGTH: 19
<212> TYPE: DNA
<213> ORGANISM: Canis familiaris

<400> SEQUENCE: 189

```
ctgtggtgtc tctgcgcct                                                   19
```

<210> SEQ ID NO 190
<211> LENGTH: 24
<212> TYPE: DNA
<213> ORGANISM: Canis familiaris

<400> SEQUENCE: 190

```
tttcagctgt agattccttt gctg                                             24
```

<210> SEQ ID NO 191
<211> LENGTH: 521
<212> TYPE: DNA
<213> ORGANISM: Canis familiaris

<400> SEQUENCE: 191

| | | | | | |
|---|---|---|---|---|---|
| cgcgggatcc | ctgtggtgtc | tcagcgcctg | acagagtctc | cgtgtgctct | ggtggccagc | 60 |
| cagtatggat | ggtctggcaa | catggagaga | atcatgaaag | ctcaagcata | ccagacgggc | 120 |
| aaagacatct | ctacaaatta | ctatgccagc | caaaagaaaa | catttgaaat | taatcccaga | 180 |
| catcccctga | tcaaagacat | gcttcgacga | gttaaggaag | atgaggatga | caaaacggta | 240 |
| tcggatcttg | ctgtggtttt | gtttgagaca | gcaacgctga | gatcaggcta | tctgctacca | 300 |
| gacactaaag | catatggaga | tcgaatagaa | agaatgcttc | gcctcagttt | aaacattgac | 360 |
| cctgatgcaa | aggtggaaga | agaaccagaa | gaagaacccg | aagagacaac | cgaggacacc | 420 |
| acagaagaca | cagagcagga | cgatgaagaa | gaaatggatg | caggaacaga | cgacgaagaa | 480 |
| caagaaacag | caaaggaatc | tacagctgaa | aaagcttggc | c | | 521 |

<210> SEQ ID NO 192
<211> LENGTH: 20
<212> TYPE: DNA
<213> ORGANISM: Canis familiaris

<400> SEQUENCE: 192

| | | |
|---|---|---|
| cagagaagcc | caagctccac | 20 |

<210> SEQ ID NO 193
<211> LENGTH: 20
<212> TYPE: DNA
<213> ORGANISM: Canis familiaris

<400> SEQUENCE: 193

| | | |
|---|---|---|
| accagatgaa | tgtcagcccg | 20 |

<210> SEQ ID NO 194
<211> LENGTH: 498
<212> TYPE: DNA
<213> ORGANISM: Canis familiaris

<400> SEQUENCE: 194

| | | | | | |
|---|---|---|---|---|---|
| cgcgggatcc | cagagaagcc | caagctccac | tacttcaatg | gacgaggcag | aatggagtcc | 60 |
| atccggtggc | tcctggcttc | agctggagta | gagtttgaag | agaaatttat | aaatgctcca | 120 |
| gaagacttgg | ataaattaaa | aaatgatgga | agtctgatgt | tccagcaagt | gccaatggtg | 180 |
| gaaattgatg | gaatgaagct | ggtacagacc | agagccattc | tcaactacat | tgccaccaaa | 240 |
| tacaacctct | atgggaaaga | cataaaggag | agagctctga | tagatatgta | cacagaaggt | 300 |
| atagtagatt | tgaatgaaat | gatcatggtt | ttgcctctat | gcccacctga | tcaaaaagat | 360 |
| gccaagatta | ctctgatcag | agagagaaca | acagatcgtt | atctcccgt | gtttgaaaaa | 420 |
| gtgttaaaga | gccatggaca | agactacctt | gttggcaaca | agctgagccg | ggctgacatt | 480 |
| catctggtct | cgagggcc | | | | | 498 |

<210> SEQ ID NO 195
<211> LENGTH: 27
<212> TYPE: DNA
<213> ORGANISM: Canis familiaris

<400> SEQUENCE: 195
gtccgtggca gagtccctca gctctat                                            27

<210> SEQ ID NO 196
<211> LENGTH: 27
<212> TYPE: DNA
<213> ORGANISM: Canis familiaris

<400> SEQUENCE: 196
caccgtgatg ccacatagct atcttcg                                            27

<210> SEQ ID NO 197
<211> LENGTH: 509
<212> TYPE: DNA
<213> ORGANISM: Canis familiaris

<400> SEQUENCE: 197
gtccgtggca gagtccctca gctctataga ctctctcacc acagaggctg accaggacta        60
cgactatctg acagactggg aaccccgctt taaagtcttg cagacatgt ttggggaaga       120 agagagttat aaccctgata aagtcactta gggcagaagc caaggataaa acacaaccaa      180
aaggagaaat ttaaaagaaa cacaaataga aatctctctc tctcacacac acacacatgc      240
atacatgcac gtgcacacac agacacacag acacacacac caggctttgt aggacacaat      300
catttgatga tctggtttct agcaagttgc tgtagttatc atattgtcaa gttttgtttt      360
actctgccaa cacaagataa atcctattac atgtacttgc ttggttttgt tttgttcttt      420
tggatacaca ctgagacaag ctcaggccta ttaaatacaa tttactgaca tgacaacata      480
gaacgaagat agctattggc atcacggtg                                         509

<210> SEQ ID NO 198
<211> LENGTH: 23
<212> TYPE: DNA
<213> ORGANISM: Canis familiaris

<400> SEQUENCE: 198
ggagcctgat gccatcaagc ctg                                                23

<210> SEQ ID NO 199
<211> LENGTH: 23
<212> TYPE: DNA
<213> ORGANISM: Canis familiaris

<400> SEQUENCE: 199
ggtttgcagc ctatgccaaa gcc                                                23

<210> SEQ ID NO 200
<211> LENGTH: 473
<212> TYPE: DNA
<213> ORGANISM: Canis familiaris
<220> FEATURE:
<221> NAME/KEY: misc_feature
<222> LOCATION: (1)...(473)
<223> OTHER INFORMATION: n = A, T, C or G

<400> SEQUENCE: 200
ggagcctgat gccatcaagc ctgtaggaat ccgacgattg gatgagagac ccatccacgc        60
cgaaccccag tacccggncc gatctgcagc cccgcaccct ggggacatcg ggacttcat       120 taatgagggc cttaaagctg ctgacaatga tccacagct ccaccatatg actccctctt       180
agtctttgac tacgaaggca gtggctctac cgctgggtct ttgagctccc ttaattcttc      240

```
aagtagtggt ggcgagcagg actatgacta cctgaacgac tgggggccac ggttcaagaa    300
acttgctgac atgtatggtg gaggtgatga ctgaacttca gggtgaactt ggtcttttgg    360
acaagtacaa acaatttcaa ctgatattcc caaaaagcat tcagaagcta ggctttaact    420
ttgtagtcta ctagcacagt gcttgctgga ggctttggca taggctgcaa acc           473
```

<210> SEQ ID NO 201
<211> LENGTH: 24
<212> TYPE: DNA
<213> ORGANISM: Canis familiaris

<400> SEQUENCE: 201

```
tcatggatgg gggatctttg gatg                                            24
```

<210> SEQ ID NO 202
<211> LENGTH: 24
<212> TYPE: DNA
<213> ORGANISM: Canis familiaris

<400> SEQUENCE: 202

```
gggtggccca tcaattcttc aggt                                            24
```

<210> SEQ ID NO 203
<211> LENGTH: 466
<212> TYPE: DNA
<213> ORGANISM: Canis familiaris

<400> SEQUENCE: 203

```
gggtggccca tcaattcttc aggtgctggt ctttctttcg gttgttttcg catgcactga    60
gtgatgaaat gtacaaatgg ctcggagaac tctccaaccg gaaggacggg cgaatcctca   120
tcaacaatgc actgcagaag ctggagaggc tccatgaaag agattcctaa actccggaca   180
tcagaatgga ttccatactg ctcccctgaa attctttcag gcgccatata agcatttgtt   240
ccaacatacg tcttggctat agaattcacc agctgagtgc taactccaaa atcgcacagc   300
ttgacctgtc ctcttgtgtt tactagcgta ttggagggct tcacatctct atgtaaaatc   360
tttaaactcc acaagtaggt aaggccttta acaactgcta ttgcaattct tccaaggaca   420
tgctctggaa ttttctata tacatccaaa gatcccccat ccatga                  466
```

<210> SEQ ID NO 204
<211> LENGTH: 22
<212> TYPE: DNA
<213> ORGANISM: Canis familiaris

<400> SEQUENCE: 204

```
gcagcagcct gtgtatgcca cc                                              22
```

<210> SEQ ID NO 205
<211> LENGTH: 23
<212> TYPE: DNA
<213> ORGANISM: Canis familiaris

<400> SEQUENCE: 205

```
aagccggaag cgatctcatc gaa                                             23
```

<210> SEQ ID NO 206
<211> LENGTH: 492
<212> TYPE: DNA
<213> ORGANISM: Canis familiaris

```
<400> SEQUENCE: 206
aagccggaag cgatctcatc gaaggtccgg cctttggtct caggaacttt gaagtaggtg      60
aagatgaaga acagaaccag gagcacggtg aagatgatga agacgtacgg accacacagt     120
tgctctacat actggaagca catgcccaca atgaaatttg aggtccagtt ggagaagcca     180
gcaacagcaa tggcagctgg gcgaggaccc tggctgagga gttcagccac aatgaaccat     240
gggatggggc cagggcccac ttcaaagaag gccacaaagc caaagatggc cacgatgctg     300
agatacgaca tccagggcag ttgttccagc agcgccagcg cgatggtcat gagcacggca     360 cagccccgcca tgccagccag gcctatgagg tgcagggtcc gccggccggc gcgttccacc     420
acgaacagcg acaccacggt gaaggccgtg ttcacgatgc cggagccgat ggtggcatac     480
acaggctgct gc                                                         492

<210> SEQ ID NO 207
<211> LENGTH: 23
<212> TYPE: DNA
<213> ORGANISM: Canis familiaris

<400> SEQUENCE: 207
cgccgatgag tacgaccagc ctt                                              23

<210> SEQ ID NO 208
<211> LENGTH: 23
<212> TYPE: DNA
<213> ORGANISM: Canis familiaris

<400> SEQUENCE: 208
gctcagcccc tttgatgggt agc                                              23

<210> SEQ ID NO 209
<211> LENGTH: 494
<212> TYPE: DNA
<213> ORGANISM: Canis familiaris

<400> SEQUENCE: 209
cgccgatgag tacgaccagc cttgggagtg gaaccgggtc accatcccag ctctggcagc      60 ccagttttaat ggcaacgaga acggcaatc atccccctct ccttcccggg accggcggcg     120
ccagcttcga gctcctggag ggggcttcaa gcccattaag catgggagcc ctgagttctg     180
tgggatcttg ggagaaagag tggatcctgc tgtcccgctg gaaaagcaaa tctggtatca     240
cggagccatc agcagaggag atgctgagaa ccttctgcgg ctctgcaagg agtgcagcta     300
ccttgtccgg aacagccaga caagcaagca cgactattcc ctctctttga agagcaacca     360
gggctttatg cacatgaaac tggccaaaac caaagagaag tatgttctgg gtcagaacag     420
ccccccgttc gacagtgtcc cagaagtcat ccactactat accaccagaa agctacccat     480
caaaggggct gagc                                                       494

<210> SEQ ID NO 210
<211> LENGTH: 23
<212> TYPE: DNA
<213> ORGANISM: Canis familiaris

<400> SEQUENCE: 210
tgcagatcac cgaccaggtg tcc                                              23

<210> SEQ ID NO 211
<211> LENGTH: 26
```

```
<212> TYPE: DNA
<213> ORGANISM: Canis familiaris

<400> SEQUENCE: 211
catatcgcgg atgagagttt cgatgg                                          26

<210> SEQ ID NO 212
<211> LENGTH: 492
<212> TYPE: DNA
<213> ORGANISM: Canis familiaris

<400> SEQUENCE: 212
tgcagatcac ccgaccaggt gtccctgctt cgcctcacct ggagcgagct gtttgtgctg     60
aatgcagcac agtgctccat gcccctccac gtcgccccgc tcctggccgc cgcaggccta    120
cacgcctcac ccatgtccgc cgaccgagtg gtcgccttta tggaccacat acggatcttc    180
caagagcaag tggagaagct caaagcgctg cacgtcgact ccgccgagta cagctgtctc    240
aaggccatag tcctgttcac ctcagatgcc tgtggtctct ctgatgtagc ccatgtggaa    300
agcttgcagg aaaagtccca gtgtgctttg gaagaatacg ttaggagcca gtaccccaac    360
caaccaacac gattcggaaa gcttttactt cgcctcccct ccctccgcac ggtctcctcc    420
tcagtcatag agcaattgtt tttcgtccgt ttggtaggta aaacccccat cgaaactctc    480
atccgcgata tg                                                        492

<210> SEQ ID NO 213
<211> LENGTH: 160
<212> TYPE: DNA
<213> ORGANISM: Canis familiaris
<220> FEATURE:
<221> NAME/KEY: misc_feature
<222> LOCATION: (1)...(160)
<223> OTHER INFORMATION: n = A, T, C or G

<400> SEQUENCE: 213
gactgagacc atttattcna gacacgcagc tgaccaagga gtgagggagg gaccaggtgt     60
gcaagctaat aaatagagga gggggagact tcctggagct gtagccattc agtcttcatt    120
cttctcaggc atgaaggcat ctcttttctg accaaagctt                          160

<210> SEQ ID NO 214
<211> LENGTH: 128
<212> TYPE: DNA
<213> ORGANISM: Canis familiaris

<400> SEQUENCE: 214
aagctttggt cagcaattat attagtttgc attttagtga caggtgtaag agaaaggccc     60
cttcttccct tactgggaca aatctagaaa tcttacacag atgtgcaaat aaagctcgcg    120
tggtgttc                                                             128

<210> SEQ ID NO 215
<211> LENGTH: 125
<212> TYPE: DNA
<213> ORGANISM: Homo sapiens

<400> SEQUENCE: 215
gcaaagttac aaatttattg gtctggaaat aaatacaaat atctgattaa gaaacttctc     60
tggaaagact tgtacacaac agttttcctg tctcgattca gccactcctg ccctgaccaa    120
agctt                                                                125
```

```
<210> SEQ ID NO 216
<211> LENGTH: 116
<212> TYPE: DNA
<213> ORGANISM: Canis familiaris

<400> SEQUENCE: 216
gagcagcagt gagcaaaacc cacgaagttg ttttaaggtt acagctatga ataaacattg      60
tccaaacaat gaagatttag ggctgaagaa cgagcgtatg tctacagtcg aagctt        116

<210> SEQ ID NO 217
<211> LENGTH: 248
<212> TYPE: DNA
<213> ORGANISM: Canis familiaris

<400> SEQUENCE: 217
caggtgcaag aggtttgttt gggaggtaat cctagaaacc acagaagggg gtggggatag      60
gagggatggc aggaaaacca gtaagaactg tgttattgag aagttatca ctgtggacaa     120 ctggcacaga atacacttca gagctgtcgc cctgagggac aatgacgcca aggtcttttt     180
ctctaagtcc tgtttcttat aggccgaggg tggctcctgg gagcagtaac tgccaacagt     240
cgaagctt                                                              248

<210> SEQ ID NO 218
<211> LENGTH: 231
<212> TYPE: DNA
<213> ORGANISM: Canis familiaris

<400> SEQUENCE: 218
aagcttgatt gcccatacct gagccattga tatatttgaa aattatggca caaatggaag      60
agaaccacat ttgaaaagct tccagccttt caacagaaga taactcttct tgttttgcag     120
attgagcaga taatttcttt tgaaggtgat agtttcctaa attggataaa accgtggctg     180
ccattatatt cacagaaaat aaaatgaaaa cttcagttaa ttgtggattt g               231

<210> SEQ ID NO 219
<211> LENGTH: 231
<212> TYPE: DNA
<213> ORGANISM: Homo sapiens

<400> SEQUENCE: 219
caatattctt aagagtttat tataaactag tttcacaggc tacaaggaag tatttaggac      60
tatgtacagc ctgacgggaa acaggcaggg agctgaggag ggccaagatg agtctagggc     120
cttggtgggc gcattcccgg gggaggggc cctgaaaggg aaaccagaca atcctgtgag     180
actccaagaa caacggcata acaaacaaac acgtctgtgg caatcaagct t               231

<210> SEQ ID NO 220
<211> LENGTH: 180
<212> TYPE: DNA
<213> ORGANISM: Canis familiaris

<400> SEQUENCE: 220
agtagatggg accgagaata atttagggt taagggatag gaggagtagg ggcagtaggt      60
gcaaggtcat tagggcattt tctcgtgtga atgatggttt gatattttg atatggtggg     120 aatatttacc acgttgtgtg gtgattaata tataaagtga gtatagggcg gtaaaagctt     180

<210> SEQ ID NO 221
<211> LENGTH: 342
```

```
<212> TYPE: DNA
<213> ORGANISM: Homo sapiens

<400> SEQUENCE: 221
actaagaaat atttattgag cacctgctgt gtacccagca ctgcgggagg ggctgtgaga      60
gacccagggc agtacaggac ttgttcttgc ccttcagagg cttatagtct aggtggaaac    120
aggagaacca ggacacatga ggagccagga gaaaacagta caggccagga tgttacagga    180
gcttacagtg tttggggtca gacccactaa gtgcttcagt acctctaggg gctcaatgtt    240
cagggccaga agagacaata actcacaact agcccatgta gcatgccta tccacagcgt     300
ctacctctgc tatcttaaaa catctgactc ctcgttaagc tt                       342

<210> SEQ ID NO 222
<211> LENGTH: 276
<212> TYPE: DNA
<213> ORGANISM: Homo sapiens

<400> SEQUENCE: 222
caaagaattt tgttttatta tagtacatga gctggactga tgggaaaggg taggtgtatg     60
ggcaaccact gcccagatta gcatcggatg cccatcccga tggccatgaa tgtgccaaat   120
gtgccgccac tctgcatcat ggttttcccg atgccgccca tcagctcccg accccgcatt   180
ccgatcctga gacaggaaaa ggtgccgaag agcgccccgg ccgccatgcc cactgcacaa   240
cccatcacaa agcccatctt cacgcggtaa aagctt                             276

<210> SEQ ID NO 223
<211> LENGTH: 239
<212> TYPE: DNA
<213> ORGANISM: Canis familiaris

<400> SEQUENCE: 223
catatatatt cttttttatt tcttgttata cctteccaaa acagagacat tcaacagtag     60
ttagaatggc catctcccaa cattttaaaa aaactgcacc ccccaatggg tgaacaaagt   120
aaagagtagt aacctagagt tcagctgagt aagccactgt ggagccttaa gtggtgaggt   180
cttccaattt cagagtgatg tgtcttcaac ttgtatcatc attttagcgg taaaagctt    239

<210> SEQ ID NO 224
<211> LENGTH: 142
<212> TYPE: DNA
<213> ORGANISM: Canis familiaris

<400> SEQUENCE: 224
ccaaagaagt gtttattaac atttggggcc tcagcggggc cagagaggaa gtgggtgcta     60
gaggctcctg aggctcaggg caaggcctgc aagacagatc ccattgctca ggaggcagcc   120
cagattgcaa atggaagaca gg                                             142

<210> SEQ ID NO 225
<211> LENGTH: 174
<212> TYPE: DNA
<213> ORGANISM: Homo sapiens

<400> SEQUENCE: 225
aagcttttac cgcaatgagg gatttataca tgaaaaatgg acaaggcttt gcattagttt     60
actccatcac agcacagtct acatttaatg atttacaaga tctgagagag cagattcttc   120
gagttaaaga cactgatgat gtaagctgac ttcctaataa atatatttta cttg          174
```

```
<210> SEQ ID NO 226
<211> LENGTH: 213
<212> TYPE: DNA
<213> ORGANISM: Bos taurus

<400> SEQUENCE: 226
aagcttaacg aggacaggcc atcagggctg ccaaggaagc aaaaaaggct aaacaagcat      60
ctaaaaagac agcaatggct gctgctaagg ctcccacaaa ggcagcacat aagcaaaaga     120
ttgtgaagcc tgtgaaggtt ccgcacccc gagttggtga aaaacgctaa gttttagtgg      180
atcagatttt taaataaaca tctgactcta act                                  213

<210> SEQ ID NO 227
<211> LENGTH: 146
<212> TYPE: DNA
<213> ORGANISM: Rattus norvegicus
<220> FEATURE:
<221> NAME/KEY: misc_feature
<222> LOCATION: (1)...(146)
<223> OTHER INFORMATION: n = A, T, C or G

<400> SEQUENCE: 227
catggagcng ttttataccct ttatttgaca atcagcgatt agttctcatc cacattaaca     60
gtctgtagat ttttgaaagt ggtgacaggt acgtaggtaa ccagcgtgta gagcttgttt    120
ggtgaatctt catcctcgtt aagctt                                         146

<210> SEQ ID NO 228
<211> LENGTH: 138
<212> TYPE: DNA
<213> ORGANISM: Canis familiaris

<400> SEQUENCE: 228
caatggtgtc actgggctcg acctcaaggg tgatagtttt gcccgtcagg gtcttcacaa     60
agatctgcat ctctgcgtct gctggagcga actcgcaagg ccgccgccac caaaccgctc   120
gcccacctcg ttaagctt                                                  138

<210> SEQ ID NO 229
<211> LENGTH: 220
<212> TYPE: DNA
<213> ORGANISM: Canis familiaris

<400> SEQUENCE: 229
aagcttgcac catatatata actcttgggc agagggtctg gcatacataa gtagatactc     60
agaaatatct gttggattgt gttgatttaa ttatttttgt gttgcttctt ttaaagatga    120
gcactttcta ttagatattt ttttgatcaa aaaaaagata ttttttttgat catacagatt   180 taagcaggat ttttattaat tcgtttctct tcctggttgg                          220

<210> SEQ ID NO 230
<211> LENGTH: 238
<212> TYPE: DNA
<213> ORGANISM: Canis familiaris

<400> SEQUENCE: 230
catgagagag acggaaagag aggcagagac acaggcagag agagaagcag gctccatgca     60
gggagcctga cgagggactc gatcccaaga ctccaagatc gtaccctggg ccaaaggcag    120
gagcttaacc gctgagccac ccaggtgtcc caactgtcag ggttttaaaa gagtgagtga    180
aatttgggga aatatcaagg cacagtcata ttcataaaca taatacgttg agaagctt      238
```

<210> SEQ ID NO 231
<211> LENGTH: 237
<212> TYPE: DNA
<213> ORGANISM: Homo sapiens

<400> SEQUENCE: 231

```
aagcttctca acgtatatgg tgtacagttt ttgtaaggtt ttaattttac aatcattctg        60
aatagttatg gtcaagtaca aattatggta tctattactt tttaaatggt tttaatttgt       120
atatcttttg tacatgtaac tatcttagtt atttggctaa ttttaagtgg ttttgttaaa       180
gtattaatga tgccacctgt cagcacaata agagtaagaa ctaataaatg gatttgg          237
```

<210> SEQ ID NO 232
<211> LENGTH: 204
<212> TYPE: DNA
<213> ORGANISM: Homo sapiens

<400> SEQUENCE: 232

```
aagcttctca acgtattcaa gagaaaactt ctaaattgcc agatatgtta aaagaccatt        60
atccatgtgt gtcttcactg gagcagttaa cagagttggg aggtgaaact gatgtttttg       120
tatgccgtcc taacacagcc ctatgcccga tgtactcaga gactggaaca gcacaagaga       180
aataaagcaa caatcagtaa tggg                                              204
```

<210> SEQ ID NO 233
<211> LENGTH: 572
<212> TYPE: DNA
<213> ORGANISM: Homo sapiens
<220> FEATURE:
<221> NAME/KEY: misc_feature
<222> LOCATION: (1)...(572)
<223> OTHER INFORMATION: n = A, T, C or G

<400> SEQUENCE: 233

```
aagctttggt caggcaggaa taggaatgag taatttgggc tttgaaatct ctcccagaag        60
acaaactact tcgatgggaa aaagctttga cattttgtgt tttatttgta gaggggggtta      120
ttggatacag aggagcctgg tctcatacat tttcatcttc agtctgaaaa gatctgtaat       180
tctgtagacc ctgaagcggg ggaacttttc tttctgccat ctccctttgc tttcatatga       240
acacctcttc tgtaccaatc atttggaaaa gaagtgagca tatctcttgt tttaaaagtt       300
ttgcttgnct ggttagcatt ccttttgagc tcaacatata tggaacaata aatgtcattt       360
aatgctgngn gctatttga attcctcatc aggttttaga agtgggggtca agaacactta       420
aaagctcatt ggactttgaa attatnccag ccgccnttga ccattatctg gcccancaaa       480
gcaggttaaa ttatggcncc ngcaaatttg cttttttttt taatagnngg angnntacnt       540
ttcagnttaa taaatgtttt ccgatggttt gc                                     572
```

<210> SEQ ID NO 234
<211> LENGTH: 448
<212> TYPE: DNA
<213> ORGANISM: Homo sapiens

<400> SEQUENCE: 234

```
ggtcaaagtg tatagttttg acttaccccct cccagatcct gaatgtcctt ttggagtttt       60
tcagatacgg tgacagaagg taagtcaatg taaaatattt ttccccagag tggcttatat      120
ttgtattttt ctggtttgtt atcagttttc atagatttca tagatctgtt tttttcattt      180
```

| | |
|---|---|
| ttgacttgga ttccacctgt tgttaaaaaa agtagaatc agatcatgat ttatgtggac | 240 |
| agaaaatttc tcttttaaaa atactttta tacagtcatc atttcataga gggggaaaaa | 300 |
| atctttataa taccaccaat taaacactca atagcatttt actgtatttc ttcgtagtat | 360 |
| cacttaggat aaaaccagaa taccatattt gttttaacag atcccatact gtaaaataat | 420 |
| catcgttcac agcctacagt cgaagctt | 448 |

<210> SEQ ID NO 235
<211> LENGTH: 136
<212> TYPE: DNA
<213> ORGANISM: Canis familiaris

<400> SEQUENCE: 235

| | |
|---|---|
| ggggcagata aaaacactta atgtaaaatt taccctctca gaaaaatttc cagtatgcta | 60 |
| tacggtatca ctaactatag tcactatagt atacagtaga tccctaggat ttattcatga | 120 |
| tgtacagtcg aagctt | 136 |

<210> SEQ ID NO 236
<211> LENGTH: 465
<212> TYPE: DNA
<213> ORGANISM: Homo sapiens

<400> SEQUENCE: 236

| | |
|---|---|
| aagcttgatt gccagagtta cgaaaagcat caaagcatct ttatggtcag cttaaatttg | 60 |
| gtacactaga ttgtacaatt catgagggac tctgtaacat gtataacatt caggcttatc | 120 |
| caacaatagt ggtgttcaac cagtccaacg ttcatgaata cgaaggccat cactctgctg | 180 |
| aacagatctt ggaattcata gaggacctta tgaatccttc agtgatctcc ctgacaccca | 240 |
| ccactttcaa tgaactggtt aaacagagaa acatgacca agtctggatg gttgatttct | 300 |
| attctccatg gtgtcatcca tgtcaagtcc taatgccaga atggaaaaga atggcccgga | 360 |
| cattaactgg actgatcaat gtgggcagcg tagactgcca acagtatcat tctttttgtg | 420 |
| cccaagaaaa tgttcggaga tccctgagat aagaatttac ccccc | 465 |

<210> SEQ ID NO 237
<211> LENGTH: 262
<212> TYPE: DNA
<213> ORGANISM: Homo sapiens

<400> SEQUENCE: 237

| | |
|---|---|
| aagctttggt cagggctctc gttcttgccg cgtctgttca aaccggcacg gtctgatccc | 60 |
| ggaaatacgg cctcaacatg tgccggccag tgtttccgtc agtacgccaa ggatataggc | 120 |
| ttcattaagt tggattaagt gaacttcctt gaatgggtca tccaagatac ctaccttaac | 180 |
| tgcagatgtc caagatacct actttgatgc caactcattg tatataaaat aaaaatactc | 240 |
| caattatgag tgttttaatg tg | 262 |

<210> SEQ ID NO 238
<211> LENGTH: 280
<212> TYPE: DNA
<213> ORGANISM: Canis familiaris

<400> SEQUENCE: 238

| | |
|---|---|
| caagttttac cattgtttta attattgaaa caaaattaac gtaagtagaa tcatgtgcaa | 60 |
| cagtgtctct aacatatgga agaggtaaat atgaatttta caataagg tatattatcc | 120 |
| actgtaacaa atttccaata atttggcatt tatctttcac aaaatgtctc ccaaattcta | 180 |

```
agcaaagtat gcaaattgga gattaactct aaacaggcat aattatcttc ttatccagtt    240
tttctgaaga gactgaagag ttcaggtctg accaaagctt                          280

<210> SEQ ID NO 239
<211> LENGTH: 202
<212> TYPE: DNA
<213> ORGANISM: Homo sapiens

<400> SEQUENCE: 239
cagatgtgat aaaatcgttt tcattactgt caaaggcatc aaccagattt gggaatttgt    60
taaaaggtta aaaattcata caaaacctgc tgtaaattaa gacaaaggta gattaaaatg    120
catcattatc tgtctcttaa ataaagtaat gctttccata aaaagcaaag gtgggctttt    180
gccttgatgc tgaccaaagc tt                                             202

<210> SEQ ID NO 240
<211> LENGTH: 276
<212> TYPE: DNA
<213> ORGANISM: Homo sapiens

<400> SEQUENCE: 240
gggaagtgtc aaggatcagt tccgtggcac cctctgacca cagactggga gcaacacgca    60
tctgtggcat ttaaaaatgg aattggcaac ttcatgacat ggaatgcat atcacactta     120 cagtgtctag actttcctat gtgtgctcag ttacaagtag tgaagcaaaa gtatacatat    180 caccccctact gctattcggt tgctacagag ccataaatgt gaaaagcaat actctgaaat   240
aaagattttt gttttttgcc ctagcctact aagctt                              276

<210> SEQ ID NO 241
<211> LENGTH: 192
<212> TYPE: DNA
<213> ORGANISM: Canis familiaris

<400> SEQUENCE: 241
aagcttgcac catactcctc ctctacatat gctcccaaat taccttctaa aaaggctgta    60
ttaatttact ttcaccagta gtattatgag agtgcccatg tcccttagcc ttttaaaatt    120
cactatgagc aatctttaaa tcatgtacta aatcttatag gcaaagaata gggccttgcc    180
cctgcccctg tt                                                        192

<210> SEQ ID NO 242
<211> LENGTH: 137
<212> TYPE: DNA
<213> ORGANISM: Canis familiaris

<400> SEQUENCE: 242
attccttttc caaggacctc tcttctatgt gatcactgag taagttcagt cactcccatc    60
atctctagat tggagatttc caaatttatg gcctttccta actttgaagt ccttatttct   120
aactgcctac taagctt                                                   137

<210> SEQ ID NO 243
<211> LENGTH: 155
<212> TYPE: DNA
<213> ORGANISM: Homo sapiens

<400> SEQUENCE: 243
ataaatagag atgggggtct tgctatgttg ccaggctggt cttgaacttc tgggatcaag    60
```

```
caatctgcct gccttggcct cctaaagtgc tgggattaca ggtgtgagtc actgtgcctg    120
gcctcatata gtcactataa cagcctacta agctt                              155

<210> SEQ ID NO 244
<211> LENGTH: 203
<212> TYPE: DNA
<213> ORGANISM: Canis familiaris

<400> SEQUENCE: 244
aagcttagta ggcaataata gagaagtaga aattgaatgt ggaacattaa ccattaaaaa    60
tcatactttt gaatgtgctg aggtcatgaa ttgtttttac cttctttgta atttgtgttt   120
ttcagatttt ctgtagttag catatattct ataatcagaa aaagatgctt caagtttttt   180
gcagatttca cagaattttg ttt                                           203

<210> SEQ ID NO 245
<211> LENGTH: 203
<212> TYPE: DNA
<213> ORGANISM: Canis familiaris

<400> SEQUENCE: 245
aaacaaaatt ctgtgaaatc tgcaaaaaac ttgaagcatc ttttttctgat tatagaatat    60 ctgctaacta cagaaaatct gaaaaacaca aattacaaag aagataaaaa caattcatga   120
cctcagcaca ttcaaaagta tgattttttaa tggttaatgt tccacattca atttctactt   180
ctctattatt gcctactaag ctt                                           203

<210> SEQ ID NO 246
<211> LENGTH: 219
<212> TYPE: DNA
<213> ORGANISM: Canis familiaris

<400> SEQUENCE: 246
aattgtcacg aacagggctg actgacactg cagtgtgtcc ttgtttgttg atccctgatc    60
taggcctcgg cttttcaaac tgcagttgat caaactggga tatgcttcgg ctgaatctgc   120
tctctggtgc ttctctttaa tcgttttctc cttaaatggg ttactttctt actaggaaaa   180
aaaaaatgtt ccacctctgg aattaacgtt gagaagctt                          219

<210> SEQ ID NO 247
<211> LENGTH: 265
<212> TYPE: DNA
<213> ORGANISM: Homo sapiens

<400> SEQUENCE: 247
aggtcaaggt gagtttattg tccaaatagc ataacctaat tgcattcaaa accattttca    60
aatccatctt taaactagtc agaaaacagg ttattatttt tttaaatcac ttaacactga   120
acagataaga cctcttaaaa ggcagctgac tatatcatgt caccatcata gccaatacaa   180
catttttgcc atacttccta aaaacctttt cgcatacact gatcatgcta cttatcagca   240 cttttttaaca tcctgaccaa agctt                                        265

<210> SEQ ID NO 248
<211> LENGTH: 309
<212> TYPE: DNA
<213> ORGANISM: Homo sapiens

<400> SEQUENCE: 248
actaaaataa acctgttcgg ggggaacagc tactagatga atttaagggt tttatgcacc    60
```

```
ttatagaact tatagcaaaa atagttttag ttgatttcat tataaataac gttttcaaga      120
acctgtgcaa aactgtcaat aatttcctaa agcacaattg atcagaaaaa tccatgattg      180
ttcagccttc acaccttct tcatgtaaga cacccttct gtacatctca cagttactta       240
ttaggttgaa aggtatatgg tgaatggtca ttagacgtct cgacagccac ctgctgctga      300
ccaaagctt                                                              309

<210> SEQ ID NO 249
<211> LENGTH: 169
<212> TYPE: DNA
<213> ORGANISM: Mustela sp

<400> SEQUENCE: 249
acattaaatg cccagtgcaa gccaggaaca ttgcagaatg ctaaatttat ctgctaggtg       60
atgatattga acgatctaga caataatttc accttactta aataacaatg aacagaattc      120
ctttttttcc actctgagtg gatatttctg tcatctctga ccaaagctt                 169

<210> SEQ ID NO 250
<211> LENGTH: 368
<212> TYPE: DNA
<213> ORGANISM: Canis familiaris

<400> SEQUENCE: 250
aagcttcgac tgtcgcatca atgaatgttt taagtaataa ctttgctggt tatcagcttg       60
atggtgcatt aattttatgg ctcatttcct ttattttgac cattgtcgga ttcttcattt      120
tatattggac gatccccaat cgaacggtac caattttttc agctgtgatt gcggcatgtt      180
tcaacgcgac cgttttgaa attttaaaac atttatttgg ctgggtcatg agtaatttca       240
ccagctatga aatcgtttat ggtgcttttg cagcagttcc tatttttcta ctttggatct      300
atctgtcttg gaatatcatt ttattgggtg tagaagtgag ttatgcactc accgccttcc      360
attctggt                                                               368

<210> SEQ ID NO 251
<211> LENGTH: 261
<212> TYPE: DNA
<213> ORGANISM: Canis familiaris

<400> SEQUENCE: 251
agaatcaagc caccaggtgt ttatttttgc actataaata gagttcccta gtcccatttt       60
gttacataat atatgagata acagagaacc taaaattcat ttggtgaaaa tcaagtgtgt      120
agtataccta ataccaatg agctagtaag acttgtaagg cactgaagct aaggctaaca      180
gcaacagagt cctttatgaa aataatttca gaaccacaac gcattctctg atggtgcatt      240 ccctgggac agtcgaagct t                                                 261

<210> SEQ ID NO 252
<211> LENGTH: 193
<212> TYPE: DNA
<213> ORGANISM: Canis familiaris

<400> SEQUENCE: 252
catcgcagac atttatttta gttttgttaa tttcaaatat tcattaacct cttgtatcag       60
atttaaggca gagaaaagat acacgcccct ggttaactga accggggttt agatagtgta      120
gtccaccctg ggttccacca gggagacctc acccgagatg acaggtccgg ttgctggtgc      180
```
acagtcgaag ctt 193

<210> SEQ ID NO 253
<211> LENGTH: 252
<212> TYPE: DNA
<213> ORGANISM: Sus scrofa

<400> SEQUENCE: 253

| ccatttaaaa tgttttattt tccttttaa actagattgt gaagtgccac tgaaataggc | 60 |
| aatgttggca aaacaatgtc tgttacaata aaatacatta gacatttaaa taaataacct | 120 |
| taaaaactac atgggggac atgaacccag tcgattgaat ctggaacaat gttttctgca | 180 |
| caagcgagaa caggcatacc tcttgttaag actgatgtaa acagaaccat cggaacccta | 240 |
| cagtcgaagc tt | 252 |

<210> SEQ ID NO 254
<211> LENGTH: 429
<212> TYPE: DNA
<213> ORGANISM: Homo sapiens

<400> SEQUENCE: 254

| cacgttttaa aactttattt gcatattaaa aaaattgtgc attccaataa ttaaaatcat | 60 |
| ttgaacaaaa aaatggcact ctgattaaac tgcattttaa cagcctgcaa gatacccttgg | 120 |
| gccagcttgg ttttttactc tagatctcac tgtcctccca cccagcttct ccttcacca | 180 |
| acatgcaagt tcttttcctt ccctgccagc cagccagaca ggcagatggg aaaggcaggc | 240 |
| gccttcgttg tcagtagttc tccattcttt gatgtgaaaa ggggcagcac agtcatttaa | 300 |
| actcgatcca accgctttgc atcttacaaa gttaaacagc taaagaagt aaaataagaa | 360 |
| ggcaatgctt gtggaatgta cagtgcatat tggcggcgca cgcctcatta cgattcggct | 420 |
| actaagctt | 429 |

<210> SEQ ID NO 255
<211> LENGTH: 323
<212> TYPE: DNA
<213> ORGANISM: Oryctolagus cuniculus

<400> SEQUENCE: 255

| ctcattaaac ttttgtttta atgggtctca aaattctgtg acagattttt ggtcaagttg | 60 |
| tttccattaa aaagtactga ttttaaaaac taataactta aaactgccac acacgcacaa | 120 |
| aaaaaaaaaa aaaacaaat ggtccacaaa acattctcct ttccttctga aggttttacg | 180 |
| atgcattgtt atcattagcc agtcttttac tattaaactt aaatggccaa ttgacacaaa | 240 |
| cagttctgag accgttcttc caccactgat taagactggg gtggcaggta ttagggataa | 300 |
| tattcattta gcctactaag ctt | 323 |

<210> SEQ ID NO 256
<211> LENGTH: 253
<212> TYPE: DNA
<213> ORGANISM: Canis familiaris

<400> SEQUENCE: 256

| aagcttagta ggcacgcaat aaataggaga atgaatcaga gtcctccaac gcgtcctccc | 60 |
| taatgtccct ttgagctgcc tcctcttcca ctctgcctca gcttgtccat gtcacttcgc | 120 |
| tccagagcag ccgcaagagc atcttaacac cttgtggcct gaactctctc ccatcctcca | 180 |
| ctgtacagtg atatgactga aacctcattt aaccttttag aactaccagg aggaggttcc | 240 |

```
caaggatccc agg                                                          253

<210> SEQ ID NO 257
<211> LENGTH: 260
<212> TYPE: DNA
<213> ORGANISM: Canis familiaris

<400> SEQUENCE: 257
cactgaatct caatcaggaa actcttaatg cacggcacaa ctgcccagat gtgcaggaaa        60
gaaagaatgg caaagtaaat gccccatatg agtgccattg ggatgccaaa gagggcagac       120
agcaagcggt aaaaccagta ttttgtcaca gtgaaggtgg tgaagctggc cttccagatg       180
ccatcaaaac tgtgtgttcc ttctggttct gcaatcacat cttcaaaatc aatcttgacc       240
acgtcgtcgt tgagaagctt                                                  260

<210> SEQ ID NO 258
<211> LENGTH: 188
<212> TYPE: DNA
<213> ORGANISM: Canis familiaris

<400> SEQUENCE: 258 ccattttgc tcttaaagag catcttaagt gagagatcat gacaatcttt ggccactcca        60
ggttttctca tctactacat gatctgttcc caacaataag ccattgaaat taaggtctc       120 cagaagtttt atctggggtc tgtgattgaa agaaggaaa atgagatgag agactgccta       180
ctaagctt                                                               188

<210> SEQ ID NO 259
<211> LENGTH: 186
<212> TYPE: DNA
<213> ORGANISM: Homo sapiens

<400> SEQUENCE: 259
caagcccatc aattagtgtt cttttatag acattacaca caacacatat atagtgacac        60
aaacacaaga ttcaacactt gtaagatttt ttatttgcca gtttcttaat tggattactg      120 gcatcaggt ggaaacttta gaggaagaga gccaggtagc atgcatttct agggcctact      180
aagctt                                                                 186

<210> SEQ ID NO 260
<211> LENGTH: 189
<212> TYPE: DNA
<213> ORGANISM: Canis familiaris

<400> SEQUENCE: 260
cccataagaa acatctttaa aacattcaga atactcagga taatcaaggc taatattcct        60
ataaattcct tacgtgtatt atgtacattc agaaaagtgt aaattactca atatattac       120 tcaaaacccc ttatagtctg ctaacttgca tgtagaaaca tctgaagtaa catgctgcct      180
actaagctt                                                              189

<210> SEQ ID NO 261
<211> LENGTH: 174
<212> TYPE: DNA
<213> ORGANISM: Canis familiaris

<400> SEQUENCE: 261
aagcttagta ggcatcaatt ggatcctttc ctatgttgaa atggaagaat taatgagctt        60
```

```
acattaatta gtattgtaat gtgtaaagga agcccagcaa aatttttga aaacttgatg      120 atcccaacgt atttaccatt gtatgttaaa gcaaaataaa tcaccatttt ttta          174

<210> SEQ ID NO 262
<211> LENGTH: 115
<212> TYPE: DNA
<213> ORGANISM: Canis familiaris

<400> SEQUENCE: 262
aagcttctca acggcctcca cctcctttct gccctcacag cctcctggct ctggcccaaa     60
aagtgattca tttgtaaatt atcatggttt tctgcattaa aatggccatt tctgg         115

<210> SEQ ID NO 263
<211> LENGTH: 451
<212> TYPE: DNA
<213> ORGANISM: Canis familiaris
<220> FEATURE:
<221> NAME/KEY: misc_feature
<222> LOCATION: (0)...(0)
<223> OTHER INFORMATION: n = A, G, T or G

<400> SEQUENCE: 263
aagcttttac cgccatcttg gctcctgtgg aggcctgctg ggaccaggac tcctaaagcg     60
acganttttt ntggaaggct ttggtccaag gccattttg ccggctataa acggggtctc    120
cggaaccaaa gggagcacac agctcttctt aaaattgaag gtgtttacgc ccgagatgaa   180
acagaattct atttgggcaa gagatgcgct tatgtatata aagcaaaaga acaacacagt   240
cactcctggc ggcaaaccaa acaaaaccag nagtcatctg gggaaaagta actctgggcc   300
catggaaaca agtggcatgn gttccgtgcc aaattccgaa gcaatnttcc tgctaatgcc   360
attggacaca gaatccgagt gatgctgtac ccctcanagg atttaaaact aacgaanaan   420
caataaataa atgtggattt gcgntcttng g                                   451

<210> SEQ ID NO 264
<211> LENGTH: 242
<212> TYPE: DNA
<213> ORGANISM: Canis familiaris
<220> FEATURE:
<221> NAME/KEY: misc_feature
<222> LOCATION: (1)...(451)
<223> OTHER INFORMATION: n = A, T, C or G

<400> SEQUENCE: 264
caattggttt agttttattt caaaattgta caaaatggcc ataagcggct ataaaaaatt     60
tcgttttcgg aacacgtgga aattcagaaa gaacaacaaa gcaggttatc atttcacagt   120
gtaatggaaa agctctctct gaggcaggaa tcacaactct tccttcttct tccccagtct   180
ctcgtggtct ccttcccgga gcgctcgaat gaaactggta accccgatt ccgtccgatc    240 gc                                                                   242

<210> SEQ ID NO 265
<211> LENGTH: 333
<212> TYPE: DNA
<213> ORGANISM: Homo sapiens
<220> FEATURE:
<221> NAME/KEY: misc_feature
<222> LOCATION: (0)...(0)
<223> OTHER INFORMATION: n = A, T, C or G

<400> SEQUENCE: 265
cgatgttgag atccagatga cacaggaaat tcttttgtta atgttacctg gcttttggt     60
```

```
ggagttggct tgctgcagc aatattcaga ttgaaaaaaa tgggtttggg ttcactgagt      120
ttaaagggat gatgataaaa aggaggttct tcttcctctt catcccgaaa catgaggctt      180
attcactatt acatcatcat cttctttact ctgtgcgatc tgtttgcatt tctcaagtta      240
gttcttctat agtngctcct cctgattttt tagcaacttt ctcttctatt gtgggtggag      300
gtgcacgctt ttaggtttgg cgggtaaaag ctt                                   333

<210> SEQ ID NO 266
<211> LENGTH: 239
<212> TYPE: DNA
<213> ORGANISM: Canis familiaris
<220> FEATURE:
<221> NAME/KEY: misc_feature
<222> LOCATION: (1)...(333)
<223> OTHER INFORMATION: n = A, T, C or G

<400> SEQUENCE: 266
catatatatt ctttttatt tcttgttata ccttcccaaa acagagacat tcaacagtag       60
ttagaatggc catctcccaa catttaaaaa aaactgcacc ccccaatggg tgaacaaagt     120
aaagagtagt aacctagagt tcagctgagt aagccactgt ggagccttaa gtggtgaggt     180
cttccaattt cagagtgatg tgtcttcaac ttgtatcatc attttagcgg taaaagctt      239

<210> SEQ ID NO 267
<211> LENGTH: 123
<212> TYPE: DNA
<213> ORGANISM: Homo sapiens

<400> SEQUENCE: 267
cgccggccag aaagcgtaat attctttaaa ggaaccttaa caaaacttta cacttaataa      60
tgtaaatctc accatgttcc tagtcaaaaa tttactacac agactcagta gcggtaaaag     120
ctt                                                                   123

<210> SEQ ID NO 268
<211> LENGTH: 163
<212> TYPE: DNA
<213> ORGANISM: Canis familiaris

<400> SEQUENCE: 268
ccaaagaagt gtttattaac atttggggcc tcagcggggc cagagaggaa gtgggtgcta      60
gaggctcctg aggctcaggg caaggcctgc aagacagatc ccattgctca ggaggcagcc     120
cagattgcaa atgaagacag gccatggta gcggtaaaag ctt                        163

<210> SEQ ID NO 269
<211> LENGTH: 312
<212> TYPE: DNA
<213> ORGANISM: Homo sapiens

<400> SEQUENCE: 269
aagcttaacg aggagacaga ggtcatgatt ctgagatgat tggagacctt caagctcgaa      60
ttacatcctt acaagaggag gtgaagcatc tcaaacataa tcttgaaaga gtggagggag     120
aaaggaaaga agctcaggac ttgcttaatc actcggaaaa ggaaaagaat aatttagaga     180
tagatttaaa ctataagctt aaatcattac aacaacggct agaacaagag gtgaatgaac     240
ataaagtaac caaagctcgt ttaactgaca aacatcaatc tattgaagaa gcaaagtctg     300
ttgcaatgtg tg                                                         312
```

<210> SEQ ID NO 270
<211> LENGTH: 180
<212> TYPE: DNA
<213> ORGANISM: Homo sapiens

<400> SEQUENCE: 270

```
aagcttaacg aggacccaag aagcagaagg agaacaagcc aggaaaaccc cgaaaacgca      60
agaagcttga cagtgaggag gaatttggct ctgagcgaga tgagtaccgg gagaagtcag     120
agagtggagg cagcgaatat ggaactggac caggtcggaa acggaggcgg aagcacaggg     180
```

<210> SEQ ID NO 271
<211> LENGTH: 174
<212> TYPE: DNA
<213> ORGANISM: Homo sapiens

<400> SEQUENCE: 271

```
aagcttaacg aggcatgtga aaattatgag cagagaaaac tcaaggggctc agaagagacc     60
agggatctgg aagaaaaatt gaaaaggaac ttagaagaaa acaagatctc aaagacagaa    120
ttagattggt tccttgaaga cttggaaaag gaaatcaaga aatggcaaca ggag           174
```

<210> SEQ ID NO 272
<211> LENGTH: 146
<212> TYPE: DNA
<213> ORGANISM: Rattus norvegicus

<400> SEQUENCE: 272

```
aagcttaacg aggatgaaga ttcaccaaac aagctctaca cgctggttac ctacgtacct      60
gtcaccactc tcaaaaatct acagactgtt aatgtggatg agaactaatc gctgattgtc     120
aaataaaggt ataaaactgc tccatg                                          146
```

<210> SEQ ID NO 273
<211> LENGTH: 241
<212> TYPE: DNA
<213> ORGANISM: Homo sapiens

<400> SEQUENCE: 273

```
ctaaagggcc agatagtagc tgtgggctgg ggtctcaaac tgtgttgccc actactcaac      60
tctgccattg taatgtgaaa gtagtcacag acaaaatata agaaatgag tgtgactgtg     120
ttccaataaa actttattta caaaagcatt cagtgggctg gatttggctt ttgggccata     180
attaaatccc ctctggtaaa ataatcacta ttttagctgg atcatgagta cgtggaagct     240
t                                                                     241
```

<210> SEQ ID NO 274
<211> LENGTH: 224
<212> TYPE: DNA
<213> ORGANISM: Homo sapiens

<400> SEQUENCE: 274

```
acaggtttca tctgaataca tatttattag ataaatatta gaggttgtca catcatctaa      60
ctacatacag ctttgcaaga ctagaaatca caattagttt tttgaccagt ttaaagtatg    120
aaatgattgc attgtacata cgatgtacaa agacgatgat ggtttctgtg ggagttactt    180
caggctgcac tggtgggtgt gtttatgtgt gtacgtggaa gctt                      224
```

<210> SEQ ID NO 275
<211> LENGTH: 161

```
<212> TYPE: DNA
<213> ORGANISM: Canis familiaris

<400> SEQUENCE: 275
gcactaaatt caaaccaatg acctcccatg ttctaattct gattgtttaa tccaactggg      60
agggtaaacg ggagactctt tggcctgtca gtgacaaaat ggtttgtaaa aagaaaaaa      120
taaatacgat atacaagtaa gtataactag cactcaagct t                         161

<210> SEQ ID NO 276
<211> LENGTH: 158
<212> TYPE: DNA
<213> ORGANISM: Human sapiens

<400> SEQUENCE: 276
ggggtgttga agagccttgt tttgtcatat taccagagtt ggttttctgg ttccttctca      60
tttgggtagg ctctgtcaga gagaaggtct agggctgaag gctgttgttc agattctttt     120
gtcccaagtg gtgttccctt gatgtagcac tcaagctt                             158

<210> SEQ ID NO 277
<211> LENGTH: 295
<212> TYPE: DNA
<213> ORGANISM: Homo sapiens

<400> SEQUENCE: 277
aagcttgagt gctgttgctg atgtacaact taaaaatgtg aagtttgtag ctttaacttt      60
ttgtaataaa aactaataac actggcttaa gtgctgactt gaaatgctat tttataaagt     120
ttggatgtaa ataatcaatc gaggtcagca gtttgtatat gtaggagaca tagcttcctc     180
cctgcacccc ccattttttt aaatttgag gtgcttcctg tgtgttttta tgttagaatt      240
gttctccctc cttcctacac gtggtcacct ttgtttttaaa taaactgtcc tttgg         295

<210> SEQ ID NO 278
<211> LENGTH: 245
<212> TYPE: DNA
<213> ORGANISM: Homo sapiens

<400> SEQUENCE: 278
aagcttgagt gctgtatcct gtgcttttc tgtgggacca ttccattcag gagcaaagag       60
caccatgatt ccaatcttgt gtgtgtttac taacccttcc ctgaggtttg tgtatgttgg     120
atattgtggt gttttagatc actgagtgta cagaagagag aaattcaaac aaaatattgc     180
tgttcttcag ttttgtttgt ggaatttgaa attactcaaa tttaaaataa attactggac     240
tgtgg                                                                 245

<210> SEQ ID NO 279
<211> LENGTH: 253
<212> TYPE: DNA
<213> ORGANISM: Canis familiaris

<400> SEQUENCE: 279
agcatatgta agatctctgg cttgtagaag acaagtttat atagcactta aaaaccatt       60
tgttacatta aatgtcgaac tcaaactttt aaagagtata gagaactaca aaatggaaaa     120
aggaagcaga tatacgcttt atgaggaaat tgtgttaatg atctctcctc taaaaaagga    180
ctcttcccta ttatcataat gaccacactg cccgtcctta aaccactgg tcgctgacat      240
tatgccgaag ctt                                                        253
```

<210> SEQ ID NO 280
<211> LENGTH: 299
<212> TYPE: DNA
<213> ORGANISM: Homo sapiens

<400> SEQUENCE: 280

```
aacatataaa aacatttatt cactaggaat aattgtggca gacacaatcc agtgaaagca      60
gctcaatcct gctcagttag gctagttgaa gaaccatact ttaaaaaaag aaaggaagac     120
aggcaaacaa gtgttttaca ggagcaacag acttcaaggt caccccccaca agacaccctg   180
cacagcaggg acgggacag ggaggatgac ctcttagggc ctgtgccttc gcagaggtgc      240
tcggcggatg ggtgtggtct tcttgggtgt ctcctcttct gtcatctatg ccgaagctt     299
```

<210> SEQ ID NO 281
<211> LENGTH: 222
<212> TYPE: DNA
<213> ORGANISM: Canis familiaris

<400> SEQUENCE: 281

```
aagcttcggc atagttactg tttgatttta agtttttata tagttcttag ttttgaagaa      60
atccttcaag aacagtttct ctaaagagca tgttttaatt aaatgctaat taattacctt    120
tcttagtttt ccaatttagt aggccacttt caatgtctat taaagtgaaa taaaccttct    180
gaacttaaac atttttaaat cgattaaaaa ttgtgtcaaa at                       222
```

<210> SEQ ID NO 282
<211> LENGTH: 291
<212> TYPE: DNA
<213> ORGANISM: Canis familiaris

<400> SEQUENCE: 282

```
aagctttttt tttttcaaaa cggatttgta aaaactgtat ttcttacact gtgcacaaac      60
cttttatact aaataaatat caaactacat tcttcagaaa gatgtttcta gtattttct     120
taggtcactt ccatatgtag tatgtacagt gagaccactt tttaaaaagc aatgacttag    180
gcaaaccaac cctaatggtt tgttagacca tttccctgtt tttaattaaa aatcataggg    240
ttgtgcttct gtataaagtt tgtacatttc acaatgtaaa atactgacat t              291
```

<210> SEQ ID NO 283
<211> LENGTH: 423
<212> TYPE: DNA
<213> ORGANISM: Canis familiaris

<400> SEQUENCE: 283

```
atgcaaccac acggaattta ttgaacattt tcacaagtga tttcattaaa ggaaggcttt      60
ttcgtgccta tattggttac catcactttt gcccctatca caatctcatg gtgtagtcct    120
tgcatgtagc aggaactcaa caaatgtctg ctaaattgac agatggagcc ccagacgacc    180
taaaacttgc actttagaag cacttacttc atcctgagct attatgaata aggaactcaa    240
gtgactgtta aaagcattct actgatgagt tggtaatgtt ctaaagcaac atatctcaaa    300
ggaaaggata ttgagtttgt ctccaccata aaatcctatt tttaaacaaa ggtactactt    360
aaaaatggtc ttccaaaggc ctcagcagag gttctaaaga gatgtgacaa tatgccgaag    420
ctt                                                                   423
```

<210> SEQ ID NO 284
<211> LENGTH: 299

```
<212> TYPE: DNA
<213> ORGANISM: Canis familiaris

<400> SEQUENCE: 284
aacatataaa aacatttatt cactaggaat aattgtggca gacacaatcc agtgaaagca      60
gctcaatcct gctcagttag gctagttgaa gaaccatact ttaaaaaaag aaaggaagac     120
aggcaaacaa gtgttttaca ggagcaacag acttcaaggt caccccacaa agacaccctg     180
cacagcaggg acgggacagg gaggatgac ctcttagggc ctgtgccttc gcagaggtgc      240
tcggcggatg ggtgtggtct tcttgggtgt ctcctcttct gtcatctatg ccgaagctt      299

<210> SEQ ID NO 285
<211> LENGTH: 223
<212> TYPE: DNA
<213> ORGANISM: Canis familiaris

<400> SEQUENCE: 285
aagcttcggc ataaacgatc cattctcctc ggcctcccaa agtgctaagg ttccaggcgt      60
gaaccaccat gcccagcctg ttcttttttt tatctctagg tggtgctctc cagctgtagt     120
agaaatagca tttgtattgg atctattttt ttaaataggg actaaataca gaccattttg     180
ttagagtgaa atgccaaaca gaacgagat ttttctcttg gct                       223

<210> SEQ ID NO 286
<211> LENGTH: 467
<212> TYPE: DNA
<213> ORGANISM: Bos taurus

<400> SEQUENCE: 286
ctcagttcaa gtttaataga aacaacaaaa gatcaaaagt gatgccttgc tactactgta      60
catatcagtt ggcctgcccc atagcacacc tcagaccatc ctctccagag gaagaaaggc     120
tggcctcccc aaccctgca ggaaagggcg gtcttgtccc ataccacata ccacatctgc      180
agagtctaaa gtcttgttat aagcatgaca atagtacaaa aaaagattct gttttcatgg     240
atcccccact acagcccgga cctaaaatgg cgaggcgctc acttctgctt agagaaatat     300
tcttttgctct tctggacatc aggcttgatg gtatcactgc caggcttcca gccagctggg     360
cacacttccc catgcttgtc agtaaactgg aaggcctgaa ccagtcgcag tgtctcatcc     420
acagagcgac caacaggaag gtcgtttaca gtgatatgcc gaagctt                  467

<210> SEQ ID NO 287
<211> LENGTH: 387
<212> TYPE: DNA
<213> ORGANISM: Bos taurus

<400> SEQUENCE: 287
ctagttagag tcagatgttt atttaaaaat ctgatccact aaaacttagc gttttccacc      60
aactcggggt gcggaaacct tcacaggctt cacaatcttt tgcttaggtg ctgcctttgt     120
gggagcctta gcagcagcca ttgctgtctt tttagatgct tgcttagcct ttttttgcttc    180
cttggcagcc ctgatggcct gttctcgttg agccttccta acttcaggtt tctgattcct     240
cttagccatt atatcagcaa gagatgcccc agtgatggcc ctctggaatt tgactgcacg     300
gcgggttctt ttcttctgaa tttcttccga ctgtcccttt ttgtgctttc ttctgtagag     360
gacagtccag ttgatatgcc gaagctt                                        387

<210> SEQ ID NO 288
```

<211> LENGTH: 309
<212> TYPE: DNA
<213> ORGANISM: Homo sapiens

<400> SEQUENCE: 288

```
ctaaggtgat atagaagtgg actaagggag agccaaagtt ggcaatccca ttaatcttac      60
aacttcctaa attatggcaa tcacaatgcc tgcctgaatg aatatagcaa gtcctaaagg     120
atgtcttctg tgagggcaga tggaagttta cttcaactca actccatcta ctatttaagg     180
gaaggataag tcaaagtaag agttaattat ttcaacatgg tttgttccat tcatgattta     240
accacactat ggaccccaga agcagttagg taaaagggat tttctagaag cttaattatg     300
ccgaagctt                                                             309
```

<210> SEQ ID NO 289
<211> LENGTH: 420
<212> TYPE: DNA
<213> ORGANISM: Canis familiaris

<400> SEQUENCE: 289

```
aaaagagcat acttatcagt tgaatgggga tagaggtttt agatattttc caaatatttt      60
ataaaacact tcattgttga gaaatcactt acagaatggt ggctatcaaa caataattta    120
taaattttta aagcacaagt cacatgtttt gtaactcctg tgtgaattta ttttagctgt     180
gacatttaat tgaaaacatc agatatgttt tggaaaagtc ttaatttgag aacaactgaa     240
ggaagttaat ccagaatcta tatgtagtta gctattaatg atgatgcttt attgacagta     300
tattgctaat atatttcttc atgaaatctg aagttaaata gtttcgttgt ggaatagtgt     360
cactgtaaca tttcccttac gaagttcaat aaaccagctt tgccataaaa aaaaaagctt     420
```

<210> SEQ ID NO 290
<211> LENGTH: 237
<212> TYPE: DNA
<213> ORGANISM: Homo sapiens

<400> SEQUENCE: 290

```
aagctttttt ttttaagct gatgtcttat gacttttat gagtcgaaat tgttttgatt      60
tcagcaagtc aaatcttgta aaggcccgcg tatttttttt aagattatat gaagtctgtg     120
caaaagcttt aaaaagaaat gcctctgcct tgcctgcaat acatgcaatg tacgttaact     180
tcgtctctgt cctcagacac tgtccgtatt tacttccttg ttttccttttt tcttaat       237
```

<210> SEQ ID NO 291
<211> LENGTH: 398
<212> TYPE: DNA
<213> ORGANISM: Homo sapiens

<400> SEQUENCE: 291

```
caaaagaaaa aaaatagtgt tttattaact accacactgt tataatacac tttaaacgta      60
caataaggta gcctttaaat ttgaggtggt cttaagaata caaatgaac agaattccaa     120
atttttgaaa taggtgaact gctgtagtta taggtataca tttaggaaaa ttgtatagct     180
tttacaagac cagcaatgaa actttatttt gtacattttt ttaataattg aaaatataaa     240
caataattaa aaaataaaag aaaatacagc ataataaaaa acatcatttt ctcaattaaa     300
tgtactggat acatataaat ttaaagggaa gaagcaaaaa aggaaaatgg ttgatattta     360
agtgcagact gactacctag acgaaaaaaa aaaagctt                             398
```

<210> SEQ ID NO 292
<211> LENGTH: 390
<212> TYPE: DNA
<213> ORGANISM: Homo sapiens
<220> FEATURE:
<221> NAME/KEY: misc_feature
<222> LOCATION: (0)...(0)
<223> OTHER INFORMATION: n=a, t, g or c

<400> SEQUENCE: 292

| | | | | | |
|---|---|---|---|---|---|
| aagcttcatt | ccgacgaccc | aagaccctgc | gtctccgaag | gcagccnaaa | tatcctcgaa | 60 |
| agagcgcccc | caggagaaac | aagcttgatc | actatgccat | catcaagttc | cccttaacta | 120 |
| ctgagtcagc | catgaagaaa | atagaagaca | acaacacact | tgtgttcatt | gtggatgtca | 180 |
| aggccaataa | gcaccagatc | aaacaggctg | tgaagaagct | ctatgacatt | gatgtggcca | 240 |
| aggtcaacac | cttgatcagg | cctgatggag | agaagaaagc | atatgttcga | ctggctcctg | 300 |
| actatgatgc | tttggatgtt | gccaacaaaa | ttgggatcat | ctaaactgag | tccagccggc | 360 |
| tataaatcta | aatataaatt | ttttcaccat | | | | 390 |

<210> SEQ ID NO 293
<211> LENGTH: 418
<212> TYPE: DNA
<213> ORGANISM: Homo sapiens
<220> FEATURE:
<221> NAME/KEY: misc_feature
<222> LOCATION: (1)...(390)
<223> OTHER INFORMATION: n = A, T, C or G

<400> SEQUENCE: 293

| | | | | | |
|---|---|---|---|---|---|
| aagcttttt | tttttgggac | tgcttttgat | taatgcagtt | atccaattta | agtgttttta | 60 |
| ctttaactca | agtaaaaag | aaattctcac | atggtaacta | ctctatttaa | atggtcctgg | 120 |
| aaacattaaa | cagctttctg | ctgcttgctt | aatggtaata | cctttgatt | cttgattcta | 180 |
| ggacatagct | gatttattag | gtaaagtact | ctgtcaattt | taccttcacc | caagactgtc | 240 |
| atgtttaaaa | tactttagct | gtgggagaaa | tccttgtctg | tttttattgt | gagaggaatg | 300 |
| gtcatcctca | aagtctgttt | ctactacata | atgtggacta | attatttttt | ctatcacagt | 360 |
| attaacaaat | ggatttattg | taaatacaaa | gaagatatta | atatactatt | cttatgtc | 418 |

<210> SEQ ID NO 294
<211> LENGTH: 421
<212> TYPE: DNA
<213> ORGANISM: Canis familiaris

<400> SEQUENCE: 294

| | | | | | |
|---|---|---|---|---|---|
| atggcaaagc | tggtttattg | aacttcgtaa | gggaaatgtt | acagtgacac | tattccacaa | 60 |
| cgaaattatt | taacttcaga | tttcatgaag | aaatatatta | gcaatatact | gtcaataaag | 120 |
| catcatcatt | aatagctaac | tacatataga | ttctggatta | acttccttca | gttgttctca | 180 |
| aattaagact | tttccaaaac | atatctgatg | ttttcaatta | aatgtcacag | ctaaaataaa | 240 |
| ttcacacagg | agttacaaaa | catgtgactt | gtgcttaaa | aatttataat | tatttgtttg | 300 |
| atagccacca | ttctgtaagt | gatttctcaa | caatgaagtg | ttttataaat | attttggaaa | 360 |
| atatctaaaa | cctctatccc | cattcaactg | ataagtatgc | tcttttaaaa | aaaaaaagct | 420 |
| t | | | | | | 421 |

<210> SEQ ID NO 295
<211> LENGTH: 356
<212> TYPE: DNA

<213> ORGANISM: Canis familiaris

<400> SEQUENCE: 295

```
aaagaaagta attatggaac tagattttta acattgtaaa atactaaatg atccttcagt      60
tgtaagttga tatatatttg taacctttgt gaaattgtat ccttatgaaa ataccacttt     120
tgtggaagag agaatccaac tatgtaatat ttaattaaaa caatccatgt ttaccctatc     180
cctgctcaat taaacagtgt ataggtct aataatagct ctggagcaac ttttatcatg      240
agtcaaatat attaaacaca ttgatgtctt cttggtatat ctgaaaacaa gaggtagaag     300
tcctgttgag agtctttaaa ataaactatt tttacaaatg taaaaaaaaa aagctt         356
```

<210> SEQ ID NO 296
<211> LENGTH: 390
<212> TYPE: DNA
<213> ORGANISM: Homo sapiens

<400> SEQUENCE: 296

```
aagcttcatt ccgacgaccc aagaccctgc gtctccgaag gcagccgaaa tatcctcgaa      60
agagcgcccc caggagaaac aagcttgatc actatgccat catcaagttc cccttaacta     120
ctgagtcagc catgaagaaa atagaagaca acaacacact tgtgttcatt gtggatgtca     180
aggccaataa gcaccagatc aaacaggctg tgaagaagct ctatgacatt gatgtggcca     240
aggtcaacac cttgatcagg cctgatggag agaagaaagc atatgttcga ctggctcctg     300
actatgatgc tttggatgtt gccaacaaaa ttgggatcat ctaaactgag tccagccggc     360
tataaatcta aatataaatt ttttcaccat                                       390
```

<210> SEQ ID NO 297
<211> LENGTH: 216
<212> TYPE: DNA
<213> ORGANISM: Homo sapiens

<400> SEQUENCE: 297

```
aagcttcatt ccggggacac atagccagag aggaggcaaa gaaatgaaa acaaatagtc       60
ttcaaaatga ggaaaaagag gaaaacaagt gaggacactg gttttacctc caggaaacat     120
gaaaaataat ccaaatccat caaccttctt attaatgtca tttcttcctg aggaaggaag     180
atttgatgtt gtgaaataac attcgttact gttgtg                                216
```

<210> SEQ ID NO 298
<211> LENGTH: 165
<212> TYPE: DNA
<213> ORGANISM: Canis familiaris
<220> FEATURE:
<221> NAME/KEY: misc_feature
<222> LOCATION: (0)...(0)
<223> OTHER INFORMATION: n = A, T, C or G

<400> SEQUENCE: 298

```
ccaaaaagag ccatgcccag agggaaagtt ggaaacgaaa gccaagtttt catttaaaag      60
gaaacantaa agaggttagc cagagaaact tgaaccaaag aaaagacagc acgctgttca     120
gaatggtcaa taagagccta aaacggtacc ctcggaatga agctt                     165
```

<210> SEQ ID NO 299
<211> LENGTH: 165
<212> TYPE: DNA
<213> ORGANISM: Canis familiaris
<220> FEATURE:
<221> NAME/KEY: misc_feature

```
<222> LOCATION: (1)...(165)
<223> OTHER INFORMATION: n = A, T, C or G

<400> SEQUENCE: 299
ccaaaaagag ccatgcccag agggaaagtt ggaaacgaaa gccaagtttt catttaaaag      60
gaaacattaa agaggttagc cagagaaact tgaaccaaag aaaagacagc acgctgttca     120
gaatggtcaa taagagccta aaacggtacc ctcggaatga agctt                    165

<210> SEQ ID NO 300
<211> LENGTH: 150
<212> TYPE: DNA
<213> ORGANISM: Homo sapiens

<400> SEQUENCE: 300
ccatcaaatg taatttattt aaataacaat tcaattgcat gttaagtaaa ccagttgtag      60
caatataaaa atacagaatt ttgagaaaat ctggcaaatt aaacctgtat ctaaatgcag     120
catattctgt gatactacgg aatgaagctt                                      150

<210> SEQ ID NO 301
<211> LENGTH: 124
<212> TYPE: DNA
<213> ORGANISM: Canis familiaris

<400> SEQUENCE: 301
aagatttcaa agagtgagca agtgcattag cagggcagag agagaggcag cagcagactc      60
cctgctgagc tgggagccaa cttgggactc gatgccggga ccccaggatc attacccgaa     120
gctt                                                                  124

<210> SEQ ID NO 302
<211> LENGTH: 249
<212> TYPE: DNA
<213> ORGANISM: Canis familiaris

<400> SEQUENCE: 302
gggtaaatcc gtccagttta ctgtaaatat gcctttgaca aactggtaac tcatgtccca      60
tcccagtccc gagtactgga ccagggaaac tccagccaca gttgagggaa ggccacctgt     120
tggctctggg gcagcaggtc atccagtggg cttcaggagt caccaggcct ctgaccagtt     180 cctcccacc aagcagtttc agagttgtcc gccaagtcta tttcacacct ctcgtgtatg     240
ccgaagctt                                                             249

<210> SEQ ID NO 303
<211> LENGTH: 214
<212> TYPE: DNA
<213> ORGANISM: Canis familiaris

<400> SEQUENCE: 303
ggactgataa taataggatt ttatttctaa aatttatctt agagctttca aagagtataa      60
cacacagatc tttaccacca cacccccctt gcctatacag gaaacaacca agttgtgaga     120
acatttatca tgcacagaca catcagggct tgcaggtgct acacaggaat cacaaatgct     180
gttccacatc atgtcttctg ttatgccgaa gctt                                 214

<210> SEQ ID NO 304
<211> LENGTH: 253
<212> TYPE: DNA
<213> ORGANISM: Homo sapiens
```

```
<400> SEQUENCE: 304
agcatatgta agatctctgg cttgtagaag acaagtttat atagcactta aaaaaccatt      60
tgttacatta aatgtcgaac tcaaactttt aaagagtata gagaactaca aaatggaaaa     120
aggaagcaga tatacgcttt atgaggaaat tgtgttaatg atctctcctc taaaaaagga     180
ctcttcccta ttatcataat gaccacactg cccgtcctta aaaccactgg tcgctgacat     240
tatgccgaag ctt                                                        253

<210> SEQ ID NO 305
<211> LENGTH: 311
<212> TYPE: DNA
<213> ORGANISM: Canine familiaris

<400> SEQUENCE: 305
aggaagaata aaaacatata aaaacattta ttcactagga ataattgtgg cagacacaat      60
ccagtgaaag cagctcaatc ctgctcagtt aggctagttg aagaaccata ctttaaaaaa     120
agaaaggaag acaggcaaac aagtgtttta caggagcaac agacttcaag gtcacccccca    180 caagacaccc tgcacagcag ggacggggac agggaggatg acctcttagg gcctgtgcct     240
tcgcagaggt gctcggcgga tgggtgtggt cttcttgggt gtctcctctt ctgtcatcta     300
tgccgaagct t                                                          311

<210> SEQ ID NO 306
<211> LENGTH: 253
<212> TYPE: DNA
<213> ORGANISM: Canis familiaris

<400> SEQUENCE: 306
agcatatgta agatctctgg cttgtagaag acaagtttac atagcactta aaaaaccatt      60
tgttacatta aatgtcgaac tcaaactttt aaagagtata gagaactaca aaatggaaaa     120
aggaagcaga tatacgcttt atgaggaaat tgtgttaatg atctctcctc taaaaaagga     180
ctcttcccta ttatcataat gaccacactg cccgtcctta aaaccactgg tcgctgacat     240
tatgccgaag ctt                                                        253

<210> SEQ ID NO 307
<211> LENGTH: 255
<212> TYPE: DNA
<213> ORGANISM: Canis familiaris

<400> SEQUENCE: 307
aggatcctca tcaataaata gatacataca agaatagcca gactacatca acaaagtgtc      60
aatatcatgc agcggcttca atccgaagt ggtggtttga tgtgaagtgg tagtatagct      120
gtcggaggaa gcacacgatg aggaatgtag agccaataat tacgtgtaat ccgtgaaatc     180
cagtggctat aaaaaaggta gatccgtata ccccatcgga gattgtaaaa gatgtctcat     240
agtatgccga agctt                                                      255

<210> SEQ ID NO 308
<211> LENGTH: 253
<212> TYPE: DNA
<213> ORGANISM: Canis familiaris

<400> SEQUENCE: 308
agcatatgta agatctctgg cttgtagaag acaagtttat atagcactta aaaaaccatt      60
tgttacatta aatgtcgaac tcaaactttt aaagagtata gagaactaca aaatggaaaa     120
```

```
aggaagcaga tatacgcttt atgaggaaat tgtgttaatg atctctcctc taaaaaagga      180
ctcttcccta ttatcataat gaccacactg cccgtcctta aaaccactgg tcgctgacat      240
tatgccgaag ctt                                                          253

<210> SEQ ID NO 309
<211> LENGTH: 199
<212> TYPE: DNA
<213> ORGANISM: Homo sapiens

<400> SEQUENCE: 309
aagcttcggg taaccactgc taataactaa aatactctaa cttggaataa tcgactccga       60
cgtctttatt tttccaagtt gccttttctt taaaacacct ttttctgatt taatacggaa      120
taacggtctt cttttccact cgataactat ggtgtcctct tgggttactg cttaagaaaa      180
gttggtttgg gccatttcg                                                   199

<210> SEQ ID NO 310
<211> LENGTH: 562
<212> TYPE: DNA
<213> ORGANISM: Canis familiaris

<400> SEQUENCE: 310
aagctttttt tttttgaaga tacaagttag agttcaatca gtaccaaagg taaggaaaaa       60
ttaactctat gtacacagtc gagttttatc ctgcttaaaa ttgtcaagta gagaaaattc      120 tgaaatatt tatgaaaaag ctattctcat gctggcagca atggttaaaa taagatatt        180 tcctttatta aaaagaaaa agcctaaaaa acaactttaa ataatcaagt tgctgtgaag       240
tgaaagggtt tgaaagtgat gaaactgaag ttaaagttc tctatatgtg tgttttactt       300
taagcaaatt agacatagtg aataaaattt gaattttcag acaaattatt tgcttttttt      360
ttattttatt tatttattca tgagagacac agagagagag aggcagagac acaggcagag      420
ggagaagcag gctccacgca gggagcccaa tgtgggactc gatctgggaa ctccgggatc      480
aagccctgag ctgaaggtag acactcaacc gctgagccac ccaggtgccc tgatttgctt      540
tttaaagaag tctcccccctt cc                                              562

<210> SEQ ID NO 311
<211> LENGTH: 318
<212> TYPE: DNA
<213> ORGANISM: Canis familiaris

<400> SEQUENCE: 311
aagcttcggc atacggtgtg aggttacagt ccagttttgt gtgctttact acacggtttg       60
gttacaggac ttctgtgcat tgtaaaacat aaacagcatg gaaaaggtta aatacctgtg      120
tgcagattgt aagatctggt ccggacttgc tgtgtatatt gtaacgttaa gtgaaaaaga      180
accccccttt gtatcatagt catgcggtct tatgtatgat aaacagttga ataatttgtc      240
ctcagactct ttactatgct tttttaaaat taagaaaaat gtaaatatag taaaaatctt      300
cctatgcaat taacctgg                                                   318

<210> SEQ ID NO 312
<211> LENGTH: 419
<212> TYPE: DNA
<213> ORGANISM: Homo sapiens

<400> SEQUENCE: 312
```

```
aataaggctt catctagatt tttttctgtg aactgaagtt ggtcaaggat tgtaggcagc      60
agaaggctca caaacggtc agttgaggaa cagttagcag tatctgcaac atcctcaaat      120
atttccttga acaactctaa ggctagaaga gaacagtttt ctgatctgtc cagaggttgg    180
tttgaccaac gcagtagagc cacagtaggt tctaaacatt tagaacggct tcccagaatg    240
gtgttgccag atggagactg ttcaaatatc atctgagtga gcacgtggcg cagctgagtc    300
actgaacaga aggcaagaag taattctaaa acctttgaag aagaatcagg atcctttcca    360
ttgagaagac ctaatacttg actaagacat gaagaaaagt gctcatacct ggtaagctt    419
```

```
<210> SEQ ID NO 313
<211> LENGTH: 135
<212> TYPE: DNA
<213> ORGANISM: Canis familiaris

<400> SEQUENCE: 313
aagcttacca ggtagaggga ctgttggagg tatggacgca cacaggaggg ccaggccaag    60
gcacgagttt ttcagtgaag ggggtaaagc atcacaattt aaaatgtttg caattaaact   120
ggtttgttaa atatc                                                     135
```

```
<210> SEQ ID NO 314
<211> LENGTH: 143
<212> TYPE: DNA
<213> ORGANISM: Canis familiaris

<400> SEQUENCE: 314
cagcgaagag gcattaaaga ttcatgccat aagtttattt acaaacatgt tgtgtatgtt    60
gaattcaaga gattgatcca tttttcagag actgcacctc ttaaaatgtt cctttttcaca  120 tctgtttagt ggatcaaaag ctt                                            143
```

```
<210> SEQ ID NO 315
<211> LENGTH: 219
<212> TYPE: DNA
<213> ORGANISM: Canis familiaris

<400> SEQUENCE: 315
atggtgtgtg tgtgggttca aatagtttat tcacctctgt agtggaaaaa caaggagaaa    60
taaaatctgc ttacaatggc caaaatttat ggagaagccc taagttgct ttccccaaat   120 cacaaatctg attcaagaga aggaaaaaaa tgatgaaaaa catctcatca cacaaaactc   180
agtgtggtgt ctctgatagt catcagccag cagaagctt                           219
```

```
<210> SEQ ID NO 316
<211> LENGTH: 209
<212> TYPE: DNA
<213> ORGANISM: Homo sapiens

<400> SEQUENCE: 316
atcatttcaa aaataatcat ttaatgttcc ataattaaac tgtacacgac ctagtcttgg    60
gacatagaag ccagtgaggt gagtttggag cagtcccagg agccaggagt cgagttttca   120
ttggcctttt ttttcttttt tcttttgtc attctgttca tctaagatta tttggatact    180
tggcacaatc tggctctgct gctaagctt                                      209
```

```
<210> SEQ ID NO 317
<211> LENGTH: 217
<212> TYPE: DNA
<213> ORGANISM: Canis familiaris
```

<400> SEQUENCE: 317

```
agaaaaaaaa ttgataatta ggtgcagata gaaaatatga attagaagag gttaattcaa      60
gtgatcagcc tgaaagttca gcttcattag ctttgtggta aatccaccac ttcagatagt     120
aactaaagta aattttaaat ttcataagaa taaagtaatc cctgaaaaga attcactttt     180
ttcccagaag aagcttataa ttaaaaaaaa aaagctt                              217
```

<210> SEQ ID NO 318
<211> LENGTH: 222
<212> TYPE: DNA
<213> ORGANISM: Homo sapiens

<400> SEQUENCE: 318

```
attaagaaaa aggaaagcaa ggaagtaaat acggacagtg tctgagaaca gagacgaagt      60
taacgtacat tgcatgtatt gcaggcaagg cagaggcatt tctttttaaa gcttttgcac     120
agacttcata taatcttaaa aaaaatacgc gggcctttac aagatttgac ttgctgaaat     180
caaaacaatt tccactcata aaaagtcata agacatcagc tt                        222
```

<210> SEQ ID NO 319
<211> LENGTH: 232
<212> TYPE: DNA
<213> ORGANISM: Homo sapiens

<400> SEQUENCE: 319

```
caggctggtg ttataggtga agataggcat ctcttacaga tgggggtggg ggctgttgtt      60
actggtgaag ataggcatct agccagagct gcccagactc cttcagtgag tagataatgt     120
cggcgaaggc tgagagcagg ggcttggact ggtactctat gccatgcttg gcacacaggg     180
actgcaccag gggagccact ttatggtaat tgtgtcgagg catcgtaagc tt             232
```

<210> SEQ ID NO 320
<211> LENGTH: 126
<212> TYPE: DNA
<213> ORGANISM: Canis familiaris

<400> SEQUENCE: 320

```
ctagaggaag tgcttttat ttttagatca accaaacata tttaatataa aaaccttta       60
atatacaaac tgtaatcaca attgcatcca cgtagcagcg agggaatggg gtgttgcagg    120
aagctt                                                                126
```

<210> SEQ ID NO 321
<211> LENGTH: 236
<212> TYPE: DNA
<213> ORGANISM: Canis familiaris

<400> SEQUENCE: 321

```
aagcttagag gcagtaaaca ggagcgtccc caagaaaaag aggaaattct cttctaagga      60
ggagccactt agcagtggac ctgaagaggc tgctggcaac aagagcggca gctccaagaa     120
aaagaaaaag ctccagaagc tatcccagga agattagaat ggacatttta ccaggtgggg    180
caaacccaca tgattccaaa cccaccctta tatcccaata aaaacaaatt cacagg         236
```

<210> SEQ ID NO 322
<211> LENGTH: 201
<212> TYPE: DNA
<213> ORGANISM: Canis familiaris

```
<400> SEQUENCE: 322
aggcagttgc tttgaacttt atttgagaaa acaaaaggt  aaatgtatca aaagagcata      60
caggttagtg tgcagggacg gtcagtgatg gctactgagg tgaggatgtg ggctaagcag     120
ggctaaggcc tttacttggc tccagactgc tccgactttc cagcttctgg gccccccaatc   180 tgggcacgtg cctctaagct t                                               201

<210> SEQ ID NO 323
<211> LENGTH: 148
<212> TYPE: DNA
<213> ORGANISM: Canis familiaris

<400> SEQUENCE: 323
aagcttacca ggtgaagagt ggggttgtca tgaccttggc tatgacgccc agcatttcga      60
ggtggctccc tctattcttt actttgggca tcatagaaaa cgtgtctctg ggggattaat     120
cttagagaaa aataaagcct ttctgctg                                        148

<210> SEQ ID NO 324
<211> LENGTH: 130
<212> TYPE: DNA
<213> ORGANISM: Homo sapiens

<400> SEQUENCE: 324
ccaaggttca ccaagctttc aacaagcact gttcttctaa taattcctgc cacaatatat      60
taatttcttg tagcctactc caacgttcct ctgtccaacg gcacactgct gtccagcgtt     120
caccaagctt                                                            130

<210> SEQ ID NO 325
<211> LENGTH: 206
<212> TYPE: DNA
<213> ORGANISM: Homo sapiens

<400> SEQUENCE: 325
aagcttagca gcacagcaca ccaacatata caaacaccga gtgactacag tacatgccga      60
ggtaagaaaa gtacattcgg ggagactatc actgacactc aagccatttt tatttccaat     120
atgttttgct ttcacccttc ccagtgccaa aaaaaaaaa acctagtcac aaattggagt     180
aaataagaat cggtgccagt tgacct                                          206

<210> SEQ ID NO 326
<211> LENGTH: 346
<212> TYPE: DNA
<213> ORGANISM: Canis familiaris

<400> SEQUENCE: 326
aagcttctgc tggtatggaa agccttcaag gaagagggta atgaggggga agaagtgctg      60
tgccaaagtg acagcattca gtgaggaata agaaaggag ctcagtggta gcaggatgtt     120
gagcttccaa gaaaatctgg tggtggtgag aaagtggctg ctgtgcactg caaggaaaca    180
gagcgattaa agaaagagat gtgacagggt aggtggaaga gatagccaga agttagaaat    240
gggttacact gaagaagtaa attatttgat taaacaataa gtaaatatac tggggataac    300
aaaagcctga tttctccact gtctcagaag ggatttgcaa gtatgg                   346

<210> SEQ ID NO 327
<211> LENGTH: 375
<212> TYPE: DNA
<213> ORGANISM: Canis familiaris
```

```
<220> FEATURE:
<221> NAME/KEY: misc_feature
<222> LOCATION: (0)...(0)
<223> OTHER INFORMATION: n = A, T, C, or G

<400> SEQUENCE: 327
aagctttctc tggatgaaca gttaaatgga acctggaaac ctcttcctgg gattattcct      60
taagcaaggc agtgtcaaag gcaaccctcc cagcaagact tcagaaaaca gctggcagaa     120
ctacaggatc tggtgtctgg tgtgtaaaat actctcctcc ctgttcaaat gattcagaac     180
atgtgcaaag tgtgctagct ttcatcacat atacataaca gcattatgta tcaagttacc     240
ctgttcaaac aaggagcagg cttcctcttt ttgacttaaa tgacatgaag tgagaaaaaa     300
aatgagaata accntcnngg gaattataga gggttataat tctatcccna ctatttcaat     360
aaaagccatc acggg                                                      375

<210> SEQ ID NO 328
<211> LENGTH: 328
<212> TYPE: DNA
<213> ORGANISM: Canis familiaris
<220> FEATURE:
<221> NAME/KEY: misc_feature
<222> LOCATION: (1)...(375)
<223> OTHER INFORMATION: n = A, T, C or G

<400> SEQUENCE: 328
aagctttctc tggctttccg aaggtaaaac tgttgccgaa gttgctgcgt tacaagagcg      60
tatcccagaa accataaggc tacaacgccg aaattgggag ctacatcagt ttgaatcgat     120
tcaagaaggt catcgctcag gccgtcccaa tacactgacc tcaaactatc aggctcaaat     180
cttagagtgg gtcaacacaa gcccactcaa tgcagaacaa atccgagtca aactgcatga     240
aaaacacggt gtgtccgtgt ctgttgaaac tcttcgcaag ttttttgcgag attcaggcat     300 ggtcttcaaa cgcacccgcc acagcttg                                        328

<210> SEQ ID NO 329
<211> LENGTH: 160
<212> TYPE: DNA
<213> ORGANISM: Canis familiaris
<220> FEATURE:
<221> NAME/KEY: misc_feature
<222> LOCATION: (0)...(0)
<223> OTHER INFORMATION: n = A, T, C or G

<400> SEQUENCE: 329
gactgagacc atttattcna gacacgcagc tgaccaagga gtgagggagg gaccaggtgt      60
gcaagctaat aaatagagga gggggagact tcctggagct gtagccattc agtcttcatt     120
cttctcaggc atgaaggcat ctcttttctg accaaagctt                           160

<210> SEQ ID NO 330
<211> LENGTH: 128
<212> TYPE: DNA
<213> ORGANISM: Canis familiaris
<220> FEATURE:
<221> NAME/KEY: misc_feature
<222> LOCATION: (1)...(160)
<223> OTHER INFORMATION: n = A, T, C or G

<400> SEQUENCE: 330
aagctttggt cagcaattat attagtttgc attttagtga caggtgtaag agaaaggccc      60
cttcttccct tactgggaca aatctagaaa tcttacacag atgtgcaaat aaagctcgcg     120
```

```
tggtgttc                                                             128

<210> SEQ ID NO 331
<211> LENGTH: 116
<212> TYPE: DNA
<213> ORGANISM: Canis familiaris

<400> SEQUENCE: 331
gagcagcagt gagcaaaacc cacgaagttg ttttaaggtt acagctatga ataaacattg      60
tccaaacaat gaagatttag ggctgaagaa cgagcgtatg tctacagtcg aagctt        116

<210> SEQ ID NO 332
<211> LENGTH: 248
<212> TYPE: DNA
<213> ORGANISM: Canis familiaris

<400> SEQUENCE: 332
caggtgcaag aggtttgttt gggaggtaat cctagaaacc acagaagggg gtggggatag      60
gagggatggc aggaaaacca gtaagaactg tgttattgag aaggttatca ctgtggacaa     120
ctggcacaga atacacttca gagctgtcgc cctgagggac aatgacgcca aggtctttt     180 ctctaagtcc tgtttcttat aggccgaggg tggctcctgg gagcagtaac tgccaacagt     240
cgaagctt                                                            248

<210> SEQ ID NO 333
<211> LENGTH: 231
<212> TYPE: DNA
<213> ORGANISM: Canis familiaris

<400> SEQUENCE: 333
aagcttgatt gcccatacct gagccattga tatatttgaa aattatggca caaatggaag      60
agaaccacat ttgaaaagct tccagccttt caacagaaga taactcttct tgttttgcag     120
attgagcaga taatttcttt tgaaggtgat agtttcctaa attggataaa accgtggctg     180
ccattatatt cacagaaaat aaaatgaaaa cttcagttaa ttgtggattt g              231

<210> SEQ ID NO 334
<211> LENGTH: 239
<212> TYPE: DNA
<213> ORGANISM: Canis familiaris

<400> SEQUENCE: 334
catatatatt ctttttttatt tcttgttata ccttcccaaa acagagacat tcaacagtag     60
ttagaatggc catctcccaa cattttaaaa aaactgcacc ccccaatggg tgaacaaagt     120
aaagagtagt aacctagagt tcagctgagt aagccactgt ggagccttaa gtggtgaggt     180
cttccaattt cagagtgatg tgtcttcaac ttgtatcatc attttagcgg taaaagctt     239

<210> SEQ ID NO 335
<211> LENGTH: 142
<212> TYPE: DNA
<213> ORGANISM: Canis familiaris

<400> SEQUENCE: 335
ccaaagaagt gtttattaac atttggggcc tcagcggggc cagagaggaa gtgggtgcta      60
gaggctcctg aggctcaggg caaggcctgc aagacagatc ccattgctca ggaggcagcc     120
cagattgcaa atggaagaca gg                                            142
```

```
<210> SEQ ID NO 336
<211> LENGTH: 220
<212> TYPE: DNA
<213> ORGANISM: Canis familiaris

<400> SEQUENCE: 336
aagcttgcac catatatata actcttgggc agagggtctg gcatacataa gtagatactc      60
agaaatatct gttggattgt gttgatttaa ttattttttgt gttgcttctt ttaaagatga   120
gcactttcta ttagatattt ttttgatcaa aaaaaagata ttttttttgat catacagatt   180 taagcaggat ttttattaat tcgtttctct tcctggttgg                             220

<210> SEQ ID NO 337
<211> LENGTH: 136
<212> TYPE: DNA
<213> ORGANISM: Canis familiaris

<400> SEQUENCE: 337
ggggcagata aaacactta atgtaaaatt taccctctca gaaaaatttc cagtatgcta        60
tacggtatca ctaactatag tcactatagt atacagtaga tccctaggat ttattcatga    120
tgtacagtcg aagctt                                                       136

<210> SEQ ID NO 338
<211> LENGTH: 280
<212> TYPE: DNA
<213> ORGANISM: Canis familiaris

<400> SEQUENCE: 338
caagttttac cattgtttta attattgaaa caaaattaac gtaagtagaa tcatgtgcaa       60
cagtgtctct aacatatgga agaggtaaat atgaatttta acaataagg tatattatcc     120 actgtaacaa atttccaata atttggcatt tatctttcac aaaatgtctc ccaaattcta    180
agcaaagtat gcaaattgga gattaactct aaacaggcat aattatcttc ttatccagtt   240
tttctgaaga gactgaagag ttcaggtctg accaaagctt                            280

<210> SEQ ID NO 339
<211> LENGTH: 192
<212> TYPE: DNA
<213> ORGANISM: Canis familiaris

<400> SEQUENCE: 339
aagcttgcac catactcctc ctctacatat gctcccaaat taccttctaa aaaggctgta       60
ttaatttact ttcaccagta gtattatgag agtgcccatg tcccttagcc ttttaaaatt    120
cactatgagc aatctttaaa tcatgtacta aatcttatag gcaaagaata gggccttgcc    180
cctgcccctg tt                                                          192

<210> SEQ ID NO 340
<211> LENGTH: 137
<212> TYPE: DNA
<213> ORGANISM: Canis familiaris

<400> SEQUENCE: 340
attccttttc caaggacctc tcttctatgt gatcactgag taagttcagt cactcccatc       60
atctctagat tggagatttc caaatttatg gcctttccta actttgaagt ccttatttct    120
aactgcctac taagctt                                                     137
```

```
<210> SEQ ID NO 341
<211> LENGTH: 203
<212> TYPE: DNA
<213> ORGANISM: Canis familiaris

<400> SEQUENCE: 341
aagcttagta ggcaataata gagaagtaga aattgaatgt ggaacattaa ccattaaaaa      60
tcatactttt gaatgtgctg aggtcatgaa ttgtttttac cttctttgta atttgtgttt     120
ttcagatttt ctgtagttag catatattct ataatcagaa aaagatgctt caagtttttt     180
gcagatttca cagaattttg ttt                                              203

<210> SEQ ID NO 342
<211> LENGTH: 203
<212> TYPE: DNA
<213> ORGANISM: Canis familiaris

<400> SEQUENCE: 342
aaacaaaatt ctgtgaaatc tgcaaaaaac ttgaagcatc ttttctgat tatagaatat       60 ctgctaacta cagaaaatct gaaaacaca aattacaaag aagataaaaa caattcatga      120
cctcagcaca ttcaaaagta tgatttttaa tggttaatgt tccacattca atttctactt     180
ctctattatt gcctactaag ctt                                              203

<210> SEQ ID NO 343
<211> LENGTH: 219
<212> TYPE: DNA
<213> ORGANISM: Canis familiaris

<400> SEQUENCE: 343
aattgtcacg aacagggctg actgacactg cagtgtgtcc ttgtttgttg atccctgatc      60
taggcctcgg cttttcaaac tgcagttgat caaactggga tatgcttcgg ctgaatctgc     120
tctctggtgc ttctctttaa tcgttttctc cttaaatggg ttactttctt actaggaaaa     180
aaaaaatgtt ccacctctgg aattaacgtt gagaagctt                             219

<210> SEQ ID NO 344
<211> LENGTH: 368
<212> TYPE: DNA
<213> ORGANISM: Canis familiaris

<400> SEQUENCE: 344
aagcttcgac tgtcgcatca atgaatgttt taagtaataa ctttgctggt tatcagcttg      60
atggtgcatt aatttttatgg ctcatttcct ttattttgac cattgtcgga ttcttcattt    120
tatattggac gatccccaat cgaacggtac caattttttc agctgtgatt gcggcatgtt     180
tcaacgcgac cgttttttgaa attttaaaac atttatttgg ctgggtcatg agtaatttca    240
ccagctatga aatcgtttat ggtgcttttg cagcagttcc tatttttcta ctttggatct     300
atctgtcttg gaatatcatt ttattgggtg tagaagtgag ttatgcactc accgccttcc     360
attctggt                                                               368

<210> SEQ ID NO 345
<211> LENGTH: 261
<212> TYPE: DNA
<213> ORGANISM: Canis familiaris

<400> SEQUENCE: 345
agaatcaagc caccaggtgt ttattttttgc actataaata gagttcccta gtcccatttt     60
```

```
gttacataat atatgagata acagagaacc taaaattcat ttggtgaaaa tcaagtgtgt      120
agtataccta ataccaatg agctagtaag acttgtaagg cactgaagct aaggctaaca      180
gcaacagagt cctttatgaa ataatttca gaaccacaac gcattctctg atggtgcatt      240
cccctgggac agtcgaagct t                                               261

<210> SEQ ID NO 346
<211> LENGTH: 193
<212> TYPE: DNA
<213> ORGANISM: Canis familiaris

<400> SEQUENCE: 346
catcgcagac atttatttta gttttgttaa tttcaaatat tcattaacct cttgtatcag       60
atttaaggca gagaaaagat acacgcccct ggttaactga accggggttt agatagtgta      120
gtccaccctg ggttccacca gggagacctc acccgagatg acaggtccgg ttgctggtgc      180
acagtcgaag ctt                                                        193

<210> SEQ ID NO 347
<211> LENGTH: 253
<212> TYPE: DNA
<213> ORGANISM: Canis familiaris

<400> SEQUENCE: 347
aagcttagta ggcacgcaat aaataggaga atgaatcaga gtcctccaac gcgtcctccc       60
taatgtccct ttgagctgcc tcctcttcca ctctgcctca gcttgtccat gtcacttcgc      120
tccagagcag ccgcaagagc atcttaacac cttgtggcct gaactctctc ccatcctcca      180
ctgtacagtg atatgactga aacctcattt aaccttttag aactaccagg aggaggttcc      240
caaggatccc agg                                                        253

<210> SEQ ID NO 348
<211> LENGTH: 188
<212> TYPE: DNA
<213> ORGANISM: Canis familiaris

<400> SEQUENCE: 348 ccattttgc tcttaaagag catcttaagt gagagatcat gacaatcttt ggccactcca        60
ggttttctca tctactacat gatctgttcc caacaataag ccattgaaat taaggtctc       120 cagaagtttt atctggggtc tgtgattgaa aagaaggaaa atgagatgag agactgccta      180
ctaagctt                                                              188

<210> SEQ ID NO 349
<211> LENGTH: 189
<212> TYPE: DNA
<213> ORGANISM: Canis familiaris

<400> SEQUENCE: 349
cccataagaa acatctttaa aacattcaga atactcagga taatcaaggc taatattcct       60
ataaattcct tacgtgtatt atgtacattc agaaaagtgt aaattactca atatattatac    120 tcaaaacccc ttatagtctg ctaacttgca tgtagaaaca tctgaagtaa catgctgcct     180
actaagctt                                                             189

<210> SEQ ID NO 350
<211> LENGTH: 174
<212> TYPE: DNA
<213> ORGANISM: Canis familiaris
```

<400> SEQUENCE: 350

| aagcttagta ggcatcaatt ggatcctttc ctatgttgaa atggaagaat taatgagctt | 60 |
| acattaatta gtattgtaat gtgtaaagga agcccagcaa aattttttga aaacttgatg | 120 |
| atcccaacgt atttaccatt gtatgttaaa gcaaaataaa tcaccatttt ttta | 174 |

<210> SEQ ID NO 351
<211> LENGTH: 115
<212> TYPE: DNA
<213> ORGANISM: Canis familiaris

<400> SEQUENCE: 351

| aagcttctca acggcctcca cctcctttct gccctcacag cctcctggct ctggcccaaa | 60 |
| aagtgattca tttgtaaatt atcatggttt tctgcattaa aatggccatt tctgg | 115 |

<210> SEQ ID NO 352
<211> LENGTH: 451
<212> TYPE: DNA
<213> ORGANISM: Canis familiaris
<220> FEATURE:
<221> NAME/KEY: misc_feature
<222> LOCATION: (0)...(0)
<223> OTHER INFORMATION: n = A, T, C or G

<400> SEQUENCE: 352

| aagcttttac cgccatcttg gctcctgtgg aggcctgctg ggaccaggac tcctaaagcg | 60 |
| acganttttt ntggaaggct ttggtccaag gccattttttg ccggctataa acgggtctc | 120 |
| cggaaccaaa gggagcacac agctcttctt aaaattgaag gtgtttacgc ccgagatgaa | 180 |
| acagaattct atttgggcaa gagatgcgct tatgtatata aagcaaaaga acaacacagt | 240 |
| cactcctggc ggcaaaccaa acaaaaccag nagtcatctg gggaaaagta actctgggcc | 300 |
| catgaaaaca agtggcatgn gttccgtgcc aaattccgaa gcaatnttcc tgctaatgcc | 360 |
| attggacaca gaatccgagt gatgctgtac ccctcanagg atttaaaact aacgaanaan | 420 |
| caataaataa atgtggattt gcgntcttng g | 451 |

<210> SEQ ID NO 353
<211> LENGTH: 242
<212> TYPE: DNA
<213> ORGANISM: Canis familiaris
<220> FEATURE:
<221> NAME/KEY: misc_feature
<222> LOCATION: (1)...(451)
<223> OTHER INFORMATION: n = A, T, C or G

<400> SEQUENCE: 353

| caattggttt agttttattt caaaattgta caaaatggcc ataagcggct ataaaaaatt | 60 |
| tcgttttcgg aacacgtgga aattcagaaa gaacaacaaa gcaggttatc atttcacagt | 120 |
| gtaatggaaa agctctctct gaggcaggaa tcacaactct tccttcttct tccccagtct | 180 |
| ctcgtggtct ccttcccgga gcgctcgaat gaaactggta accccgatt ccgtccgatc | 240 |
| gc | 242 |

<210> SEQ ID NO 354
<211> LENGTH: 239
<212> TYPE: DNA
<213> ORGANISM: Canis familiaris

<400> SEQUENCE: 354

```
catatatatt cttttttatt tcttgttata ccttcccaaa acagagacat tcaacagtag      60
ttagaatggc catctcccaa cattttaaaa aaactgcacc ccccaatggg tgaacaaagt     120
aaagagtagt aacctagagt tcagctgagt aagccactgt ggagccttaa gtggtgaggt    180
cttccaattt cagagtgatg tgtcttcaac ttgtatcatc attttagcgg taaaagctt    239
```

<210> SEQ ID NO 355
<211> LENGTH: 163
<212> TYPE: DNA
<213> ORGANISM: Canis familiaris

<400> SEQUENCE: 355

```
ccaaagaagt gtttattaac atttggggcc tcagcggggc cagagaggaa gtgggtgcta    60
gaggctcctg aggctcaggg caaggcctgc aagacagatc ccattgctca ggaggcagcc   120
cagattgcaa atggaagaca ggccatggta gcggtaaaag ctt                     163
```

<210> SEQ ID NO 356
<211> LENGTH: 161
<212> TYPE: DNA
<213> ORGANISM: Canis familiaris

<400> SEQUENCE: 356

```
gcactaaatt caaccaatg acctcccatg ttctaattct gattgtttaa tccaactggg     60
agggtaaacg ggagactctt tggcctgtca gtgacaaaat ggtttgtaaa aagaaaaaa    120 taaatacgat atacaagtaa gtataactag cactcaagct t                      161
```

<210> SEQ ID NO 357
<211> LENGTH: 253
<212> TYPE: DNA
<213> ORGANISM: Canis familiaris

<400> SEQUENCE: 357

```
agcatatgta agatctctgg cttgtagaag acaagtttat atagcactta aaaaaccatt     60
tgttacatta aatgtcgaac tcaaactttt aagagtata gagaactaca aaatggaaaa    120
aggaagcaga tatacgcttt atgaggaaat tgtgttaatg atctctcctc taaaaaagga   180
ctcttcccta ttatcataat gaccacactg cccgtcctta aaaccactgg tcgctgacat   240
tatgccgaag ctt                                                       253
```

<210> SEQ ID NO 358
<211> LENGTH: 222
<212> TYPE: DNA
<213> ORGANISM: Canis familiaris

<400> SEQUENCE: 358

```
aagcttcggc atagttactg tttgatttta agttttata tagttcttag ttttgaagaa     60
atccttcaag aacagtttct ctaaagagca tgttttaatt aaatgctaat taattaccttt  120 tcttagtttt ccaatttagt aggccacttt caatgtctat taaagtgaaa taaaccttct   180
gaacttaaac attttaaat cgattaaaaa ttgtgtcaaa at                       222
```

<210> SEQ ID NO 359
<211> LENGTH: 291
<212> TYPE: DNA
<213> ORGANISM: Canis familiaris

<400> SEQUENCE: 359

```
aagctttttt ttttcaaaa cggatttgta aaaactgtat ttcttacact gtgcacaaac     60
```

```
cttttatact aaataaatat caaactacat tcttcagaaa gatgtttcta gtattttct      120 taggtcactt ccatatgtag tatgtacagt gagaccactt tttaaaaagc aatgacttag    180
gcaaaccaac cctaatggtt tgttagacca tttccctgtt tttaattaaa aatcataggg    240
ttgtgcttct gtataaagtt tgtacatttc acaatgtaaa atactgacat t             291

<210> SEQ ID NO 360
<211> LENGTH: 423
<212> TYPE: DNA
<213> ORGANISM: Canis familiaris

<400> SEQUENCE: 360
atgcaaccac acggaattta ttgaacattt tcacaagtga tttcattaaa ggaaggcttt     60
ttcgtgccta tattggttac catcactttt gccctatca caatctcatg gtgtagtcct    120
tgcatgtagc aggaactcaa caaatgtctg ctaaattgac agatggagcc ccagacgacc    180
taaaacttgc actttagaag cacttacttc atcctgagct attatgaata aggaactcaa    240
gtgactgtta aaagcattct actgatgagt tggtaatgtt ctaaagcaac atatctcaaa    300
ggaaaggata ttgagtttgt ctccaccata aaatcctatt tttaaacaaa ggtactactt    360
aaaaatggtc ttccaaaggc ctcagcagag gttctaaaga gatgtgacaa tatgccgaag    420
ctt                                                                  423

<210> SEQ ID NO 361
<211> LENGTH: 299
<212> TYPE: DNA
<213> ORGANISM: Canis familiaris

<400> SEQUENCE: 361
aacatataaa aacatttatt cactaggaat aattgtggca gacacaatcc agtgaaagca     60
gctcaatcct gctcagttag gctagttgaa gaaccatact ttaaaaaaag aaaggaagac    120
aggcaaacaa gtgttttaca ggagcaacag acttcaaggt cacccccaca agacaccctg    180
cacagcaggg acgggacagg gaggatgac ctcttagggc ctgtgccttc gcagaggtgc     240
tcggcggatg ggtgtggtct tcttgggtgt ctcctcttct gtcatctatg ccgaagctt     299

<210> SEQ ID NO 362
<211> LENGTH: 223
<212> TYPE: DNA
<213> ORGANISM: Canis familiaris

<400> SEQUENCE: 362
aagcttcggc ataaacgatc cattctcctc ggcctcccaa agtgctaagg ttccaggcgt     60
gaaccaccat gcccagcctg ttctttttt tatctctagg tggtgctctc cagctgtagt     120
agaaatagca tttgtattgg atctattttt ttaaataggg actaaataca gaccattttg    180
ttagagtgaa atgccaaaca agaacgagat ttttctcttg gct                      223

<210> SEQ ID NO 363
<211> LENGTH: 420
<212> TYPE: DNA
<213> ORGANISM: Canis familiaris

<400> SEQUENCE: 363
aaaagagcat acttatcagt tgaatgggga tagaggtttt agatattttc caaatatttt     60
ataaaacact tcattgttga gaaatcactt acagaatggt ggctatcaaa caataatta    120
```

-continued

```
taaatttta aagcacaagt cacatgtttt gtaactcctg tgtgaattta ttttagctgt    180
gacatttaat tgaaacatc agatatgttt tggaaaagtc ttaatttgag aacaactgaa    240
ggaagttaat ccagaatcta tatgtagtta gctattaatg atgatgcttt attgacagta   300
tattgctaat atatttcttc atgaaatctg aagttaaata gtttcgttgt ggaatagtgt   360
cactgtaaca tttcccttac gaagttcaat aaaccagctt tgccataaaa aaaaaagctt   420
```

<210> SEQ ID NO 364
<211> LENGTH: 421
<212> TYPE: DNA
<213> ORGANISM: Canis familiaris

<400> SEQUENCE: 364

```
atggcaaagc tggtttattg aacttcgtaa gggaaatgtt acagtgacac tattccacaa    60
cgaaattatt taacttcaga tttcatgaag aaatatatta gcaatatact gtcaataaag   120
catcatcatt aatagctaac tacatataga ttctggatta acttccttca gttgttctca   180
aattaagact tttccaaaac atatctgatg tttcaatta aatgtcacag ctaaaataaa    240
ttcacacagg agttacaaaa catgtgactt gtgctttaaa aatttataat tatttgtttg   300
atagccacca ttctgtaagt gatttctcaa caatgaagtg ttttataaat attttggaaa   360
atatctaaaa cctctatccc cattcaactg ataagtatgc tcttttaaaa aaaaaaagct   420
t                                                                   421
```

<210> SEQ ID NO 365
<211> LENGTH: 356
<212> TYPE: DNA
<213> ORGANISM: Canis familiaris

<400> SEQUENCE: 365

```
aaagaaagta attatggaac tagattttta acattgtaaa atactaaatg atccttcagt    60
tgtaagttga tatatatttg taacctttgt gaaattgtat ccttatgaaa ataccacttt   120
tgtggaagag agaatccaac tatgtaatat ttaattaaaa caatccatgt ttaccctatc   180
cctgctcaat taaacagtgt ataggtct aataatagct ctggagcaac ttttatcatg    240
agtcaaatat attaaacaca ttgatgtctt cttggtatat ctgaaaacaa gaggtagaag   300
tcctgttgag agtctttaaa ataaactatt tttacaaatg taaaaaaaaa aagctt       356
```

<210> SEQ ID NO 366
<211> LENGTH: 165
<212> TYPE: DNA
<213> ORGANISM: Canis familiaris
<220> FEATURE:
<221> NAME/KEY: misc_feature
<222> LOCATION: (0)...(0)
<223> OTHER INFORMATION: n = A, T, C, or G

<400> SEQUENCE: 366

```
ccaaaaagag ccatgcccag agggaaagtt ggaaacgaaa gccaagtttt catttaaaag    60
gaaacantaa agaggttagc cagagaaact tgaaccaaag aaaagacagc acgctgttca   120
gaatggtcaa taagagccta aaacggtacc ctcggaatga agctt                    165
```

<210> SEQ ID NO 367
<211> LENGTH: 165
<212> TYPE: DNA
<213> ORGANISM: Canis familiaris
<220> FEATURE:
<221> NAME/KEY: misc_feature
<222> LOCATION: (1)...(165)
<223> OTHER INFORMATION: n = A, T, C or G

<400> SEQUENCE: 367

| ccaaaaagag ccatgcccag agggaaagtt ggaaacgaaa gccaagtttt catttaaaag | 60 |
| gaaacattaa agaggttagc cagagaaact tgaaccaaag aaaagacagc acgctgttca | 120 |
| gaatggtcaa taagagccta aaacggtacc ctcggaatga agctt | 165 |

<210> SEQ ID NO 368
<211> LENGTH: 124
<212> TYPE: DNA
<213> ORGANISM: Canis familiaris

<400> SEQUENCE: 368

| aagatttcaa agagtgagca agtgcattag cagggcagag agagaggcag cagcagactc | 60 |
| cctgctgagc tgggagccaa cttgggactc gatgccggga ccccaggatc attacccgaa | 120 |
| gctt | 124 |

<210> SEQ ID NO 369
<211> LENGTH: 249
<212> TYPE: DNA
<213> ORGANISM: Canis familiaris

<400> SEQUENCE: 369

| gggtaaatcc gtccagttta ctgtaaatat gcctttgaca aactggtaac tcatgtccca | 60 |
| tcccagtccc gagtactgga ccagggaaac tccagccaca gttgagggaa ggccacctgt | 120 |
| tggctctggg gcagcaggtc atccagtggg cttcaggagt caccaggcct ctgaccagtt | 180 |
| cctccccacc aagcagtttc agagttgtcc gccaagtcta tttcacacct ctcgtgtatg | 240 |
| ccgaagctt | 249 |

<210> SEQ ID NO 370
<211> LENGTH: 214
<212> TYPE: DNA
<213> ORGANISM: Canis familiaris

<400> SEQUENCE: 370

| ggactgataa taataggatt ttatttctaa aatttatctt agagctttca aagagtataa | 60 |
| cacacagatc tttaccacca cacccccctt gcctatacag gaaacaacca agttgtgaga | 120 |
| acatttatca tgcacagaca catcagggct tgcaggtgct acacaggaat cacaaatgct | 180 |
| gttccacatc atgtcttctg ttatgccgaa gctt | 214 |

<210> SEQ ID NO 371
<211> LENGTH: 311
<212> TYPE: DNA
<213> ORGANISM: Canis familiaris

<400> SEQUENCE: 371

| aggaagaata aaaacatata aaacatttta ttcactagga ataattgtgg cagacacaat | 60 |
| ccagtgaaag cagctcaatc ctgctcagtt aggctagttg aagaaccata ctttaaaaaa | 120 |
| agaaaggaag acaggcaaac aagtgtttta caggagcaac agacttcaag gtcaccccca | 180 |
| caagacaccc tgcacagcag ggacggggac agggaggatg acctcttagg gcctgtgcct | 240 |
| tcgcagaggt gctcggcgga tgggtgtggt cttcttgggt gtctcctctt ctgtcatcta | 300 |
| tgccgaagct t | 311 |

<210> SEQ ID NO 372
<211> LENGTH: 253
<212> TYPE: DNA
<213> ORGANISM: Canis familiaris

<400> SEQUENCE: 372

| agcatatgta agatctctgg cttgtagaag acaagtttac atagcactta aaaaaccatt | 60 |
| tgttacatta aatgtcgaac tcaaactttt aaagagtata gagaactaca aaatggaaaa | 120 |
| aggaagcaga tatacgcttt atgaggaaat tgtgttaatg atctctcctc taaaaaagga | 180 |
| ctcttcccta ttatcataat gaccacactg cccgtcctta aaaccactgg tcgctgacat | 240 |
| tatgccgaag ctt | 253 |

<210> SEQ ID NO 373
<211> LENGTH: 253
<212> TYPE: DNA
<213> ORGANISM: Canis familiaris

<400> SEQUENCE: 373

| agcatatgta agatctctgg cttgtagaag acaagtttat atagcactta aaaaaccatt | 60 |
| tgttacatta aatgtcgaac tcaaactttt aaagagtata gagaactaca aaatggaaaa | 120 |
| aggaagcaga tatacgcttt atgaggaaat tgtgttaatg atctctcctc taaaaaagga | 180 |
| ctcttcccta ttatcataat gaccacactg cccgtcctta aaaccactgg tcgctgacat | 240 |
| tatgccgaag ctt | 253 |

<210> SEQ ID NO 374
<211> LENGTH: 318
<212> TYPE: DNA
<213> ORGANISM: Canis familiaris

<400> SEQUENCE: 374

| aagcttcggc atacggtgtg aggttacagt ccagttttgt gtgctttact acacggtttg | 60 |
| gttacaggac ttctgtgcat tgtaaaacat aaacagcatg gaaaaggtta atacctgtg | 120 |
| tgcagattgt aagatctggt ccggacttgc tgtgtatatt gtaacgttaa gtgaaaaaga | 180 |
| accccccttt gtatcatagt catgcggtct tatgtatgat aaacagttga ataatttgtc | 240 |
| ctcagactct ttactatgct ttttaaaat taagaaaaat gtaaatatag taaaaatctt | 300 |
| cctatgcaat taacctgg | 318 |

<210> SEQ ID NO 375
<211> LENGTH: 135
<212> TYPE: DNA
<213> ORGANISM: Canis familiaris

<400> SEQUENCE: 375

| aagcttacca ggtagaggga ctgttggagg tatggacgca cacaggaggg ccaggccaag | 60 |
| gcacgagttt ttcagtgaag ggggtaaagc atcacaattt aaaatgtttg caattaaact | 120 |
| ggtttgttaa atatc | 135 |

<210> SEQ ID NO 376
<211> LENGTH: 143
<212> TYPE: DNA
<213> ORGANISM: Canis familiaris

<400> SEQUENCE: 376

| cagcgaagag gcattaaaga ttcatgccat aagtttattt acaaacatgt tgtgtatgtt | 60 |

```
gaattcaaga gattgatcca tttttcagag actgcacctc ttaaaatgtt ccttttcaca    120
tctgtttagt ggatcaaaag ctt                                           143

<210> SEQ ID NO 377
<211> LENGTH: 219
<212> TYPE: DNA
<213> ORGANISM: Canis familiaris

<400> SEQUENCE: 377
atggtgtgtg tgtgggttca aatagtttat tcacctctgt agtggaaaaa caaggagaaa    60
taaaatctgc ttacaatggc caaaatttat ggagaagccc taagttgct ttccccaaat    120 cacaaatctg attcaagaga aggaaaaaaa tgatgaaaaa catctcatca cacaaaactc    180
agtgtggtgt ctctgatagt catcagccag cagaagctt                          219

<210> SEQ ID NO 378
<211> LENGTH: 217
<212> TYPE: DNA
<213> ORGANISM: Canis familiaris

<400> SEQUENCE: 378
agaaaaaaaa ttgataatta ggtgcagata gaaaatatga attagaagag gttaattcaa    60
gtgatcagcc tgaaagttca gcttcattag ctttgtggta aatccaccac ttcagatagt    120
aactaaagta aattttaaat ttcataagaa taaagtaatc cctgaaaaga attcacttt    180 ttcccagaag aagcttataa ttaaaaaaaa aaagctt                            217

<210> SEQ ID NO 379
<211> LENGTH: 126
<212> TYPE: DNA
<213> ORGANISM: Canis familiaris

<400> SEQUENCE: 379
ctagaggaag tgcttttat ttttagatca accaaacata tttaatataa aaacctttta    60
atatacaaac tgtaatcaca attgcatcca cgtagcagcg agggaatggg gtgttgcagg    120
aagctt                                                              126

<210> SEQ ID NO 380
<211> LENGTH: 236
<212> TYPE: DNA
<213> ORGANISM: Canis familiaris

<400> SEQUENCE: 380
aagcttagag gcagtaaaca ggagcgtccc caagaaaaag aggaaattct cttctaagga    60
ggagccactt agcagtggac ctgaagaggc tgctggcaac aagagcggca gctccaagaa    120
aaagaaaaag ctccagaagc tatcccagga agattagaat ggacatttta ccaggtgggg    180
caaacccaca tgattccaaa cccacccta tatcccaata aaaacaaatt cacagg         236

<210> SEQ ID NO 381
<211> LENGTH: 148
<212> TYPE: DNA
<213> ORGANISM: Canis familiaris

<400> SEQUENCE: 381
aagcttacca ggtgaagagt ggggttgtca tgaccttggc tatgacgccc agcatttcga    60
ggtggctccc tctattcttt actttgggca tcatagaaaa cgtgtctctg ggggattaat   120
```

```
cttagagaaa aataaagcct ttctgctg                                      148
```

```
<210> SEQ ID NO 382
<211> LENGTH: 346
<212> TYPE: DNA
<213> ORGANISM: Canis familiaris

<400> SEQUENCE: 382
aagcttctgc tggtatggaa agccttcaag gaagagggta atgaggggga agaagtgctg    60
tgccaaagtg acagcattca gtgaggaata agaaaggag ctcagtggta gcaggatgtt   120
gagcttccaa gaaatctgg tggtggtgag aaagtggctg ctgtgcactg caaggaaaca   180
gagcgattaa agaaagagat gtgacagggt aggtggaaga gatagccaga agttagaaat   240
gggttacact gaagaagtaa attatttgat taaacaataa gtaaatatac tgggataac   300 aaaagcctga tttctccact gtctcagaag ggatttgcaa gtatgg                346

<210> SEQ ID NO 383
<211> LENGTH: 375
<212> TYPE: DNA
<213> ORGANISM: Canis familiaris
<220> FEATURE:
<221> NAME/KEY: misc_feature
<222> LOCATION: (0)...(0)
<223> OTHER INFORMATION: n = A, C, T or G

<400> SEQUENCE: 383
aagctttctc tggatgaaca gttaaatgga acctggaaac ctcttcctgg gattattcct    60
taagcaaggc agtgtcaaag gcaaccctcc cagcaagact tcagaaaaca gctggcagaa   120
ctacaggatc tggtgtctgg tgtgtaaaat actctcctcc ctgttcaaat gattcagaac   180
atgtgcaaag tgtgctagct ttcatcacat atacataaca gcattatgta tcaagttacc   240
ctgttcaaac aaggagcagg cttcctcttt ttgacttaaa tgacatgaag tgagaaaaaa   300
aatgagaata accntcnngg gaattataga gggttataat tctatcccna ctatttcaat   360
aaaagccatc acggg                                                   375

<210> SEQ ID NO 384
<211> LENGTH: 328
<212> TYPE: DNA
<213> ORGANISM: Canis familiaris
<220> FEATURE:
<221> NAME/KEY: misc_feature
<222> LOCATION: (1)...(375)
<223> OTHER INFORMATION: n = A,T,C or G

<400> SEQUENCE: 384
aagctttctc tggctttccg aaggtaaaac tgttgccgaa gttgctgcgt tacaagagcg    60
tatcccagaa accataaggc tacaacgccg aaattgggag ctacatcagt ttgaatcgat   120
tcaagaaggt catcgctcag gccgtcccaa tacactgacc tcaaactatc aggctcaaat   180
cttagagtgg gtcaacacaa gcccactcaa tgcagaacaa atccgagtca aactgcatga   240
aaaacacggt gtgtccgtgt ctgttgaaac tcttcgcaag tttttgcgag attcaggcat   300
ggtcttcaaa cgcacccgcc acagcttg                                    328

<210> SEQ ID NO 385
<211> LENGTH: 45
<212> TYPE: DNA
<213> ORGANISM: Canis familiaris

<400> SEQUENCE: 385
```

-continued

```
tctagtcgac ggccagtgaa ttgtaatacg actcactata gggcg                45
```

<210> SEQ ID NO 386
<211> LENGTH: 30
<212> TYPE: DNA
<213> ORGANISM: Canis familiaris

<400> SEQUENCE: 386

```
aagcagtggt atcaacgcag agtacgcggg                                 30
```